US007118872B2

(12) United States Patent
Beltzer et al.

(10) Patent No.: US 7,118,872 B2
(45) Date of Patent: Oct. 10, 2006

(54) BINDING POLYPEPTIDES FOR B LYMPHOCYTE STIMULATOR PROTEIN (BLYS)

(75) Inventors: James P. Beltzer, Carlisle, MA (US); M. Daniel Potter, deceased, late of Acton, MA (US); by Marilou Potter, legal representative, Acton, MA (US); Tony J. Fleming, Waltham, MA (US); Robert Charles Ladner, Ijamsville, MD (US)

(73) Assignee: Dyax Corp., Cambridge, MA (US)

( * ) Notice: Subject to any disclaimer, the term of this patent is extended or adjusted under 35 U.S.C. 154(b) by 333 days.

(21) Appl. No.: 09/932,322

(22) Filed: Aug. 17, 2001

(65) Prior Publication Data

US 2003/0194743 A1  Oct. 16, 2003

Related U.S. Application Data

(60) Provisional application No. 60/226,489, filed on Aug. 18, 2000.

(51) Int. Cl.
G01N 33/53 (2006.01)
A61K 38/00 (2006.01)

(52) U.S. Cl. .......................... 435/7.1; 514/12; 514/13; 514/15

(58) Field of Classification Search .................. 435/6, 435/7.1, 235.1; 530/327, 328; 536/23.1; 514/2, 17, 16, 13
See application file for complete search history.

(56) References Cited

U.S. PATENT DOCUMENTS

| | | | |
|---|---|---|---|
| 4,179,337 A | 12/1979 | Davis et al. | |
| 5,223,409 A | 6/1993 | Ladner et al. | |
| 5,403,484 A | 4/1995 | Ladner et al. | |
| 5,474,981 A | 12/1995 | Ladner et al. | |
| 5,571,698 A | 11/1996 | Ladner et al. | |
| 5,576,195 A | 11/1996 | Robinson et al. | |
| 5,643,575 A | 7/1997 | Martinez et al. | |
| 5,795,724 A | 8/1998 | Hillman et al. | |
| 5,846,818 A | 12/1998 | Robinson et al. | |
| 5,869,331 A | 2/1999 | Dornburg | 435/320.1 |
| 6,207,160 B1 * | 3/2001 | Victoria et al. | 424/185.1 |
| 6,475,981 B1 | 11/2002 | Shu | |
| 2002/0081296 A1 | 6/2002 | Theill et al. | |

FOREIGN PATENT DOCUMENTS

| | | |
|---|---|---|
| EP | 439095 | 5/1998 |
| WO | WO 93/21232 | 10/1993 |
| WO | WO 97/46251 | 12/1997 |
| WO | WO 98/50547 | 11/1998 |
| WO | WO 00/43032 | 7/2000 |
| WO | WO 01/81417 A2 | 11/2001 |
| WO | WO 02/24909 | 3/2002 |
| WO | WO 02/092620 A2 | 11/2002 |
| WO | WO 02/094852 A2 | 11/2002 |
| WO | WO 03/030833 A2 | 4/2003 |

OTHER PUBLICATIONS

Sauge-Merle et al., 1999, European Journal of Biochemistry, vol. 266, pp. 62-69.*
Han et al., 1998, Virology, vol. 251, pp. 253-263.*
Caliceti et al., *Bioconjug. Chem.*, 10:638-646 (1999).
Moore et al., *Science*, 285: 260-263 (1999).
Morpurgo et al., *Appl. Biochem. Biotechnol.*, 56:59-72 (1996).
Vorobjev et al., *Nucleosides & Nucleotides*, 18: 2745-2750 (1999).
Koo et al., *FEMS Microbiology Letters*, 134: 159-164 (1995).
Malvar et al., *Genetics*, 132: 951-962 (1992).
Vandenberghe et al., *Biochemistry*, 37(8): 13075-13081 (1998).
Xia et al., *J. Experimental Medicine*, 192(1): 137-143 (2000).
Yan et al., *Nature Immunology*, 1(1): 37-41 (2000).
U.S. Appl. No. 09/932,613, filed Aug. 17, 2001, Beltzer et al.
U.S. Appl. No. 60/132,892, filed Jan. 2002, Shu.
U.S. Appl. No. 60/201,012, filed Jan. 2002, Shu.
U.S. Appl. No. 60/204,039, filed Jan. 2002, Theill.
U.S. Appl. No. 60/214,591, filed Jan. 2002, Theill.
Cull et al., *Proc. Natl. Acad. Sci. USA*, "Screening for receptor ligands using large libraries of peptides linked to the C terminus of the *lac* repressor", vol. 89: pp. 1865-1869 (1992).
Cwirla et al., *Proc. Natl. Acad. Sci. USA*, "Peptides on phage: A vast library of peptides for identifying ligands", vol. 87: pp. 6378-6382 (1990).
Devlin, *Science*, "Random Peptide Libraries: A Source of Specific Protein Binding Molecules", vol. 249: pp. 404-406 (1990).
Fell et al., *J. Immunol.*, "Genetic Construction and Characterization of a Fusion Protein Consisting of a Chimeric F(ab') with Specificity for Carcinomas and Human IL-2", vol. 246: pp. 2446/2452 (1991).
Felici, *J.Mol.Bio.*, "Selection of Antibody Ligands from a Large Library of Oligopeptides Expressed on a Mulivalent Exposition Vector", vol. 222: pp. 301-310 (1991).
Fodor, *Nature*, "Multiplexed biochemical assays with biological chips", vol. 364: pp. 555-556 (1993).
Gillies et al., *Proc. Natl. Acad. Sci. USA*, "Antibody-targeted interleukin 2 stimulates T-cell killing of autologous tumor cells", vol. 89: pp. 1428-1432 (1992).
Hahne et al. *J.Exp. Med.*, "APRIL, a New Ligand of the Tumor Necrosis Factor Family, Stimulates Tumor Cell Growth", vol. 188(6): pp. 1185-1190 (1998).
Houghten, *Bio/Techniques*, "The Use of Synthetic Peptide Combinatorial Libraries for the Identification of Bioactive Peptides", vol. 13: pp. 412-411 (1992).

(Continued)

Primary Examiner—B. Dell Chism
(74) *Attorney, Agent, or Firm*—Fish & Richardson P.C.

(57) ABSTRACT

Binding polypeptides comprising specific amino acid sequences are disclosed that bind B Lymphocyte Stimulator (BLyS) protein or BLyS-like polypeptides. The binding polypeptides can be used in methods of the invention for detecting or isolating BLyS protein or BLyS-like polypeptides in solutions or mixtures, such as blood, tissue samples, or conditioned media.

31 Claims, No Drawings

OTHER PUBLICATIONS

Kwon et al., *J.Biol. Chem.*, "Identification of a Novel Activation-inducible Protein of the Tumor Necrosis Factor Receptor Superfamily and It's Ligand", vol. 274(10): pp. 6056-6061 (1999).

Lam, *Nature*, "A new type of synthetic peptide library for identifying ligand-binding activity", vol. 354: pp. 82-84 (1991).

Mauri et al., *Immunity*, "LIGHT, a New Member of the TNF Superfamily, and Lymphotoxin α Are Ligands for Herpesvirus Entry Mediator", vol. 8(1), pp. 21-30 (1998).

Moore et al., *Science*, "BLys: Member of the Tumor Necrosis Factor Family and B Lymphocyte Stimulator", vol. 285: pp. 260-263 (1999).

Naramura et al., *Immunol. Lett.*, "Mechanisms of cellular cytotoxicity mediated by a recombinant antibody-IL2 fusion protein against human melanoma cells", vol. 39: pp. 91-99 (1994).

Nedwin et al., *J. Immunol.*, "Effect of Interleukin 2, Interferon-γ, and Mitogens on the Production of Tumor Necrosis Factors α and β", vol. 135(4), pp. 2492-2497 (1985).

Scott and Smith, *Science*, "Searching for Peptide Ligands with an Epitope Library", vol. 249: pp. 386-390 (1990).

Suda et al., *Cell*, "Molecular Cloning and Expression of the Fas Ligand, a Novel Member of the Tumor Necrosis Factor Family", vol. 75(6): pp. 1169-1178 (1993).

Von Bulow and Brann, *Science*, "NF-AT Activation Induced by a CAML-Interacting Member of Tumor Necrosis Factor Receptor Superfamily", vol. 278: pp. 138-141 (1997).

Wiley et al., *Immunity*, "Identification and Characterization of a New Member of the TNF Family that Induces Apoptosis", vol. 3(6): pp. 673-682 (1995).

Durner et al., *Arthritis Res.*, "B cells, BAFF/zTNF4, TACI, and systemic lupus erythematosus", vol. 3: pp. 197-199 (2001).

Xia et al., *J. Exp.*, "Identification of a receptor for BLyS demonstrates a crucial role in humoral immunity", vol. 192(1): pp. 137-143 (2000).

Gross et al., *Nature*, "TACI Is a TRAF-interacting Receptor for TALL-1, a Tumor Necrosis Factor Family Member Involved in B Cell Regulation", vol. 404: pp. 995-999 (2000).

Yan et al., *Nature Immunology*, "TACI and BCMA are receptors for a TNF homologue implicated in B-cell autoimmune disease", vol. 1(1): pp. 37-41 (2000).

European Patent Office Communication pursuant to Article 96(2) EPC, dated Sep. 9, 2005.

* cited by examiner

SEQUENCE LISTING

```
<160> NUMBER OF SEQ ID NOS: 458
<210> SEQ ID NO 1
<211> LENGTH: 13
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (1)..(1)
<223> OTHER INFORMATION: X1 is Ala, Asn, Lys, or Ser;
<221> NAME/KEY: MISC_FEATURE
<222> LOCATION: (2)..(2)
<223> OTHER INFORMATION: X2 is Ala, Glu, Met, Ser, or Val;
<221> NAME/KEY: MISC_FEATURE
<222> LOCATION: (3)..(3)
<223> OTHER INFORMATION: X3 is Ala, Asn, Lys, or Pro (preferably Lys);
<221> NAME/KEY: MISC_FEATURE
<222> LOCATION: (5)..(5)
<223> OTHER INFORMATION: X5 is Phe, Trp, or Tyr (preferably Tyr);
<221> NAME/KEY: MISC_FEATURE
<222> LOCATION: (7)..(7)
<223> OTHER INFORMATION: X7 is Pro or Tyr (preferably Pro);
<221> NAME/KEY: MISC_FEATURE
<222> LOCATION: (11)..(11)
<223> OTHER INFORMATION: X11 is Ala, Gln, His, Phe, or Val;
<221> NAME/KEY: MISC_FEATURE
<222> LOCATION: (12)..(12)
<223> OTHER INFORMATION: X12 is Asn, Gln, Gly, His, Ser, or Val;
<221> NAME/KEY: MISC_FEATURE
<222> LOCATION: (13)..(13)
<223> OTHER INFORMATION: X13 is Ala, Asn, Gly, Ile, Pro, or Ser,

<400> SEQUENCE: 1

Xaa Xaa Xaa Cys Xaa Pro Xaa Thr Gly Cys Xaa Xaa Xaa
1               5                   10

<210> SEQ ID NO 2
<211> LENGTH: 14
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (1)..(1)
<223> OTHER INFORMATION: X1 is Ala, Asp, Gln, Glu, Gly, His, Ile, Leu,
     Lys, Met, Phe, Pro,Ser, Thr, Trp, Tyr, Val, or is absent;
<221> NAME/KEY: MISC_FEATURE
```

-continued

```
<222> LOCATION: (2)..(2)
<223> OTHER INFORMATION: X2 is Ala, Asn, Asp, Gln, Gly, His, Ile, Leu,
      Lys, Met, Phe, Pro,Ser, Thr, Trp, Tyr, or Val;
<221> NAME/KEY: MISC_FEATURE
<222> LOCATION: (3)..(3)
<223> OTHER INFORMATION: X3 is Ala, Arg, Asn, Asp, Gln, Glu, Gly, His,
      Ile, Leu, Lys, Met,Phe, Pro, Ser, Trp, Tyr, or Val
      (preferably Asp);
<221> NAME/KEY: MISC_FEATURE
<222> LOCATION: (5)..(5)
<223> OTHER INFORMATION: X5 is Asp, Ile, Leu, or Tyr
      (preferably Asp or Leu);
<221> NAME/KEY: MISC_FEATURE
<222> LOCATION: (6)..(6)
<223> OTHER INFORMATION: X6 is Arg, Asp, Glu, His, Ile, Leu, Lys, Phe,
      Pro, Tyr,  or Val (preferably Glu or Leu);
<221> NAME/KEY: MISC_FEATURE
<222> LOCATION: (7)..(7)
<223> OTHER INFORMATION: X is His, Leu, Lys, or Phe
<221> NAME/KEY: MISC_FEATURE
<222> LOCATION: (8)..(8)
<223> OTHER INFORMATION: X is Leu, Pro, or Thr
<221> NAME/KEY: MISC_FEATURE
<222> LOCATION: (9)..(9)
<223> OTHER INFORMATION: X is Arg, Asn, Gly, His, Ile, Lys, Met, or Trp
<221> NAME/KEY: MISC_FEATURE
<222> LOCATION: (10)..(10)
<223> OTHER INFORMATION: X10 is Ala, Gln, Glu, Gly, His, Ile, Leu, Met,
      Phe, Ser, Trp, Tyr, or Val;
<221> NAME/KEY: MISC_FEATURE
<222> LOCATION: (12)..(12)
<223> OTHER INFORMATION: X12 is Asp, Gln, Glu, Gly, Ile, Leu, Lys, Phe,
      Ser, Trp, Tyr, or Val;
<221> NAME/KEY: MISC_FEATURE
<222> LOCATION: (13)..(13)
<223> OTHER INFORMATION: X13 is Ala, Arg, Asn, Asp, Gln, Glu, Gly, His,
      Leu, Lys, Met, Phe, Pro, Ser, Thr, Trp, Tyr, or Val;
<221> NAME/KEY: MISC_FEATURE
<222> LOCATION: (14)..(14)
<223> OTHER INFORMATION: X14 is Ala, Arg, Asn, Asp, Gln, Glu, Gly, His,
      Ile, Leu, Lys, Phe, Pro, Trp, Tyr, Val, or is absent

<400> SEQUENCE: 2

Xaa Xaa Xaa Cys Xaa Xaa Xaa Xaa Xaa Xaa Cys Xaa Xaa Xaa
1               5                   10

<210> SEQ ID NO 3
<211> LENGTH: 15
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (1)..(1)
<223> OTHER INFORMATION: X1 is Ala, Arg, Asn, Asp, Leu, Lys, Phe, Pro,
      Ser, or Thr;
<221> NAME/KEY: MISC_FEATURE
<222> LOCATION: (2)..(2)
<223> OTHER INFORMATION: X2 is Asn, Asp, Gln, His, Ile, Lys, Pro, Thr,
      or Trp;
<221> NAME/KEY: MISC_FEATURE
<222> LOCATION: (3)..(3)
<223> OTHER INFORMATION: X3 is Ala, Arg, Asn, Gln, Glu, His, Phe, Pro,
      or Thr (preferably Ala);
<221> NAME/KEY: MISC_FEATURE
<222> LOCATION: (5)..(5)
<223> OTHER INFORMATION: X5 is Asn, Asp, Pro, Ser, or Thr
      (preferably Asp);
<221> NAME/KEY: MISC_FEATURE
<222> LOCATION: (6)..(6)
<223> OTHER INFORMATION: X6 is Arg, Asp, Ile, Leu, Met, Pro, or Val
      (preferably Ile);
<221> NAME/KEY: MISC_FEATURE
<222> LOCATION: (7)..(7)
<223> OTHER INFORMATION: X7 is Ala, Ile, Leu , Pro, Thr, or Val
      (preferably Val or Leu);
<221> NAME/KEY: MISC_FEATURE
```

```
<222> LOCATION: (8)..(8)
<223> OTHER INFORMATION: X8 is Asn, His, Ile, Leu, Lys, Phe, or Thr
      (preferably Thr);
<221> NAME/KEY: MISC_FEATURE
<222> LOCATION: (9)..(9)
<223> OTHER INFORMATION: X9 is Asn, Glu, Gly, His, Leu, Lys, Met, Pro,
      or Thr (preferably Leu);
<221> NAME/KEY: MISC_FEATURE
<222> LOCATION: (10)..(10)
<223> OTHER INFORMATION: X10 is Arg, Asn, Asp, Gln, Glu, Gly, Ile, Lys,
      Met, Pro, Ser, or Trp;
<221> NAME/KEY: MISC_FEATURE
<222> LOCATION: (11)..(11)
<223> OTHER INFORMATION: X11 is Arg, Glu, Gly, Lys, Phe, Ser, Trp, or
      Tyr (preferably Ser) ;
<221> NAME/KEY: MISC_FEATURE
<222> LOCATION: (13)..(13)
<223> OTHER INFORMATION: X13 is Gln, Glu, Ile, Leu, Phe, Pro, Ser, Tyr,
      or Val (preferably Val);
<221> NAME/KEY: MISC_FEATURE
<222> LOCATION: (14)..(14)
<223> OTHER INFORMATION: X14 is Asn, Gly, Ile, Phe, Pro, Thr, Trp, or
      Tyr;
<221> NAME/KEY: MISC_FEATURE
<222> LOCATION: (15)..(15)
<223> OTHER INFORMATION: X15 is Asn, Asp, Glu, Leu, Lys, Met, Pro, or
      Thr (preferably Glu or Pro),

<400> SEQUENCE: 3

Xaa Xaa Xaa Cys Xaa Xaa Xaa Xaa Xaa Xaa Xaa Cys Xaa Xaa Xaa
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (1)..(1)
<223> OTHER INFORMATION: X1 is Asn, Asp, His, Leu, Phe, Pro, Ser, Tyr,
      or is absent (preferably Ser);
<221> NAME/KEY: MISC_FEATURE
<222> LOCATION: (2)..(2)
<223> OTHER INFORMATION: X2 is Arg, Asn, Asp, His, Phe, Ser, or Trp
      (preferably Arg);
<221> NAME/KEY: MISC_FEATURE
<222> LOCATION: (3)..(3)
<223> OTHER INFORMATION: X3 is Asn, Asp, Leu, Pro, Ser, or Val
      (preferably Asn or Asp);
<221> NAME/KEY: MISC_FEATURE
<222> LOCATION: (5)..(5)
<223> OTHER INFORMATION: X5 is Asp, Gln, His, Ile, Leu, Lys, Met, Phe,
      or Thr;
<221> NAME/KEY: MISC_FEATURE
<222> LOCATION: (6)..(6)
<223> OTHER INFORMATION: X6 is His, Ile, Leu, Met, Phe, Pro, Trp, or
      Tyr;
<221> NAME/KEY: MISC_FEATURE
<222> LOCATION: (7)..(7)
<223> OTHER INFORMATION: X7 is Asp, His, Leu, or Ser (preferably Asp);
<221> NAME/KEY: MISC_FEATURE
<222> LOCATION: (8)..(8)
<223> OTHER INFORMATION: X8 is Ala, Arg, Asp, Glu, Leu, Phe, Pro, or Thr
      (preferably Glu or Pro);
<221> NAME/KEY: MISC_FEATURE
<222> LOCATION: (9)..(9)
<223> OTHER INFORMATION: X9 is Ala, Arg, Asn, or Leu (preferably Leu);
<221> NAME/KEY: MISC_FEATURE
<222> LOCATION: (10)..(10)
<223> OTHER INFORMATION: X10 is Ile, Leu, Met, Pro, Ser, or Thr
      (preferably Thr);
<221> NAME/KEY: MISC_FEATURE
<222> LOCATION: (11)..(11)
<223> OTHER INFORMATION: X11 is Ala, Arg, Asn, Gly, His, Lys, Ser, or
      Tyr;
<221> NAME/KEY: MISC_FEATURE
```

```
<222> LOCATION: (12)..(12)
<223> OTHER INFORMATION: X12 is Ala, Arg, Asn, Gln, Leu, Met, Ser, Trp,
      Tyr, or Val;
<221> NAME/KEY: MISC_FEATURE
<222> LOCATION: (14)..(14)
<223> OTHER INFORMATION: X14 is Asp, Gly, Leu, Phe, Tyr, or Val
      (preferably Leu);
<221> NAME/KEY: MISC_FEATURE
<222> LOCATION: (15)..(15)
<223> OTHER INFORMATION: X15 is Asn, His, Leu, Pro, or Tyr (preferably
      His, Leu or Pro);
<221> NAME/KEY: MISC_FEATURE
<222> LOCATION: (16)..(16)
<223> OTHER INFORMATION: X16 is Asn, Asp, His, Phe, Ser, or Tyr,
      (preferably Asp or Ser),

<400> SEQUENCE: 4

Xaa Xaa Xaa Cys Xaa Xaa Xaa Xaa Xaa Xaa Xaa Xaa Cys Xaa Xaa Xaa
 1               5                  10                  15

<210> SEQ ID NO 5
<211> LENGTH: 18
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (1)..(1)
<223> OTHER INFORMATION: X1 is Arg, Asp, Gly, His, Leu, Phe, Pro, Ser,
      Trp, Tyr, or is absent (preferably Arg);
<221> NAME/KEY: MISC_FEATURE
<222> LOCATION: (2)..(2)
<223> OTHER INFORMATION: X2 is Ala, Arg, Asn, Asp, Gly, Pro, Ser, or is
      absent (preferably Asn, Asp, Gly, or Pro);
<221> NAME/KEY: MISC_FEATURE
<222> LOCATION: (3)..(3)
<223> OTHER INFORMATION: X3 is Arg, Asn, Gln, Glu, Gly, Lys, Met, Pro,
      Trp or Val (preferably Gly or Met);
<221> NAME/KEY: MISC_FEATURE
<222> LOCATION: (5)..(5)
<223> OTHER INFORMATION: X5 is Arg, Asn, Gln, Glu, His, Leu, Phe, Pro,
      Trp, Tyr, or Val (preferably Trp, Tyr, or Val);
<221> NAME/KEY: MISC_FEATURE
<222> LOCATION: (6)..(6)
<223> OTHER INFORMATION: X is  Arg, Asp, Gln, Gly, Ile, Lys, Phe, Thr,
      Trp, or Tyr
<221> NAME/KEY: MISC_FEATURE
<222> LOCATION: (7)..(7)
<223> OTHER INFORMATION: X7 is Ala, Arg, Asp, Glu, Gly, Leu, Ser, or
      Tyr (preferably Asp);
<221> NAME/KEY: MISC_FEATURE
<222> LOCATION: (8)..(8)
<223> OTHER INFORMATION: X8 is Asp, Gln, Glu, Leu, Met, Phe, Pro, Ser,
      or Tyr (preferably Leu);
<221> NAME/KEY: MISC_FEATURE
<222> LOCATION: (9)..(9)
<223> OTHER INFORMATION: X9 is Asp, Leu, Pro, Thr, or Val (preferably
      Leu or Thr);
<221> NAME/KEY: MISC_FEATURE
<222> LOCATION: (10)..(10)
<223> OTHER INFORMATION: X is Arg, Gln, His, Ile, Leu, Lys, Met, Phe,
      Thr, Trp, or Tyr
<221> NAME/KEY: MISC_FEATURE
<222> LOCATION: (11)..(11)
<223> OTHER INFORMATION: X11 is Ala, Arg, Asn, Gln, Glu, His, Leu, Lys,
      Met, or Thr (preferably Arg or Leu);
<221> NAME/KEY: MISC_FEATURE
<222> LOCATION: (12)..(12)
<223> OTHER INFORMATION: X12 is Ala, Asn, Gln, Gly, Leu, Lys, Phe, Pro,
      Thr, Trp, or Tyr (preferably Thr or Trp);
<221> NAME/KEY: MISC_FEATURE
<222> LOCATION: (13)..(13)
<223> OTHER INFORMATION: X13 is Ala, Arg, Gln, His, Lys, Met, Phe, Pro,
      Thr, Trp, or Tyr (preferably Met or Phe);
<221> NAME/KEY: MISC_FEATURE
<222> LOCATION: (14)..(14)
<223> OTHER INFORMATION: X14 is Arg, Gln, Glu, Gly, His, Leu, Met, Phe,
```

```
        Pro, Ser, Thr, Tyr, or Val (preferably Val);
<221> NAME/KEY: MISC_FEATURE
<222> LOCATION: (16)..(16)
<223> OTHER INFORMATION: X16 is Arg, Asp, Gly, His, Lys, Met, Phe, Pro,
        Ser, or Trp (preferably Met);
<221> NAME/KEY: MISC_FEATURE
<222> LOCATION: (17)..(17)
<223> OTHER INFORMATION: X is Arg, Asn, Asp, Gly, His, Phe, Pro, Ser,
        Trp, or Tyr
<221> NAME/KEY: MISC_FEATURE
<222> LOCATION: (18)..(18)
<223> OTHER INFORMATION: X18 is Ala, Arg, Asn, Asp, His, Leu, Phe, or
        Trp (preferably His or Asn),

<400> SEQUENCE: 5

Xaa Xaa Xaa Cys Xaa Xaa Xaa Xaa Xaa Xaa Xaa Xaa Xaa Xaa Cys Xaa
1               5                   10                  15

Xaa Xaa

<210> SEQ ID NO 6
<211> LENGTH: 12
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (1)..(1)
<223> OTHER INFORMATION: X1 is Ala, Arg, Gly, His, Leu, Lys, Met, Phe,
        Trp, Tyr, or Val (preferably Gly, Tyr, or Val);
<221> NAME/KEY: MISC_FEATURE
<222> LOCATION: (2)..(2)
<223> OTHER INFORMATION: X2 is Ala, Arg, Gln, His, Ile, Leu, Phe, Thr,
        Trp, or Tyr (preferably His or Tyr);
<221> NAME/KEY: MISC_FEATURE
<222> LOCATION: (3)..(3)
<223> OTHER INFORMATION: X3 is Ala, Asp, Lys, Phe, Thr, Trp or Tyr
        (preferably Asp or Tyr);
<221> NAME/KEY: MISC_FEATURE
<222> LOCATION: (4)..(4)
<223> OTHER INFORMATION: X4 is Arg, Asp, Gln, Lys, Met, Phe, Pro, Ser,
        Tyr, or Val (preferably Asp or Gln);
<221> NAME/KEY: MISC_FEATURE
<222> LOCATION: (5)..(5)
<223> OTHER INFORMATION: X5 is Asp, Leu, Lys, Phe, Pro, Ser, or Val
        (preferably Leu or Ser);
<221> NAME/KEY: MISC_FEATURE
<222> LOCATION: (6)..(6)
<223> OTHER INFORMATION: X6 is His, Ile, Leu, Pro, Ser, or Thr
        (preferably Leu or Thr);
<221> NAME/KEY: MISC_FEATURE
<222> LOCATION: (7)..(7)
<223> OTHER INFORMATION: X7 is Arg, Gly, His, Leu, Lys, Met, or Thr
        (preferably Lys or Thr);
<221> NAME/KEY: MISC_FEATURE
<222> LOCATION: (8)..(8)
<223> OTHER INFORMATION: X8 is Ala, Arg, Asn, Ile, Leu, Lys, Met, or
        Thr (preferably Leu or Lys);
<221> NAME/KEY: MISC_FEATURE
<222> LOCATION: (9)..(9)
<223> OTHER INFORMATION: X9 is Ala, Asn, Arg, Asp, Glu, Gly, His, Leu,
        Met, Ser, Trp, Tyr, or Val (preferably Met or Ser);
<221> NAME/KEY: MISC_FEATURE
<222> LOCATION: (10)..(10)
<223> OTHER INFORMATION: X10 is Ile, Leu, Phe, Ser, Thr, Trp, Tyr, or
        Val (preferably Thr or Leu);
<221> NAME/KEY: MISC_FEATURE
<222> LOCATION: (11)..(11)
<223> OTHER INFORMATION: X11 is Ala, Arg, Gly, His, Ile, Leu, Lys, Pro,
        Ser, Thr, Trp, Tyr, or Val (preferably Pro or Thr);
<221> NAME/KEY: MISC_FEATURE
<222> LOCATION: (12)..(12)
<223> OTHER INFORMATION: X12 is Arg, Asp, His, Leu, Lys, Met, Phe, Pro,
        Ser, Trp, Tyr, or Val (preferably Arg or Pro),

<400> SEQUENCE: 6
```

```
Xaa Xaa Xaa Xaa Xaa Xaa Xaa Xaa Xaa Xaa Xaa Xaa
1               5                   10

<210> SEQ ID NO 7
<211> LENGTH: 13
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (1)..(1)
<223> OTHER INFORMATION: X1 is Asp, Gln, Glu, Gly, His, Lys, Met, or
      Trp (preferably Glu,
      Lys);
<221> NAME/KEY: MISC_FEATURE
<222> LOCATION: (2)..(2)
<223> OTHER INFORMATION: X2 is Arg, Gln, His, Ile, Leu, or Pro
      (preferably His or Pro);
<221> NAME/KEY: MISC_FEATURE
<222> LOCATION: (3)..(3)
<223> OTHER INFORMATION: X3 is Asp, Gly, Ile, Lys, Thr, Tyr or Val
      (preferably Tyr);
<221> NAME/KEY: MISC_FEATURE
<222> LOCATION: (4)..(4)
<223> OTHER INFORMATION: X4 is Asn, Asp, Gln, Glu, Met, Pro, Ser, or Tyr
      (preferably Asp or Gln);
<221> NAME/KEY: MISC_FEATURE
<222> LOCATION: (5)..(5)
<223> OTHER INFORMATION: X5 is Asn, Asp, His, Ile, Leu, Met, Pro, Thr
      or Val (preferably Asn or Thr);
<221> NAME/KEY: MISC_FEATURE
<222> LOCATION: (6)..(6)
<223> OTHER INFORMATION: X6 is Asp, Glu, His, Leu, Lys, Pro, or Val
      (preferably Asp or Pro);
<221> NAME/KEY: MISC_FEATURE
<222> LOCATION: (7)..(7)
<223> OTHER INFORMATION: X7 is Arg, Asn, Gln, His, Ile, Leu, Met, Pro,
      or Thr (preferably Ile or Pro);
<221> NAME/KEY: MISC_FEATURE
<222> LOCATION: (8)..(8)
<223> OTHER INFORMATION: X8 is Gln, Gly, His, Leu, Met, Ser, or Thr
      (preferably Leu or Thr);
<221> NAME/KEY: MISC_FEATURE
<222> LOCATION: (9)..(9)
<223> OTHER INFORMATION: X9 is Asn, Gln, Gly, His, Leu, Lys, Ser, or
      Thr (preferably Lys);
<221> NAME/KEY: MISC_FEATURE
<222> LOCATION: (10)..(10)
<223> OTHER INFORMATION: X10 is Ala, Gly, Ile, Leu, Lys, Met, or Phe
      (preferably Gly or Met);
<221> NAME/KEY: MISC_FEATURE
<222> LOCATION: (11)..(11)
<223> OTHER INFORMATION: X11 is Ala, Glu, His, Ile, Leu, Met, Ser, Thr,
      Trp, Tyr, or Val (preferably Ala or Thr);
<221> NAME/KEY: MISC_FEATURE
<222> LOCATION: (12)..(12)
<223> OTHER INFORMATION: X12 is Arg, Gln, Glu, Gly, His, Ile, Lys, Tyr,
      or Val (preferably Arg or His);
<221> NAME/KEY: MISC_FEATURE
<222> LOCATION: (13)..(13)
<223> OTHER INFORMATION: X13 is Arg, Asn, Glu, His, Ile, Ser, Thr, Trp,
      or Val (preferably His),

<400> SEQUENCE: 7

Xaa Xaa Xaa Xaa Xaa Xaa Xaa Xaa Xaa Xaa Xaa Xaa Xaa
1               5                   10

<210> SEQ ID NO 8
<211> LENGTH: 7
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (2)..(2)
<223> OTHER INFORMATION: X2 is Phe, Trp, or Tyr (preferably Tyr);
```

-continued

```
<221> NAME/KEY: MISC_FEATURE
<222> LOCATION: (4)..(4)
<223> OTHER INFORMATION: X4 is Pro or Tyr (preferably Pro);

<400> SEQUENCE: 8

Cys Xaa Pro Xaa Thr Gly Cys
1               5

<210> SEQ ID NO 9
<211> LENGTH: 8
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (2)..(2)
<223> OTHER INFORMATION: X2 is Asp, Ile, Leu, or Tyr (preferably Asp or
      Leu);
<221> NAME/KEY: MISC_FEATURE
<222> LOCATION: (3)..(3)
<223> OTHER INFORMATION: X3 is Arg, Asp, Glu, His, Ile, Leu, Lys, Phe,
      Pro, Tyr,  or Val (preferably Glu or Leu);
<221> NAME/KEY: MISC_FEATURE
<222> LOCATION: (4)..(4)
<223> OTHER INFORMATION: X4 is His, Leu, Lys, or Phe (preferably His
      or Leu);
<221> NAME/KEY: MISC_FEATURE
<222> LOCATION: (5)..(5)
<223> OTHER INFORMATION: X5 is Leu, Pro, or Thr (preferably Thr or Pro);
<221> NAME/KEY: MISC_FEATURE
<222> LOCATION: (6)..(6)
<223> OTHER INFORMATION: X6 is Arg, Asn, Gly, His, Ile, Lys, Met, or Trp
      (preferably Lys);
<221> NAME/KEY: MISC_FEATURE
<222> LOCATION: (7)..(7)
<223> OTHER INFORMATION: X7 is Ala, Asn, Gln, Glu, Gly, His, Ile, Leu,
      Met, Phe, Ser, Trp,Tyr, or Val;

<400> SEQUENCE: 9

Cys Xaa Xaa Xaa Xaa Xaa Xaa Cys
1               5

<210> SEQ ID NO 10
<211> LENGTH: 9
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (2)..(2)
<223> OTHER INFORMATION: X2 is Asn, Asp, Pro, Ser, or Thr (preferably
      Asp);
<221> NAME/KEY: MISC_FEATURE
<222> LOCATION: (3)..(3)
<223> OTHER INFORMATION: X3 is Arg, Asp, Ile, Leu, Met, Pro, or Val
      (preferably Ile);
<221> NAME/KEY: MISC_FEATURE
<222> LOCATION: (4)..(4)
<223> OTHER INFORMATION: X4 is Ala, Ile, Leu , Pro, Thr, or Val
      (preferably Val or Leu);
<221> NAME/KEY: MISC_FEATURE
<222> LOCATION: (5)..(5)
<223> OTHER INFORMATION: X5 is Asn, His, Ile, Leu, Lys, Phe, or Thr
      (preferably Thr);
<221> NAME/KEY: MISC_FEATURE
<222> LOCATION: (6)..(6)
<223> OTHER INFORMATION: X6 is Asn, Glu, Gly, His, Leu, Lys, Met, Pro,
      or Thr (preferably Leu);
<221> NAME/KEY: MISC_FEATURE
<222> LOCATION: (7)..(7)
<223> OTHER INFORMATION: X7 is Arg, Asn, Asp, Gln, Glu, Gly, Ile, Lys,
      Met, Pro, Ser, or Trp;
<221> NAME/KEY: MISC_FEATURE
<222> LOCATION: (8)..(8)
<223> OTHER INFORMATION: X8 is Arg, Glu, Gly, Lys, Phe, Ser, Trp, or Tyr
```

-continued (preferably Ser);

<400> SEQUENCE: 10

Cys Xaa Xaa Xaa Xaa Xaa Xaa Xaa Cys
1               5

<210> SEQ ID NO 11
<211> LENGTH: 10
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (2)..(2)
<223> OTHER INFORMATION: X2 is Asp, Gln, His, Ile, Leu, Lys, Met, Phe,
      or Thr;
<221> NAME/KEY: MISC_FEATURE
<222> LOCATION: (3)..(3)
<223> OTHER INFORMATION: X3 is His, Ile, Leu, Met, Phe, Pro, Trp, or
      Tyr;
<221> NAME/KEY: MISC_FEATURE
<222> LOCATION: (4)..(4)
<223> OTHER INFORMATION: X4 is Asp, His, Leu, or Ser (preferably Asp);
<221> NAME/KEY: MISC_FEATURE
<222> LOCATION: (5)..(5)
<223> OTHER INFORMATION: X5 is Ala, Arg, Asp, Glu, Leu, Phe, Pro, or
      Thr (preferably Glu or Pro);
<221> NAME/KEY: MISC_FEATURE
<222> LOCATION: (6)..(6)
<223> OTHER INFORMATION: X6 is Ala, Arg, Asn, or Leu (preferably Leu);
<221> NAME/KEY: MISC_FEATURE
<222> LOCATION: (7)..(7)
<223> OTHER INFORMATION: X7 is Ile, Leu, Met, Pro, Ser, or Thr
      (preferably Thr);
<221> NAME/KEY: MISC_FEATURE
<222> LOCATION: (8)..(8)
<223> OTHER INFORMATION: X8 is Ala, Arg, Asn, Gly, His, Lys, Ser, or
      Tyr;
<221> NAME/KEY: MISC_FEATURE
<222> LOCATION: (9)..(9)
<223> OTHER INFORMATION: X9 is Ala, Arg, Asn, Gln, Leu, Met, Ser, Trp,
      Tyr, or Val;

<400> SEQUENCE: 11

Cys Xaa Xaa Xaa Xaa Xaa Xaa Xaa Xaa Cys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (2)..(2)
<223> OTHER INFORMATION: X2 is Arg, Asn, Gln, Glu, His, Leu, Phe, Pro,
      Trp, Tyr, or Val (preferably Trp, Tyr, or Val);
<221> NAME/KEY: MISC_FEATURE
<222> LOCATION: (3)..(3)
<223> OTHER INFORMATION: X3 is Arg, Asp, Gln, Gly, Ile, Lys, Phe, Thr,
      Trp or Tyr (preferably Asp);
<221> NAME/KEY: MISC_FEATURE
<222> LOCATION: (4)..(4)
<223> OTHER INFORMATION: X4 is Ala, Arg, Asp, Glu, Gly, Leu, Ser, or Tyr
      (preferably Asp);
<221> NAME/KEY: MISC_FEATURE
<222> LOCATION: (5)..(5)
<223> OTHER INFORMATION: X5 is Asp, Gln, Glu, Leu, Met, Phe, Pro, Ser,
      or Tyr (preferably leu);
<221> NAME/KEY: MISC_FEATURE
<222> LOCATION: (6)..(6)
<223> OTHER INFORMATION: X6 is Asp, Leu, Pro, Thr, or Val (preferably
      Leu or Thr);
<221> NAME/KEY: MISC_FEATURE
<222> LOCATION: (7)..(7)

```
<223> OTHER INFORMATION: X7 is Arg, Gln, His, Ile, Leu, Lys, Met, Phe,
      Thr, Trp or Tyr (preferably Lys or Thr);
<221> NAME/KEY: MISC_FEATURE
<222> LOCATION: (8)..(8)
<223> OTHER INFORMATION: X8 is Ala, Arg, Asn, Gln, Glu, His, Leu, Lys,
      Met, or Thr (preferably Arg or Leu);
<221> NAME/KEY: MISC_FEATURE
<222> LOCATION: (9)..(9)
<223> OTHER INFORMATION: X9 is Ala, Asn, Gln, Gly, Leu, Lys, Phe, Pro,
      Thr, Trp, or Tyr (preferably Thr or Trp);
<221> NAME/KEY: MISC_FEATURE
<222> LOCATION: (10)..(10)
<223> OTHER INFORMATION: X10 is Ala, Arg, Gln, His, Lys, Met, Phe, Pro,
      Thr, Trp, or Tyr (preferably Met or Phe);
<221> NAME/KEY: MISC_FEATURE
<222> LOCATION: (11)..(11)
<223> OTHER INFORMATION: X11 is Arg, Gln, Glu, Gly, His, Leu, Met, Phe,
      Pro, Ser, Thr, Tyr, or Val (preferably Val);

<400> SEQUENCE: 12

Cys Xaa Xaa Xaa Xaa Xaa Xaa Xaa Xaa Xaa Cys
1               5                   10

<210> SEQ ID NO 13
<211> LENGTH: 8
<212> TYPE: PRT
<213> ORGANISM: Artificial Sequence
<220> FEATURE:
<223> OTHER INFORMATION: c-terminal linker

<400> SEQUENCE: 13

Pro Gly Pro Glu Gly Gly Gly Lys
1               5

<210> SEQ ID NO 14
<211> LENGTH: 12
<212> TYPE: PRT
<213> ORGANISM: Artificial Sequence
<220> FEATURE:
<223> OTHER INFORMATION: phage display library template
<221> NAME/KEY: MISC_FEATURE
<222> LOCATION: (1)..(3)
<223> OTHER INFORMATION: X is any amino acid except Cys
<221> NAME/KEY: MISC_FEATURE
<222> LOCATION: (5)..(8)
<223> OTHER INFORMATION: X is any amino acid except Cys
<221> NAME/KEY: MISC_FEATURE
<222> LOCATION: (10)..(12)
<223> OTHER INFORMATION: X is any amino acid except Cys

<400> SEQUENCE: 14

Xaa Xaa Xaa Cys Xaa Xaa Xaa Xaa Cys Xaa Xaa Xaa
1               5                   10

<210> SEQ ID NO 15
<211> LENGTH: 13
<212> TYPE: PRT
<213> ORGANISM: Artificial Sequence
<220> FEATURE:
<223> OTHER INFORMATION: phage display library template
<221> NAME/KEY: MISC_FEATURE
<222> LOCATION: (1)..(3)
<223> OTHER INFORMATION: X is any amino acid except Cys
<221> NAME/KEY: MISC_FEATURE
<222> LOCATION: (5)..(9)
<223> OTHER INFORMATION: X is any amino acid except Cys
<221> NAME/KEY: MISC_FEATURE
<222> LOCATION: (11)..(13)
<223> OTHER INFORMATION: X is any amino acid except Cys

<400> SEQUENCE: 15

Xaa Xaa Xaa Cys Xaa Xaa Xaa Xaa Xaa Cys Xaa Xaa Xaa
```

```
<210> SEQ ID NO 16
<211> LENGTH: 14
<212> TYPE: PRT
<213> ORGANISM: Artificial Sequence
<220> FEATURE:
<223> OTHER INFORMATION: phage display library template
<221> NAME/KEY: MISC_FEATURE
<222> LOCATION: (1)..(14)
<223> OTHER INFORMATION: X is any amino acid except Cys

<400> SEQUENCE: 16

Xaa Xaa Xaa Cys Xaa Xaa Xaa Xaa Xaa Xaa Cys Xaa Xaa Xaa
1               5                   10

<210> SEQ ID NO 17
<211> LENGTH: 15
<212> TYPE: PRT
<213> ORGANISM: Artificial Sequence
<220> FEATURE:
<223> OTHER INFORMATION: phage display library template
<221> NAME/KEY: MISC_FEATURE
<222> LOCATION: (1)..(3)
<223> OTHER INFORMATION: X is any amino acid except Cys
<221> NAME/KEY: MISC_FEATURE
<222> LOCATION: (5)..(11)
<223> OTHER INFORMATION: X is any amino acid except Cys
<221> NAME/KEY: MISC_FEATURE
<222> LOCATION: (13)..(15)
<223> OTHER INFORMATION: X is any amino acid except Cys

<400> SEQUENCE: 17

Xaa Xaa Xaa Cys Xaa Xaa Xaa Xaa Xaa Xaa Xaa Cys Xaa Xaa Xaa
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: phage display library template
<221> NAME/KEY: MISC_FEATURE
<222> LOCATION: (1)..(3)
<223> OTHER INFORMATION: X is any amino acid except Cys
<221> NAME/KEY: MISC_FEATURE
<222> LOCATION: (5)..(12)
<223> OTHER INFORMATION: X is any amino acid except Cys
<221> NAME/KEY: MISC_FEATURE
<222> LOCATION: (14)..(16)
<223> OTHER INFORMATION: X is any amino acid except Cys

<400> SEQUENCE: 18

Xaa Xaa Xaa Cys Xaa Xaa Xaa Xaa Xaa Xaa Xaa Xaa Cys Xaa Xaa Xaa
1               5                   10                  15

<210> SEQ ID NO 19
<211> LENGTH: 18
<212> TYPE: PRT
<213> ORGANISM: Artificial Sequence
<220> FEATURE:
<223> OTHER INFORMATION: phage display library template
<221> NAME/KEY: MISC_FEATURE
<222> LOCATION: (1)..(3)
<223> OTHER INFORMATION: X is any amino acid except Cys
<221> NAME/KEY: MISC_FEATURE
<222> LOCATION: (5)..(14)
<223> OTHER INFORMATION: X is any amino acid except Cys
<221> NAME/KEY: MISC_FEATURE
<222> LOCATION: (16)..(18)
<223> OTHER INFORMATION: X is any amino acid except Cys
```

-continued

```
<400> SEQUENCE: 19

Xaa Xaa Xaa Cys Xaa Xaa Xaa Xaa Xaa Xaa Xaa Xaa Xaa Cys Xaa
1               5                   10                  15

Xaa Xaa

<210> SEQ ID NO 20
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 20

His Leu Arg Cys Trp Ser Thr Asn Cys Arg Tyr Asp
1               5                   10

<210> SEQ ID NO 21
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 21

Val Met Asp Cys Leu Ile Asn Arg Cys Asp Thr Val
1               5                   10

<210> SEQ ID NO 22
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 22

Lys Ser Lys Cys Phe Phe Pro Trp Glu Cys Gln Gln Ala
1               5                   10

<210> SEQ ID NO 23
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 23

Ala Met Lys Cys Tyr Phe Pro Trp Glu Cys Ala Asn Gly
1               5                   10

<210> SEQ ID NO 24
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 24

Glu Asn Val Ala Cys Tyr Phe Pro Trp Glu Cys His His Pro
1               5                   10

<210> SEQ ID NO 25
<211> LENGTH: 13
<212> TYPE: PRT
<213> ORGANISM: Artificial Sequence
<220> FEATURE:
<223> OTHER INFORMATION: BLyS binding polypeptide
```

-continued

```
<400> SEQUENCE: 25

Asn Ala Pro Cys Tyr Phe Pro Trp Glu Cys Phe Ser Ile
1               5                   10

<210> SEQ ID NO 26
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 26

Ser Val Asn Cys Trp Phe Pro Trp Glu Cys Val Gly Asn
1               5                   10

<210> SEQ ID NO 27
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 27

Lys Glu Pro Cys Tyr Phe Tyr Trp Glu Cys Ala Val Ser
1               5                   10

<210> SEQ ID NO 28
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 28

Asp Thr Asn Cys Asp Leu Leu Thr Lys Met Cys Gly Pro Gln
1               5                   10

<210> SEQ ID NO 29
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 29

Gly Thr Pro Cys Asp Leu Leu Thr Lys Leu Cys Leu Leu Trp
1               5                   10

<210> SEQ ID NO 30
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 30

Met Ser Glu Cys Asp Leu Leu Thr Lys Ile Cys Leu Met Gly
1               5                   10

<210> SEQ ID NO 31
<211> LENGTH: 14
<212> TYPE: PRT
<213> ORGANISM: Artificial Sequence
<220> FEATURE:
<223> OTHER INFORMATION: BLyS binding polypeptide
```

-continued

```
<400> SEQUENCE: 31

Val Pro Phe Cys Asp Leu Leu Thr Lys His Cys Phe Glu Ala
1               5                   10

<210> SEQ ID NO 32
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 32

Val Pro Phe Cys Asp Leu Leu Thr Lys His Cys Phe Glu Ala
1               5                   10

<210> SEQ ID NO 33
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 33

Trp Ser Ala Cys Asp Leu Leu Thr Lys Gln Cys Val Gln Val
1               5                   10

<210> SEQ ID NO 34
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 34

Asp Gly Cys Asp Glu Leu Thr Lys Ile Cys Gly Met Lys
1               5                   10

<210> SEQ ID NO 35
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 35

Lys Ser Trp Cys Asp Glu Leu Thr Lys Val Cys Phe Asp Pro
1               5                   10

<210> SEQ ID NO 36
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 36

Lys Trp Met Cys Asp Glu Leu Thr Lys Gln Cys Gln Tyr Val
1               5                   10

<210> SEQ ID NO 37
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 37
```

```
Met Lys Tyr Cys Asp Glu Leu Thr Lys Ile Cys Val Gly Trp
1               5                   10
```

<210> SEQ ID NO 38
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 38

```
Tyr Phe Gln Cys Asp Glu Leu Thr Lys Met Cys Trp Gln Lys
1               5                   10
```

<210> SEQ ID NO 39
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 39

```
Ala Met His Cys Asp Lys Leu Thr Lys His Cys Lys Phe His
1               5                   10
```

<210> SEQ ID NO 40
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 40

```
Val Pro Tyr Cys Asp Lys Leu Thr Lys Ile Cys Gln Trp
1               5                   10
```

<210> SEQ ID NO 41
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 41

```
Glu Val Phe Cys Asp Val Leu Thr Lys Val Cys Phe His Asp
1               5                   10
```

<210> SEQ ID NO 42
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 42

```
Lys Pro Lys Cys Asp Val Leu Thr Lys Met Cys Asp Trp Leu
1               5                   10
```

<210> SEQ ID NO 43
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 43

```
Thr Gln His Cys Asp Val Leu Thr Lys Gln Cys Phe Thr Ile
1               5                   10
```

<210> SEQ ID NO 44
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 44

```
Gly His Phe Cys Asp Arg Leu Thr Lys Tyr Cys Phe Glu Pro
1               5                   10
```

<210> SEQ ID NO 45
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 45

```
His Ile Gln Cys Asp Arg Leu Thr Lys Ser Cys Leu Ser Val
1               5                   10
```

<210> SEQ ID NO 46
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 46

```
Ile Lys Ala Cys Asp Ile Leu Thr Lys Val Cys Trp Pro Pro
1               5                   10
```

<210> SEQ ID NO 47
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 47

```
Gln Phe Asp Cys Asp Pro Leu Thr Lys Tyr Cys Gly Glu Phe
1               5                   10
```

<210> SEQ ID NO 48
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 48

```
Lys Met Tyr Cys Asp His Leu Thr Gly Tyr Cys Trp Pro Glu
1               5                   10
```

<210> SEQ ID NO 49
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 49

```
Met Gln Ser Cys Asp Ile Leu Thr Gly Tyr Cys Phe Lys Arg
```

-continued

```
1               5                   10

<210> SEQ ID NO 50
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 50

Gly Pro Trp Cys Asp Ile Leu Thr Gly Phe Cys Leu Ala Gln
1               5                   10

<210> SEQ ID NO 51
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 51

Ser Val Arg Cys Asp Leu Leu Thr Gly Trp Cys Pro Val Trp
1               5                   10

<210> SEQ ID NO 52
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 52

Pro Ala Asp Cys Asp Pro Leu Thr Asn Ile Cys Phe Trp Lys
1               5                   10

<210> SEQ ID NO 53
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 53

Thr Asn Val Cys Asp Pro Leu Thr Asn Val Cys Phe Met Asn
1               5                   10

<210> SEQ ID NO 54
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 54

Glu His Trp Cys Asp Asp Leu Thr His Leu Cys Phe Arg Leu
1               5                   10

<210> SEQ ID NO 55
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 55

Gly Tyr Trp Cys Asp Val Leu Thr Asn Asn Cys Trp Lys Ile
1               5                   10
```

```
<210> SEQ ID NO 56
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 56

Leu Tyr Asn Cys Asp Tyr Leu Thr Arg Leu Cys Phe Glu Pro
 1               5                  10

<210> SEQ ID NO 57
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 57

His Val Asp Cys Leu Leu His Pro Lys Ala Cys Tyr Lys Tyr
 1               5                  10

<210> SEQ ID NO 58
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 58

Val Gln Asp Cys Leu Leu His Pro Lys Ala Cys Gln Met Gln
 1               5                  10

<210> SEQ ID NO 59
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 59

Lys Phe Asp Cys Leu Leu Lys Pro Met Phe Cys Ser Asn His
 1               5                  10

<210> SEQ ID NO 60
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 60

Phe Ala Asp Cys Leu Ile His Pro Lys Ser Cys Lys Pro Leu
 1               5                  10

<210> SEQ ID NO 61
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 61

His Gly Asn Cys Tyr Pro Phe Pro Trp Glu Cys Glu Ser Lys
 1               5                  10
```

-continued

<210> SEQ ID NO 62
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 62

```
Met Ile Ile Val Leu Leu Leu Leu Arg Phe Ala Ile Ser Arg
1               5                   10
```

<210> SEQ ID NO 63
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 63

```
Ser Leu Leu Val Ile Phe Leu Leu Ile Gly Ala Gly Ser Leu
1               5                   10
```

<210> SEQ ID NO 64
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 64

```
Phe His Pro Cys Asp Met Leu Thr Gly Ile Trp Cys Gln Pro Asn
1               5                   10                  15
```

<210> SEQ ID NO 65
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 65

```
Ser Lys Arg Cys Asp Leu Leu Thr Lys Met Trp Cys Glu Thr Glu
1               5                   10                  15
```

<210> SEQ ID NO 66
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 66

```
Thr Lys Phe Cys Asp Arg Leu Thr Met Pro Lys Cys Val Trp Lys
1               5                   10                  15
```

<210> SEQ ID NO 67
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 67

```
Asn Thr Phe Cys Pro Asp Pro Leu Thr Gly Arg Cys Val Asn Pro
1               5                   10                  15
```

<210> SEQ ID NO 68
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 68

Asp Trp Thr Cys Asp Pro Leu Phe His Arg Glu Cys Ile Phe Glu
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 69

Pro Gln Pro Cys Asp Leu Leu Phe Glu Lys Lys Cys Ser Ile Lys
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 70

Arg Trp His Cys Asp Met Leu Ile Asn Pro Ser Cys Leu Pro Asp
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 71

Lys Ile Gln Cys Asp Ile Val Asn Leu Ser Ser Cys Val Tyr Pro
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 72

Leu Asn Ala Cys Asp Ile Val His Pro Asn Tyr Cys Ser Gly Met
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 73

Ala Lys Ala Cys Ser Ile Val Asn Leu Glu Ser Cys Glu Tyr Leu
1               5                   10                  15

<210> SEQ ID NO 74

```
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 74

Arg Gln Ala Cys Ser Ile Ile Thr Pro Trp Gly Cys Pro Ile Pro
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 75

Ala Asp Asn Cys Thr Val Ala Thr Leu Asp Phe Cys Tyr Trp Thr
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 76

Lys Pro Glu Cys Asn Ile Thr Lys Pro Gln Phe Cys Phe Gly Glu
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 77

Asn Asn Cys Gln Trp Asp Glu Leu Thr Ser Met Cys Asp Pro Phe
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 78

Ser Arg Leu Cys His Met Asp Glu Leu Thr His Val Cys Val His Phe
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 79

Ser Arg Pro Cys Gln Ile Asp Glu Leu Thr Lys Ala Cys Phe Tyr Asn
1               5                   10                  15

<210> SEQ ID NO 80
<211> LENGTH: 16
```

```
<212> TYPE: PRT
<213> ORGANISM: Artificial Sequence
<220> FEATURE:
<223> OTHER INFORMATION: BLyS binding polypeptide

<400> SEQUENCE: 80

Asp Arg Val Cys Lys Leu Asp Phe Leu Thr Tyr Asn Cys Leu Asn His
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 81

His Ser Asn Cys Ile Met Asp Leu Leu Thr Asn Arg Cys Phe Tyr Asp
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 82

Pro Phe Asn Cys Phe His Asp Pro Leu Thr Gly Leu Cys Leu His Ser
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 83

Tyr Asp Ser Cys Thr Tyr Asp Arg Leu Thr Lys Gln Cys Tyr Pro Ser
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 84

Phe His Asp Cys Met Tyr Asp Ala Leu Leu Gly Tyr Cys Leu Pro Tyr
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: BLyS binding polypeptide

<400> SEQUENCE: 85

Asn Arg Ser Cys Asp Pro Leu Thr Arg Pro Lys Ser Cys Gly Leu
1               5                   10                  15

<210> SEQ ID NO 86
<211> LENGTH: 16
<212> TYPE: PRT
```

```
<213> ORGANISM: Artificial Sequence
<220> FEATURE:
<223> OTHER INFORMATION: BLyS binding polypeptide

<400> SEQUENCE: 86

Leu Ser Asn Cys Asp Trp Asp Asp Leu Ile Arg Gln Cys Leu His Asp
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 87

Phe Trp Asp Cys Leu Phe His Pro Asn Ser Arg Tyr Cys Val Leu Ser
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 88

Ser Arg Asp Cys Leu Leu Ser Pro Ala Met Ala Trp Cys Gly Leu Asp
1               5                   10                  15

<210> SEQ ID NO 89
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 89

Gly Gly Asn Cys Tyr Thr Asp Ser Leu Thr Lys Leu His Phe Cys Met
1               5                   10                  15

Gly Asp

<210> SEQ ID NO 90
<211> LENGTH: 16
<212> TYPE: PRT
<213> ORGANISM: Artificial Sequence
<220> FEATURE:
<223> OTHER INFORMATION: BLyS binding polypeptide

<400> SEQUENCE: 90

Met Cys Pro Arg Asp Pro Leu Thr Lys Ala Lys Leu Cys Asn Trp His
1               5                   10                  15

<210> SEQ ID NO 91
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 91

Pro Asn Gln Cys Gln Asp Asp Leu Thr Lys Gln Trp Tyr Ser Cys His
1               5                   10                  15

Tyr His
```

<210> SEQ ID NO 92
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 92

Phe Asp Met Cys Phe Asp Ala Leu Thr Lys Gln Asn Phe Tyr Cys Arg
1               5                   10                  15

Phe His

<210> SEQ ID NO 93
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 93

Arg Asn Met Cys Val Asp Arg Leu Thr Lys Leu Gln His Gly Cys Glu
1               5                   10                  15

Gly Ala

<210> SEQ ID NO 94
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 94

Asp Pro Glu Cys Leu Thr Ser Phe Asp Arg Leu Thr Lys Met Cys Trp
1               5                   10                  15

Pro Trp

<210> SEQ ID NO 95
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 95

Asp Asp Glu Cys His Tyr Asp Tyr Leu Thr His Tyr Met Arg Cys Asp
1               5                   10                  15

Tyr Arg

<210> SEQ ID NO 96
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 96

Phe Gly Gly Cys Asn Ile Asp Leu Leu Thr Asn Thr Met Met Cys His
1               5                   10                  15

Arg Asn

<210> SEQ ID NO 97
<211> LENGTH: 18
<212> TYPE: PRT
<213> ORGANISM: Artificial Sequence

```
<220> FEATURE:
<223> OTHER INFORMATION: BLyS binding polypeptide

<400> SEQUENCE: 97

His Gly Pro Cys Tyr Trp Asp Glu Leu Thr Met Gln Trp His Cys Asn
1               5                   10                  15

His His

<210> SEQ ID NO 98
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 98

Gly Ala Met Cys Val Asp Leu Leu Thr Tyr Thr Phe Arg Pro Cys Met
1               5                   10                  15

Tyr Ala

<210> SEQ ID NO 99
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 99

Ser Asn Lys Cys Trp Asp Glu Leu Thr His Ala Trp Ala Glu Cys Gly
1               5                   10                  15

Arg Phe

<210> SEQ ID NO 100
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 100

Arg Pro Val Cys Tyr Lys Gly Tyr Asp Ile Leu Thr Thr Gln Cys Met
1               5                   10                  15

Pro Trp

<210> SEQ ID NO 101
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 101

Pro Ser Arg Cys Trp Phe Asp Leu Leu Phe Asn Lys Phe Val Cys Lys
1               5                   10                  15

Arg Asn

<210> SEQ ID NO 102
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 102
```

```
Arg Ser Gly Cys Val Tyr Asp Met Leu Leu Met Thr Met Tyr Cys Pro
1               5                   10                  15

Ser Asn

<210> SEQ ID NO 103
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 103

Ser Asn Arg Cys Glu Gly Asp Gln Leu Met Arg Pro Pro Ser Cys Arg
1               5                   10                  15

His Leu

<210> SEQ ID NO 104
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 104

Tyr Arg Met Cys Trp Trp Asp Asp Leu Leu Arg Gly Phe Val Cys Asp
1               5                   10                  15

Phe His

<210> SEQ ID NO 105
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 105

His Asp Gly Cys Tyr Asp Glu Leu Leu Tyr Arg Trp Thr Arg Cys Glu
1               5                   10                  15

His Arg

<210> SEQ ID NO 106
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 106

Trp Ala Trp Cys Phe Asp Glu Leu Val Gln Arg Tyr Phe Thr Cys Phe
1               5                   10                  15

Asp His

<210> SEQ ID NO 107
<211> LENGTH: 18
<212> TYPE: PRT
<213> ORGANISM: Artificial Sequence
<220> FEATURE:
<223> OTHER INFORMATION: BLyS binding polypeptide

<400> SEQUENCE: 107

Leu Pro Glu Cys Arg Gln Tyr Phe Pro Trp Glu Lys Gln Val Cys Ser
1               5                   10                  15
```

Tyr Trp

<210> SEQ ID NO 108
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 108

Val His Tyr Asp Ser Leu Thr Lys Met Trp Thr Arg
1               5                   10

<210> SEQ ID NO 109
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 109

Phe Thr Asp Pro Leu Thr Lys Met Ser Leu His Ser
1               5                   10

<210> SEQ ID NO 110
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 110

Gly Tyr Asp Val Leu Thr Lys Leu Tyr Phe Val Pro
1               5                   10

<210> SEQ ID NO 111
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 111

Tyr Tyr Asp Arg Leu Thr Lys Leu Tyr Ser Ser Met
1               5                   10

<210> SEQ ID NO 112
<211> LENGTH: 12
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (2)..(2)
<223> OTHER INFORMATION: X is unknown

<400> SEQUENCE: 112

Leu Xaa Lys Asp Pro Leu Thr Lys Leu Tyr Ile Ser
1               5                   10

<210> SEQ ID NO 113
<211> LENGTH: 12
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (9)..(9)

<223> OTHER INFORMATION: X is unknown

<400> SEQUENCE: 113

Gly Tyr Asp Val Leu Thr Lys Leu Xaa Phe Val Pro
1               5                   10

<210> SEQ ID NO 114
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 114

Arg Leu Tyr Asp Pro Leu Thr Lys Leu Val Leu Ser
1               5                   10

<210> SEQ ID NO 115
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 115

Met Phe Asp Pro Leu Thr Lys Ile Ala Phe Pro Ala
1               5                   10

<210> SEQ ID NO 116
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 116

Phe Tyr Asp Ser Leu Thr Lys Thr Asn Leu Arg Asp
1               5                   10

<210> SEQ ID NO 117
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 117

Gly Ile Tyr Asp Lys Leu Thr Arg Ala Trp Leu Pro
1               5                   10

<210> SEQ ID NO 118
<211> LENGTH: 12
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (10)..(10)
<223> OTHER INFORMATION: X is unknown

<400> SEQUENCE: 118

Lys Tyr Asp Pro Leu Thr Arg Ala Arg Xaa Pro Leu
1               5                   10

<210> SEQ ID NO 119
<211> LENGTH: 12
<212> TYPE: PRT

```
<213> ORGANISM: Artificial Sequence
<220> FEATURE:
<223> OTHER INFORMATION: BLyS binding polypeptide

<400> SEQUENCE: 119

Tyr Ile Asp Gln Leu Thr Arg Leu Ser Leu Pro Ser
1               5                   10

<210> SEQ ID NO 120
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 120

His Gln Thr Phe Asp Ile Leu Thr Arg Leu His Phe
1               5                   10

<210> SEQ ID NO 121
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 121

Trp Gln Phe Asp Val Leu Thr Arg Ser Trp Thr Pro
1               5                   10

<210> SEQ ID NO 122
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 122

Gly Ala Ala Tyr Asp His Leu Thr Arg Thr Trp Leu
1               5                   10

<210> SEQ ID NO 123
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 123

Tyr Phe Asp Gln Leu Thr His Leu Ser Ile Lys Lys
1               5                   10

<210> SEQ ID NO 124
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 124

Ala Trp Asp Pro Leu Thr Met Leu Val Leu Pro Trp
1               5                   10

<210> SEQ ID NO 125
<211> LENGTH: 12
<212> TYPE: PRT
<213> ORGANISM: Artificial Sequence
```

```
<220> FEATURE:
<223> OTHER INFORMATION: BLyS binding polypeptide

<400> SEQUENCE: 125

Ala Leu Trp Met Asp Pro Leu Thr Gly Leu Ala Phe
1               5                   10

<210> SEQ ID NO 126
<211> LENGTH: 12
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (8)..(8)
<223> OTHER INFORMATION: X is unknown

<400> SEQUENCE: 126

Trp Gln Phe Asp Val Leu Thr Xaa Ser Trp Thr Pro
1               5                   10

<210> SEQ ID NO 127
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 127

Trp Thr Asp Pro Leu Thr His Met Glu Ile Tyr His
1               5                   10

<210> SEQ ID NO 128
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 128

Trp Thr Asp Ser Leu Thr Gly Leu Trp Phe Pro Asp
1               5                   10

<210> SEQ ID NO 129
<211> LENGTH: 12
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (10)..(10)
<223> OTHER INFORMATION: X is unknown

<400> SEQUENCE: 129

Tyr Thr Asp Pro Leu Thr Gly Ile Val Xaa Pro Phe
1               5                   10

<210> SEQ ID NO 130
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 130

Tyr Trp Asp Lys Leu Thr Met Leu His Leu Gly Val
1               5                   10
```

```
<210> SEQ ID NO 131
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 131

Tyr Tyr Asp Phe Leu Thr Arg Thr Val Leu Pro Ser
1               5                   10

<210> SEQ ID NO 132
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 132

Arg Leu Asp Pro Leu Ser Lys Asn Asp Phe Pro Arg
1               5                   10

<210> SEQ ID NO 133
<211> LENGTH: 12
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (10)..(10)
<223> OTHER INFORMATION: X is unknown

<400> SEQUENCE: 133

Leu Arg Tyr Asp Pro Leu Leu Lys Ser Xaa Ile Tyr
1               5                   10

<210> SEQ ID NO 134
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 134

Leu Arg Tyr Asp Pro Leu Leu Lys Ser Tyr Ile Tyr
1               5                   10

<210> SEQ ID NO 135
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 135

Tyr Phe Asp Gln Phe Thr His Leu Ser Ile Lys Lys
1               5                   10

<210> SEQ ID NO 136
<211> LENGTH: 12
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (5)..(5)
<223> OTHER INFORMATION: X is unknown
```

```
<400> SEQUENCE: 136

Tyr Phe Asp Gln Xaa Thr His Leu Ser Ile Lys Lys
1               5                   10

<210> SEQ ID NO 137
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 137

Glu His Tyr Tyr Thr Asp Pro Leu Thr Gly Ala Arg Ile
1               5                   10

<210> SEQ ID NO 138
<211> LENGTH: 13
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (4)..(4)
<223> OTHER INFORMATION: X is unknown

<400> SEQUENCE: 138

Glu His Tyr Xaa Thr Asp Pro Leu Thr Gly Ala Arg Ile
1               5                   10

<210> SEQ ID NO 139
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 139

Glu His Tyr Ser Thr Asp Pro Leu Thr Gly Ala Arg Ile
1               5                   10

<210> SEQ ID NO 140
<211> LENGTH: 13
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (9)..(9)
<223> OTHER INFORMATION: X is unknown
<221> NAME/KEY: MISC_FEATURE
<222> LOCATION: (11)..(11)
<223> OTHER INFORMATION: X is unknown

<400> SEQUENCE: 140

Glu His Tyr Tyr Thr Asp Pro Leu Xaa Gly Xaa Arg Ile
1               5                   10

<210> SEQ ID NO 141
<211> LENGTH: 13
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (9)..(9)
<223> OTHER INFORMATION: X is unknown
<221> NAME/KEY: MISC_FEATURE
<222> LOCATION: (11)..(11)
<223> OTHER INFORMATION: X is unknown
```

```
<221> NAME/KEY: MISC_FEATURE
<222> LOCATION: (13)..(13)
<223> OTHER INFORMATION: X is unknown

<400> SEQUENCE: 141

Glu His Tyr Tyr Thr Asp Pro Leu Xaa Gly Xaa Arg Xaa
1               5                   10

<210> SEQ ID NO 142
<211> LENGTH: 13
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (9)..(9)
<223> OTHER INFORMATION: X is unknown
<221> NAME/KEY: MISC_FEATURE
<222> LOCATION: (13)..(13)
<223> OTHER INFORMATION: X is unknown

<400> SEQUENCE: 142

Glu His Tyr Tyr Thr Asp Pro Leu Xaa Gly Ala Arg Xaa
1               5                   10

<210> SEQ ID NO 143
<211> LENGTH: 13
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (3)..(3)
<223> OTHER INFORMATION: X is unknown
<221> NAME/KEY: MISC_FEATURE
<222> LOCATION: (13)..(13)
<223> OTHER INFORMATION: X is unknown

<400> SEQUENCE: 143

Glu His Xaa Tyr Thr Asp Pro Leu Asn Gly Ala Arg Xaa
1               5                   10

<210> SEQ ID NO 144
<211> LENGTH: 13
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (13)..(13)
<223> OTHER INFORMATION: X is unknown

<400> SEQUENCE: 144

Glu His Tyr Tyr Asn Asp Pro Leu Asn Gly Ala Arg Xaa
1               5                   10

<210> SEQ ID NO 145
<211> LENGTH: 13
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (1)..(1)
<223> OTHER INFORMATION: X is unknown
<221> NAME/KEY: MISC_FEATURE
<222> LOCATION: (3)..(3)
<223> OTHER INFORMATION: X is unknown
<221> NAME/KEY: MISC_FEATURE
<222> LOCATION: (13)..(13)
<223> OTHER INFORMATION: X is unknown
```

```
<400> SEQUENCE: 145

Xaa His Xaa Tyr Asn Asp Pro Leu Asn Gly Ala Arg Xaa
1               5                   10

<210> SEQ ID NO 146
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 146

Lys Pro Tyr Tyr Asp Pro Ile Thr Lys Met Thr His His
1               5                   10

<210> SEQ ID NO 147
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 147

Lys Pro Tyr Tyr Asp Pro Ile Thr Lys Met Ser His His
1               5                   10

<210> SEQ ID NO 148
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 148

Lys Pro Tyr Tyr Asp Pro Ile Ser Lys Met Thr His His
1               5                   10

<210> SEQ ID NO 149
<211> LENGTH: 13
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (3)..(4)
<223> OTHER INFORMATION: X is unknown

<400> SEQUENCE: 149

Lys Pro Xaa Xaa Asp Pro Ile Ser Lys Met Thr His His
1               5                   10

<210> SEQ ID NO 150
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 150

Gln Ile Gly Tyr Asp Glu Leu Thr Lys Ala Trp Val Thr
1               5                   10

<210> SEQ ID NO 151
<211> LENGTH: 13
<212> TYPE: PRT
<213> ORGANISM: Artificial Sequence
```

```
<220> FEATURE:
<223> OTHER INFORMATION: BLyS binding polypeptide

<400> SEQUENCE: 151

Gln Leu Gly Tyr Asp Glu Leu Thr Lys Ala Trp Val Thr
1               5                   10

<210> SEQ ID NO 152
<211> LENGTH: 13
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (6)..(6)
<223> OTHER INFORMATION: X is unknown

<400> SEQUENCE: 152

Lys Ile Asp Glu Leu Xaa Met Gln Asn Ile Ile Ile Trp
1               5                   10

<210> SEQ ID NO 153
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 153

Asp His Thr Asp Pro Leu Ile Gln Gly Leu Thr Lys Arg
1               5                   10

<210> SEQ ID NO 154
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 154

Trp His Asp Pro Leu Lys His Met His Phe His His Glu
1               5                   10

<210> SEQ ID NO 155
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 155

Lys His Ile Asp Met Glu Thr Gly Leu Ile Leu Gln Asn
1               5                   10

<210> SEQ ID NO 156
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 156

Met Gln Val Asp Pro Glu Thr Gly Leu Lys Tyr Glu His
1               5                   10

<210> SEQ ID NO 157
<211> LENGTH: 13
```

```
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (1)..(1)
<223> OTHER INFORMATION: X is unknown
<221> NAME/KEY: MISC_FEATURE
<222> LOCATION: (8)..(10)
<223> OTHER INFORMATION: X is unknown

<400> SEQUENCE: 157

Xaa Leu Asp Gln His Val Asn Xaa Xaa Xaa Tyr Gln Ser
1               5                   10

<210> SEQ ID NO 158
<211> LENGTH: 13
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (2)..(4)
<223> OTHER INFORMATION: X is unknown
<221> NAME/KEY: MISC_FEATURE
<222> LOCATION: (6)..(7)
<223> OTHER INFORMATION: X is unknown
<221> NAME/KEY: MISC_FEATURE
<222> LOCATION: (13)..(13)
<223> OTHER INFORMATION: X is unknown

<400> SEQUENCE: 158

Glu Xaa Xaa Xaa Thr Xaa Xaa Leu Thr Gly Ala Arg Xaa
1               5                   10

<210> SEQ ID NO 159
<211> LENGTH: 13
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (9)..(9)
<223> OTHER INFORMATION: X is unknown
<221> NAME/KEY: MISC_FEATURE
<222> LOCATION: (6)..(6)
<223> OTHER INFORMATION: X is unknown
<221> NAME/KEY: MISC_FEATURE
<222> LOCATION: (13)..(13)
<223> OTHER INFORMATION: X is unknown

<400> SEQUENCE: 159

Gly Pro Tyr Asn Ile Xaa Arg Leu Xaa Gly Glu Arg Xaa
1               5                   10

<210> SEQ ID NO 160
<211> LENGTH: 13
<212> TYPE: PRT
<213> ORGANISM: Artificial Sequence
<220> FEATURE:
<223> OTHER INFORMATION: BLyS binding polypeptide

<400> SEQUENCE: 160

His Ile Lys Met Leu His Gln Gly Ser Phe Val Gly Val
1               5                   10

<210> SEQ ID NO 161
<211> LENGTH: 13
<212> TYPE: PRT
<213> ORGANISM: Artificial Sequence
<220> FEATURE:
```

```
<223> OTHER INFORMATION: BLyS binding polypeptide
<221> NAME/KEY: MISC_FEATURE
<222> LOCATION: (6)..(7)
<223> OTHER INFORMATION: X is unknown
<221> NAME/KEY: MISC_FEATURE
<222> LOCATION: (10)..(10)
<223> OTHER INFORMATION: X is unknown

<400> SEQUENCE: 161

His Pro Thr Asn Thr Xaa Xaa His Gln Xaa Val Tyr Ser
1               5                   10

<210> SEQ ID NO 162
<211> LENGTH: 13
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (6)..(7)
<223> OTHER INFORMATION: X is unknown
<221> NAME/KEY: MISC_FEATURE
<222> LOCATION: (12)..(12)
<223> OTHER INFORMATION: X is unknown
<221> NAME/KEY: MISC_FEATURE
<222> LOCATION: (13)..(13)
<223> OTHER INFORMATION: X is unknown

<400> SEQUENCE: 162

His Arg Gly Gln Val Xaa Xaa Leu Asn Gly Met Val Xaa
1               5                   10

<210> SEQ ID NO 163
<211> LENGTH: 24
<212> TYPE: PRT
<213> ORGANISM: Artificial Sequence
<220> FEATURE:
<223> OTHER INFORMATION: BLyS binding polypeptide

<400> SEQUENCE: 163

Ala Gly Lys Glu Pro Cys Tyr Phe Tyr Trp Glu Cys Ala Val Ser Gly
1               5                   10                  15

Pro Gly Pro Glu Gly Gly Gly Lys
            20

<210> SEQ ID NO 164
<211> LENGTH: 25
<212> TYPE: PRT
<213> ORGANISM: Artificial Sequence
<220> FEATURE:
<223> OTHER INFORMATION: BLyS binding polypeptide

<400> SEQUENCE: 164

Ala Gly Val Pro Phe Cys Asp Leu Leu Thr Lys His Cys Phe Glu Ala
1               5                   10                  15

Gly Pro Gly Pro Glu Gly Gly Gly Lys
            20                  25

<210> SEQ ID NO 165
<211> LENGTH: 28
<212> TYPE: PRT
<213> ORGANISM: Artificial Sequence
<220> FEATURE:
<223> OTHER INFORMATION: BLyS binding polypeptide

<400> SEQUENCE: 165

Gly Ser Ser Arg Leu Cys His Met Asp Glu Leu Thr His Val Cys Val
1               5                   10                  15
```

His Phe Ala Pro Pro Gly Pro Glu Gly Gly Gly Lys
            20                  25

<210> SEQ ID NO 166
<211> LENGTH: 29
<212> TYPE: PRT
<213> ORGANISM: Artificial Sequence
<220> FEATURE:
<223> OTHER INFORMATION: BLyS binding polypeptide

<400> SEQUENCE: 166

Gly Asp Gly Gly Asn Cys Tyr Thr Asp Ser Leu Thr Lys Leu His Phe
1               5                   10                  15

Cys Met Gly Asp Glu Pro Gly Pro Glu Gly Gly Gly Lys
            20                  25

<210> SEQ ID NO 167
<211> LENGTH: 22
<212> TYPE: PRT
<213> ORGANISM: Artificial Sequence
<220> FEATURE:
<223> OTHER INFORMATION: BLyS binding polypeptide

<400> SEQUENCE: 167

Gly Tyr Asp Val Leu Thr Lys Leu Tyr Phe Val Pro Gly Gly Pro Gly
1               5                   10                  15

Pro Glu Gly Gly Gly Lys
            20

<210> SEQ ID NO 168
<211> LENGTH: 22
<212> TYPE: PRT
<213> ORGANISM: Artificial Sequence
<220> FEATURE:
<223> OTHER INFORMATION: BLyS binding polypeptide

<400> SEQUENCE: 168

Trp Thr Asp Ser Leu Thr Gly Leu Trp Phe Pro Asp Gly Gly Pro Gly
1               5                   10                  15

Pro Glu Gly Gly Gly Lys
            20

<210> SEQ ID NO 169
<211> LENGTH: 24
<212> TYPE: PRT
<213> ORGANISM: Artificial Sequence
<220> FEATURE:
<223> OTHER INFORMATION: modified BLyS binding polypeptide

<400> SEQUENCE: 169

Ala Gly Lys Glu Pro Cys Tyr Phe Tyr Trp Glu Cys Ala Val Ser Gly
1               5                   10                  15

Pro Gly Pro Glu Gly Gly Gly Lys
            20

<210> SEQ ID NO 170
<211> LENGTH: 24
<212> TYPE: PRT
<213> ORGANISM: Artificial Sequence
<220> FEATURE:
<223> OTHER INFORMATION: modified BLyS binding polypeptide

<400> SEQUENCE: 170

Ala Gly Arg Glu Pro Cys Tyr Phe Tyr Trp Glu Cys Ala Val Ser Gly

```
1               5                   10                  15
Pro Gly Pro Glu Gly Gly Gly Lys
            20

<210> SEQ ID NO 171
<211> LENGTH: 24
<212> TYPE: PRT
<213> ORGANISM: Artificial Sequence
<220> FEATURE:
<223> OTHER INFORMATION: modified BLyS binding polypeptide

<400> SEQUENCE: 171

Ala Gly Gln Glu Pro Cys Tyr Phe Tyr Trp Glu Cys Ala Val Ser Gly
1               5                   10                  15
Pro Gly Pro Glu Gly Gly Gly Lys
            20

<210> SEQ ID NO 172
<211> LENGTH: 25
<212> TYPE: PRT
<213> ORGANISM: Artificial Sequence
<220> FEATURE:
<223> OTHER INFORMATION: modified BLyS binding polypeptide
<221> NAME/KEY: MISC_FEATURE
<222> LOCATION: (4)..(4)
<223> OTHER INFORMATION: X is norleucine

<400> SEQUENCE: 172

Ala Gly Asn Xaa Glu Pro Cys Tyr Phe Tyr Trp Glu Cys Ala Val Ser
1               5                   10                  15
Gly Pro Gly Pro Glu Gly Gly Gly Lys
            20                  25

<210> SEQ ID NO 173
<211> LENGTH: 285
<212> TYPE: PRT
<213> ORGANISM: Homo Sapiens

<400> SEQUENCE: 173

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
```

```
                 165                 170                 175
Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
        210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
            245                 250                 255

Asp Glu Leu Gln Leu Ala Ile Pro Arg Glu Asn Ala Gln Ile Ser Leu
        260                 265                 270

Asp Gly Asp Val Thr Phe Phe Gly Ala Leu Lys Leu Leu
        275                 280                 285

<210> SEQ ID NO 174
<211> LENGTH: 266
<212> TYPE: PRT
<213> ORGANISM: Homo Sapiens

<400> SEQUENCE: 174

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Gly Ser Tyr
    130                 135                 140

Thr Phe Val Pro Trp Leu Leu Ser Phe Lys Arg Gly Ser Ala Leu Glu
145                 150                 155                 160

Glu Lys Glu Asn Lys Ile Leu Val Lys Glu Thr Gly Tyr Phe Phe Ile
                165                 170                 175

Tyr Gly Gln Val Leu Tyr Thr Asp Lys Thr Tyr Ala Met Gly His Leu
            180                 185                 190

Ile Gln Arg Lys Lys Val His Val Phe Gly Asp Glu Leu Ser Leu Val
        195                 200                 205

Thr Leu Phe Arg Cys Ile Gln Asn Met Pro Glu Thr Leu Pro Asn Asn
    210                 215                 220

Ser Cys Tyr Ser Ala Gly Ile Ala Lys Leu Glu Glu Gly Asp Glu Leu
225                 230                 235                 240

Gln Leu Ala Ile Pro Arg Glu Asn Ala Gln Ile Ser Leu Asp Gly Asp
                245                 250                 255
```

```
Val Thr Phe Phe Gly Ala Leu Lys Leu Leu
            260                 265
```

<210> SEQ ID NO 175
<211> LENGTH: 309
<212> TYPE: PRT
<213> ORGANISM: mouse

<400> SEQUENCE: 175

```
Met Asp Glu Ser Ala Lys Thr Leu Pro Pro Cys Leu Cys Phe Cys
1               5                   10                  15

Ser Glu Lys Gly Glu Asp Met Lys Val Gly Tyr Asp Pro Ile Thr Pro
                20                  25                  30

Gln Lys Glu Glu Gly Ala Trp Phe Gly Ile Cys Arg Asp Gly Arg Leu
            35                  40                  45

Leu Ala Ala Thr Leu Leu Ala Leu Leu Ser Ser Ser Phe Thr Ala
    50                  55                  60

Met Ser Leu Tyr Gln Leu Ala Ala Leu Gln Ala Asp Leu Met Asn Leu
65                  70                  75                  80

Arg Met Glu Leu Gln Ser Tyr Arg Gly Ser Ala Thr Pro Ala Ala Ala
                85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
        115                 120                 125

Gln Gly Pro Glu Glu Thr Glu Gln Asp Val Asp Leu Ser Ala Pro Pro
    130                 135                 140

Ala Pro Cys Leu Pro Gly Cys Arg His Ser Gln His Asp Asp Asn Gly
145                 150                 155                 160

Met Asn Leu Arg Asn Ile Ile Gln Asp Cys Leu Gln Leu Ile Ala Asp
                165                 170                 175

Ser Asp Thr Pro Thr Ile Arg Lys Gly Thr Tyr Thr Phe Val Pro Trp
            180                 185                 190

Leu Leu Ser Phe Lys Arg Gly Asn Ala Leu Glu Glu Lys Glu Asn Lys
        195                 200                 205

Ile Val Val Arg Gln Thr Gly Tyr Phe Phe Ile Tyr Ser Gln Val Leu
    210                 215                 220

Tyr Thr Asp Pro Ile Phe Ala Met Gly His Val Ile Gln Arg Lys Lys
225                 230                 235                 240

Val His Val Phe Gly Asp Glu Leu Ser Leu Val Thr Leu Phe Arg Cys
                245                 250                 255

Ile Gln Asn Met Pro Lys Thr Leu Pro Asn Asn Ser Cys Tyr Ser Ala
            260                 265                 270

Gly Ile Ala Arg Leu Glu Glu Gly Asp Glu Ile Gln Leu Ala Ile Pro
        275                 280                 285

Arg Glu Asn Ala Gln Ile Ser Arg Asn Gly Asp Asp Thr Phe Phe Gly
    290                 295                 300

Ala Leu Lys Leu Leu
305
```

<210> SEQ ID NO 176
<211> LENGTH: 290
<212> TYPE: PRT
<213> ORGANISM: mouse

<400> SEQUENCE: 176

```
Met Asp Glu Ser Ala Lys Thr Leu Pro Pro Cys Leu Cys Phe Cys
1               5                   10                  15

Ser Glu Lys Gly Glu Asp Met Lys Val Gly Tyr Asp Pro Ile Thr Pro
                20                  25                  30

Gln Lys Glu Glu Gly Ala Trp Phe Gly Ile Cys Arg Asp Gly Arg Leu
            35                  40                  45

Leu Ala Ala Thr Leu Leu Leu Ala Leu Leu Ser Ser Ser Phe Thr Ala
    50                  55                  60

Met Ser Leu Tyr Gln Leu Ala Ala Leu Gln Ala Asp Leu Met Asn Leu
65                  70                  75                  80

Arg Met Glu Leu Gln Ser Tyr Arg Gly Ser Ala Thr Pro Ala Ala Ala
                85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
        115                 120                 125

Gln Gly Pro Glu Glu Thr Glu Gln Asp Val Asp Leu Ser Ala Pro Pro
    130                 135                 140

Ala Pro Cys Leu Pro Gly Cys Arg His Ser Gln His Asp Asp Asn Gly
145                 150                 155                 160

Met Asn Leu Arg Asn Arg Thr Tyr Thr Phe Val Pro Trp Leu Leu Ser
                165                 170                 175

Phe Lys Arg Gly Asn Ala Leu Glu Glu Lys Glu Asn Lys Ile Val Val
            180                 185                 190

Arg Gln Thr Gly Tyr Phe Phe Ile Tyr Ser Gln Val Leu Tyr Thr Asp
        195                 200                 205

Pro Ile Phe Ala Met Gly His Val Ile Gln Arg Lys Lys Val His Val
    210                 215                 220

Phe Gly Asp Glu Leu Ser Leu Val Thr Leu Phe Arg Cys Ile Gln Asn
225                 230                 235                 240

Met Pro Lys Thr Leu Pro Asn Asn Ser Cys Tyr Ser Ala Gly Ile Ala
                245                 250                 255

Arg Leu Glu Glu Gly Asp Glu Ile Gln Leu Ala Ile Pro Arg Glu Asn
            260                 265                 270

Ala Gln Ile Ser Arg Asn Gly Asp Asp Thr Phe Phe Gly Ala Leu Lys
        275                 280                 285

Leu Leu
    290

<210> SEQ ID NO 177
<211> LENGTH: 239
<212> TYPE: PRT
<213> ORGANISM: rat

<400> SEQUENCE: 177

Ala Val Gln Ala Asp Leu Met Ser Leu Arg Met Glu Leu Gln Ser Tyr
1               5                   10                  15

Arg Ser Ser Ala Thr Pro Ala Ala Pro Gly Ala Pro Gly Leu Ser Ala
                20                  25                  30

Gly Val Lys Leu Pro Thr Pro Ala Ala Pro Gly Pro His Asn Ser Ser
            35                  40                  45

Arg Gly Gln Arg Asn Arg Arg Ala Phe Gln Gly Pro Glu Glu Thr Glu
        50                  55                  60

Gln Asp Val Asp Leu Ser Ala Thr Pro Ala Pro Ser Leu Pro Gly Asn
65                  70                  75                  80
```

```
Cys His Ala Ser His His Asp Glu Asn Gly Leu Asn Leu Arg Thr Ile
                85                  90                  95

Ile Gln Asp Cys Leu Gln Leu Ile Ala Asp Ser Asn Thr Pro Thr Ile
            100                 105                 110

Arg Lys Gly Thr Tyr Thr Phe Val Pro Trp Leu Leu Ser Phe Lys Arg
        115                 120                 125

Gly Asn Ala Leu Glu Glu Lys Glu Asn Lys Ile Val Val Arg Gln Thr
    130                 135                 140

Gly Tyr Phe Phe Ile Tyr Ser Gln Val Leu Tyr Thr Asp Pro Ile Phe
145                 150                 155                 160

Ala Met Gly His Val Ile Gln Arg Lys Lys Ile His Val Phe Gly Asp
                165                 170                 175

Glu Leu Ser Leu Val Thr Leu Phe Arg Cys Ile Gln Asn Met Pro Lys
            180                 185                 190

Thr Leu Pro Asn Asn Ser Cys Tyr Ser Ala Gly Ile Ala Lys Leu Glu
        195                 200                 205

Glu Gly Asp Glu Ile Gln Leu Ala Ile Pro Arg Glu Asn Ala Gln Ile
    210                 215                 220

Ser Arg Asn Gly Asp Asp Thr Phe Phe Gly Ala Leu Lys Leu Leu
225                 230                 235

<210> SEQ ID NO 178
<211> LENGTH: 220
<212> TYPE: PRT
<213> ORGANISM: rat

<400> SEQUENCE: 178

Ala Val Gln Ala Asp Leu Met Ser Leu Arg Met Glu Leu Gln Ser Tyr
1               5                   10                  15

Arg Ser Ser Ala Thr Pro Ala Ala Pro Gly Ala Pro Gly Leu Ser Ala
            20                  25                  30

Gly Val Lys Leu Pro Thr Pro Ala Ala Pro Gly Pro His Asn Ser Ser
        35                  40                  45

Arg Gly Gln Arg Asn Arg Arg Ala Phe Gln Gly Pro Glu Glu Thr Glu
    50                  55                  60

Gln Asp Val Asp Leu Ser Ala Thr Pro Val Pro Ser Leu Pro Gly Asn
65                  70                  75                  80

Cys His Ala Ser His His Asp Glu Asn Gly Leu Asn Leu Arg Thr Arg
                85                  90                  95

Thr Tyr Thr Phe Val Pro Trp Leu Leu Ser Phe Lys Arg Gly Asn Ala
            100                 105                 110

Leu Glu Glu Lys Glu Asn Lys Ile Val Val Arg Gln Thr Gly Tyr Phe
        115                 120                 125

Phe Ile Tyr Ser Gln Val Leu Tyr Thr Asp Pro Ile Phe Ala Met Gly
    130                 135                 140

His Val Ile Gln Arg Lys Lys Ile His Val Phe Gly Asp Glu Leu Ser
145                 150                 155                 160

Leu Val Thr Leu Phe Arg Cys Ile Gln Asn Met Pro Lys Thr Leu Pro
                165                 170                 175

Asn Asn Ser Cys Tyr Ser Ala Gly Ile Ala Lys Leu Glu Glu Gly Asp
            180                 185                 190

Glu Ile Gln Leu Ala Ile Pro Arg Glu Asn Ala Gln Ile Ser Arg Asn
        195                 200                 205

Gly Asp Asp Thr Phe Phe Gly Ala Leu Lys Leu Leu
    210                 215                 220
```

-continued

```
            210                 215                 220

<210> SEQ ID NO 179
<211> LENGTH: 207
<212> TYPE: PRT
<213> ORGANISM: rat

<400> SEQUENCE: 179

Ala Val Gln Ala Asp Leu Met Ser Leu Arg Met Glu Leu Gln Ser Tyr
1               5                   10                  15

Arg Ser Ser Ala Thr Pro Ala Ala Pro Gly Ala Pro Gly Leu Ser Ala
            20                  25                  30

Gly Val Lys Leu Pro Thr Pro Ala Ala Pro Gly Pro His Asn Ser Ser
        35                  40                  45

Arg Gly Gln Arg Asn Arg Arg Ala Phe Gln Gly Pro Glu Glu Thr Val
    50                  55                  60

Ile Gln Asp Cys Leu Gln Leu Ile Ala Asp Ser Asn Thr Pro Thr Ile
65                  70                  75                  80

Arg Lys Gly Thr Tyr Thr Phe Val Pro Trp Leu Leu Ser Phe Lys Arg
                85                  90                  95

Gly Asn Ala Leu Glu Glu Lys Glu Asn Lys Ile Val Val Arg Gln Thr
            100                 105                 110

Gly Tyr Phe Phe Ile Tyr Ser Gln Val Leu Tyr Thr Asp Pro Ile Phe
        115                 120                 125

Ala Met Gly His Val Ile Gln Arg Lys Lys Ile His Val Phe Gly Asp
    130                 135                 140

Glu Leu Ser Leu Val Thr Leu Phe Arg Cys Ile Gln Asn Met Pro Lys
145                 150                 155                 160

Thr Leu Pro Asn Asn Ser Cys Tyr Ser Ala Gly Ile Ala Lys Leu Glu
                165                 170                 175

Glu Gly Asp Glu Val Gln Leu Ala Ile Pro Arg Glu Asn Ala Gln Ile
            180                 185                 190

Ser Arg Asn Gly Asp Asp Thr Phe Phe Gly Ala Leu Lys Leu Leu
        195                 200                 205

<210> SEQ ID NO 180
<211> LENGTH: 188
<212> TYPE: PRT
<213> ORGANISM: rat

<400> SEQUENCE: 180

Ala Val Gln Ala Asp Leu Met Ser Leu Arg Met Glu Leu Gln Ser Tyr
1               5                   10                  15

Arg Ser Ser Ala Thr Pro Ala Ala Pro Gly Ala Pro Gly Leu Ser Ala
            20                  25                  30

Gly Val Lys Leu Pro Thr Pro Ala Ala Pro Gly Pro His Asn Ser Ser
        35                  40                  45

Arg Gly Gln Arg Asn Arg Arg Ala Phe Gln Gly Pro Glu Glu Thr Gly
    50                  55                  60

Thr Tyr Thr Phe Val Pro Trp Leu Leu Ser Phe Lys Arg Gly Asn Ala
65                  70                  75                  80

Leu Glu Glu Lys Glu Asn Lys Ile Val Val Arg Gln Thr Gly Tyr Phe
                85                  90                  95

Phe Ile Tyr Ser Gln Val Leu Tyr Thr Asp Pro Ile Phe Ala Met Gly
            100                 105                 110

His Val Ile Gln Arg Lys Lys Ile His Val Phe Gly Asp Glu Leu Ser
```

```
            115                 120                 125
Leu Val Thr Leu Phe Arg Cys Ile Gln Asn Met Pro Lys Thr Leu Pro
    130                 135                 140

Asn Asn Ser Cys Tyr Ser Ala Gly Ile Ala Lys Leu Glu Glu Gly Asp
145                 150                 155                 160

Glu Ile Gln Leu Ala Ile Pro Arg Glu Asn Ala Gln Ile Ser Arg Asn
                165                 170                 175

Gly Asp Asp Thr Phe Phe Gly Ala Leu Lys Leu Leu
                180                 185
```

<210> SEQ ID NO 181
<211> LENGTH: 243
<212> TYPE: PRT
<213> ORGANISM: monkey

<400> SEQUENCE: 181

```
Lys Asp Arg Lys Leu Leu Ala Ala Ala Leu Leu Ala Leu Leu Ser
1               5                   10                  15

Cys Cys Leu Met Val Val Ser Phe Tyr Gln Val Ala Ala Leu Gln Gly
                20                  25                  30

Asp Leu Ala Ser Leu Arg Ala Glu Leu Gln Gly His His Ala Glu Lys
            35                  40                  45

Leu Pro Ala Arg Ala Arg Ala Pro Lys Ala Gly Leu Gly Glu Ala Pro
        50                  55                  60

Ala Val Thr Ala Gly Leu Lys Ile Phe Glu Pro Pro Ala Pro Gly Glu
65                  70                  75                  80

Gly Asn Ser Ser Gln Ser Ser Arg Asn Lys Arg Ala Ile Gln Gly Ala
                85                  90                  95

Glu Glu Thr Val Ile Gln Asp Cys Leu Gln Leu Ile Ala Asp Ser Glu
                100                 105                 110

Thr Pro Thr Ile Gln Lys Gly Ser Tyr Thr Phe Val Pro Trp Leu Leu
                115                 120                 125

Ser Phe Lys Arg Gly Ser Ala Leu Glu Glu Lys Glu Asn Lys Ile Leu
    130                 135                 140

Val Lys Glu Thr Gly Tyr Phe Phe Ile Tyr Gly Gln Val Leu Tyr Thr
145                 150                 155                 160

Asp Lys Thr Tyr Ala Met Gly His Leu Ile Gln Arg Lys Lys Val His
                165                 170                 175

Val Phe Gly Asp Glu Leu Ser Leu Val Thr Leu Phe Arg Cys Ile Gln
                180                 185                 190

Asn Met Pro Glu Thr Leu Pro Asn Asn Ser Cys Tyr Ser Ala Gly Ile
                195                 200                 205

Ala Lys Leu Glu Glu Gly Asp Glu Leu Gln Leu Ala Ile Pro Arg Glu
    210                 215                 220

Asn Ala Gln Ile Ser Leu Asp Gly Asp Val Thr Phe Phe Gly Ala Leu
225                 230                 235                 240

Lys Leu Leu
```

<210> SEQ ID NO 182
<211> LENGTH: 219
<212> TYPE: PRT
<213> ORGANISM: monkey

<400> SEQUENCE: 182

```
Tyr Gln Val Ala Ala Val Gln Gly Asp Leu Ala Ser Leu Arg Ala Glu
1               5                   10                  15
```

```
Leu Gln Ser His His Ala Glu Lys Leu Pro Ala Arg Ala Arg Ala Pro
             20                  25                  30

Lys Ala Gly Leu Gly Glu Ala Pro Ala Val Thr Ala Gly Leu Lys Ile
         35                  40                  45

Phe Glu Pro Pro Ala Pro Gly Glu Gly Asn Ser Ser Gln Ser Ser Arg
     50                  55                  60

Asn Lys Arg Ala Ile Gln Gly Ala Glu Glu Thr Val Ile Gln Asp Cys
 65                  70                  75                  80

Leu Gln Leu Ile Ala Asp Ser Glu Thr Pro Thr Ile Gln Lys Gly Ser
                 85                  90                  95

Tyr Thr Phe Val Pro Trp Leu Leu Ser Phe Lys Arg Gly Ser Ala Leu
            100                 105                 110

Glu Glu Lys Glu Asn Lys Ile Leu Val Lys Glu Thr Gly Tyr Phe Phe
        115                 120                 125

Ile Tyr Gly Gln Val Leu Tyr Thr Asp Lys Thr Tyr Ala Met Gly His
    130                 135                 140

Leu Ile Gln Arg Lys Lys Val His Val Phe Gly Asp Glu Leu Ser Leu
145                 150                 155                 160

Val Thr Leu Phe Arg Cys Ile Gln Asn Met Pro Glu Thr Leu Pro Asn
                165                 170                 175

Asn Ser Cys Tyr Ser Ala Gly Ile Ala Lys Leu Glu Glu Gly Asp Glu
            180                 185                 190

Leu Gln Leu Ala Ile Pro Arg Glu Asn Ala Gln Ile Ser Leu Asp Gly
        195                 200                 205

Asp Val Thr Phe Phe Gly Ala Leu Lys Leu Leu
    210                 215

<210> SEQ ID NO 183
<211> LENGTH: 8
<212> TYPE: PRT
<213> ORGANISM: Artificial Sequence
<220> FEATURE:
<223> OTHER INFORMATION: epitope tag

<400> SEQUENCE: 183

Asp Tyr Lys Asp Asp Asp Asp Lys
1               5

<210> SEQ ID NO 184
<211> LENGTH: 14
<212> TYPE: PRT
<213> ORGANISM: Artificial Sequence
<220> FEATURE:
<223> OTHER INFORMATION: concensus BLyS binding polypeptide

<400> SEQUENCE: 184

Ala Asn Trp Tyr Asp Ser Leu Thr Lys Leu Trp Leu Pro Asp
1               5                   10

<210> SEQ ID NO 185
<211> LENGTH: 42
<212> TYPE: DNA
<213> ORGANISM: Artificial Sequence
<220> FEATURE:
<223> OTHER INFORMATION: coding sequence for BLyS affinity maturation
      library template
<221> NAME/KEY: misc_feature
<222> LOCATION: (4)..(12)
<223> OTHER INFORMATION: N=A or G or C or T
<221> NAME/KEY: misc_feature
<222> LOCATION: (16)..(18)
```

<223> OTHER INFORMATION: N=A or G or C or T
<221> NAME/KEY: misc_feature
<222> LOCATION: (25)..(27)
<223> OTHER INFORMATION: N=A or G or C or T
<221> NAME/KEY: misc_feature
<222> LOCATION: (31)..(42)
<223> OTHER INFORMATION: N=A or G or C or T

<400> SEQUENCE: 185
gctnnnnnnn nngatnnnct tactnnnctc nnnnnnnnnn nn        42

<210> SEQ ID NO 186
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 186

Ala Asn Trp Tyr Asp Pro Leu Thr Lys Leu Trp Leu Pro Asp
1               5                   10

<210> SEQ ID NO 187
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 187

Ala Asn Trp Tyr Asp Pro Leu Thr Lys Leu Trp Leu Pro Glu
1               5                   10

<210> SEQ ID NO 188
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 188

Ala Asn Trp Tyr Asp Pro Leu Thr Lys Leu Trp Leu Pro Gly
1               5                   10

<210> SEQ ID NO 189
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 189

Ala Asn Trp Tyr Asp Pro Leu Thr Lys Leu Trp Leu Pro Val
1               5                   10

<210> SEQ ID NO 190
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 190

Ala Asn Trp Tyr Asp Pro Leu Thr Lys Leu Trp Leu Ser Asp
1               5                   10

<210> SEQ ID NO 191

-continued

```
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 191

Ala Asn Trp Tyr Asp Pro Leu Thr Lys Leu Trp Leu Asn Asp
1               5                   10

<210> SEQ ID NO 192
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 192

Ala Asn Trp Tyr Asp Pro Leu Thr Lys Leu Trp Leu Pro Thr
1               5                   10

<210> SEQ ID NO 193
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 193

Ala Asn Trp Tyr Asp Pro Leu Thr Lys Leu Trp Leu Pro Ala
1               5                   10

<210> SEQ ID NO 194
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 194

Ala Asn Trp Tyr Asp Pro Leu Thr Lys Leu Trp Leu Pro Asn
1               5                   10

<210> SEQ ID NO 195
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 195

Ala Asn Trp Tyr Asp Pro Leu Thr Lys Leu Trp Leu Val Asp
1               5                   10

<210> SEQ ID NO 196
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 196

Ala Asn Trp Tyr Asp Pro Leu Thr Lys Leu Trp Leu His Asp
1               5                   10

<210> SEQ ID NO 197
<211> LENGTH: 14
```

-continued

<212> TYPE: PRT
<213> ORGANISM: Artificial Sequence
<220> FEATURE:
<223> OTHER INFORMATION: BLyS binding polypeptide

<400> SEQUENCE: 197

Ala Asn Trp Tyr Asp Pro Leu Thr Lys Leu Trp Leu Thr Asp
1 5 10

<210> SEQ ID NO 198
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 198

Ala Asn Trp Tyr Asp Pro Leu Thr Lys Leu Trp Leu Pro His
1 5 10

<210> SEQ ID NO 199
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 199

Ala Asn Trp Tyr Asp Pro Leu Thr Lys Leu Trp Leu Thr Val
1 5 10

<210> SEQ ID NO 200
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 200

Ala Asn Trp Tyr Asp Pro Leu Thr Lys Leu Trp Leu Leu Asp
1 5 10

<210> SEQ ID NO 201
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 201

Ala Asn Trp Tyr Asp Pro Leu Thr Lys Leu Trp Leu Leu Glu
1 5 10

<210> SEQ ID NO 202
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 202

Ala Asn Trp Tyr Asp Pro Leu Thr Lys Leu Trp Leu His Glu
1 5 10

<210> SEQ ID NO 203
<211> LENGTH: 14
<212> TYPE: PRT

```
<213> ORGANISM: Artificial Sequence
<220> FEATURE:
<223> OTHER INFORMATION: BLyS binding polypeptide

<400> SEQUENCE: 203

Ala Asn Trp Tyr Asp Pro Leu Thr Lys Leu Trp Leu Pro Arg
1               5                   10

<210> SEQ ID NO 204
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 204

Ala Asn Trp Tyr Asp Pro Leu Thr Lys Leu Trp Leu Ala Asp
1               5                   10

<210> SEQ ID NO 205
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 205

Ala Asn Trp Tyr Asp Pro Leu Thr Lys Leu Trp Leu Pro Tyr
1               5                   10

<210> SEQ ID NO 206
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 206

Ala Asn Trp Tyr Asp Pro Leu Thr Lys Leu Trp Leu Pro Ile
1               5                   10

<210> SEQ ID NO 207
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 207

Ala Asn Trp Tyr Asp Pro Leu Thr Lys Leu Trp Leu Ile Asp
1               5                   10

<210> SEQ ID NO 208
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 208

Ala Asn Trp Tyr Asp Pro Leu Thr Lys Leu Trp Leu Arg Asp
1               5                   10

<210> SEQ ID NO 209
<211> LENGTH: 14
<212> TYPE: PRT
<213> ORGANISM: Artificial Sequence
```

```
<220> FEATURE:
<223> OTHER INFORMATION: BLyS binding polypeptide

<400> SEQUENCE: 209

Ala Tyr Trp Tyr Asp Pro Leu Thr Lys Leu Trp Leu Pro Asp
1               5                   10

<210> SEQ ID NO 210
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 210

Ala Tyr Trp Tyr Asp Pro Leu Thr Lys Leu Trp Leu Leu Glu
1               5                   10

<210> SEQ ID NO 211
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 211

Ala Tyr Trp Tyr Asp Pro Leu Thr Lys Leu Trp Leu Arg Val
1               5                   10

<210> SEQ ID NO 212
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 212

Ala Tyr Trp Tyr Asp Pro Leu Thr Lys Leu Trp Leu Pro Glu
1               5                   10

<210> SEQ ID NO 213
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 213

Ala Tyr Trp Tyr Asp Pro Leu Thr Lys Leu Trp Leu Pro Val
1               5                   10

<210> SEQ ID NO 214
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 214

Ala Tyr Trp Tyr Asp Pro Leu Thr Lys Leu Trp Leu His Gln
1               5                   10

<210> SEQ ID NO 215
<211> LENGTH: 14
<212> TYPE: PRT
<213> ORGANISM: Artificial Sequence
<220> FEATURE:
```

<223> OTHER INFORMATION: BLyS binding polypeptide

<400> SEQUENCE: 215

Ala Tyr Trp Tyr Asp Pro Leu Thr Lys Leu Trp Leu Pro Ala
1               5                   10

<210> SEQ ID NO 216
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 216

Ala Tyr Trp Tyr Asp Pro Leu Thr Lys Leu Trp Leu Arg Val
1               5                   10

<210> SEQ ID NO 217
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 217

Ala Tyr Trp Tyr Asp Pro Leu Thr Lys Leu Trp Leu Pro Gly
1               5                   10

<210> SEQ ID NO 218
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 218

Ala Tyr Trp Tyr Asp Pro Leu Thr Lys Leu Trp Leu Arg Tyr
1               5                   10

<210> SEQ ID NO 219
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 219

Ala Tyr Trp Tyr Asp Pro Leu Thr Lys Leu Trp Leu Pro Tyr
1               5                   10

<210> SEQ ID NO 220
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 220

Ala Tyr Trp Tyr Asp Pro Leu Thr Lys Leu Trp Leu Leu Tyr
1               5                   10

<210> SEQ ID NO 221
<211> LENGTH: 14
<212> TYPE: PRT
<213> ORGANISM: Artificial Sequence
<220> FEATURE:
<223> OTHER INFORMATION: BLyS binding polypeptide -continued

<400> SEQUENCE: 221

Ala Tyr Trp Tyr Asp Pro Leu Thr Lys Leu Trp Leu Arg Asp
1 5 10

<210> SEQ ID NO 222
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 222

Ala Tyr Trp Tyr Asp Pro Leu Thr Lys Leu Trp Leu Pro Val
1 5 10

<210> SEQ ID NO 223
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 223

Ala Tyr Trp Tyr Asp Pro Leu Thr Lys Leu Trp Leu Leu Gly
1 5 10

<210> SEQ ID NO 224
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 224

Ala Tyr Trp Tyr Asp Pro Leu Thr Lys Leu Trp Leu Thr His
1 5 10

<210> SEQ ID NO 225
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 225

Ala Tyr Trp Tyr Asp Pro Leu Thr Lys Leu Trp Leu Pro Thr
1 5 10

<210> SEQ ID NO 226
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 226

Ala Tyr Trp Tyr Asp Pro Leu Thr Lys Leu Trp Leu Leu Val
1 5 10

<210> SEQ ID NO 227
<211> LENGTH: 14
<212> TYPE: PRT
<213> ORGANISM: Artificial Sequence
<220> FEATURE:
<223> OTHER INFORMATION: BLyS binding polypeptide

```
<400> SEQUENCE: 227

Ala Tyr Trp Tyr Asp Pro Leu Thr Lys Leu Trp Leu Tyr Tyr
1               5                   10

<210> SEQ ID NO 228
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 228

Ala Tyr Trp Tyr Asp Pro Leu Thr Lys Leu Trp Leu Ser Asp
1               5                   10

<210> SEQ ID NO 229
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 229

Ala Ser Trp Tyr Asp Pro Leu Thr Lys Leu Trp Leu Pro Ala
1               5                   10

<210> SEQ ID NO 230
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 230

Ala Ser Trp Tyr Asp Pro Leu Thr Lys Leu Trp Leu His Asp
1               5                   10

<210> SEQ ID NO 231
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 231

Ala Ser Trp Tyr Asp Pro Leu Thr Lys Leu Trp Leu Pro Gly
1               5                   10

<210> SEQ ID NO 232
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 232

Ala Ser Trp Tyr Asp Pro Leu Thr Lys Leu Trp Leu Pro Gln
1               5                   10

<210> SEQ ID NO 233
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 233
```

Ala Ser Trp Tyr Asp Pro Leu Thr Lys Leu Trp Leu Pro Tyr
1               5                   10

<210> SEQ ID NO 234
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 234

Ala Ser Trp Tyr Asp Pro Leu Thr Lys Leu Trp Leu Pro His
1               5                   10

<210> SEQ ID NO 235
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 235

Ala Ser Trp Tyr Asp Pro Leu Thr Lys Leu Trp Leu Pro Val
1               5                   10

<210> SEQ ID NO 236
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 236

Ala Ser Trp Tyr Asp Pro Leu Thr Lys Leu Trp Leu Pro Ile
1               5                   10

<210> SEQ ID NO 237
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 237

Ala Ser Trp Tyr Asp Pro Leu Thr Lys Leu Trp Leu Pro Glu
1               5                   10

<210> SEQ ID NO 238
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 238

Ala Phe Trp Tyr Asp Pro Leu Thr Lys Leu Trp Leu Arg Val
1               5                   10

<210> SEQ ID NO 239
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 239

```
Ala Phe Trp Tyr Asp Pro Leu Thr Lys Leu Trp Leu Pro Glu
1               5                   10

<210> SEQ ID NO 240
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 240

Ala Phe Trp Tyr Asp Pro Leu Thr Lys Leu Trp Leu Leu Glu
1               5                   10

<210> SEQ ID NO 241
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 241

Ala Phe Trp Tyr Asp Pro Leu Thr Lys Leu Trp Leu Pro Val
1               5                   10

<210> SEQ ID NO 242
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 242

Ala Ile Trp Tyr Asp Pro Leu Thr Lys Leu Trp Leu Pro Glu
1               5                   10

<210> SEQ ID NO 243
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 243

Ala Ile Trp Tyr Asp Pro Leu Thr Lys Leu Trp Leu Pro Asp
1               5                   10

<210> SEQ ID NO 244
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 244

Ala Ile Trp Tyr Asp Pro Leu Thr Lys Leu Trp Leu His Asp
1               5                   10

<210> SEQ ID NO 245
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 245

Ala Ile Trp Tyr Asp Pro Leu Thr Lys Leu Trp Leu Thr Asp
```

```
                1               5                   10

<210> SEQ ID NO 246
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 246

Ala Ile Trp Tyr Asp Pro Leu Thr Lys Leu Trp Leu Pro Phe
1               5                   10

<210> SEQ ID NO 247
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 247

Ala Ile Trp Tyr Asp Pro Leu Thr Lys Leu Trp Leu Leu Asp
1               5                   10

<210> SEQ ID NO 248
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 248

Ala Ile Trp Tyr Asp Pro Leu Thr Lys Leu Trp Leu Pro Arg
1               5                   10

<210> SEQ ID NO 249
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 249

Ala Ile Trp Tyr Asp Pro Leu Thr Lys Leu Trp Leu Pro Ala
1               5                   10

<210> SEQ ID NO 250
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 250

Ala Ile Trp Tyr Asp Pro Leu Thr Lys Leu Trp Leu Thr Ala
1               5                   10

<210> SEQ ID NO 251
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 251

Ala Ile Trp Tyr Asp Pro Leu Thr Lys Leu Trp Leu Ala Val
1               5                   10
```

<210> SEQ ID NO 252
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 252

Ala Ile Trp Tyr Asp Pro Leu Thr Lys Leu Trp Leu Pro Gly
1               5                   10

<210> SEQ ID NO 253
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 253

Ala Ile Trp Tyr Asp Pro Leu Thr Lys Leu Trp Leu Arg Val
1               5                   10

<210> SEQ ID NO 254
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 254

Ala Ile Trp Tyr Asp Pro Leu Thr Lys Leu Trp Leu Pro His
1               5                   10

<210> SEQ ID NO 255
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 255

Ala Ile Trp Tyr Asp Pro Leu Thr Lys Leu Trp Leu Arg Glu
1               5                   10

<210> SEQ ID NO 256
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 256

Ala Ile Trp Tyr Asp Pro Leu Thr Lys Leu Trp Leu Ser Asp
1               5                   10

<210> SEQ ID NO 257
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 257

Ala Thr Trp Tyr Asp Pro Leu Thr Lys Leu Trp Leu Pro Ala
1               5                   10

<210> SEQ ID NO 258
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 258

Ala Thr Trp Tyr Asp Pro Leu Thr Lys Leu Trp Leu Ala Asp
1               5                   10

<210> SEQ ID NO 259
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 259

Ala Thr Trp Tyr Asp Pro Leu Thr Lys Leu Trp Leu Thr Ser
1               5                   10

<210> SEQ ID NO 260
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 260

Ala Thr Trp Tyr Asp Pro Leu Thr Lys Leu Trp Leu Pro Gly
1               5                   10

<210> SEQ ID NO 261
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 261

Ala Thr Trp Tyr Asp Pro Leu Thr Lys Leu Trp Leu Pro Tyr
1               5                   10

<210> SEQ ID NO 262
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 262

Ala Thr Trp Tyr Asp Pro Leu Thr Lys Leu Trp Leu Ser Gly
1               5                   10

<210> SEQ ID NO 263
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 263

Ala Thr Trp Tyr Asp Pro Leu Thr Lys Leu Trp Leu Pro Val
1               5                   10

```
<210> SEQ ID NO 264
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 264

Ala Thr Trp Tyr Asp Pro Leu Thr Lys Leu Trp Leu Pro Asp
1               5                   10

<210> SEQ ID NO 265
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 265

Ala Asp Trp Tyr Asp Pro Leu Thr Lys Leu Trp Leu Pro Val
1               5                   10

<210> SEQ ID NO 266
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 266

Ala Asp Trp Tyr Asp Pro Leu Thr Lys Leu Trp Leu Pro Lys
1               5                   10

<210> SEQ ID NO 267
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 267

Ala Asp Trp Tyr Asp Pro Leu Thr Lys Leu Trp Leu Pro Asp
1               5                   10

<210> SEQ ID NO 268
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 268

Ala Asp Trp Tyr Asp Pro Leu Thr Lys Leu Trp Leu Pro Glu
1               5                   10

<210> SEQ ID NO 269
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 269

Ala Asp Trp Tyr Asp Pro Leu Thr Lys Leu Trp Leu His Gln
1               5                   10

<210> SEQ ID NO 270
```

```
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 270

Ala Glu Trp Tyr Asp Pro Leu Thr Lys Leu Trp Leu Arg Asp
1               5                   10

<210> SEQ ID NO 271
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 271

Ala Glu Trp Tyr Asp Pro Leu Thr Lys Leu Trp Leu Pro Asp
1               5                   10

<210> SEQ ID NO 272
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 272

Ala Glu Trp Tyr Asp Pro Leu Thr Lys Leu Trp Leu Pro Tyr
1               5                   10

<210> SEQ ID NO 273
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 273

Ala Leu Trp Tyr Asp Pro Leu Thr Lys Leu Trp Leu Pro Ala
1               5                   10

<210> SEQ ID NO 274
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 274

Ala Leu Trp Tyr Asp Pro Leu Thr Lys Leu Trp Leu Pro Asp
1               5                   10

<210> SEQ ID NO 275
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 275

Ala Leu Trp Tyr Asp Pro Leu Thr Lys Leu Trp Leu Arg Gly
1               5                   10

<210> SEQ ID NO 276
<211> LENGTH: 14
```

```
<212> TYPE: PRT
<213> ORGANISM: Artificial Sequence
<220> FEATURE:
<223> OTHER INFORMATION: BLyS binding polypeptide

<400> SEQUENCE: 276

Ala Leu Trp Tyr Asp Pro Leu Thr Lys Leu Trp Leu Leu Gly
1               5                   10

<210> SEQ ID NO 277
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 277

Ala Met Trp Tyr Asp Pro Leu Thr Lys Leu Trp Leu Pro Ala
1               5                   10

<210> SEQ ID NO 278
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 278

Ala Met Trp Tyr Asp Pro Leu Thr Lys Leu Trp Leu Gln Val
1               5                   10

<210> SEQ ID NO 279
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 279

Ala Met Trp Tyr Asp Pro Leu Thr Lys Leu Trp Leu Leu Gly
1               5                   10

<210> SEQ ID NO 280
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 280

Ala Ala Trp Tyr Asp Pro Leu Thr Lys Leu Trp Leu Pro Asp
1               5                   10

<210> SEQ ID NO 281
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 281

Ala Ala Trp Tyr Asp Pro Leu Thr Lys Leu Trp Leu Ala Asp
1               5                   10

<210> SEQ ID NO 282
<211> LENGTH: 14
<212> TYPE: PRT
```

-continued

<213> ORGANISM: Artificial Sequence
<220> FEATURE:
<223> OTHER INFORMATION: BLyS binding polypeptide

<400> SEQUENCE: 282

Ala Ala Trp Tyr Asp Pro Leu Thr Lys Leu Trp Leu Leu Asp
1 5 10

<210> SEQ ID NO 283
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 283

Ala His Trp Tyr Asp Pro Leu Thr Lys Leu Trp Leu Thr Asp
1 5 10

<210> SEQ ID NO 284
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 284

Ala His Trp Tyr Asp Pro Leu Thr Lys Leu Trp Leu Pro Val
1 5 10

<210> SEQ ID NO 285
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 285

Ala His Trp Tyr Asp Pro Leu Thr Lys Leu Trp Leu His Asp
1 5 10

<210> SEQ ID NO 286
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 286

Ala His Trp Tyr Asp Pro Leu Thr Lys Leu Trp Leu Pro Asp
1 5 10

<210> SEQ ID NO 287
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 287

Ala Pro Trp Tyr Asp Pro Leu Thr Lys Leu Trp Leu His Asp
1 5 10

<210> SEQ ID NO 288
<211> LENGTH: 14
<212> TYPE: PRT
<213> ORGANISM: Artificial Sequence

```
<220> FEATURE:
<223> OTHER INFORMATION: BLyS binding polypeptide

<400> SEQUENCE: 288

Ala Pro Trp Tyr Asp Pro Leu Thr Lys Leu Trp Leu Pro Val
1               5                   10

<210> SEQ ID NO 289
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 289

Ala Gln Trp Tyr Asp Pro Leu Thr Lys Leu Trp Leu Pro Glu
1               5                   10

<210> SEQ ID NO 290
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 290

Ala Gln Trp Tyr Asp Pro Leu Thr Lys Leu Trp Leu Pro Tyr
1               5                   10

<210> SEQ ID NO 291
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 291

Ala Gln Trp Tyr Asp Pro Leu Thr Lys Leu Trp Leu Pro Arg
1               5                   10

<210> SEQ ID NO 292
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 292

Ala Lys Trp Tyr Asp Pro Leu Thr Lys Leu Trp Leu Pro Asp
1               5                   10

<210> SEQ ID NO 293
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 293

Ala Lys Trp Tyr Asp Pro Leu Thr Lys Leu Trp Leu Pro Val
1               5                   10

<210> SEQ ID NO 294
<211> LENGTH: 14
<212> TYPE: PRT
<213> ORGANISM: Artificial Sequence
<220> FEATURE:
```

<223> OTHER INFORMATION: BLyS binding polypeptide

<400> SEQUENCE: 294

Ala Lys Trp Tyr Asp Pro Leu Thr Lys Leu Trp Leu Pro Val
1               5                   10

<210> SEQ ID NO 295
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 295

Ala Lys Trp Tyr Asp Pro Leu Thr Lys Leu Trp Leu Asn Gly
1               5                   10

<210> SEQ ID NO 296
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 296

Ala Trp Trp Tyr Asp Pro Leu Thr Lys Leu Trp Leu Pro Ala
1               5                   10

<210> SEQ ID NO 297
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 297

Ala Val Trp Tyr Asp Pro Leu Thr Lys Leu Trp Leu Thr Asp
1               5                   10

<210> SEQ ID NO 298
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 298

Ala Tyr Glu Tyr Asp Pro Leu Thr Lys Leu Trp Leu Leu Tyr
1               5                   10

<210> SEQ ID NO 299
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 299

Ala Thr Lys Tyr Asp Pro Leu Thr Lys Leu Trp Leu Pro Asp
1               5                   10

<210> SEQ ID NO 300
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 300

Ala Thr Leu Tyr Asp Pro Leu Thr Lys Leu Trp Leu Pro Gly
1               5                   10

<210> SEQ ID NO 301
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 301

Ala Ile Arg Tyr Asp Pro Leu Thr Lys Leu Trp Leu Pro Tyr
1               5                   10

<210> SEQ ID NO 302
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 302

Ala Glu Arg Tyr Asp Pro Leu Thr Lys Leu Trp Leu Pro His
1               5                   10

<210> SEQ ID NO 303
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 303

Ala Asp Arg Tyr Asp Pro Leu Thr Lys Leu Trp Leu Pro Gln
1               5                   10

<210> SEQ ID NO 304
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 304

Ala Asn Ser Tyr Asp Pro Leu Thr Lys Leu Trp Leu Pro Glu
1               5                   10

<210> SEQ ID NO 305
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 305

Ala Ile Leu Tyr Asp Pro Leu Thr Lys Leu Trp Leu Pro Asp
1               5                   10

<210> SEQ ID NO 306
<211> LENGTH: 14
<212> TYPE: PRT
<213> ORGANISM: Artificial Sequence
<220> FEATURE:
<223> OTHER INFORMATION: BLyS binding polypeptide -continued

<400> SEQUENCE: 306

Ala Asn Trp Phe Asp Pro Leu Thr Lys Leu Trp Leu Pro Gln
1 5 10

<210> SEQ ID NO 307
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 307

Ala Asn Trp Phe Asp Pro Leu Thr Lys Leu Trp Leu Pro Val
1 5 10

<210> SEQ ID NO 308
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 308

Ala Asn Trp Phe Asp Pro Leu Thr Lys Leu Trp Leu Thr Asp
1 5 10

<210> SEQ ID NO 309
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 309

Ala Asn Trp Phe Asp Pro Leu Thr Lys Leu Trp Leu Pro Asp
1 5 10

<210> SEQ ID NO 310
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 310

Ala Asn Trp Phe Asp Pro Leu Thr Lys Leu Trp Leu Pro Gly
1 5 10

<210> SEQ ID NO 311
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 311

Ala Asn Trp Phe Asp Pro Leu Thr Lys Leu Trp Leu Pro Glu
1 5 10

<210> SEQ ID NO 312
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 312

Ala Asn Trp Phe Asp Pro Leu Thr Lys Leu Trp Leu Pro Ala
1               5                   10

<210> SEQ ID NO 313
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 313

Ala Asn Trp Phe Asp Pro Leu Thr Lys Leu Trp Leu Pro Asn
1               5                   10

<210> SEQ ID NO 314
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 314

Ala Asn Trp Phe Asp Pro Leu Thr Lys Leu Trp Leu Ser Glu
1               5                   10

<210> SEQ ID NO 315
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 315

Ala Asn Trp Phe Asp Pro Leu Thr Lys Leu Trp Leu His Asp
1               5                   10

<210> SEQ ID NO 316
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 316

Ala Asn Trp Phe Asp Pro Leu Thr Lys Leu Trp Leu Val Asp
1               5                   10

<210> SEQ ID NO 317
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 317

Ala Tyr Trp Phe Asp Pro Leu Thr Lys Leu Trp Leu Pro Asp
1               5                   10

<210> SEQ ID NO 318
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 318

Ala Tyr Trp Phe Asp Pro Leu Thr Lys Leu Trp Leu Pro Val
1               5                   10

<210> SEQ ID NO 319
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 319

Ala Tyr Trp Phe Asp Pro Leu Thr Lys Leu Trp Leu Pro Ala
1               5                   10

<210> SEQ ID NO 320
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 320

Ala Gln Trp Phe Asp Pro Leu Thr Lys Leu Trp Leu Pro Asp
1               5                   10

<210> SEQ ID NO 321
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 321

Ala His Trp Phe Asp Pro Leu Thr Lys Leu Trp Leu Pro Asp
1               5                   10

<210> SEQ ID NO 322
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 322

Ala Thr Trp Phe Asp Pro Leu Thr Lys Leu Trp Leu Pro Val
1               5                   10

<210> SEQ ID NO 323
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 323

Ala Tyr Trp Tyr Asp Ser Leu Thr Lys Leu Trp Leu Pro Val
1               5                   10

<210> SEQ ID NO 324
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 324

Ala Tyr Trp Tyr Asp Ser Leu Thr Lys Leu Trp Leu His Asp

```
1               5                   10
```

<210> SEQ ID NO 325
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 325

```
Ala Asn Trp Tyr Asp Ser Leu Thr Lys Leu Trp Ile Pro Asp
1               5                   10
```

<210> SEQ ID NO 326
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 326

```
Ala Asn Trp Tyr Asp Ser Leu Thr Lys Leu Trp Leu Pro Val
1               5                   10
```

<210> SEQ ID NO 327
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 327

```
Ala Asn Trp Tyr Asp Ser Leu Thr Lys Leu Trp Leu Pro Asp
1               5                   10
```

<210> SEQ ID NO 328
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 328

```
Ala Asn Trp Tyr Asp Ser Leu Thr Lys Leu Trp Leu Ala Asp
1               5                   10
```

<210> SEQ ID NO 329
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 329

```
Ala Asn Trp Tyr Asp Ser Leu Thr Lys Leu Trp Leu Pro Ala
1               5                   10
```

<210> SEQ ID NO 330
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 330

```
Ala Asn Trp Tyr Asp Ser Leu Thr Lys Leu Trp Leu Tyr Glu
1               5                   10
```

-continued

<210> SEQ ID NO 331
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 331

Ala Gly Trp Tyr Asp Ser Leu Thr Lys Leu Trp Leu Pro Asp
1 5 10

<210> SEQ ID NO 332
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 332

Ala Val Trp Tyr Asp Ser Leu Thr Lys Leu Trp Leu Thr Asp
1 5 10

<210> SEQ ID NO 333
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 333

Ala Asn Trp Tyr Asp Ala Leu Thr Lys Leu Trp Leu Pro Val
1 5 10

<210> SEQ ID NO 334
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 334

Ala Tyr Trp Tyr Asp Thr Leu Thr Lys Leu Trp Leu Pro Asn
1 5 10

<210> SEQ ID NO 335
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 335

Ala Phe Trp Tyr Asp Pro Leu Thr Asn Leu Trp Leu Leu Glu
1 5 10

<210> SEQ ID NO 336
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 336

Ala Tyr Trp Tyr Asp Pro Leu Thr Gly Leu Trp Leu Leu Val
1 5 10

```
<210> SEQ ID NO 337
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 337

Ala Tyr Trp Tyr Asp Pro Leu Thr Gly Leu Trp Leu Leu Tyr
1               5                   10

<210> SEQ ID NO 338
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 338

Ala Tyr Trp Tyr Asp Pro Leu Thr Gly Leu Trp Leu Arg Val
1               5                   10

<210> SEQ ID NO 339
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 339

Ala Tyr Trp Tyr Asp Pro Leu Thr Glu Leu Trp Leu Arg Leu
1               5                   10

<210> SEQ ID NO 340
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 340

Ala Met Trp Tyr Asp Pro Leu Thr Lys Leu Ser Leu Pro Asp
1               5                   10

<210> SEQ ID NO 341
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 341

Ala Tyr Trp Tyr Asp Pro Leu Thr Lys Leu Ser Leu Leu Val
1               5                   10

<210> SEQ ID NO 342
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 342

Ala Ile Trp Tyr Asp Pro Leu Thr Lys Leu Ser Leu Thr Val
1               5                   10
```

```
<210> SEQ ID NO 343
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 343

Ala Ile Trp Tyr Asp Pro Leu Thr Lys Leu Ser Leu Leu Val
1               5                   10

<210> SEQ ID NO 344
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 344

Ala Asp Trp Tyr Asp Pro Leu Thr Lys Leu Ser Leu Leu Leu
1               5                   10

<210> SEQ ID NO 345
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 345

Ala Tyr Trp Tyr Asp Pro Leu Thr Lys Leu Arg Leu Leu Glu
1               5                   10

<210> SEQ ID NO 346
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 346

Ala Asp Trp Tyr Asp Pro Leu Thr Lys Leu Arg Leu Leu Val
1               5                   10

<210> SEQ ID NO 347
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 347

Ala Asp Trp Tyr Asp Pro Leu Thr Lys Leu Arg Leu Ile Val
1               5                   10

<210> SEQ ID NO 348
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 348

Ala Ile Trp Tyr Asp Pro Leu Thr Lys Leu Tyr Leu Pro Asp
1               5                   10

<210> SEQ ID NO 349
```

```
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 349

Ala Ile Trp Tyr Asp Pro Leu Thr Lys Leu Gly Leu Leu Val
1               5                   10

<210> SEQ ID NO 350
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 350

Ala Asn Trp Tyr Asp Pro Leu Thr Lys Leu Thr Leu Leu Val
1               5                   10

<210> SEQ ID NO 351
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 351

Ala Asn Trp Tyr Asp Pro Leu Thr Lys Leu Leu Leu Pro Asn
1               5                   10

<210> SEQ ID NO 352
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 352

Ala Ser Trp Tyr Asp Pro Leu Thr Lys Leu Trp Phe Pro Asp
1               5                   10

<210> SEQ ID NO 353
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 353

Ala Asn Trp Tyr Asp Pro Leu Thr Lys Leu Trp Phe Pro Asp
1               5                   10

<210> SEQ ID NO 354
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 354

Ala Asn Trp Tyr Asp Pro Leu Thr Lys Leu Trp Phe Ser Asp
1               5                   10

<210> SEQ ID NO 355
<211> LENGTH: 14
```

```
<212> TYPE: PRT
<213> ORGANISM: Artificial Sequence
<220> FEATURE:
<223> OTHER INFORMATION: BLyS binding polypeptide

<400> SEQUENCE: 355

Ala Ser Trp Tyr Asp Pro Leu Thr Lys Leu Trp Phe Pro Val
1               5                   10

<210> SEQ ID NO 356
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 356

Ala Asp Trp Tyr Asp Pro Leu Thr Lys Leu Trp Phe Pro Val
1               5                   10

<210> SEQ ID NO 357
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 357

Ala Ser Trp Tyr Asp Pro Leu Thr Lys Leu Trp Phe Pro Lys
1               5                   10

<210> SEQ ID NO 358
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 358

Ala Lys Trp Tyr Asp Pro Leu Thr Lys Leu Trp Phe Pro Asp
1               5                   10

<210> SEQ ID NO 359
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 359

Ala Ser Trp Tyr Asp Pro Leu Thr Lys Leu Trp Phe Leu Glu
1               5                   10

<210> SEQ ID NO 360
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 360

Ala Asn Trp Tyr Asp Pro Leu Thr Lys Leu Trp Phe Pro Ala
1               5                   10

<210> SEQ ID NO 361
<211> LENGTH: 14
<212> TYPE: PRT
```

<213> ORGANISM: Artificial Sequence
<220> FEATURE:
<223> OTHER INFORMATION: BLyS binding polypeptide

<400> SEQUENCE: 361

Ala Thr Trp Tyr Asp Pro Leu Thr Lys Leu Trp Phe Pro Asp
1               5                   10

<210> SEQ ID NO 362
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 362

Ala Ile Trp Tyr Asp Pro Leu Thr Lys Leu Trp Phe Pro Glu
1               5                   10

<210> SEQ ID NO 363
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 363

Ala Ile Trp Tyr Asp Pro Leu Thr Lys Leu Trp Phe Pro Asp
1               5                   10

<210> SEQ ID NO 364
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 364

Ala Ile Trp Tyr Asp Pro Leu Thr Lys Leu Trp Phe Pro Gly
1               5                   10

<210> SEQ ID NO 365
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 365

Ala Tyr Trp Tyr Asp Pro Leu Thr Lys Leu Trp Phe Pro His
1               5                   10

<210> SEQ ID NO 366
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 366

Ala Asn Trp Tyr Asp Pro Leu Thr Lys Leu Trp Phe Pro Val
1               5                   10

<210> SEQ ID NO 367
<211> LENGTH: 14
<212> TYPE: PRT
<213> ORGANISM: Artificial Sequence

```
<220> FEATURE:
<223> OTHER INFORMATION: BLyS binding polypeptide

<400> SEQUENCE: 367

Ala Tyr Trp Tyr Asp Pro Leu Thr Lys Leu Trp Phe Pro Asp
1               5                   10

<210> SEQ ID NO 368
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 368

Ala Gly Trp Tyr Asp Pro Leu Thr Lys Leu Trp Phe Pro Asp
1               5                   10

<210> SEQ ID NO 369
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 369

Ala Ile Trp Tyr Asp Pro Leu Thr Lys Leu Trp Phe Pro Thr
1               5                   10

<210> SEQ ID NO 370
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 370

Ala Lys Trp Tyr Asp Pro Leu Thr Lys Leu Trp Phe Pro Ala
1               5                   10

<210> SEQ ID NO 371
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 371

Ala Tyr Trp Tyr Asp Pro Leu Thr Lys Leu Trp Phe Phe Asp
1               5                   10

<210> SEQ ID NO 372
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 372

Ala Asn Trp Tyr Asp Pro Leu Thr Lys Leu Trp Phe Ala Asp
1               5                   10

<210> SEQ ID NO 373
<211> LENGTH: 14
<212> TYPE: PRT
<213> ORGANISM: Artificial Sequence
<220> FEATURE:
```

-continued

<223> OTHER INFORMATION: BLyS binding polypeptide

<400> SEQUENCE: 373

Ala Asn Trp Tyr Asp Pro Leu Thr Lys Leu Trp Phe Pro Tyr
1               5                   10

<210> SEQ ID NO 374
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 374

Ala Asp Trp Tyr Asp Pro Leu Thr Lys Leu Trp Phe Arg Asp
1               5                   10

<210> SEQ ID NO 375
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 375

Ala Asn Trp Tyr Asp Pro Leu Thr Lys Leu Trp Val Pro Asp
1               5                   10

<210> SEQ ID NO 376
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 376

Ala Asp Trp Tyr Asp Pro Leu Thr Lys Leu Trp Val Pro Ala
1               5                   10

<210> SEQ ID NO 377
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 377

Ala Asn Trp Tyr Asp Pro Leu Thr Lys Leu Trp Val Pro Asn
1               5                   10

<210> SEQ ID NO 378
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 378

Ala Asn Trp Tyr Asp Pro Leu Thr Lys Leu Trp Val Pro Glu
1               5                   10

<210> SEQ ID NO 379
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 379

Ala Asn Trp Tyr Asp Pro Leu Thr Lys Leu Trp Val Pro Gln
1               5                   10

<210> SEQ ID NO 380
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 380

Ala Glu Trp Tyr Asp Pro Leu Thr Lys Leu Trp Val Pro Lys
1               5                   10

<210> SEQ ID NO 381
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 381

Ala Gln Trp Tyr Asp Pro Leu Thr Lys Leu Trp Val Pro Val
1               5                   10

<210> SEQ ID NO 382
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 382

Ala Asn Trp Tyr Asp Pro Leu Thr Lys Leu Trp Val Pro Tyr
1               5                   10

<210> SEQ ID NO 383
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 383

Ala Leu Trp Tyr Asp Pro Leu Thr Lys Leu Trp Val Pro Tyr
1               5                   10

<210> SEQ ID NO 384
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 384

Ala Asn Trp Tyr Asp Pro Leu Thr Lys Leu Trp Val Pro Gly
1               5                   10

<210> SEQ ID NO 385
<211> LENGTH: 14
<212> TYPE: PRT
<213> ORGANISM: Artificial Sequence
<220> FEATURE:
<223> OTHER INFORMATION: BLyS binding polypeptide

```
<400> SEQUENCE: 385

Ala Ser Trp Tyr Asp Pro Leu Thr Lys Leu Trp Ile Pro Tyr
1               5                   10

<210> SEQ ID NO 386
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 386

Ala Asp Trp Tyr Asp Pro Leu Thr Lys Leu Trp Ile Pro Gly
1               5                   10

<210> SEQ ID NO 387
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 387

Ala Asn Trp Tyr Asp Pro Leu Thr Lys Leu Trp Ile Pro Tyr
1               5                   10

<210> SEQ ID NO 388
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 388

Ala Lys Trp Tyr Asp Pro Leu Thr Lys Leu Trp Ile Pro Tyr
1               5                   10

<210> SEQ ID NO 389
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 389

Ala Ile Trp Tyr Asp Pro Leu Thr Lys Leu Trp Ile Pro Asn
1               5                   10

<210> SEQ ID NO 390
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 390

Ala Thr Trp Tyr Asp Pro Leu Thr Lys Leu Trp Ile Pro Gln
1               5                   10

<210> SEQ ID NO 391
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 391
```

Ala Ser Trp Tyr Asp Pro Leu Thr Asn Leu Trp Val Pro Asp
1               5                   10

<210> SEQ ID NO 392
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 392

Ala Tyr Glu Tyr Asp Pro Leu Thr Asn Leu Trp Leu Leu Tyr
1               5                   10

<210> SEQ ID NO 393
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 393

Ala Tyr Trp Tyr Asp Pro Leu Thr Asn Leu Ser Leu Leu Val
1               5                   10

<210> SEQ ID NO 394
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 394

Ala Tyr Trp Tyr Asp Pro Leu Thr Lys Leu Ser Ile Leu Glu
1               5                   10

<210> SEQ ID NO 395
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 395

Ala Asn Trp Tyr Asp Ser Leu Thr Lys Leu Trp Ile Pro Tyr
1               5                   10

<210> SEQ ID NO 396
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 396

Ala His Trp Phe Asp Pro Leu Thr Gln Leu Lys Ile Arg Val
1               5                   10

<210> SEQ ID NO 397
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 397

```
Ala Tyr Trp Cys Asp Pro Leu Thr Lys Leu Cys Ile Leu Glu
1               5                   10
```

<210> SEQ ID NO 398
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 398

```
Ala Asn Ser Tyr Asp Pro Leu Thr Lys Leu Trp Phe Pro Tyr
1               5                   10
```

<210> SEQ ID NO 399
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 399

```
Ala Asn Leu Tyr Asp Pro Leu Thr Lys Leu Trp Val Pro Tyr
1               5                   10
```

<210> SEQ ID NO 400
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 400

```
Ala Asn Trp Tyr Asp Ala Leu Thr Lys Leu Trp Leu His Asp
1               5                   10
```

<210> SEQ ID NO 401
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 401

```
Ala Asn Trp Tyr Asp Ser Leu Thr Lys Leu Trp Phe Pro Asp
1               5                   10
```

<210> SEQ ID NO 402
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 402

```
Ala Thr Ser Tyr Asp Ser Leu Thr Lys Leu Trp Leu Pro Ala
1               5                   10
```

<210> SEQ ID NO 403
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 403

```
Ala Cys Trp Tyr Asp Ser Leu Thr Lys Leu Cys His Arg Glu
```

<210> SEQ ID NO 404
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 404

Ala Ile Gly Asn Asp Pro Leu Thr Lys Leu Trp Ile Pro Tyr
1               5                   10

<210> SEQ ID NO 405
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 405

Ala Asn Trp Gln Asp Cys Leu Thr Lys Leu Cys Leu Ala Gly
1               5                   10

<210> SEQ ID NO 406
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 406

Ala Tyr Trp Phe Asp Pro Leu Thr Asn Leu Trp Leu Leu Glu
1               5                   10

<210> SEQ ID NO 407
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 407

Ala Tyr Trp Tyr Asp Pro Leu Thr Asn Leu Ser Leu Leu Val
1               5                   10

<210> SEQ ID NO 408
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 408

Ala Asn Cys Phe Asp Ser Leu Thr Arg Leu Trp Leu Cys Asp
1               5                   10

<210> SEQ ID NO 409
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 409

Ala Cys Ala Tyr Asp Ala Leu Thr Lys Leu Cys Leu Pro Ala
1               5                   10

```
<210> SEQ ID NO 410
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 410

Ala Asn Trp Tyr Asp Pro Leu Thr Asn Leu Ser Leu Leu Leu
1               5                   10

<210> SEQ ID NO 411
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 411

Ala Tyr Trp Tyr Asp Pro Leu Thr Gln Leu Ser Leu Leu Val
1               5                   10

<210> SEQ ID NO 412
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 412

Ala Tyr Arg Tyr Asp Ala Leu Thr Gly Leu Trp Leu Leu Tyr
1               5                   10

<210> SEQ ID NO 413
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 413

Ala Tyr Trp Asn Asp Pro Leu Thr Lys Leu Lys Leu Arg Leu
1               5                   10

<210> SEQ ID NO 414
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 414

Ala Tyr Trp Tyr Asp Pro Leu Thr Gln Leu Ser Leu Leu Val
1               5                   10

<210> SEQ ID NO 415
<211> LENGTH: 14
<212> TYPE: PRT
<213> ORGANISM: Artificial Sequence
<220> FEATURE:
<223> OTHER INFORMATION: BL

```
<210> SEQ ID NO 416
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 416

Ala Tyr Arg Tyr Asp Ser Leu Thr Asn Leu Trp Leu Leu Tyr
1               5                   10

<210> SEQ ID NO 417
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 417

Ala Tyr Trp Tyr Asp Pro Leu Thr Lys Leu Ser Ile Leu Glu
1               5                   10

<210> SEQ ID NO 418
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 418

Ala Ser Cys Tyr Asp Pro Leu Thr Lys Leu Cys Phe Pro Val
1               5                   10

<210> SEQ ID NO 419
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 419

Ala Phe Trp Phe Asp Pro Leu Thr Gly Leu Trp Leu Leu Glu
1               5                   10

<210> SEQ ID NO 420
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 420

Ala His Trp Tyr Asp Pro Leu Thr Lys Leu Ser Ile Arg Val
1               5                   10

<210> SEQ ID NO 421
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 421

Ala Pro Trp Tyr Asp Ser Leu Thr Lys Leu Trp Phe Pro Ser
1               5                   10
```

-continued

```
<210> SEQ ID NO 422
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 422

Ala Asn Cys Tyr Asp Thr Leu Thr Lys Leu Trp Leu Thr Cys
1               5                   10

<210> SEQ ID NO 423
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 423

Ala Asn Trp Tyr Asp Ser Leu Thr Lys Leu Ser Leu Pro Asp
1               5                   10

<210> SEQ ID NO 424
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 424

Ala Tyr Ala Tyr Asp Phe Leu Thr Gln Leu Ser Leu Pro Asp
1               5                   10

<210> SEQ ID NO 425
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 425

Ala Phe Arg Tyr Asp Ser Leu Thr Gly Leu Trp Leu Arg Tyr
1               5                   10

<210> SEQ ID NO 426
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 426

Ala Asn Cys Tyr Asp Ser Leu Thr Lys Leu Trp Leu Pro Cys
1               5                   10

<210> SEQ ID NO 427
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 427

Ala Asn Gly Tyr Asp Leu Leu Thr Asn Leu Ser Val Ser Asp
1               5                   10

<210> SEQ ID NO 428

```
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 428

Ala Asn Trp Tyr Asp Pro Leu Thr Arg Leu Trp Ile Pro Val
1               5                   10

<210> SEQ ID NO 429
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 429

Ala Leu Lys Phe Asp Tyr Leu Thr Lys Leu Trp Leu Pro Asp
1               5                   10

<210> SEQ ID NO 430
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 430

Ala Tyr Arg Tyr Asp Ser Leu Thr Lys Leu Trp Leu Pro Gly
1               5                   10

<210> SEQ ID NO 431
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 431

Ala Tyr Cys Tyr Asp Ser Leu Thr Lys Leu Trp Ile Pro Asp
1               5                   10

<210> SEQ ID NO 432
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 432

Ala Ser Trp Glu Asp Ser Leu Thr Lys Leu Trp Leu Ser Lys
1               5                   10

<210> SEQ ID NO 433
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 433

Ala Tyr Trp Tyr Asp Ser Leu Thr Gly Leu Ser Leu Leu Val
1               5                   10

<210> SEQ ID NO 434
<211> LENGTH: 14
```

```
<212> TYPE: PRT
<213> ORGANISM: Artificial Sequence
<220> FEATURE:
<223> OTHER INFORMATION: BLyS binding polypeptide

<400> SEQUENCE: 434

Ala Tyr Trp Tyr Asp Pro Leu Thr Tyr Leu Arg Leu Arg Val
1               5                   10

<210> S

<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 440

Ala Asn Trp Tyr Asp Pro Leu Thr Lys Leu Trp Leu Pro Val Gly Gly
1               5                   10                  15
Lys

<210> SEQ ID NO 441
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 441

Ala Asn Trp Phe Asp Pro Leu Thr Lys Leu Trp Leu Pro Asp Gly Gly
1               5                   10                  15
Lys

<210> SEQ ID NO 442
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 442

Ala Asn Trp Tyr Asp Pro Leu Thr Lys Leu Ser Leu Pro Asp Gly Gly
1               5                   10                  15
Lys

<210> SEQ ID NO 443
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 443

Ala Asn Trp Tyr Asp Pro Leu Thr Lys Leu Trp Phe Pro Asp Gly Gly
1               5                   10                  15
Lys

<210> SEQ ID NO 444
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 444

Ala Asn Trp Tyr Asp Ser Leu Thr Lys Leu Trp Leu Pro Asp Gly Gly
1               5                   10                  15
Lys

<210> SEQ ID NO 445
<211> LENGTH: 585
<212> TYPE: PRT
<213> ORGANISM: HomoSapiens

```
<400> SEQUENCE: 445

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415
```

```
               Gln Val Ser Thr Pro Thr Leu Val Glu Val Ser Arg Asn Leu Gly Lys
                       420                 425                 430

Val Gly Ser Lys Cys Cys Lys His Pro Glu Ala Lys Arg Met Pro Cys
                       435                 440                 445

Ala Glu Asp Tyr Leu Ser Val Val Leu Asn Gln Leu Cys Val Leu His
                       450                 455                 460

Glu Lys Thr Pro Val Ser Asp Arg Val Thr Lys Cys Cys Thr Glu Ser
               465                 470                 475                 480

Leu Val Asn Arg Arg Pro Cys Phe Ser Ala Leu Glu Val Asp Glu Thr
                               485                 490                 495

Tyr Val Pro Lys Glu Phe Asn Ala Glu Thr Phe Thr Phe His Ala Asp
                           500                 505                 510

Ile Cys Thr Leu Ser Glu Lys Glu Arg Gln Ile Lys Lys Gln Thr Ala
                       515                 520                 525

Leu Val Glu Leu Val Lys His Lys Pro Lys Ala Thr Lys Glu Gln Leu
                       530                 535                 540

Lys Ala Val Met Asp Asp Phe Ala Ala Phe Val Glu Lys Cys Cys Lys
               545                 550                 555                 560

Ala Asp Asp Lys Glu Thr Cys Phe Ala Glu Glu Gly Lys Lys Leu Val
                               565                 570                 575

Ala Ala Ser Gln Ala Ala Leu Gly Leu
                           580                 585

<210> SEQ ID NO 446
<211> LENGTH: 4
<212> TYPE: PRT
<213> ORGANISM: Artificial Sequence
<220> FEATURE:
<223> OTHER INFORMATION: recurring structural motif of BLyS binding
      polypeptides
<221> NAME/KEY: MISC_FEATURE
<222> LOCATION: (2)..(2)
<223> OTHER INFORMATION: X is Pro, Ser, Thr, Phe, Leu, Tyr, Cys, or Ala

<400> SEQUENCE: 446

Asp Xaa Leu Thr
1

<210> SEQ ID NO 447
<211> LENGTH: 14
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (2)..(2)
<223> OTHER INFORMATION: X2 is any amino acid except Arg;
<221> NAME/KEY: MISC_FEATURE
<222> LOCATION: (3)..(3)
<223> OTHER INFORMATION: X3 is Trp, Glu, Lys, Cys, Leu, Ala, Arg, Gly,
      or Ser;
<221> NAME/KEY: MISC_FEATURE
<222> LOCATION: (4)..(4)
<223> OTHER INFORMATION: X4 is Tyr, Phe, Glu, Cys, Asn;
<221> NAME/KEY: MISC_FEATURE
<222> LOCATION: (6)..(6)
<223> OTHER INFORMATION: X6 is Pro, Ser, Thr, Phe, Leu, Tyr, Cys, or
      Ala;
<221> NAME/KEY: MISC_FEATURE
<222> LOCATION: (9)..(9)
<223> OTHER INFORMATION: X9 is Lys, Asn, Gln, Gly, or Arg;
<221> NAME/KEY: MISC_FEATURE
<222> LOCATION: (11)..(11)
<223> OTHER INFORMATION: X11 is Trp, Ser, Thr, Arg, Cys, Tyr, or Lys;
<221> NAME/KEY: MISC_FEATURE
```

```
<222> LOCATION: (12)..(12)
<223> OTHER INFORMATION: X12 is Leu, Phe, Val, Ile, or His;
<221> NAME/KEY: MISC_FEATURE
<222> LOCATION: (13)..(13)
<223> OTHER INFORMATION: X13 is Pro, Leu, His, Ser, Arg, Asn, Gln, Thr,
      Val, Ala, Cys, Ile, Phe, or Tyr;
<221> NAME/KEY: MISC_FEATURE
<222> LOCATION: (14)..(14)
<223> OTHER INFORMATION: X14 is Asp, Glu, Asn, Val, His, Gln, Arg, Gly,
      Ser, Tyr, Ala, Cys, Lys, Ile, Thr or Leu.

<400> SEQUENCE: 447

Ala Xaa Xaa Xaa Asp Xaa Leu Thr Xaa Leu Xaa Xaa Xaa Xaa
1               5                   10

<210> SEQ ID NO 448
<211> LENGTH: 10
<212> TYPE: PRT
<213> ORGANISM: Artificial Sequence
<220> FEATURE:
<223> OTHER INFORMATION: BLyS binding polypeptide
<221> NAME/KEY: MISC_FEATURE
<222> LOCATION: (1)..(1)
<223> OTHER INFORMATION: X1 is Trp, Glu, Lys, Cys, Leu, Ala, Arg, Gly,
      or Ser;
<221> NAME/KEY: MISC_FEATURE
<222> LOCATION: (2)..(2)
<223> OTHER INFORMATION: X2 is Tyr, Phe, Glu, Cys, Asn;
<221> NAME/KEY: MISC_FEATURE
<222> LOCATION: (4)..(4)
<223> OTHER INFORMATION: X4 is Pro, Ser, Thr, Phe, Leu, Tyr, Cys, or
      Ala;
<221> NAME/KEY: MISC_FEATURE
<222> LOCATION: (7)..(7)
<223> OTHER INFORMATION: X7 is Lys, Asn, Gln, Gly, or Arg;
<221> NAME/KEY: MISC_FEATURE
<222> LOCATION: (9)..(9)
<223> OTHER INFORMATION: X9 is Trp, Ser, Thr, Arg, Cys, Tyr, or Lys;
<221> NAME/KEY: MISC_FEATURE
<222> LOCATION: (10)..(10)
<223> OTHER INFORMATION: X10 is Leu, Phe, Val, Ile, or His.

<400> SEQUENCE: 448

Xaa Xaa Asp Xaa Leu Thr Xaa Leu Xaa Xaa
1               5                   10

<210> SEQ ID NO 449
<211> LENGTH: 14
<212> TYPE: PRT
<213> ORGANISM: Artificial Sequence
<220> FEATURE:
<223> OTHER INFORMATION: BLyS affinity maturation library template
<221> NAME/KEY: MISC_FEATURE
<222> LOCATION: (2)..(4)
<223> OTHER INFORMATION: X is any amino acid;
<221> NAME/KEY: MISC_FEATURE
<222> LOCATION: (6)..(6)
<223> OTHER INFORMATION: X is any amino ac

```
<220> FEATURE:
<223> OTHER INFORMATION: BLyS binding polypeptide

<400> SEQUENCE: 450

Ala Gly Lys Glu Pro Cys Tyr Phe Tyr Trp Glu Cys Ala Val Ser Gly
1               5                   10                  15

<210> SEQ ID NO 451
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 451

Ala Gly Val Pro Phe Cys Asp Leu Leu Thr Lys His Cys Phe Glu Ala
1               5                   10                  15

Gly

<210> SEQ ID NO 452
<211> LENGTH: 20
<212> TYPE: PRT
<213> ORGANISM: Artificial Sequence
<220> FEATURE:
<223> OTHER INFORMATION: BLyS binding polypeptide

<400> SEQUENCE: 452

Gly Ser Ser Arg Leu Cys His Met Asp Glu Leu Thr His Val Cys Val
1               5                   10                  15

His Phe Ala Pro
            20

<210> SEQ ID NO 453
<211> LENGTH: 21
<212> TYPE: PRT
<213> ORGANISM: Artificial Sequence
<220> FEATURE:
<223> OTHER INFORMATION: BLyS binding polypeptide

<400> SEQUENCE: 453

Gly Asp Gly Gly Asn Cys Tyr Thr Asp Ser Leu Thr Lys Leu His Phe
1               5                   10                  15

Cys Met Gly Asp Glu
            20

<210> SEQ ID NO 454
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 454

Gly Tyr Asp Val Leu Thr Lys Leu Tyr Phe Val Pro Gly Gly
1               5                   10

<210> SEQ ID NO 455
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 455

Trp Thr Asp Ser Leu Thr Gly Leu Trp Phe Pro Asp Gly Gly
```

```
1           5                    10
```

<210> SEQ ID NO 456
<211> LENGTH: 12
<212> TYPE: PRT
<213> ORGANISM: Artificial Sequence
<220> FEATURE:
<223> OTHER INFORMATION: BLyS binding polypeptide

<400> SEQUENCE: 456

```
Trp Tyr Asp Pro Leu Thr Lys Leu Trp Leu Pro Asp
1               5                   10
```

<210> SEQ ID NO 457
<211> LENGTH: 10
<212> TYPE: PRT
<213> ORGANISM: Artificial Sequence
<220> FEATURE:
<223> OTHER INFORMATION: BLyS binding polypeptide

<400> SEQUENCE: 457

```
Trp Tyr Asp Pro Leu Thr Lys Leu Trp Leu
1               5                   10
```

<210> SEQ ID NO 458
<211> LENGTH: 14
<212> TYPE: PRT
<213> ORGANISM: Artificial Sequence
<220> FEATURE:
<223> OTHER INFORMATION: BLyS binding polypeptide

<400> SEQUENCE: 458

```
Ala Asn Trp Tyr Asp Pro Leu Thr Lys Leu Ser Leu Pro Asp
1               5                   10
```

BINDING POLYPEPTIDES FOR B LYMPHOCYTE STIMULATOR PROTEIN (BLYS)

This application claims the benefit of Provisional Application No. 60/226,489, filed Aug. 18, 2000.

FIELD OF THE INVENTION

The present invention relates to polypeptides that bind to B lymphocyte stimulator protein (BLyS). Such polypeptides have uses for example, in the detection, isolation, and/or purification of BLyS. The invention also relates to nucleic acid molecules encoding these BLyS binding polypeptides, vectors and host cells containing these nucleic acids, and methods for producing the same.

BACKGROUND OF THE INVENTION

B lymphocyte stimulator (BLyS) is a member of the tumor necrosis factor ("TNF") superfamily that induces both in vivo and in vitro B cell proliferation and differentiation (Moore et al., *Science*, 285: 260–263 (1999)). BLyS is distinguishable from other B cell growth and differentiation factors such as IL-2, IL-4, IL-5, IL-6, IL-7, IL-13, IL-15, CD40L, or CD27L (CD70) by its monocyte-specific gene and protein expression pattern and its specific receptor distribution and biological activity on B lymphocytes. BLyS expression is not detected on natural killer ("NK") cells, T cells or B cells, but is restricted to cells of myeloid origin. BLyS expression on resting monocytes is upregulated by interferon-gamma (IFN-gamma). The gene encoding BLyS has been mapped to chromosome 13q34.

BLyS is expressed as a 285 amino acid type II membrane-bound polypeptide and a soluble 152 amino acid polypeptide (Moore et al., 1999, supra). The membrane-bound form of BLyS has a predicted transmembrane spanning domain between amino acid residues 47 and 73. The NH$_2$-terminus of the soluble form of BLyS begins at Ala$^{134}$ of the membrane-bound form of BLyS. Both the soluble and membrane-bound forms of the protein form homotrimers. Soluble recombinant BLyS has been shown to induce in vitro proliferation of murine splenic B cells and to bind to a cell-surface receptor on these cells (Moore et al., 1999, supra). Soluble BLyS administration to mice has been shown to result in an increase in the proportion of CD45R$^{dull}$, Ly6D$^{bright}$ (also known as ThB) B cells and an increase in serum IgM and IgA levels (Moore et al., 1999, supra). Thus, BLyS displays a B cell tropism in both its receptor distribution and biological activity.

Based on its expression pattern and biological activity, BLyS has been suggested to be involved in the exchange of signals between B cells and monocytes or their differentiated progeny. The restricted expression patterns of BLyS receptor and ligand suggest that BLyS may function as a regulator of T cell-independent responses in a manner analogous to that of CD40 and CD40L in T cell-dependent antigen activation.

Accordingly, molecules that specifically bind BLyS would find a variety of uses in the study of the BLyS cytokine, in the manufacture and purification of BLyS in commercial and medically pure quantities, and in the development new therapeutic or diagnostic reagents.

SUMMARY OF THE INVENTION

The present invention provides new polypeptides and families of polypeptides that specifically bind to B lymphocyte stimulator protein (BLyS) and/or BLyS-like polypeptides. In particular, the invention encompasses polypeptides that specifically bind to a polypeptide or polypeptide fragment of human BLyS (SEQ ID NOs: 173 and/or 174) or BLyS expressed on human monocytes; murine BLyS (SEQ ID NOs: 175 and/or 176) or BLyS expressed on murine monocytes; rat BLyS (either the soluble forms as given in SEQ ID NOs: 177, 178, 179 and/or 180 or in a membrane associated form, e.g., on the surface of rat monocytes); or monkey BLyS (e.g., the monkey BLyS polypeptides of SEQ ID NOS: 181 and/or 182, the soluble form of monkey BLyS, or BLyS expressed on monkey monocytes), preferably human BLyS.

In specific preferred embodiments, the BLyS binding polypeptides of the invention bind BLyS and/or BLyS-like polypeptides with high affinity. In other embodiments, the BLyS binding polypeptides of the invention reversibly bind BLyS and/or BLyS-like polypeptides. In still other embodiments, the BLyS binding polypeptides of the invention irreversibly bind BLyS and/or BLyS-like polypeptides.

The cysteine residues in certain polypeptides according to the invention are believed to form a disulfide bond, which would cause the polypeptide containing these cysteine residues to form a stable loop structure under non-reducing conditions. Especially preferred BLyS binding polypeptides of the invention are polypeptide molecules that comprise amino acid sequences that form stable loop structures or other stable structures that bind BLyS or BLyS-like polypeptides.

In specific embodiments, the invention relates to BLyS binding polypeptides comprising, or alternatively consisting of, an amino acid sequence selected from the group consisting of SEQ ID NOs: 1–12, 20–172, and 186–444, preferably SEQ ID NOs: 163–172 or 436–444 as referred to above and in Tables 1–8, 14 and 15 and in Examples 2, 5 and 6 below. Analysis of the sequences of the BLyS binding polypeptides isolated as described herein shows a strong selection for polypeptides containing the tetrapeptide Asp-Xaa-Leu-Thr (SEQ ID NO:446), and therefore in its broadest aspects, the present invention relates to polypeptides capable of binding to BLyS comprising the polypeptide Asp-Xaa-Leu-Thr (SEQ ID NO:446), where Xaa is Pro, Ser, Thr, Phe, Leu, Tyr, Cys, or Ala (preferably Pro or Ser).

Seven consensus sequences (SEQ ID NOs: 1–7) have been determined based on the specific BLyS binding polypeptides shown in Tables 1–8. In specific embodiments, BLyS binding polypeptides of the invention comprise one or more of these sequences. Such preferred BLyS binding polypeptides include polypeptides with the potential to form a cyclic or loop structure between invariant Cys residues comprising, or alternatively consisting of, an amino acid sequence selected from A–E (SEQ ID NOs: 1–5):

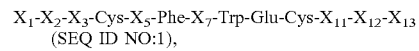
(SEQ ID NO:1), (A)

wherein

X$_1$ is Ala, Asn, Lys, or Ser;

X$_2$ is Ala, Glu, Met, Ser, or Val;

X$_3$ is Ala, Asn, Lys, or Pro (preferably Lys);

X$_5$ is Phe, Trp, or Tyr (preferably Tyr);

X$_7$ is Pro or Tyr (preferably Pro);

X$_{11}$ is Ala, Gln, His, Phe, or Val;

X$_{12}$ is Asn, Gln, Gly, His, Ser, or Val; and

X$_{13}$ is Ala, Asn, Gly, Ile, Pro, or Ser, wherein said polypeptide binds BLyS and/or BLyS-like polypeptides; or

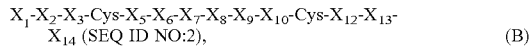
$X_1$-$X_2$-$X_3$-Cys-$X_5$-$X_6$-$X_7$-$X_8$-$X_9$-$X_{10}$-Cys-$X_{12}$-$X_{13}$-$X_{14}$ (SEQ ID NO:2), (B)

wherein $X_1$ is Ala, Asp, Gln, Glu, Gly, His, Ile, Leu, Lys, Met, Phe, Pro, Ser, Thr, Trp, Tyr, Val, or is absent;

$X_2$ is Ala, Asn, Asp, Gln, Gly, His, Ile, Leu, Lys, Met, Phe, Pro, Ser, Thr, Trp, Tyr, or Val;

$X_3$ is Ala, Arg, Asn, Asp, Gln, Glu, Gly, His, Ile, Leu, Lys, Met, Phe, Pro, Ser, Trp, Tyr, or Val (preferably Asp);

$X_5$ is Asp, Ile, Leu, or Tyr (preferably Asp or Leu);

$X_6$ is Arg, Asp, Glu, His, Ile, Leu, Lys, Phe, Pro, Tyr, or Val (preferably Glu or Leu);

$X_7$ is His, Leu, Lys, or Phe (preferably His or Leu);

$X_8$ is Leu, Pro, or Thr (preferably Thr or Pro);

$X_9$ is Arg, Asn, Gly, His, Ile, Lys, Met, or Trp (preferably Lys);

$X_{10}$ is Ala, Gln, Glu, Gly, His, Ile, Leu, Met, Phe, Ser, Trp, Tyr, or Val;

$X_{12}$ is Asp, Gln, Glu, Gly, Ile, Leu, Lys, Phe, Ser, Trp, Tyr, or Val;

$X_{13}$ is Ala, Arg, Asn, Asp, Gln, Glu, Gly, His, Leu, Lys, Met, Phe, Pro, Ser, Thr, Trp, Tyr, or Val; and $X_{14}$ is Ala, Arg, Asn, Asp, Gln, Glu, Gly, His, Ile, Leu, Lys, Phe, Pro, Trp, Tyr, Val, or is absent, wherein said polypeptide binds BLyS and/or BLyS-like polypeptides; or

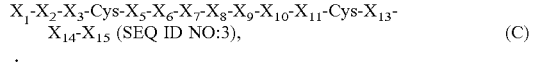
$X_1$-$X_2$-$X_3$-Cys-$X_5$-$X_6$-$X_7$-$X_8$-$X_9$-$X_{10}$-$X_{11}$-Cys-$X_{13}$-$X_{14}$-$X_{15}$ (SEQ ID NO:3), (C)

wherein $X_1$ is Ala, Arg, Asn, Asp, Leu, Lys, Phe, Pro, Ser, or Thr;

$X_2$ is Asn, Asp, Gln, His, Ile, Lys, Pro, Thr, or Trp;

$X_3$ is Ala, Arg, Asn, Gln, Glu, His, Phe, Pro, or Thr (preferably Ala);

$X_5$ is Asn, Asp, Pro, Ser, or Thr (preferably Asp);

$X_6$ is Arg, Asp, Ile, Leu, Met, Pro, or Val (preferably Ile);

$X_7$ is Ala, Ile, Leu, Pro, Thr, or Val (preferably Val or Leu);

$X_8$ is Asn, His, Ile, Leu, Lys, Phe, or Thr (preferably Thr);

$X_9$ is Asn, Glu, Gly, His, Leu, Lys, Met, Pro, or Thr (preferably Leu);

$X_{10}$ is Arg, Asn, Asp, Gln, Glu, Gly, Ile, Lys, Met, Pro, Ser, or Trp;

$X_{11}$ is Arg, Glu, Gly, Lys, Phe, Ser, Trp, or Tyr (preferably Ser);

$X_{13}$ is Gln, Glu, Ile, Leu, Phe, Pro, Ser, Tyr, or Val (preferably Val);

$X_{14}$ is Asn, Gly, Ile, Phe, Pro, Thr, Trp, or Tyr; and $X_{15}$ is Asn, Asp, Glu, Leu, Lys, Met, Pro, or Thr (preferably Glu or Pro), wherein said polypeptide binds BLyS and/or BLyS-like polypeptides; or

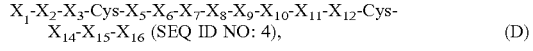
$X_1$-$X_2$-$X_3$-Cys-$X_5$-$X_6$-$X_7$-$X_8$-$X_9$-$X_{10}$-$X_{11}$-$X_{12}$-Cys-$X_{14}$-$X_{15}$-$X_{16}$ (SEQ ID NO: 4), (D)

wherein $X_1$ is Asn, Asp, His, Leu, Phe, Pro, Ser, Tyr, or is absent (preferably Ser);

$X_2$ is Arg, Asn, Asp, His, Phe, Ser, or Trp (preferably Arg);

$X_3$ is Asn, Asp, Leu, Pro, Ser, or Val (preferably Asn or Asp);

$X_5$ is Asp, Gln, His, Ile, Leu, Lys, Met, Phe, or Thr;

$X_6$ is His, Ile, Leu, Met, Phe, Pro, Trp, or Tyr;

$X_7$ is Asp, His, Leu, or Ser (preferably Asp);

$X_8$ is Ala, Arg, Asp, Glu, Leu, Phe, Pro, or Thr (preferably Glu or Pro);

$X_9$ is Ala, Arg, Asn, or Leu (preferably Leu);

$X_{10}$ is Ile, Leu, Met, Pro, Ser, or Thr (preferably Thr);

$X_{11}$ is Ala, Arg, Asn, Gly, His, Lys, Ser, or Tyr;

$X_{12}$ is Ala, Arg, Asn, Gln, Leu, Met, Ser, Trp, Tyr, or Val;

$X_{14}$ is Asp, Gly, Leu, Phe, Tyr, or Val (preferably Leu);

$X_{15}$ is Asn, His, Leu, Pro, or Tyr (preferably His, Leu or Pro); and $X_{16}$ is Asn, Asp, His, Phe, Ser, or Tyr, (preferably Asp or Ser), wherein said polypeptide binds BLyS and/or BLyS-like polypeptides; or

$X_1$-$X_2$-$X_3$-Cys-$X_5$-$X_6$-$X_7$-$X_8$-$X_9$-$X_{10}$-$X_{11}$-$X_{12}$-$X_{13}$-$X_{14}$-Cys-$X_{16}$-$X_{17}$-$X_{18}$ (SEQ ID NO:5), (E)

wherein $X_1$ is Arg, Asp, Gly, His, Leu, Phe, Pro, Ser, Trp, Tyr, or is absent (preferably Arg);

$X_2$ is Ala, Arg, Asn, Asp, Gly, Pro, Ser, or is absent (preferably Asn, Asp, Gly, or Pro);

$X_3$ is Arg, Asn, Gln, Glu, Gly, Lys, Met, Pro, Trp or Val (preferably Gly or Met);

$X_5$ is Arg, Asn, Gln, Glu, His, Leu, Phe, Pro, Trp, Tyr, or Val (preferably Trp, Tyr, or Val);

$X_6$ is Arg, Asp, Gln, Gly, Ile, Lys, Phe, Thr, Trp or Tyr (preferably Asp);

$X_7$ is Ala, Arg, Asp, Glu, Gly, Leu, Ser, or Tyr (preferably Asp);

$X_8$ is Asp, Gln, Glu, Leu, Met, Phe, Pro, Ser, or Tyr (preferably Leu);

$X_9$ is Asp, Leu, Pro, Thr, or Val (preferably Leu or Thr);

$X_{10}$ is Arg, Gln, His, Ile, Leu, Lys, Met, Phe, Thr, Trp or Tyr (preferably Lys or Thr);

$X_{11}$ is Ala, Arg, Asn, Gln, Glu, His, Leu, Lys, Met, or Thr (preferably Arg or Leu);

$X_{12}$ is Ala, Asn, Gln, Gly, Leu, Lys, Phe, Pro, Thr, Trp, or Tyr (preferably Thr or Trp);

$X_{13}$ is Ala, Arg, Gln, His, Lys, Met, Phe, Pro, Thr, Trp, or Tyr (referably Met or Phe);

$X_{14}$ is Arg, Gln, Glu, Gly, His, Leu, Met, Phe, Pro, Ser, Thr, Tyr, or Val (preferably Val);

$X_{16}$ is Arg, Asp, Gly, His, Lys, Met, Phe, Pro, Ser, or Trp (preferably Met);

$X_{17}$ is Arg, Asn, Asp, Gly, His, Phe, Pro, Ser, Trp or Tyr, (preferably Arg, His, or Tyr); and $X_{18}$ is Ala, Arg, Asn, Asp, His, Leu, Phe, or Trp (preferably His or Asn), wherein said polypeptide binds BLyS and/or BLyS-like polypeptides.

Additional preferred embodiments include linear polypeptides comprising, or alternatively consisting of, an amino acid sequence selected from F and G (SEQ ID NOs:6 and 7):

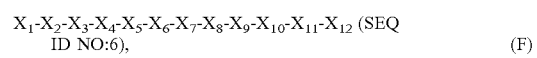
$X_1$-$X_2$-$X_3$-$X_4$-$X_5$-$X_6$-$X_7$-$X_8$-$X_9$-$X_{10}$-$X_{11}$-$X_{12}$ (SEQ ID NO:6), (F)

wherein $X_1$ is Ala, Arg, Gly, His, Leu, Lys, Met, Phe, Trp, Tyr, or Val (preferably Gly, Tyr, or Val);

$X_2$ is Ala, Arg, Gln, His, Ile, Leu, Phe, Thr, Trp, or Tyr (preferably His or Tyr);

$X_3$ is Ala, Asp, Lys, Phe, Thr, Trp or Tyr (preferably Asp or Tyr);

$X_4$ is Arg, Asp, Gln, Lys, Met, Phe, Pro, Ser, Tyr, or Val (preferably Asp or Gln);

$X_5$ is Asp, Leu, Lys, Phe, Pro, Ser, or Val (preferably Leu or Ser);

$X_6$ is His, Ile, Leu, Pro, Ser, or Thr (preferably Leu or Thr);

$X_7$ is Arg, Gly, His, Leu, Lys, Met, or Thr (preferably Lys or Thr);

$X_8$ is Ala, Arg, Asn, Ile, Leu, Lys, Met, or Thr (preferably Leu or Lys);

$X_9$ is Ala, Asn, Arg, Asp, Glu, Gly, His, Leu, Met, Ser, Trp, Tyr, or Val (preferably Met or Ser);

$X_{10}$ is Ile, Leu, Phe, Ser, Thr, Trp, Tyr, or Val (preferably Thr or Leu);

$X_{11}$ is Ala, Arg, Gly, His, Ile, Leu, Lys, Pro, Ser, Thr, Trp, Tyr, or Val (preferably Pro or Thr); and $X_{12}$ is Arg, Asp, His, Leu, Lys, Met, Phe, Pro, Ser, Trp, Tyr, or Val (preferably Arg or Pro), wherein said polypeptide binds BLyS and/or BLyS-like polypeptides; or $$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13} \text{ (SEQ ID NO:7),} \quad (G)$$

wherein $X_1$ is Asp, Gln, Glu, Gly, His, Lys, Met, or Trp (preferably Glu, Lys);

$X_2$ is Arg, Gln, His, Ile, Leu, or Pro (preferably His or Pro);

$X_3$ is Asp, Gly, Ile, Lys, Thr, Tyr or Val (preferably Tyr);

$X_4$ is Asn, Asp, Gln, Glu, Met, Pro, Ser, or Tyr (preferably Asp or Gln);

$X_5$ is Asn, Asp, His, Ile, Leu, Met, Pro, Thr or Val (preferably Asn or Thr);

$X_6$ is Asp, Glu, His, Leu, Lys, Pro, or Val (preferably Asp or Pro);

$X_7$ is Arg, Asn, Gln, His, Ile, Leu, Met, Pro, or Thr (preferably Ile or Pro);

$X_8$ is Gln, Gly, His, Leu, Met, Ser, or Thr (preferably Leu or Thr);

$X_9$ is Asn, Gln, Gly, His, Leu, Lys, Ser, or Thr (preferably Lys);

$X_{10}$ is Ala, Gly, Ile, Leu, Lys, Met, or Phe (preferably Gly or Met);

$X_{11}$ is Ala, Glu, His, Ile, Leu, Met, Ser, Thr, Trp, Tyr, or Val (preferably Ala or Thr);

$X_{12}$ is Arg, Gln, Glu, Gly, His, Ile, Lys, Tyr, or Val (preferably Arg or His); and $X_{13}$ is Arg, Asn, Glu, His, Ile, Ser, Thr, Trp, or Val (preferably His), wherein said polypeptide binds BLyS and/or BLyS-like polypeptides.

Said polypeptides may have additional amino acids attached at either or both of the N- and C-terminal ends.

Examination of the sequence information and binding data from the isolates of libraries containing polypeptides with the potential to form loop structures (i.e., libraries designated TN6, TN7, TN8, TN9, TN10 and TN12) identifies a series of BLyS binding polypeptides that may form loop structures. In specific embodiments, BLyS binding polypeptides of the invention comprise, or alternatively consist of, an amino acid sequence selected from H-L (SEQ ID NOs:8–12):

$$\text{Cys-}X_2\text{-Phe-}X_4\text{-Trp-Glu-Cys (SEQ ID NO:8),} \quad (H)$$

wherein $X_2$ is Phe, Trp, or Tyr (preferably Tyr); and
$X_4$ is Pro or Tyr (preferably Pro); or $$\text{Cys-}X_2\text{-}X_3\text{-}X_4\text{-}X_5\text{-}X_6\text{-}X_7\text{-Cys (SEQ ID NO:9),} \quad (I)$$

wherein $X_2$ is Asp, Ile, Leu, or Tyr (preferably Asp or Leu);
$X_3$ is Arg, Asp, Glu, His, Ile, Leu, Lys, Phe, Pro, Tyr, or Val (preferably Glu or Leu);

$X_4$ is His, Leu, Lys, or Phe (preferably His or Leu);
$X_5$ is Leu, Pro, or Thr (preferably Thr or Pro);
$X_6$ is Arg, Asn, Gly, His, Ile, Lys, Met, or Trp (preferably Lys); and
$X_7$ is Ala, Asn, Gln, Glu, Gly, His, Ile, Leu, Met, Phe, Ser, Trp, Tyr, or Val; or $$\text{Cys-}X_2\text{-}X_3\text{-}X_4\text{-}X_5\text{-}X_6\text{-}X_7\text{-}X_8\text{-Cys (SEQ ID NO:10),} \quad (J)$$

wherein $X_2$ is Asn, Asp, Pro, Ser, or Thr (preferably Asp);
$X_3$ is Arg, Asp, Ile, Leu, Met, Pro, or Val (preferably Ile);
$X_4$ is Ala, Ile, Leu, Pro, Thr, or Val (preferably Val or Leu);
$X_5$ is Asn, His, Ile, Leu, Lys, Phe, or Thr (preferably Thr);
$X_6$ is Asn, Glu, Gly, His, Leu, Lys, Met, Pro, or Thr (preferably Leu);
$X_7$ is Arg, Asn, Asp, Gln, Glu, Gly, Ile, Lys, Met, Pro, Ser, or Trp;
$X_8$ is Arg, Glu, Gly, Lys, Phe, Ser, Trp, or Tyr (preferably Ser); or $$\text{(K) Cys-}X_2\text{-}X_3\text{-}X_4\text{-}X_5\text{-}X_6\text{-}X_7\text{-}X_8\text{-}X_9\text{-Cys (SEQ ID NO:11),} \quad (K)$$

wherein $X_2$ is Asp, Gln, His, Ile, Leu, Lys, Met, Phe, or Thr;
$X_3$ is His, Ile, Leu, Met, Phe, Pro, Trp, or Tyr;
$X_4$ is Asp, His, Leu, or Ser (preferably Asp);
$X_5$ is Ala, Arg, Asp, Glu, Leu, Phe, Pro, or Thr (preferably Glu or Pro);
$X_6$ is Ala, Arg, Asn, or Leu (preferably Leu);
$X_7$ is Ile, Leu, Met, Pro, Ser, or Thr (preferably Thr);
$X_8$ is Ala, Arg, Asn, Gly, His, Lys, Ser, or Tyr;
$X_9$ is Ala, Arg, Asn, Gln, Leu, Met, Ser, Trp, Tyr, or Val; or $$\text{Cys-}X_2\text{-}X_3\text{-}X_4\text{-}X_5\text{-}X_6\text{-}X_7\text{-}X_8\text{-}X_9\text{-}X_{10}\text{-}X_{11}\text{-Cys (SEQ ID NO:12),} \quad (L)$$

wherein $X_2$ is Arg, Asn, Gln, Glu, His, Leu, Phe, Pro, Trp, Tyr, or Val (preferably Trp, Tyr, or Val);
$X_3$ is Arg, Asp, Gln, Gly, Ile, Lys, Phe, Thr, Trp or Tyr (preferably Asp);
$X_4$ is Ala, Arg, Asp, Glu, Gly, Leu, Ser, or Tyr (preferably Asp);
$X_5$ is Asp, Gln, Glu, Leu, Met, Phe, Pro, Ser, or Tyr (preferably Leu);
$X_6$ is Asp, Leu, Pro, Thr, or Val (preferably Leu or Thr);
$X_7$ is Arg, Gln, His, Ile, Leu, Lys, Met, Phe, Thr, Trp or Tyr (preferably Lys or Thr);
$X_8$ is Ala, Arg, Asn, Gln, Glu, His, Leu, Lys, Met, or Thr (preferably Arg or Leu);
$X_9$ is Ala, Asn, Gln, Gly, Leu, Lys, Phe, Pro, Thr, Trp, or Tyr (preferably Thr or Trp);
$X_{10}$ is Ala, Arg, Gln, His, Lys, Met, Phe, Pro, Thr, Trp, or Tyr (preferably Met or Phe);
$X_{11}$ is Arg, Gln, Glu, Gly, His, Leu, Met, Phe, Pro, Ser, Thr, Tyr, or Val (preferably Val);

wherein said polypeptides bind BLyS and/or BLyS-like polypeptides.

In additional preferred embodiments of the present invention, BLyS binding polypeptides comprise the following amino acid sequence M (SEQ ID NO:447):

$$\text{Ala-}X_2\text{-}X_3\text{-}X_4\text{-Asp-}X_6\text{-Leu-Thr-}X_9\text{-Leu-}X_{11}\text{-}X_{12}\text{-}X_{13}\text{-}X_{14} \text{ (SEQ ID NO:447),} \quad (M)$$

wherein $X_2$ is Asn, Ser, Tyr, Asp, Phe, Ile, Gln, His, Pro, Lys, Leu, Met, Thr, Val, Glu, Ala, Gly, Cys, or Trp (i.e., any amino acid except Arg; preferably Asn);

X₃ is Trp, Glu, Lys, Cys, Leu, Ala, Arg, Gly, or Ser (preferably Trp);
X₄ is Tyr, Phe, Glu, Cys, Asn (preferably Tyr);
X₆ is Pro, Ser, Thr, Phe, Leu, Tyr, Cys, or Ala (preferably Pro or Ser);
X₉ is Lys, Asn, Gln, Gly, or Arg (preferably Lys);
X₁₁ is Trp, Ser, Thr, Arg, Cys, Tyr, or Lys (preferably Tip);
X₁₂ is Leu, Phe, Val, Ile, or His (preferably Leu);
X₁₃ is Pro, Leu, His, Ser, Arg, Asn, Gln, Thr, Val, Ala, Cys, Ile, Phe, or Tyr (i.e., not Asp, Glu, Gly, Lys, Met, or Trp; preferably Pro); and
X₁₄ is Asp, Glu, Asn, Val, His, Gln, Arg, Gly, Ser, Tyr, Ala, Cys, Lys, Ile, Thr or Leu (i.e., not Phe, Met, Pro, or Trp; preferably Asp, Val or Glu).

Preferred embodiments are polypeptides comprising a core sequence of the formula N:

X₁-X₂-Asp-X₄-Leu-Thr-X₇-Leu-X₉-X₁₀ (SEQ ID NO:448),                (N)

wherein
X₁ is Trp, Glu, Lys, Cys, Leu, Ala, Arg, Gly, or Ser (preferably Trp);
X₂ is Tyr, Phe, Glu, Cys, Asn (preferably Tyr);
X₄ is Pro, Ser, Thr, Phe, Leu, Tyr, Cys, or Ala (preferably Pro or Ser);
X₇ is Lys, Asn, Gln, Gly, or Arg (preferably Lys);
X₉ is Trp, Ser, Thr, Arg, Cys, Tyr, or Lys (preferably Trp); and
X₁₀ is Leu, Phe, Val, Ile, or His (preferably Leu).

Especially preferred BLyS binding polypeptides according to the present invention comprise the core peptide Trp-Tyr-Asp-Pro-Leu-Thr-Lys-Leu-Trp-Leu (SEQ ID NO:436).

The BLyS binding polypeptides described above may have additional amino acids attached at either or both of the N- and C-terminal ends.

A further embodiment of the present invention relates to a BLyS affinity maturation library, comprising a population of at least 10³ polypeptides, preferably at least 10⁶ polypeptides, more preferably at least 10⁹ or more polypeptides, wherein the polypeptides of said population comprise the amino acid sequence:

Ala-X₂-X₃-X₄-Asp-X₆-Leu-Thr-X₉Leu-X₁₁-X₁₂-X₁₃-X₁₄ (SEQ ID NO:449), wherein
X₂ is any amino acid;
X₃ is any amino acid;
X₄ is any amino acid;
X₆ is any amino acid;
X₉ is any amino acid;
X₁₁ is any amino acid;
X₁₂ is any amino acid;
X₁₃ is any amino acid; and
X₁₄ is any amino acid.

A preferred BLyS affinity maturation library will be produced such that the variable amino acid positions (i.e., positions 2, 3, 4, 6, 9, 11, 12, 13 and 14 in SEQ ID NO:449) will not be randomly variegated but will disproportionately be a single selected amino acid. Such a library may be produced by expression of a multiplicity of polynucleotides fitting the DNA template:
GCT NNN NNN NNN GAT NNN CTT ACT NNN CTC NNN NNN NNN NNN (SEQ ID NO: 185), where each variable base (N) is A or C or G or T but one base in each instant is approximately 11-fold more probable at a given base position. One such DNA template, discussed in Example 6 below, is prepared so that the nucleotides of the DNA sequences are in the following proportions:

| in DNA template (SEQ ID NO:185) | | Proportion of Bases at Position | | | |
|---|---|---|---|---|---|
| Codon | Base Position | A | C | G | T |
| 2 | 4 | 79% | 7% | 7% | 7% |
|   | 5 | 79% | 7% | 7% | 7% |
|   | 6 | 7% | 7% | 7% | 79% |
| 3 | 7 | 7% | 7% | 7% | 79% |
|   | 8 | 7% | 7% | 79% | 7% |
|   | 9 | 7% | 7% | 79% | 7% |
| 4 | 10 | 7% | 7% | 7% | 79% |
|   | 11 | 79% | 7% | 7% | 7% |
|   | 12 | 7% | 7% | 7% | 79% |
| 6 | 16 | 7% | 7% | 7% | 79% |
|   | 17 | 7% | 79% | 7% | 7% |
|   | 18 | 7% | 7% | 7% | 79% |
| 9 | 25 | 79% | 7% | 7% | 7% |
|   | 26 | 79% | 7% | 7% | 7% |
|   | 27 | 7% | 7% | 79% | 7% |
| 11 | 31 | 7% | 7% | 7% | 79% |
|   | 32 | 7% | 7% | 79% | 7% |
|   | 33 | 7% | 7% | 79% | 7% |
| 12 | 34 | 7% | 79% | 7% | 7% |
|   | 35 | 7% | 7% | 7% | 79% |
|   | 36 | 7% | 7% | 7% | 79% |
| 13 | 37 | 7% | 79% | 7% | 7% |
|   | 38 | 7% | 79% | 7% | 7% |
|   | 39 | 7% | 7% | 7% | 79% |
| 14 | 40 | 7% | 7% | 79% | 7% |
|   | 41 | 79% | 7% | 7% | 7% |
|   | 42 | 7% | 7% | 7% | 79% |

BLyS binding polypeptide molecules of the invention may also have an amino terminal (N-terminal) capping or functional group, such as an acetyl group, which, for example, blocks the amino terminal amino group from undesirable reactions or is useful in linking the BLyS binding polypeptide to another molecule, matrix, resin, or solid support. BLyS binding polypeptides of the invention may also have a carboxy terminal (C-terminal) capping or functional group, such as an amide group, which, for example, blocks the C-terminal carboxyl group from undesirable reactions or provides a functional group useful in conjugating the binding polypeptide to other molecules, matrices, resins, or solid supports. Preferably, the N- and/or C-terminal capping groups are polypeptide linker molecules. An especially preferred C-terminal linker molecule that is useful for immobilizing a BLyS binding polypeptide of the invention to a solid support or chromatographic matrix material comprises the amino acid sequence Pro-Gly-Pro-Glu-Gly-Gly-Gly-Lys (SEQ ID NO:13). Another useful C-terminal linker, e.g., for fluoresceinating peptides, is Gly-Gly-Lys (see Table 15).

The invention also encompasses BLyS binding polypeptides that have been modified, for example, to increase or decrease the stability of the molecule, while retaining the ability to bind BLyS and/or BLyS-like polypeptides. An example of a modified BLyS binding polypeptide of the invention is a polypeptide in which one of two cysteine residues is substituted with a non-naturally occurring amino acid that is capable of condensing with the remaining cysteine side chain to form a stable thioether bridge, thereby generating a cyclic BLyS binding polypeptide. Such cyclic thioether molecules of synthetic peptides may be routinely generated using techniques known in the art, e.g., as described in PCT publication WO 97/46251, incorporated herein by reference.

In another embodiment, the invention provides BLyS binding polypeptides of the invention attached, coupled, linked or adhered to a matrix or resin or solid support. Techniques for attaching, linking or adhering polypeptides to matrices, resins and solid supports are well known in the art. Suitable matrices, resins or solid supports for these materials may be any composition known in the art to which a BLyS binding polypeptide of the invention could be attached, coupled, linked, or adhered, including but not limited to, a chromatographic resin or matrix, such as SEPHAROSE-4 FF agarose beads, the wall or floor of a well in a plastic microtiter dish, such as used in an enzyme-liked immunosorbent assay (ELISA), or a silica based biochip. Materials useful as solid supports on which to immobilize binding polypeptides of the invention include, but are not limited to, polyacrylamide, agarose, silica, nitrocellulose, paper, plastic, nylon, metal, and combinations thereof. A BLyS binding polypeptide of the invention may be immobilized on a matrix, resin or solid support material by a non-covalent association or by covalent bonding, using techniques known in the art. Preferably, a BLyS binding polypeptide of the invention is immobilized on a chromatography material such as SEPHAROSE-4 FF agarose. In an even more preferred embodiment, a BLyS binding polypeptide of the invention is coupled to a chromatography material using a linker molecule. A preferred linker molecule according to the present invention is a polypeptide comprising the amino acid sequence Pro-Gly-Pro-Glu-Gly-Gly-Gly-Lys (SEQ ID NO:13). Most preferably, the affinity chromatography material of the invention comprises a BLyS binding polypeptide comprising an amino acid sequence selected from the group consisting of SEQ ID NOs: 163–172, which is linked to a chromatography material by a polypeptide linker molecule having the amino acid sequence Pro-Gly-Pro-Glu-Gly-Gly-Gly-Lys (SEQ ID NO:13). BLyS binding polypeptides, particularly attached, coupled, linked or adhered to a matrix or resin or other solid support are useful for methods of detecting, isolating and purifying BLyS and/or BLyS like polypeptides, particularly for purification of BLyS and/or BLyS like polypeptides by affinity chromatography.

In certain preferred embodiments, the BLyS binding polypeptides of the present invention or phage displaying such binding polypeptides, irreversibly bind the BLyS protein in its native, soluble trimeric form.

In certain preferred embodiments, the BLyS binding polypeptides of the present invention or phage displaying such binding polypeptides, reversibly bind the BLyS protein in its native, soluble trimeric form.

In a further embodiment, the present invention encompasses a composition of matter comprising isolated nucleic acids, preferably DNA, encoding a BLyS binding polypeptide of the invention. In a specific embodiment, nucleic acid molecules of the invention encode a BLyS binding polypeptide of the invention as provided in SEQ ID NOs:1–12, 20–172, and 186–444. In additional embodiments, nucleic acid molecules of the invention encode a polypeptide variant or fragment of a polypeptide comprising an amino acid sequence of SEQ ID NOs:1–12, 20–172, and 186–444. In a further additional embodiment, nucleic acid molecules of the invention encode a BLyS binding polypeptide, the complementary strand of which nucleic acid hybridizes to a polynucleotide sequence encoding a polypeptide described in Tables 1–8 and 14 and in Examples 2, 5 and 6 (SEQ ID NOs:1–12, 20–172, and 186–444), under stringent conditions, e.g., hybridization to filter-bound DNA in 6× sodium chloride/sodium citrate (SSC) at about 45° C. followed by one or more washes in 0.2×SSC/0.1% SDS at about 50–65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, *Current Protocols in Molecular Biology*, Vol. 1, Green Publishing Associates, Inc. and John Wiley & Sons, Inc., New York at pages 6.3.1–6.3.6 and 2.10.3).

The present invention also relates to recombinant vectors, which include the isolated nucleic acid molecules encoding the BLyS binding polypeptides of the present invention (as well as fragments and variants thereof), and to host cells containing the recombinant vectors, as well as to methods of making such vectors and host cells. The invention further provides for the use of such recombinant vectors in the production of BLyS binding polypeptides by recombinant techniques.

The BLyS binding polypeptides, nucleic acids, transformed host cells, and genetically engineered viruses and phage of the invention (e.g., recombinant phage), have uses that include, but are not limited to, the detection, isolation, and purification of BLyS.

In another embodiment of the invention, recombinant bacteriophage displaying BLyS binding polypeptides on their surfaces are also provided. Such phage may be routinely generated using techniques known in the art and are useful, for example, as screening reagents and reagents for detecting BLyS.

In another embodiment, a BLyS binding polypeptide of the invention is used to detect or isolate BLyS or BLyS-like polypeptides in a solution. Such solutions include, but are not limited to, BLyS or BLyS-like polypeptides suspended or dissolved in water or a buffer solution as well as any fluid and/or cell obtained from an individual, biological fluid, body tissue, body cell, cell line, tissue culture, or other source which may contain BLyS or BLyS-like polypeptides, such as, cell culture medium, cell extracts, and tissue homogenates. Biological fluids include, but are not limited to, sera, plasma, lymph, blood, blood fractions, urine, synovial fluid, spinal fluid, saliva, and mucous.

In another embodiment, the present invention provides a method for detecting BLyS protein and/or BLyS-like polypeptide in a solution comprising, contacting the solution with a BLyS binding polypeptide of the invention and detecting binding of BLyS or BLyS-like polypeptide to the BLyS binding polypeptide. The BLyS binding polypeptide may be either free or immobilized. Preferably, the BLyS binding polypeptide is a polypeptide immobilized on a solid surface or chromatographic material or the well of a plastic microtiter assay dish.

Another embodiment of the present invention is a method for isolating BLyS protein and/or BLyS-like polypeptide from a solution containing it, comprising:

(a) contacting the solution with a BLyS binding polypeptide under conditions that permit binding of the BLyS and/or BLyS-like polypeptides to BLyS binding polypeptides, and (b) separating BLyS binding polypeptides (and BLyS and/or BLyS-like polypeptides bound thereto) from the rest of the solution.

A further embodiment of the present invention is a method for isolating BLyS protein and/or BLyS-like polypeptide from a solution containing it, comprising:

(a) contacting the solution with a BLyS binding polypeptide under conditions that permit binding of the BLyS and/or BLyS-like polypeptides to BLyS binding polypeptides, (b) separating the complex(es) formed by the BLyS binding polypeptide and BLyS and/or BLyS-like polypeptides from other components of the solution, (c) dissociating the BLyS binding polypeptide from the BLyS and/or BLyS-like polypeptides, and (d) recovering the dissociated, BLyS and/or BLyS-like polypeptides.

In another embodiment, the invention provides kits containing a binding polypeptide of the invention for use in methods of detecting or isolating BLyS and/or BLyS-like polypeptides.

Definitions

In order that the invention may be clearly understood, the following terms are defined:

The term "recombinant" is used to describe non-naturally altered or manipulated nucleic acids, host cells transfected with exogenous nucleic acids, or polypeptide molecules that are expressed non-naturally, through manipulation of isolated nucleic acid (typically, DNA) and transformation or transfection of host cells. "Recombinant" is a term that specifically encompasses nucleic acid molecules that have been constructed in vitro using genetic engineering techniques, and use of the term "recombinant" as an adjective to describe a molecule, construct, vector, cell, polypeptide or polynucleotide specifically excludes naturally occurring such molecules, constructs, vectors, cells, polypeptides or polynucleotides.

The term "bacteriophage" is defined as a bacterial virus containing a nucleic acid core and a protective shell built up by the aggregation of a number of different protein molecules. The terms "bacteriophage" and "phage" are synonymous and are used herein interchangeably.

The term "affinity ligand" is sometimes used herein and is synonymous with BLyS binding polypeptides of the invention.

The term "BLyS protein" as used herein encompasses both the membrane (e.g., SEQ ID NO:173) and soluble forms (e.g., SEQ ID NO:174). BLyS protein may be monomeric, dimeric, or trimeric or multivalent. Preferably, BLyS proteins are homotrimeric.

The term "BLyS-like polypeptide" as used herein encompasses natural BLyS or full-length recombinant BLyS as well as fragments and variants thereof, such as, a modified or truncated form of natural BLyS or fall-length recombinant BLyS, which BLyS and BLyS-like polypeptide retain a BLyS functional activity. BLyS or BLyS fragments that may be specifically bound by the compositions of the invention include, but are not limited to, human BLyS (SEQ ID NOs:173 and/or 174) or BLyS expressed on human monocytes; murine BLyS (SEQ ID NOs:175 and/or 176) or BLyS expressed on murine monocytes; rat BLyS (either the soluble forms as given in SEQ ID NOs:177, 178, 179 and/or 180 or in a membrane associated form, e.g., on the surface of rat monocytes); or monkey BLyS (e.g., the monkey BLyS polypeptides of SEQ ID NOS: 181 and/or 182, the soluble form of monkey BLyS, or BLyS expressed on monkey monocytes) or fragments thereof. Preferably compositions of the invention bind human BLyS (SEQ ID NOs: 173 and/or 174) or fragments thereof. BLyS and BLyS-like polypeptides retain at least one functional activity of the natural or full-length BLyS, including but not limited to the following activities: binding to BLyS receptor (e.g., TACI (GenBank accesion number AAC51790), and BCMA (GenBank accession number NP_001183)), stimulating B cell proliferation, stimulating immunoglobulin secretion by B cells, stimulating the BLyS receptor signaling cascade and/or being bound by an anti-BLyS antibody or other BLyS binding polypeptide. Assays that can be used to determine the functional activities of BLyS or BLyS like polypeptides can readily be determined by one skilled in the art (e.g., see assays disclosed in Moore et al., 1999, supra) "BLyS-like polypeptides" also include fusion polypeptides in which all or a portion of BLyS is fused or conjugated to another polypeptide. BLyS-like polypeptides that are fusion polypeptides retain at least one functional activity of BLyS, preferably the ability to stimulate B lymphocytes (see, for example, Moore et al., *Science*, 285: 260–263 (1999)), to bind the BLyS receptors (e.g., TACI or BCMA), and/or to be bound by an anti-BLyS antibody or other BLyS binding polypeptide. BLyS fusion polypeptides may be made by recombinant DNA techniques in which a gene or other polynucleotide coding sequence for BLyS or a fragment thereof is ligated in-frame (recombined) with the coding sequence of another protein or polypeptide. The resulting recombinant DNA molecule is then inserted into any of a variety of plasmid or phage expression vectors, which enable expression of the fusion protein molecule in an appropriate eukaryotic or prokaryotic host cell. BLyS fusion polypeptides may be generated by synthetic or semi-synthetic procedures as well.

The terms "BLyS target" or "BLyS target protein" are sometimes used herein and encompass BLyS and/or BLyS-like polypeptides. Thus, the BLyS binding polypeptides of the invention bind "BLyS target proteins" and can be used to bind, detect, remove, and/or purify "BLyS target proteins."

The term "binding polypeptide" is used herein to refer to any polypeptide capable of forming a binding complex with another molecule, polypeptide, peptidomimetic or transformant.

A "BLyS binding polypeptide" is a molecule of the invention that can bind BLyS target protein. Non-limiting examples of BLyS binding polypeptides of the invention are the polypeptide molecules having an amino acid sequence described herein (see SEQ ID NOs:1–12, 20–172, and 186–444). The term BLyS binding polypeptide also encompasses BLyS binding fragments and variants (including derivatives) of polypeptides having the specific amino acid sequences described herein (SEQ ID NOs:1–12, 20–172, and 186–444). By "variant" of an amino acid sequence as described herein is meant a polypeptide that binds BLyS, but does not necessarily comprise an identical or similar amino acid sequence of a BLyS binding polypeptide specified herein. BLyS binding polypeptides of the invention which are variants of a BLyS binding polypeptide specified herein satisfy at least one of the following: (a) a polypeptide comprising, or alternatively consisting of, an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% least 99%, or 100% identical to the amino acid sequence of a BLyS binding polypeptide sequence disclosed herein (SEQ ID NOs:1–12, 20–172, and 186–444), (b) a polypeptide encoded by a nucleotide sequence, the complementary sequence of which hybridizes under stringent conditions to a nucleotide sequence encoding a BLyS binding polypeptide disclosed herein (e.g., a nucleic acid sequence encoding the amino acid sequence of SEQ ID NOs:1–12, 20–172, and 186–444), and/or a fragment of a BLyS binding polypeptide disclosed herein, of at least 5 amino acid residues, at least 10 amino acid residues, at least 15 amino acid residues, or at least 20 amino acid residues. BLyS binding polypeptides of the invention also encompass polypeptide sequences that have been modified for various applications provided that such modifications do not eliminate the ability to bind a BLyS target. Specific, non-limiting examples of modifications contemplated include C-terminal or N-terminal amino acid substitutions or peptide chain elongations for the purpose of linking the BLyS binder to a chromatographic material or other solid support. Other substitutions contemplated herein include substitution of one or both of a pair of cysteine residues that normally form disulfide links, for example with non-naturally occurring amino acid residues having reactive side chains, for the purpose of forming a more stable bond between those amino acid positions than the former disulfide bond. All such modified binding polypeptides are also considered BLyS binding polypeptides according to this invention so long as the modified polypeptides retain the ability to bind BLyS and/or BLyS-like polypeptides, and therefore, may be used in one or more of the various methods described herein, such as, to detect, purify, or isolate BLyS or BLyS-like polypeptides in or from a solution. BLyS binding polypeptides of the invention also include variants of the specific BLyS binding polypeptide sequences disclosed herein (e.g., SEQ ID NOs: 1–12, 20–172, and 186–444) which have an amino acid sequence corresponding to one of these polypeptide sequences, but in which the polypeptide sequence is altered by substitutions, additions or deletions that provide for molecules that bind BLyS. Thus, the BLyS binding polypeptides include polypeptides containing, as a primary amino acid sequence, all or part of the particular BLyS binding polypeptide sequence including altered sequences in which functionally equivalent amino acid residues are substituted for residues within the sequence, resulting in a peptide which is functionally active. For example, one or more amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such BLyS binding polypeptides can be made either by chemical peptide synthesis or by recombinant production from a nucleic acid encoding the BLyS binding polypeptide which nucleic acid has been mutated. Any technique for mutagenesis known in the art can be used, including but not limited to, chemical mutagenesis, in vitro site-directed mutagenesis (Hutchinson et al., *J. Biol. Chem.*, 253:6551 (1978)), use of TAB.RTM. linkers (Pharmacia), etc.

As used and understood herein, percent homology or percent identity of two amino acid lo sequences or of two nucleic acid sequences is determined using the algorithm of Karlin and Atschul (*Proc. Natl. Acad. Sci. USA*, 87: 2264–2268 (1990)), modified as in Karlin and Altschul (*Proc. Natl. Acad. Sci. USA*, 90: 5873–5877 (1993)). Such an algorithm is incorporated into the NBLAST and XBLAST programs of Altschul et al. (*J. Mol. Biol.*, 215: 403–410 (1990)). BLAST nucleotide searches are performed with the NBLAST program to obtain nucleotide sequences homologous to a nucleic acid molecule described herein. BLAST protein searches are performed with the XBLAST program to obtain amino acid sequences homologous to a reference polypeptide. To obtain gapped alignments for comparison purposes, Gapped BLAST is utilized as described in Altschul et al. (*Nucleic Acids Res.*, 25: 3389–3402 (1997)). When utilizing BLAST and Gapped BLAST programs, the default parameters of the respective programs (e.g., XBLAST and NBLAST) are used. See, http://www.ncbi.nlm.nih.gov. Alternatively, the percent identity of two amino acid sequences or of two nucleic acid sequences can be determined once the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. The percent identity between the two sequences is a function of the number of identical positions shared by the sequences (i.e., % identity=number of identical overlapping positions/ total number of positions×100%). In one embodiment, the two sequences are the same length.

The term "polypeptide", as used herein, refers to a linear, branched, or cyclic (e.g., containing a loop structure) polymer of two or more amino acid residues linked with a peptide bond. The term "polypeptide" is not restricted to any particular upper limit of amino acid residues. Thus, the BLyS affinity ligands of the invention that comprise an amino acid sequence described herein are properly referred to as "BLyS binding polypeptides" because such binding polypeptides contain at least two amino acid residues held together by a peptide bond, even though such molecules may also contain one or more additional moieties or groups that are not amino acids, such as N-terminal and/or C-terminal capping or functional groups, and that may or may not be involved in a peptide bond. The polypeptides of the invention may be monovalent, divalent, trivalent, or multivalent and may comprise one or more of the BLyS binding polypeptides having the amino acid sequence of SEQ ID NOs:1–12, 20–172, and 186–444 and/or fragments or variants thereof. The term "peptide" is used herein to have the same meaning as "polypeptide."

"Feed stream": BLyS and BLyS-like polypeptides that are bound by a BLyS binding polypeptide of this invention may be produced by any method known in the art, including, but not limited to, chemical synthesis; production in transformed host cells; secretion into culture medium by naturally occurring cells or recombinantly transformed bacteria, yeasts, fungi, insect cells, plant cells, and mammalian cells; production in genetically engineered organisms (for example, transgenic mammals); and production in non-genetically engineered organisms. The solution, sample, or mixture that contains a BLyS or BLyS-like polypeptide as it is produced or is found present in a production solution will sometimes be referred to as the "feed stream".

The term "binding" refers to the determination by standard techniques that a binding polypeptide recognizes and binds to a given target. Such standard techniques include, but are not limited to, affinity chromatography, equilibrium dialysis, gel filtration, enzyme linked immunosorbent assay (ELISA), FACS analysis, and the monitoring of spectroscopic changes that result from binding, e.g., using fluorescence anisotropy, either by direct binding measurements or competition assays with another binder.

The term "specificity" refers to a binding polypeptide of the invention that has a higher binding affinity for one target over another. Thus, the term "BLyS target protein specificity" refers to a molecule having a higher affinity for BLyS target protein as compared with another molecule that is not a BLyS target protein.

Other terms are defined as necessary in the text below.

DETAILED DESCRIPTION OF THE INVENTION

The present invention provides novel binding moieties for BLyS. Such binding moieties make possible the efficient detection and isolation of BLyS or BLyS-like polypeptides in tissues or in a solution or system that contains BLyS or BLyS-like polypeptides. The BLyS binding polypeptides disclosed herein can also be used to immobilize BLyS targets and provide a means of removing BLyS target proteins from solutions or systems containing them. The preferred binding moieties of the present invention bind BLyS with high affinity, i.e., acting at low concentrations.

BLyS Binding Polypeptides

The present invention provides new polypeptides and families of polypeptides that specifically bind to B lymphocyte stimulator protein (BLyS) and/or BLyS-like polypeptides. In particular, the invention encompasses polypeptides that specifically bind to a polypeptide or polypeptide fragment of human BLyS (SEQ ID NOs:173 and/or 174) or BLyS expressed on human monocytes; murine BLyS (SEQ ID NOs:175 and/or 176) or BLyS expressed on murine monocytes; rat BLyS (either the soluble forms as given in SEQ ID NOs:177, 178, 179 and/or 180 or in a membrane associated form, e.g., on the surface of rat monocytes); or monkey BLyS (e.g., the monkey BLyS polypeptides of SEQ ID NOS:181 and/or 182, the soluble form of monkey BLyS, or BLyS expressed on monkey monocytes); preferably human BLyS.

In specific preferred embodiments, the BLyS binding polypeptides of the invention bind BLyS and/or BLyS-like polypeptides with high affinity. In other embodiments, the BLyS binding polypeptides of the invention reversibly bind BLyS and/or BLyS-like polypeptides. In still other embodiments, the BLyS binding polypeptides of the invention irreversibly bind BLyS and/or BLyS-like polypeptides.

The cysteine residues in polypeptides are believed to form a disulfide bond, which would cause the polypeptide containing these cysteine residues to form a stable loop structure under non-reducing conditions. Especially preferred BLyS binding polypeptides of the invention are polypeptide molecules that comprise amino acid sequences that form stable loop structures or other stable structures that bind BLyS or BLyS-like polypeptides.

In specific embodiments, the invention relates to BLyS binding polypeptides comprising, or alternatively consisting of, an amino acid sequence selected from the group consisting of SEQ ID NOs:1–12, 20–172, and 186–444, preferably SEQ ID NOs:163–172 or 436–444 as referred to above and in Tables 1–8, 14 and 15 and in Examples 2, 5 and 6 below. Analysis of the sequences of the BLyS binding polypeptides isolated as described herein shows a strong selection for polypeptides containing the tetrapeptide Asp-Xaa-Leu-Thr (SEQ ID NO:446), and therefore in its broadest aspects, the present invention relates to polypeptides capable of binding to BLyS comprising the polypeptide Asp-Xaa-Leu-Thr (SEQ ID NO:446), where Xaa is Pro, Ser, Thr, Phe, Leu, Tyr, Cys, or Ala (preferably Pro or Ser).

Seven consensus sequences (SEQ ID NOs:1–7) have been determined based on the specific BLyS binding polypeptides shown in Tables 1–8. In specific embodiments, BLyS binding polypeptides of the invention comprise one or more of these sequences. Such preferred BLyS binding polypeptides include polypeptides with the potential to formi a cyclic or loop structure between invariant Cys residues comprising, or alternatively consisting of, an amino Ad acid sequence selected from A-E (SEQ ID NOs:1–5):

(A) $X_1$-$X_2$-$X_3$-Cys-$X_5$-Phe-$X_7$-Trp-Glu-Cys-$X_{11}$-$X_{12}$-$X_{13}$ (SEQ ID NO:1), (A)

wherein
$X_1$ is Ala, Asn, Lys, or Ser;
$X_2$ is Ala, Glu, Met, Ser, or Val;
$X_3$ is Ala, Asn, Lys, or Pro preferably Lys);
$X_5$ is Phe, Trp, or Tyr (preferably Tyr);
$X_7$ is Pro or Tyr (preferably Pro);
$X_{11}$ is Ala, Gln, His, Phe, or Val;
$X_{12}$ is Asn, Gln, Gly, His, Ser, or Val; and
$X_{13}$ is Ala, Asn, Gly, Ile, Pro, or Ser,
wherein said polypeptide binds BLyS and/or BLyS-like polypeptides; or $X_1$-$X_2$-$X_3$-Cys-$X_5$-$X_6$-$X_7$-$X_8$-$X_9$-$X_{10}$-Cys-$X_{12}$-$X_{13}$-$X_{14}$ (SEQ ID NO:2), (B)

wherein
$X_1$ is Ala, Asp, Gln, Glu, Gly, His, Ile, Leu, Lys, Met, Phe, Pro, Ser, Thr, Trp, Tyr, Val, or is absent;
$X_2$ is Ala, Asn, Asp, Gln, Gly, His, Ile, Leu, Lys, Met, Phe, Pro, Ser, Thr, Trp, Tyr, or Val;
$X_3$ is Ala, Arg, Asn, Asp, Gln, Glu, Gly, His, Ile, Leu, Lys, Met, Phe, Pro, Ser, Trp, Tyr, or Val (preferably Asp);
$X_5$ is Asp, Ile, Leu, or Tyr (preferably Asp or Leu);
$X_6$ is Arg, Asp, Glu, His, Ile, Leu, Lys, Phe, Pro, Tyr, or Val (preferably Glu or Leu);
$X_7$ is His, Leu, Lys, or Phe (preferably His or Leu);
$X_8$ is Leu, Pro, or Thr (preferably Thr or Pro);
$X_9$ is Arg, Asn, Gly, His, Ile, Lys, Met, or Trp (preferably Lys);
$X_{10}$ is Ala, Gln, Glu, Gly, His, Ile, Leu, Met, Phe, Ser, Trp, Tyr, or Val;
$X_{12}$ is Asp, Gln, Glu, Gly, Ile, Leu, Lys, Phe, Ser, Trp, Tyr, or Val;
$X_{13}$ is Ala, Arg, Asn, Asp, Gln, Glu, Gly, His, Leu, Lys, Met, Phe, Pro, Ser, Thr, Trp, Tyr, or Val; and
$X_{14}$ is Ala, Arg, Asn, Asp, Gln, Glu, Gly, His, Ile, Leu, Lys, Phe, Pro, Trp, Tyr, Val, or is absent,
wherein said polypeptide binds BLyS and/or BLyS-like polypeptides; or $X_1$-$X_2$-$X_3$-Cys-$X_5$-$X_6$-$X_7$-$X_8$-$X_9$-$X_{10}$-$X_{11}$-Cys-$X_{13}$-$X_{14}$-$X_{15}$ (SEQ ID NO:3); (C)

wherein
$X_1$ is Ala, Arg, Asn, Asp, Leu, Lys, Phe, Pro, Ser, or Thr;
$X_2$ is Asn, Asp, Gln, His, Ile, Lys, Pro, Thr, or Trp;
$X_3$ is Ala, Arg, Asn, Gln, Glu, His, Phe, Pro, or Thr (preferably Ala);
$X_5$ is Asn, Asp, Pro, Ser, or Thr (preferably Asp);
$X_6$ is Arg, Asp, Ile, Leu, Met, Pro, or Val (preferably Ile);
$X_7$ is Ala, Ile, Leu, Pro, Thr, or Val (preferably Val or Leu);
$X_8$ is Asn, His, Ile, Leu, Lys, Phe, or Thr (preferably Thr);
$X_9$ is Asn, Glu, Gly, His, Leu, Lys, Met, Pro, or Thr (preferably Leu);

$X_{10}$ is Arg, Asn, Asp, Gln, Glu, Gly, Ile, Lys, Met, Pro, Ser, or Trp;

$X_{11}$ is Arg, Glu, Gly, Lys, Phe, Ser, Trp, or Tyr (preferably Ser);

$X_{13}$ is Gln, Glu, Ile, Leu, Phe, Pro, Ser, Tyr, or Val (preferably Val);

$X_{14}$ is Asn, Gly, Ile, Phe, Pro, Thr, Trp, or Tyr; and $X_{15}$ is Asn, Asp, Glu, Leu, Lys, Met, Pro, or Thr (preferably Glu or Pro), wherein said polypeptide binds BLyS and/or BLyS-like polypeptides; or $$X_1\text{-}X_2\text{-}X_3\text{-}Cys\text{-}X_5\text{-}X_6\text{-}X_7\text{-}X_8\text{-}X_9\text{-}X_{10}\text{-}X_{11}\text{-}X_{12}\text{-}Cys\text{-}X_{14}\text{-}X_{15}\text{-}X_{16} \text{ (SEQ ID NO:4)}, \quad (D)$$

wherein $X_1$ is Asn, Asp, His, Leu, Phe, Pro, Ser, Tyr, or is absent (preferably Ser);

$X_2$ is Arg, Asn, Asp, His, Phe, Ser, or Trp (preferably Arg);

$X_3$ is Asn, Asp, Leu, Pro, Ser, or Val (preferably Asn or Asp);

$X_5$ is Asp, Gln, His, Ile, Leu, Lys, Met, Phe, or Thr;

$X_6$ is His, Ile, Leu, Met, Phe, Pro, Trp, or Tyr;

$X_7$ is Asp, His, Leu, or Ser (preferably Asp);

$X_8$ is Ala, Arg, Asp, Glu, Leu, Phe, Pro, or Thr preferably Glu or Pro);

$X_9$ is Ala, Arg, Asn, or Leu (preferably Leu);

$X_{10}$ is Ile, Leu, Met, Pro, Ser, or Thr (preferably Thr);

$X_{11}$ is Ala, Arg, Asn, Gly, His, Lys, Ser, or Tyr;

$X_{12}$ is Ala, Arg, Asn, Gln, Leu, Met, Ser, Trp, Tyr, or Val;

$X_{14}$ is Asp, Gly, Leu, Phe, Tyr, or Val (preferably Leu);

$X_{15}$ is Asn, His, Leu, Pro, or Tyr (preferably His, Leu or Pro); and $X_{16}$ is Asn, Asp, His, Phe, Ser, or Tyr, (preferably Asp or Ser), wherein said polypeptide binds BLyS and/or BLyS-like polypeptides; or $$X_1\text{-}X_2\text{-}X_3\text{-}Cys\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}Cys\text{-}X_{16}\text{-}X_{17}\text{-}X_{18} \text{ (SEQ ID NO:5)}, \quad (E)$$

wherein $X_1$ is Arg, Asp, Gly, His, Leu, Phe, Pro, Ser, Trp, Tyr, or is absent (preferably Arg);

$X_2$ is Ala, Arg, Asn, Asp, Gly, Pro, Ser, or is absent (preferably Asn, Asp, Gly, or Pro);

$X_3$ is Arg, Asn, Gln, Glu, Gly, Lys, Met, Pro, Trp or Val (preferably Gly or Met);

$X_5$ is Arg, Asn, Gln, Glu, His, Leu, Phe, Pro, Trp, Tyr, or Val (preferably Trp, Tyr, or Val);

$X_6$ is Arg, Asp, Gln, Gly, Ile, Lys, Phe, Thr, Trp or Tyr (preferably Asp);

$X_7$ is Ala, Arg, Asp, Glu, Gly, Leu, Ser, or Tyr (preferably Asp);

$X_8$ is Asp, Gln, Glu, Leu, Met, Phe, Pro, Ser, or Tyr (preferably Leu);

$X_9$ is Asp, Leu, Pro, Thr, or Val (preferably Leu or Thr);

$X_{10}$ is Arg, Gln, His, Ile, Leu, Lys, Met, Phe, Thr, Trp or Tyr (preferably Lys or Thr);

$X_{11}$ is Ala, Arg, Asn, Gln, Glu, His, Leu, Lys, Met, or Thr (preferably Arg or Leu);

$X_{12}$ is Ala, Asn, Gln, Gly, Leu, Lys, Phe, Pro, Thr, Trp, or Tyr (preferably Thr or Trp);

$X_{13}$ is Ala, Arg, Gln, His, Lys, Met, Phe, Pro, Thr, Trp, or Tyr (preferably Met or Phe);

$X_{14}$ is Arg, Gln, Glu, Gly, His, Leu, Met, Phe, Pro, Ser, Thr, Tyr, or Val (preferably Val);

$X_{16}$ is Arg, Asp, Gly, His, Lys, Met, Phe, Pro, Ser, or Trp (preferably Met);

$X_{17}$ is Arg, Asn, Asp, Gly, His, Phe, Pro, Ser, Trp or Tyr, (preferably Arg, His, or Tyr); and $X_{18}$ is Ala, Arg, Asn, Asp, His, Leu, Phe, or Trp (preferably His or Asn), wherein said polypeptide binds BLyS and/or BLyS-like polypeptides.

Additional preferred embodiments include linear polypeptides comprising, or alternatively consisting of, an amino acid sequence selected from F and G (SEQ ID NOs:6 and 7):

$$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12} \text{ (SEQ ID NO:6)}, \quad (F)$$

wherein $X_1$ is Ala, Arg, Gly, His, Leu, Lys, Met, Phe, Trp, Tyr, or Val (preferably Gly, Tyr, or Val);

$X_2$ is Ala, Arg, Gln, His, Ile, Leu, Phe, Thr, Trp, or Tyr (preferably His or Tyr);

$X_3$ is Ala, Asp, Lys, Phe, Thr, Trp or Tyr (preferably Asp or Tyr);

$X_4$ is Arg, Asp, Gln, Lys, Met, Phe, Pro, Ser, Tyr, or Val (preferably Asp or Gln);

$X_5$ is Asp, Leu, Lys, Phe, Pro, Ser, or Val (preferably Leu or Ser);

$X_6$ is His, Ile, Leu, Pro, Ser, or Thr (preferably Leu or Thr);

$X_7$ is Arg, Gly, His, Leu, Lys, Met, or Thr (preferably Lys or Thr);

$X_8$ is Ala, Arg, Asn, Ile, Leu, Lys, Met, or Thr (preferably Leu or Lys);

$X_9$ is Ala, Asn, Arg, Asp, Glu, Gly, His, Leu, Met, Ser, Trp, Tyr, or Val (preferably Met or Ser);

$X_{10}$ is Ile, Leu, Phe, Ser, Thr, Trp, Tyr, or Val (preferably Thr or Leu);

$X_{11}$ is Ala, Arg, Gly, His, Ile, Leu, Lys, Pro, Ser, Thr, Trp, Tyr, or Val (preferably Pro or Thr); and $X_{12}$ is Arg, Asp, His, Leu, Lys, Met, Phe, Pro, Ser, Trp, Tyr, or Val (preferably Arg or Pro), wherein said polypeptide binds BLyS and/or BLyS-like polypeptides; or $$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13} \text{ (SEQ ID NO:7)}, \quad (G)$$

wherein $X_1$ is Asp, Gln, Glu, Gly, His, Lys, Met, or Trp (preferably Glu, Lys);

$X_2$ is Arg, Gln, His, Ile, Leu, or Pro (preferably His or Pro);

$X_3$ is Asp, Gly, Ile, Lys, Thr, Tyr or Val (preferably Tyr);

$X_4$ is Asn, Asp, Gln, Glu, Met, Pro, Ser, or Tyr (preferably Asp or Gln);

$X_5$ is Asn, Asp, His, Ile, Leu, Met, Pro, Thr or Val (preferably Asn or Thr);

$X_6$ is Asp, Glu, His, Leu, Lys, Pro, or Val (preferably Asp or Pro);

$X_7$ is Arg, Asn, Gln, His, Ile, Leu, Met, Pro, or Thr (preferably Ile or Pro);

$X_8$ is Gln, Gly, His, Leu, Met, Ser, or Thr (preferably Leu or Thr);

$X_9$ is Asn, Gln, Gly, His, Leu, Lys, Ser, or Thr (preferably Lys);

$X_{10}$ is Ala, Gly, Ile, Leu, Lys, Met, or Phe (preferably Gly or Met);

$X_{11}$ is Ala, Glu, His, Ile, Leu, Met, Ser, Thr, Trp, Tyr, or Val (preferably Ala or Thr);

$X_{12}$ is Arg, Gln, Glu, Gly, His, Ile, Lys, Tyr, or Val (preferably Arg or His); and $X_{13}$ is Arg, Asn, Glu, His, Ile, Ser, Thr, Trp, or Val (preferably His), wherein said polypeptide binds BLyS and/or BLyS-like polypeptides.

Said polypeptides may have additional amino acids attached at either or both of the N- and C-terminal ends.

Examination of the sequence information and binding data from the isolates of libraries containing polypeptides with the potential to form loop structures (i.e., libraries designated TN6, TN7, TN8, TN9, TN10 and TN12) identifies a series of BLyS binding polypeptides that may form loop structures. In specific embodiments, BLyS binding polypeptides of the invention comprise, or alternatively consist of, an amino acid sequence selected from H-L (SEQ ID NOs:8–12):

Cys-$X_2$-Phe-$X_4$Trp-Glu-Cys (SEQ ID NO:8),  (H)

wherein $X_2$ is Phe, Trp, or Tyr (preferably Tyr); and
$X_4$ is Pro or Tyr (preferably Pro); or Cys-$X_2$-$X_3$-$X_4$-$X_5$-$X_6$-$X_7$-Cys (SEQ ID NO:9),  (I)

wherein $X_2$ is Asp, Ile, Leu, or Tyr (preferably Asp or Leu);
$X_3$ is Arg, Asp, Glu, His, Ile, Leu, Lys, Phe, Pro, Tyr, or Val (preferably Glu or Leu);
$X_4$ is His, Leu, Lys, or Phe (preferably His or Leu);
$X_5$ is Leu, Pro, or Thr (preferably Thr or Pro);
$X_6$ is Arg, Asn, Gly, His, Ile, Lys, Met, or Trp (preferably Lys); and
$X_7$ is Ala, Asn, Gln, Glu, Gly, His, Ile, Leu, Met, Phe, Ser, Trp, Tyr, or Val; or Cys-$X_2$-$X_3$-$X_4$-$X_5$-$X_6$-$X_7$-$X_8$-Cys (SEQ ID NO:10),  (J)

wherein $X_2$ is Asn, Asp, Pro, Ser, or Thr (preferably Asp);
$X_3$ is Arg, Asp, Ile, Leu, Met, Pro, or Val (preferably Ile);
$X_4$ is Ala, Ile, Leu , Pro, Thr, or Val (preferably Val or Leu);
$X_5$ is Asn, His, Ile, Leu, Lys, Phe, or Thr (preferably Thr);
$X_6$ is Asn, Glu, Gly, His, Leu, Lys, Met, Pro, or Thr (preferably Leu);
$X_7$ is Arg, Asn, Asp, Gln, Glu, Gly, Ile, Lys, Met, Pro, Ser, or Trp;
$X_8$ is Arg, Glu, Gly, Lys, Phe, Ser, Trp, or Tyr (preferably Ser); or Cys-$X_2$-$X_3$-$X_4$-$X_5$-$X_6$-$X_7$-$X_8$-$X_9$-Cys (SEQ ID NO:11),  (K)

wherein $X_2$ is Asp, Gln, His, Ile, Leu, Lys, Met, Phe, or Thr;
$X_3$ is His, Ile, Leu, Met, Phe, Pro, Trp, or Tyr;
$X_4$ is Asp, His, Leu, or Ser (preferably Asp);
$X_5$ is Ala, Arg, Asp, Glu, Leu, Phe, Pro, or Thr (preferably Glu or Pro);
$X_6$ is Ala, Arg, Asn, or Leu (preferably Leu);
$X_7$ is Ile, Leu, Met, Pro, Ser, or Thr (preferably Thr);
$X_8$ is Ala, Arg, Asn, Gly, His, Lys, Ser, or Tyr;
$X_9$ is Ala, Arg, Asn, Gln, Leu, Met, Ser, Trp, Tyr, or Val; or Cys-$X_2$-$X_3$-$X_4$-$X_5$-$X_6$-$X_7$-$X_8$-$X_9$-$X_{10}$-$X_{11}$-Cys (SEQ ID NO:12),  (L)

wherein $X_2$ is Arg, Asn, Gln, Glu, His, Leu, Phe, Pro, Trp, Tyr, or Val (preferably Trp, Tyr, or Val);
$X_3$ is Arg, Asp, Gln, Gly, Ile, Lys, Phe, Thr, Trp or Tyr (preferably Asp);
$X_4$ is Ala, Arg, Asp, Glu, Gly, Leu, Ser, or Tyr (preferably Asp);
$X_5$ is Asp, Gln, Glu, Leu, Met, Phe, Pro, Ser, or Tyr (preferably Leu);
$X_6$ is Asp, Leu, Pro, Thr, or Val (preferably Leu or Thr);
$X_7$ is Arg, Gln, His, Ile, Leu, Lys, Met, Phe, Thr, Trp or Tyr (preferably Lys or Thr);
$X_8$ is Ala, Arg, Asn, Gln, Glu, His, Leu, Lys, Met, or Thr (preferably Arg or Leu);
$X_9$ is Ala, Asn, Gln, Gly, Leu, Lys, Phe, Pro, Thr, Trp, or Tyr (preferably Thr or Trp);
$X_{10}$ is Ala, Arg, Gln, His, Lys, Met, Phe, Pro, Thr, Trp, or Tyr (preferably Met or Phe);
$X_{11}$ is Arg, Gln, Glu, Gly, His, Leu, Met, Phe, Pro, Ser, Thr, Tyr, or Val (preferably Val);

wherein said polypeptides bind BLyS and/or BLyS-like polypeptides.

In additional preferred embodiments of the present invention, BLyS binding polypeptides comprise the following amino acid sequence M (SEQ ID NO:447):

Ala-$X_2$-$X_3$-$X_4$-Asp-$X_6$-Leu-Thr-$X_9$-Leu-$X_{11}$-$X_{12}$-$X_{13}$-$X_{14}$ (SEQ ID NO:447),  (M)

wherein $X_2$ is Asn, Ser, Tyr, Asp, Phe, Ile, Gln, His, Pro, Lys, Leu, Met, Thr, Val, Glu, Ala, Gly, Cys, or Trp (i.e., any amino acid except Arg; preferably Asn);
$X_3$ is Trp, Glu, Lys, Cys, Leu, Ala, Arg, Gly, or Ser (preferably Trp);
$X_4$ is Tyr, Phe, Glu, Cys, Asn (preferably Tyr);
$X_6$ is Pro, Ser, Thr, Phe, Leu, Tyr, Cys, or Ala (preferably Pro or Ser);
$X_9$ is Lys, Asn, Gln, Gly, or Arg (preferably Lys);
$X_{11}$ is Trp, Ser, Thr, Arg, Cys, Tyr, or Lys (preferably Trp);
$X_{12}$ is Leu, Phe, Val, Ile, or His (preferably Leu);
$X_{13}$ is Pro, Leu, His, Ser, Arg, Asn, Gln, Thr, Val, Ala, Cys, Ile, Phe, or Tyr (i.e., not Asp, Glu, Gly, Lys, Met, or Trp; preferably Pro); and
$X_{14}$ is Asp, Glu, Asn, Val, His, Gln, Arg, Gly, Ser, Tyr, Ala, Cys, Lys, Ile, Thr or Leu (i.e., not Phe, Met, Pro, or Trp; preferably Asp, Val or Glu).

Preferred embodiments are polypeptides comprising a core sequence of the formula N:

$X_1$-$X_2$-Asp-$X_4$-Leu-Thr-$X_7$-Leu-$X_9$-$X_{10}$ (SEQ ID NO:448),  (N)

wherein $X_1$ is Trp, Glu, Lys, Cys, Leu, Ala, Arg, Gly, or Ser (preferably Trp);
$X_2$ is Tyr, Phe, Glu, Cys, Asn (preferably Tyr);
$X_4$ is Pro, Ser, Thr, Phe, Leu, Tyr, Cys, or Ala (preferably Pro or Ser);
$X_7$ is Lys, Asn, Gln, Gly, or Arg (preferably Lys);
$X_9$ is Trp, Ser, Thr, Arg, Cys, Tyr, or Lys (preferably Trp); and
$X_{10}$ is Leu, Phe, Val, Ile, or His (preferably Leu).

Especially preferred BLyS binding polypeptides according to the present invention comprise the core peptide Trp-Tyr-Asp-Pro-Leu-Thr-Lys-Leu-Trp-Leu (SEQ ID NO:436).

The BLyS binding polypeptides described above may have additional amino acids attached at either or both of the N- and C-terminal ends.

BLyS binding polypeptide molecules of the invention may also have an amino terminal (N-terminal) capping or functional group, such as an acetyl group, which, for example, blocks the amino terminal amino group from undesirable reactions or is useful in linking the BLyS binding polypeptide to another molecule, matrix, resin, or solid support. BLyS binding polypeptides of the invention may also have a carboxy terminal (C-terminal) capping or functional group, such as an amide group, which, for example, blocks the C-terminal carboxyl group from undesirable reactions or provides a functional group useful in conjugating the binding polypeptide to other molecules, matrices, resins, or solid supports. Preferably, the N- and/or C-terminal capping groups are polypeptide linker molecules. An especially preferred C-terminal linker molecule that is useful for immobilizing a BLyS binding polypeptide of the invention to a solid support or chromatographic matrix material comprises the amino acid sequence Pro-Gly-Pro-Glu-Gly-Gly-Gly-Lys (SEQ ID NO:13). Another useful C-terminal linker, e.g., for fluoresceinating peptides, is Gly-Gly-Lys (see Table 15).

The invention also encompasses, BLyS binding polypeptides that have been modified, for example, to increase or decrease the stability of the molecule, while retaining the ability to bind BLyS and/or BLyS-like polypeptides. An example of a modified BLyS binding polypeptide of the invention is a polypeptide in which one of two cysteine residues is substituted with a non-naturally occurring amino acid that is capable of condensing with the remaining cysteine side chain to form a stable thioether bridge, thereby generating a cyclic BLyS binding polypeptide. Such cyclic thioether molecules of synthetic peptides may be routinely generated using techniques known in the art and described, e.g., in PCT publication WO 97/46251, incorporated herein by reference.

In another embodiment, the invention provides BLyS binding polypeptides of the invention attached, coupled, linked or adhered to a matrix or resin or solid support. Techniques for attaching linking or adhering polypeptides to matrices, resins and solid supports are well known in the art. Suitable matrices, resins or solid supports for these materials may be any composition known in the art to which binding polypeptides are commonly attached, coupled, linked, or adhered, including but not limited to, a chromatographic resin or matrix, such as SEPHAROSE-4 FF agarose beads, the wall or floor of a well in a plastic microtiter dish, such as used in an enzyme-liked immunosorbent assay (ELISA), or a silica based biochip. Materials useful as solid supports on which to immobilize binding polypeptides of the invention include, but are not limited to, polyacrylamide, agarose, silica, nitrocellulose, paper, plastic, nylon, metal, and combinations thereof. A BLyS binding polypeptide of the invention may be immobilized on a matrix, resin or solid support material by a non-covalent association or by covalent bonding, using techniques known in the art. Preferably, a BLyS binding polypeptide of the invention is immobilized on SEPHAROSE-4 FF agarose chromatographic material. More preferably, a BLyS binding polypeptide of the invention is coupled to a chromatography material such as SEPHAROSE-4FF (agarose). In an even more preferred embodiment, a BLyS binding polypeptide of the invention is coupled to a chromatography material using a linker molecule. A preferred linker molecule according to the present invention is a polypeptide comprising the amino acid sequence Pro-Gly-Pro-Glu-Gly-Gly-Gly-Lys (SEQ ID NO:13). Most preferably, the affinity chromatography material of the invention comprises a BLyS binding polypeptide comprising an amino acid sequence selected from the group consisting of SEQ ID NOs:163–172, which is linked to a chromatography material by a polypeptide linker molecule having the amino acid sequence Pro-Gly-Pro-Glu-Gly-Gly-Gly-Lys (SEQ ID NO:13). BLyS binding polypeptides of the invention attached, coupled, linked or adhered to a matrix or resin or solid support are useful for methods of detecting, isolating and purifying BLyS and/or BLyS like polypeptides, particularly for purification of BLyS and/or BLyS like polypeptides by affinity chromatography.

In certain preferred embodiments, the BLyS binding polypeptides of the present invention or phage displaying such binding polypeptides, irreversibly bind the BLyS protein in its native, soluble trimeric form.

In certain preferred embodiments, the BLyS binding polypeptides of the present invention or phage displaying such binding polypeptides, reversibly bind the BLyS protein in its native, soluble trimeric form.

BLyS binding polypeptides of the invention bind BLyS target protein with high affinity. In specific embodiments, BLyS binding polypeptides of the invention bind BLyS target proteins with a dissociation constant or $K_D$ of less than or equal to $5 \times 10^{-2}$ M, $10^{-2}$ M, $5 \times 10^{-3}$ M, $5 \times 10^{-4}$ M, $10^{-4}$ M, $5 \times 10^{-5}$ M, or $10^{-5}$ M. More preferably, BLyS binding polypeptides of the invention bind BLyS target proteins with a dissociation constant or $K_D$ less than or equal to $5 \times 10^{-6}$ M, $10^{-6}$ M, $5 \times 10^{-7}$ M, $10^{-7}$ M, $5 \times 10^{-8}$ M, or $10^{-8}$ M. Even more preferably, BLyS binding polypeptides of the invention bind BLyS target proteins with a dissociation constant or $K_D$ less than or equal to $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In certain preferred embodiments, BLyS binding polypeptides of the invention reversibly bind BLyS and/or BLyS-like polypeptides and release bound BLyS protein in an active form, preferably in the native soluble trimeric form, under specific release conditions. In specific embodiments, BLyS binding polypeptides of the invention bind BLyS target proteins with off-rates or $k_{off}$ greater than or equal to $10^{-10}$ s$^{-1}$, $5 \times 10^{-9}$ s$^{-1}$, $10^{-9}$ s$^{-1}$, $5 \times 10^{-8}$ s$^{-1}$, $10^{-8}$ s$^{-1}$, $5 \times 10^{-7}$ s$^{-1}$, $10^{-7}$ s$^{-1}$, $5 \times 10^{-6}$ s$^{-1}$, $10^{-6}$ s$^{-1}$, $5 \times 10^{-5}$ s$^{-1}$, $10^{-5}$ s$^{-1}$, $5 \times 10^{-4}$ s$^{-1}$, $10^{-4}$ s$^{-1}$, $5 \times 10^{-3}$ s$^{-1}$, $10^{-3}$ s$^{-1}$, $5 \times 10^{-2}$ s$^{311}$, $10^{-2}$ s$^{-1}$, $5 \times 10^{-1}$ s$^{-1}$, or $10^{-1}$ s$^{-1}$.

Binding experiments to determine $K_D$ and off-rates can be performed in a number of conditions including, but not limited to, [pH 6.0, 0.01% Tween 20], [pH 6.0, 0.1% gelatin], [pH5.0, 0.01% Tween 20], [pH9.0, 0.1% Tween 20], [pH6.0, 15% ethylene glycol, 0.01% Tween20], [pH5.0, 15% ethylene glycol, 0.01% Tween 20], and [pH9.0, 15% ethylene glycol, 0.01% Tween 20] The buffers in which to make these solutions can readily be determined by one of skill in the art, and depend largely on the desired pH of the final solution. Low pH solutions (<pH 5.5) can be made, for example, in citrate buffer, glycine-HCl buffer, or in succinic acid buffer. High pH solutions can be made, for example, in Tris-HCl, phosphate buffers, or sodium bicarbonate buffers. A number of conditions may be used to determine $K_D$ and off-rates for the purpose of determining, for example, optimal pH and/or salt concentrations.

In certain embodiments, BLyS binding polypeptides of the invention reversibly bind BLyS and/or BLyS-like polypeptides, preferably in the native soluble, trimeric form.

In preferred embodiments, BLyS binding polypeptides of the invention reversibly bind only the native soluble, trimeric form of BLyS.

In certain embodiments, BLyS binding polypeptides of the invention irreversibly bind BLyS and/or BLyS-like polypeptides, preferably in the native soluble, trimeric form.

In preferred embodiments, BLyS binding polypeptides of the invention irreversibly bind only the native soluble, trimeric form of BLyS.

In some screening or assay procedures, it is possible and more convenient to use recombinant bacteriophage that display a particular BLyS binding polypeptide instead of using isolated BLyS binding polypeptide. Such procedures include phage-based ELISA protocols and immobilization of phage displaying a binding polypeptide to chromatographic materials. Such screening assays and procedures are routine in the art and may be readily adapted for procedures using the recombinant bacteriophage of the present invention.

The invention also encompasses BLyS binding polypeptides that competitively inhibit the binding of a BLyS binding polypeptide disclosed herein (e.g., a polypeptide having the amino acid sequence of SEQ ID NOS: 163–168) for binding to BLyS. Competitive inhibition can be determined by any suitable method known in the art, for example, using the competitive binding assays described herein. In preferred embodiments, the polypeptide competitively inhibits the binding of a BLyS binding polypeptide disclosed herein (e.g., a polypeptide having the amino acid sequence of SEQ ID NOS: 163–168) to BLyS by at least 95%, at least 90%, at least 85%, at least 80%, at least 75%, at least 70%, at least 60%, or at least 50%. In a more preferred embodiment, the BLyS binding polypeptide competitively inhibits the binding of a BLyS binding polypeptide disclosed herein (e.g., a polypeptide having the amino acid sequence of SEQ ID NOS: 163–168) to the native soluble trimeric form of BLyS, by at least 95%, at least 90%, at least 85%, at least 80%, at least 75%, at least 70%, at least 60%, or at least 50%.

In a further embodiment, the present invention encompasses a composition of matter comprising isolated nucleic acids, preferably DNA, encoding a BLyS binding polypeptide of the invention. In a specific embodiment, nucleic acid molecules of the invention encode a BLyS binding polypeptide of the invention as provided in SEQ ID NOs:1–12, 20–172, and 186–444. In additional embodiments, nucleic acid molecules of the invention encode a polypeptide variant or fragment of a polypeptide having an amino acid sequence of SEQ ID NOs:1–12, 20–172, and 186–444. In a further additional embodiment, nucleic acid molecules of the invention encode a BLyS binding polypeptide, the complementary strand of which nucleic acid hybridizes to a polynucleotide sequence encoding a polypeptide described in Tables 1–8 and in Examples 2 and 5 (SEQ ID NOs:1–12, 20–172, and 186–444), under stringent conditions, e.g., hybridization to filter-bound DNA in 6× sodium chloride/sodium citrate (SSC) at about 45° C. followed by one or more washes in 0.2×SSC/0.1% SDS at about 50–65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel et al., eds., 1989, Current Protocols in Molecular Biology, Vol. I, Green Publishing Associates, Inc. and John Wiley & Sons, Inc., New York at pages 6.3.1–6.3.6 and 2.10.3).

The present invention also relates to recombinant vectors that include the isolated nucleic acid molecules encoding the BLyS binding polypeptides of the present invention (as well as fragments and variants thereof), and to host cells containing the recombinant vectors, as well as to methods of making such vectors and host cells. The invention further provides for the use of such recombinant vectors in the production of BLyS binding polypeptides by recombinant techniques.

The BLyS binding polypeptides, nucleic acids, transformed host cells, and genetically engineered viruses and phage of the invention (e.g., recombinant phage), have uses that include, but are not limited to, the detection, isolation, and purification of BLyS.

In another embodiment of the invention, recombinant bacteriophage displaying BLyS binding polypeptides on their surfaces are also provided. Such phage may be routinely generated using techniques known in the art and are useful, for example, as screening reagents and reagents for detecting BLyS.

Production and Modification of BLyS Binding Polypeptides

BLyS binding polypeptides of the invention may be produced by chemical synthesis, semi-synthetic methods, and recombinant DNA methodologies known in the art.

In certain embodiments, BLyS binding polypeptides of the present invention are produced by chemical or semi-synthetic methodologies known in the art (see, Kelley et al. in *Genetic Engineering Principles and Methods*, Setlow, J. K., ed. (Plenum Press, NY., 1990), vol. 12, pp. 1–19; Stewart et al., *Solid-Phase Peptide Synthesis*, W. H. Freeman Co., San Francisco, 1989). One advantage of these methodologies is that they allow for the incorporation of non-natural amino acid residues into the sequence of the BLyS binding polypeptide.

In preferred embodiments, BLyS binding polypeptides of the invention are chemically synthesized (see, e.g., Merrifield, *J. Am. Chem. Soc.*, 85: 2149 (1963); Houghten, *Proc. Natl. Acad. Sci. USA*, 82: 5132 (1985)). For example, polypeptides can be synthesized by solid phase techniques, cleaved from the resin, and purified by preparative high performance liquid chromatography (see, e.g., Creighton, *Proteins: Structures and Molecular Properties* (W. H. Freeman and Co., N.Y., 1983), pp. 50–60). BLyS binding polypeptides can also be synthesized by use of a peptide synthesizer. The composition of the synthetic polypeptides may be confirmed by amino acid analysis or sequencing (e.g., the Edman degradation procedure; see Creighton, *Proteins: Structures and Molecular Properties* (W. H. Freeman and Co., N.Y., 1983), pp. 34–49). Furthermore, if desired, BLyS binding polypeptides of the invention may contain non-classical amino acids or chemical amino acid analogs, which can routinely be introduced during chemical synthesis as a substitution or addition into the BLyS binding polypeptides of the invention. Non-classical amino acids include, but are not-limited to, the D-isomers of the common amino acids, 2,4-diaminobutyric acid, alpha-aminoisobutyric acid, 4-aminobutyric acid (4Abu), 2-aminobutyric acid (Abu), 6-aminohexanoic acid (epsilon-Ahx), 2-aminoisobutyric acid (Aib), 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine (bAla), fluoro-amino acids, designer amino acids such as beta-methyl amino acids, Calpha-methyl amino acids, Nalpha-methyl amino acids, and amino acid analogs in general. Furthermore, the amino acid can be D (dextrorotary) or L (levorotary).

Solid phase peptide synthesis begins at the carboxy (C) terminus of the putative polypeptide by coupling a protected amino acid to a suitable resin, which reacts with the carboxyl group of the C-terminal amino acid to form a bond that is readily cleaved later, for example, a halomethyl resin such as chloromethyl resin, bromomethyl resin, hydroxymethyl resin, aminomethyl resin, benzhydrylamine resin, or t-alkyloxycarbonyl-hydrazide resin. After removal of the α-amino protecting group with, for example, trifluoroacetic acid (TFA) in methylene chloride and neutralization with, for example TEA, the next cycle in the synthesis is ready to proceed. The remaining α-amino and, if necessary, side-chain-protected amino acids are then coupled sequentially in the desired order by condensation to obtain an intermediate compound connected to the resin. Alternatively, some amino acids may be coupled to one another forming an oligopeptide prior to addition to the growing solid phase polypeptide chain.

The condensation between two amino acids, or an amino acid and a peptide, or a peptide and a peptide can be carried out according to condensation methods known in the art, including but not limited to, the azide method, mixed acid anhydride method, DCC (dicyclohexylcarbodiimide) method, active ester method (p-nitrophenyl ester method, BOP [benzotriazole-1-yl-oxy-tris (dimethylamino) phosphonium hexafluorophosphate] method, N-hydroxysuccinic acid imido ester method), and Woodward reagent K method.

Common to chemical synthesis of peptides is the protection or capping (blocking) of the reactive side chain groups of the various amino acid residues with suitable protecting or capping groups at that site until the group is ultimately removed after the polypeptide chain has been completely assembled. Also common is the protection or capping of the α-amino group on an amino acid or a fragment while that entity reacts at the carboxyl group followed by the selective removal of the α-amino-protecting group to allow subsequent reaction to take place at that location. Accordingly, during synthesis, intermediate compounds are produced which includes each of the amino acid residues located in the desired sequence in the peptide chain with various of these residues having side-chain protecting or capping groups. These protecting or capping groups on amino acid side chains are then removed substantially at the same time so as to produce the desired resultant product following purification.

The typical protective, capping, or blocking groups for α- and ε-amino side chain groups found in amino acids are exemplified by benzyloxycarbonyl (Z), isonicotinyloxycarbonyl (iNOC), O-chlorobenzyloxycarbonyl [Z(NO$_2$)], p-methoxybenzyloxycarbonyl [Z(OMe)], t-butoxycarbonyl (Boc), t-amyioxycarbonyl (Aoc), isobornyloxycarbonyl, adamatyloxycarbonyl, 2-(4-biphenyl)-2-propyloxycarbonyl (Bpoc), 9-fluorenylmethoxycarbonyl (Fmoc), methylsulfonyiethoxycarbonyl (Msc), trifluoroacetyl, phthalyl, formyl, 2-nitrophenylsulphenyl (NPS), diphenylphosphinothioyl (Ppt), dimethylophosphinothioyl (Mpt), and the like.

Protective, capping, or blocking groups for the carboxyl group of amino acids include, for example, benzyl ester (OBzl), cyclohexyl ester (Chx), 4-nitrobenzyl ester (ONb), t-butyl ester (Obut), 4-pyridylmethyl ester (OPic), and the like. It is usually also desirable that side chain groups of specific amino acids such as arginine, cysteine, and serine, are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2,6-dimethylbenzenesulfonyl (Mds), 1,3,5-trimethylphenylsulfonyl (Mts), and the like. The thiol group in cysteine may be protected with p-methoxybenzyl, triphenylmethyl, acetylaminomethyl ethylcarbamoyl, 4-methylbenzyl, 2,4,6-trimethy-benzyl (Tmb), etc., and the hydroxyl group in the serine can be protected with benzyl, t-butyl, acetyl, tetrahydropyranyl, etc.

After the desired amino acid sequence has been completed, the intermediate polypeptide is removed from the resin support by treatment with a reagent, such as liquid HF and one or more thio-containing scavengers, which cleaves the peptide molecule from the resin and all the remaining side-chain protecting groups. Following HF cleavage, the protein sequence is washed with ether, transferred to a large volume of dilute acetic acid, and stirred at pH adjusted to about 8.0 with ammonium hydroxide. Upon pH adjustment, the polypeptide takes its desired conformational arrangement.

By way of example but not by way of limitation, polypeptides of the invention can be chemically synthesized and purified as follows: Peptides can be synthesized by employing the N-alpha-9-fluorenylmethyloxycarbonyl or Fmoc solid phase peptide synthesis chemistry using a Rainin Symphony Multiplex Peptide Synthesizer. The standard cycle used for coupling of an amino acid to the peptide-resin growing chain generally includes: (1) washing the peptide-resin three times for 30 seconds with N,N-dimethylformamide (DMF); (2) removing the Fmoc protective group on the amino terminus by deprotection to with 20% piperdine in DMF by two washes for 15 minutes each, during which process mixing is effected by bubbling nitrogen through the reaction vessel for one second every 10 seconds to prevent peptide-resin settling; (3) washing the peptide-resin three times for 30 seconds with DMF; (4) coupling the amino acid to the peptide resin by addition of equal volumes of a 250 mM solution of the Fmoc derivative of the appropriate amino acid and an activator mix consisting or 400 mM N-methylmorpholine and 250 mM (2-(1H-benzotriazol-1–4))-1,1,3,3-tetramethyluronium hexafluorophosphate (HBTU) in DMF; (5) allowing the solution to mix for 45 minutes; and (6) washing the peptide-resin three times for 30 seconds of DMF. This cycle can be repeated as necessary with the appropriate amino acids in sequence to produce the desired peptide. Exceptions to this cycle program are amino acid couplings predicted to be difficult by nature of their hydrophobicity or predicted inclusion within a helical formation during synthesis. For these situations, the above cycle can be modified by repeating step 4 a second time immediately upon completion of the first 45 minute coupling step to "double couple" the amino acid of interest. Additionally, in the first coupling step in peptide synthesis, the resin can be allowed to swell for more efficient coupling by increasing the time of mixing in the initial DMF washes to three 15 minute washes rather than three 30 second washes.

After peptide synthesis, the peptide can be cleaved from the resin as follows: (1) washing the peptide-resin three times for 30 seconds with DMF; (2) removing the Fmoc protective group on the amino terminus by washing two times for 15 minutes it 20% piperdine in DMF; (3) washing the peptide-resin three times for 30 seconds with DMF; and (4) mixing a cleavage cocktail consisting of 95% trifluoroacetic acid (TFA), 2.4% water, 2.4% phenol, and 0.2% triisopropysilane with the peptide-resin for two hours, then filtering the peptide in the cleavage cocktail away from the resin, and precipitating the peptide out of solution by addition of two volumes of ethyl ether. Specifically, to isolate the peptide, the ether-peptide solution can be allowed to sit at –20° C. for 20 minutes, then centrifuged at 6,000×G for 5 minutes to pellet the peptide, and the peptide can be washed three times with ethyl ether to remove residual cleavage cocktail ingredients. The final peptide product can be purified by reversed phase high pressure liquid chromatography (RP-HPLC) with the primary solvent consisting of 0.1% TFA and the eluting buffer consisting of 80% acetonitrile and 0.1% TFA. The purified peptide can then be lyophilized to a powder.

In other specific embodiments, branched versions of the BLyS binding polypeptides described herein are provided, e.g., by substituting one or more amino acids within the BLyS binding polypeptide sequence with an amino acid or amino acid analog with a free side chain capable of forming a peptide bond with one or more amino acids (and thus capable of forming a "branch").

Branched peptides may be prepared by any method known in the art for covalently linking any naturally occurring or synthetic amino acid to any naturally occurring or synthetic amino acid in a peptide chain which has a side chain group able to react with the amino or carboxyl group on the amino acids so as to become covalently attached to the peptide chain. In particular, amino acids with a free amino side chain group, such as, but not limited to, diaminobutyric acid, lysine, arginine, ornithine, diaminopropionic acid and citrulline, can be incorporated into a peptide so that an amino acid can form a branch therewith, for example, by forming a peptide bond to the free amino side group, from that residue. Alternatively, amino acids with a free carboxyl side chain group, such as, but not limited to, glutamic acid, aspartic acid and homocitrulline, can be incorporated into the peptide so that an amino acid can form a branch therewith, for example, by forming a peptide bond to the free carboxyl side group, from that residue. The amino acid forming the branch can be linked to a side chain group of an amino acid in the peptide chain by any type of covalent bond, including, but not limited to, peptide bonds, ester bonds and disulfide bonds. In a specific embodiment, amino acids, such as those described above, that are capable of forming a branch point, are substituted for BLyS binding polypeptide residues within a peptide including a BLyS binding polypeptide sequence.

Branched peptides can be prepared by any method known in the art. For example, but not by way of limitation, branched peptides can be prepared as follows: (1) the amino acid to be branched from the main peptide chain can be purchased as an N-alpha-tert-butyloxycarbonyl (Boc) protected amino acid pentafluorophenyl (Opfp) ester and the residue within the main chain to which this branched amino acid will be attached can be an N-Fmoc-alpha-gamma-diaminobutyric acid; (2) the coupling of the Boc protected amino acid to diaminobutyric acid can be achieved by adding 5 grams of each precursor to a flask containing 150 ml DMF, along with 2.25 ml pyridine and 50 mg dimethylaminopyridine and allowing the solution to mix for 24 hours; (3) the peptide can then be extracted from the 150 ml coupling reaction by mixing the reaction with 400 ml dichlormethane (DCM) and 200 ml 0.12N HCl in a 1 liter separatory funnel, and allowing the phases to separate, saving the bottom aqueous layer and re-extracting the top layer two more times with 200 ml 0.12N HCl; (4) the solution containing the peptide can be dehydrated by adding 2–5 grams magnesium sulfate, filtering out the magnesium sulfate, and evaporating the remaining solution to a volume of about 2–5 ml; (5) the dipeptide can then be precipitated by addition of ethyl acetate and then 2 volumes of hexanes and then collected by filtration and washed two times with cold hexanes; and (6) the resulting filtrate can be lyophilized to achieve a light powder form of the desired dipeptide. Branched peptides prepared by this method will have a substitution of diaminobutyric acid at the amino acid position which is branched. Branched peptides containing an amino acid or amino acid analog substitution other than diaminobutyric acid can be prepared analogously to the procedure described above, using the N-Fmoc coupled form of the amino acid or amino acid analog.

In a preferred embodiment, the BLyS binding polypeptide of the invention is a cyclic peptide. Cyclization can be, for example, but not by way of limitation, via a disulfide bond between two cysteine residues or via an amide linkage. For example, but not by way of limitation, disulfide bridge formation can be achieved by (1) dissolving the purified peptide at a concentration of between 0.1–0.5 mg/ml in 0.01 M ammonium acetate, pH 7.5; (2) adding to the dissolved peptide 0.01 M potassium ferricyanide dropwise until the solution appears pale yellow in color and allowing this solution to mix for 24 hours; (3) concentrating the cyclized peptide to 5–10 ml of solution, repurifying the peptide by reverse phase-high pressure liquid chromatography (RP-HPLC) and finally lyophilizing the peptide. In a specific embodiment, in which the peptide does not contain two appropriately situated cysteine residues, cysteine residues can be introduced at the amino-terminus and/or carboxy-terminus and/or internally such that the peptide to be cyclized contains two cysteine residues spaced such that the residues can form a disulfide bridge. Alternatively, a cyclic peptide can be obtained by generating an amide linkage using, for example but not limited to, the following protocol: An allyl protected amino acid, such as aspartate, glutamate, asparagine or glutamine, can be incorporated into the peptide as the first amino acid, and then the remaining amino acids are coupled on. The allyl protective group can U be removed by a two hour mixing of the peptide-resin with a solution of tetrakistriphenylphosphine palladium (0) in a solution of chloroform containing 5% acetic acid and 2.5% N-methylmorpholine. The peptide resin can be washed three times with 0.5% N,N-diisopropylethylamine (DIEA) and 0.5% sodium diethyldithiocabamate in DMF. The amino terminal Fmoc group on the peptide chain can be removed by two incubations for 15 minutes each in 20% piperdine in DMF, and washed three times with DMF for 30 seconds each. The activator mix, N-methylmorpholine and HBTU in DMF, can be brought onto the column and allowed to couple the free amino terminal end to the carboxyl group generated by removal of the allyl group to cyclize the peptide. The peptide can be cleaved from the resin as described in the general description of chemical peptide synthesis above and the peptide purified by reverse phase-high pressure liquid chromatography (RP-HPLC). In a specific embodiment, in which the peptide to be cyclized does not contain an allyl protected amino acid, an allyl protected amino acid can be introduced into the sequence of the peptide, at the amino-terminus, carboxy-terminus or internally, such that the peptide can be cyclized.

In addition, according to certain embodiments, it is preferable that the BLyS binding polypeptides of the invention are produced having or retaining an amino terminal (N-terminal) and/or a carboxy terminal (C-terminal) capping group, which may protect the N-terminal or C-terminal amino acid from undesirable chemical reactions during use or which may permit further conjugations or manipulations of the binding polypeptide, for example, in conjugating the binding polypeptide to a chromatographic support resin or matrix or to another peptide to tether the binding polypeptide to a resin or support. Such N-terminal and C-terminal groups may also be used to label or tag the binding polypeptide to detect bound complexes or to locate the binding polypeptide (whether bound or unbound to a BLyS target protein) for example, at some point in a separation procedure. Accordingly, a BLyS binding polypeptide of the invention synthesized in its final form for use in a detection or separation procedure may contain an N-terminal and/or a C-terminal capping group. A particularly preferred N-terminal capping group, which may be present or retained in binding polypeptides of the invention, is an acetyl group (Ac). A particularly preferred C-terminal capping group, which may be present or retained in binding polypeptides of the invention, is an amide group. In a further preferred embodiment, the BLyS binding polypeptides of the invention have an acetyl group as an N-terminal capping group and an amide group as a C terminal capping group.

The BLyS binding polypeptides of the invention may also be prepared commercially by companies providing polypeptide synthesis as a service (e.g., BACHEM Bioscience, Inc., King of Prussia, Pa.; Quality Controlled Biochemicals, Inc., Hopkinton, Mass.).

The nucleic acid sequence encoding a BLyS binding polypeptide of the invention can be produced and isolated using well-known techniques in the art. In one example, nucleic acids encoding the BLyS binding polypeptides of the invention are chemically synthesized based on knowledge of the amino acid sequence of the BLyS binding polypeptide (preferably the sequence is codon optimized to the host system in which the polypeptide will be expressed). In another example, nucleic acids encoding a BLyS binding polypeptide are obtained by screening an expression library (e.g., a phage display library) to identify phage expressing BLyS binding polypeptides, and isolating BLyS binding polypeptide encoding nucleic acid sequences from the identified library member (e.g., via polymerase chain reaction methodology using primers flanking the polypeptide encoding sequences).

The present invention also relates to vectors which include nucleic acid sequences encoding the BLyS binding polypeptides of the invention, host cells which are genetically engineered with the recombinant vectors, or which are otherwise engineered to produce the polypeptides of the invention, and the production of BLyS binding polypeptides, or fragments thereof, by recombinant, chemical or synthetic techniques.

Thus, according to the present invention, BLyS binding polypeptidess can also be obtained by recombinant expression techniques. (See, e.g., Sambrook et al., 1989, *Molecular Cloning, A Laboratory Manual*, 2d Ed., Glover, D. M. (ed.), (Cold Spring Harbor Laboratory, Cold Spring Harbor, N.Y., 1989); *DNA Cloning: A Practical Approach* (MRL Press, Ltd., Oxford, U.K., 1985), Vols. I, II.

To produce a recombinant BLyS binding polypeptide, a nucleic acid sequence encoding the BLyS binding polypeptide is operatively linked to a promoter such that the BLyS binding polypeptide is produced from said sequence. For example, a vector can be introduced into a cell, within which cell the vector or a portion thereof is expressed, producing the BLyS binding polypeptides. In a preferred embodiment, the nucleic acid is DNA if the source of RNA polymerase is DNA-directed RNA polymerase, but the nucleic acid may also be RNA if the source of polymerase is RNA-directed RNA polymerase or if reverse transcriptase is present in the cell or provided to produce DNA from the RNA. Such a vector can remain episomal or, become chromosomally integrated, as long as it can be transcribed to produce the desired RNA. Such vectors can be constructed by recombinant DNA technology methods standard in the art. Vectors can be bacteriophage, plasmid, viral, retroviral, or others known in the art, used for replication and expression in bacterial, fungal, plant, insect or mammalian cells. Retroviral vectors may be replication competent or replication defective. In the latter case, viral propagation generally will occur only in complementing host cells. Introduction of the vector construct into the host cell can be effected by techniques known in the art which include, but are not limited to, calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, for example, stabilization or simplified purification of expressed recombinant product.

In one embodiment, the nucleic acid encoding a BLyS binding polypeptide of the invention is operatively associated with an appropriate heterologous regulatory element (e.g., promoter or enhancer), such as, the phage lambda PL promoter, the *E. coli* lac, trp, phoA, and tac promoters, the SV40 early and late promoters, and promoters of retroviral LTRs, to name a few. Other suitable promoters will be known to the skilled artisan.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells (e.g., *Saccharomyces cerevisiae* or *Pichia pastoris* (ATCC Accession No. 201178)); insect cells such as Drosophila S2 and Spodoptera Sf9 cells; animal cells such as CHO, COS, 293, NSO and Bowes melanoma cells; and plant cells. Appropriate culture mediums and conditions for the above-described host cells are known in the art.

The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of at the inserted nucleic acid sequences encoding the BLyS polypeptides of the invention, or modifies and processes the Blys binding polypeptide in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed. Selection of appropriate vectors and promoters for expression in a host cell is a well-known procedure and the requisite techniques for expression vector construction, introduction of the vector into the host and expression in the host are routine skills in the art.

Useful expression vectors for bacterial use are constructed by inserting a structural DNA sequence encoding a desired protein together with suitable translation initiation and termination signals in operable reading phase with a functional promoter. The vector will preferably comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium*, and various species within the genera Pseudomonas, Streptomyces, and Staphylococcus, although others may also be employed as a matter of choice. As a representative, but i nonlimiting example, useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed. Among vectors preferred for use in bacteria are pHE4–5 (ATCC Accession No. 209311) and variations thereof), pQE70, pQE60 and pQE-9, available from QIAGEN, Inc.; pBS vectors, Phagescript vectors, Bluescript vectors, pNH8A, pNH16a, pNH18A, pNH46A, available from Stratagene; and ptrc99a, pKK223–3, pKK233-3, pDR540, pRIT5 available from Pharmacia. Preferred expression vectors for use in yeast systems include, but are not limited to, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, pPIC9K, and PAO815 (all available from Invitrogen, Carlsbad, Calif.). Among preferred eukaryotic vectors are pWL-NEO, pSV2CAT, pOG44, pXT1 and pSG available from Stratagene; and pSVK3, pBPV, pMSG and pSVL (available from Pharmacia). Other suitable vectors will be readily apparent to the skilled artisan.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

In one embodiment, the yeast *Pichia pastoris* is used to express a BLyS binding polypeptide in a eukaryotic system. *Pichia pastoris* is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis et al., *Mol. Cell. Biol.*, 5:1111–21 (1985); Koutz et al., *Yeast*, 5:167–77 (1989); Tschopp et al., *Nucl. Acids Res.*, 15:3859–76 (1987). Thus, a heterologous coding sequence, such as, for example, a polynucleotide encoding a BLyS binding polypeptide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a BLyS binding polypeptide of the invention, as set forth herein, in a Pichea yeast system essentially as described in "*Pichia Protocols: Methods in Molecular Biology*," D. R. Higgins and J. Cregg, eds. (The Humana Press, Totowa, N.J., 1998). This expression vector allows expression and secretion of a BLyS binding polypeptide of the invention by virtue of the strong AOX1 promoter linked to the *Pichia pastoris* alkaline phosphatase (PHO) secretory signal peptide (i.e., leader) located upstream of a multiple cloning site.

Many other yeast vectors may be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In one embodiment, high-level expression of a heterologous coding sequence, such as, for example, a nucleic acid encoding a BLyS binding polypeptide of the invention, may be achieved by cloning the heterologous nucleic acid sequence of the invention into an expression vector such as, for example, pGAPZ or pGAPZalpha, and growing the yeast culture in the absence of methanol.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Various mammalian cell culture systems can also be employed to express recombinant protein. Examples of mammalian expression systems include the COS-7 lines of monkey kidney fibroblasts, described by Gluzman (*Cell*, 23:175 (1981)), and other cell lines capable of expressing a compatible vector, for example, the C127, 3T3, CHO, 293, NSO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The host cells described herein may be used in a conventional manner to produce the gene product encoded by the recombinant sequence. Alternatively, cell-free translation systems can also be employed to produce the polypeptides of the invention using RNAs derived from the DNA constructs of the present invention.

The polypeptides of the invention may be expressed or synthesized in a modified form, such as a fusion protein (comprising the polypeptide joined via a peptide bond to a heterologous protein sequence (of a different protein)), and may include not only secretion signals, but also additional heterologous functional regions. Such a fusion protein can be made by ligating polynucleotides of the invention and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. Particular mention is made of the hexa-histidine polypeptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA*, 86:821–824 (1989), for instance, hexa-histidine provides for convenient purification of the fusion protein. Other peptide tags useful for purification include, but are not limited to, the hemagglutinin"HA" tag, which corresponds to an epitope derived from the influenza hemagglutinin protein (Wilson et al., *Cell*, 37:767 (1984)) and the "flag" tag (DYKDDDDK, (SEQ ID NO:183) Stratagene, La Jolla, Calif.).

In one embodiment, nucleic acids encoding a BLyS binding polypeptides of the invention may be fused to the pelB pectate lyase signal sequence to increase the efficiency to expression and purification of such polypeptides in Gram-negative bacteria. See, U.S. Pat. Nos. 5,576,195 and 5,846,818, the contents of which are herein incorporated by reference in their entireties.

Polypeptides of the present invention include products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The invention encompasses BLyS binding polypeptides which are modified during or after synthesis or translation, e.g., by glycosylation, acetylation, benzylation, phosphorylation, amidation, pegylation, formylation, derivatization by known protecting/blocking groups, proteolytic cleavage, linkage to an antibody molecule, hydroxylation, iodination, methylation, myristoylation, oxidation, pegylation, proteolytic processing, phosphorylation, prenylation, racemization, selenoylation, sulfation, ubiquitination, etc. (See, for instance, Creighton, *Proteins: Structures and Molecular Properties*, 2d Ed. (W. H. Freeman and Co., N.Y., 1992); *Postranslational Covalent Modification of Proteins*, Johnson, ed. (Academic Press, New York, 1983), pp. 1–12; Seifter et al., *Meth. Enzymol.*, 182:626–646 (1990); Rattan et al., *Ann. NY Acad. Sci.*, 663:48–62 (1992).) In specific embodiments, the peptides are acetylated at the N-terminus and/or amidated at the C-terminus.

In further embodiments, BLyS binding polypeptides of the invention containing two or more residues that have the potential to interact, such as for example, two cysteine residues in a polypeptide, may be treated under oxidizing conditions or other conditions that promote interaction of these residues (e.g., disulfide bridge formation).

Further BLyS binding polypeptide modifications encompassed by the invention include, for example, any of numerous chemical modifications carried out by known techniques, including but not limited to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Additional post-translational /post-synthesis modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression.

Also provided by the invention are chemically modified derivatives of BLyS binding polypeptides of the invention which may provide additional advantages such as increased affinity, decreased off-rate, solubility, stability and in vivo or in vitro circulating time of the polypeptide, or decreased immunogenicity (see, U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any, on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.*, 56:59–72 (1996); Vorobjev et al., *Nucleosides Nucleotides*, 18:2745–2750 (1999); and Caliceti et al., *Bioconjug. Chem.*, 10:638–646 (1999), the disclosures of each of which are incorporated herein by reference.

The polyethylene glycol molecules (or other chemical moieties) should be attached to the BLyS binding poypeptide with consideration of effects on functional domains of the polypeptide. There are a number of attachment methods available to those skilled in the art, e.g., EP 0 401 384, herein incorporated by reference (coupling PEG to G-CSF), see also Malik et al., *Exp. Hematol.*, 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include, for example, lysine residues and the N-terminal amino acid residues; those having a free carboxyl group may include aspartic acid residues, glutamic acid residues, and the C-terminal amino acid residue. Sulfhydryl groups may also be used as a reactive group for attaching the polyethylene glycol molecules. In a preferred embodiment, the polyethylene glycol molecule is attached at an amino group, such as attachment at the N-terminus or to a lysine side chain amino group.

As suggested above, polyethylene glycol may be attached to polypeptides via linkage to any of a number of amino acid residues. For example, polyethylene glycol can be linked to a polypeptide via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the polypeptide or to more than one type of amino acid residue (e.g., lysine, histidine, aspartic acid, glutamic acid, cysteine and combinations thereof) of the polypeptide.

One may specifically desire proteins chemically modified at the N-terminus. Using polyethylene glycol as an illustration, one may select from a variety of polyethylene glycol molecules (by molecular weight, branching, etc.), the proportion of polyethylene glycol molecules to polypeptide molecules in the reaction mix, the type of pegylation reaction to be performed, and the method of obtaining the selected N-terminally pegylated polypeptide. The method of obtaining the N-terminally pegylated preparation (i.e., separating this moiety from other monopegylated moieties if necessary) may be by purification of the N-terminally pegylated material from a population of pegylated polypeptide molecules. Selective N-terminal modification of proteins may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As indicated above, pegylation of the polypeptides of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.*, 9:249–304 (1992); Francis et al., *Intern. J. of Hematol.*, 68:1–18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of polypeptides without an intervening linker employs tresylated MPEG, which is produced by the modification of monomethoxy polyethylene glycol (PEG) using tresylchloride ($ClSO_2CH_2CF_3$). Upon reaction of protein with tresylated MPEG, polyethylene glycol is directly attached to amine groups of the polyeptide. Thus, the invention includes polypeptide-polyethylene glycol conjugates produced by reacting polypeptides of the invention with a polyethylene glycol molecule having a 2,2,2-trifluoreothane sulphonyl group.

Polyethylene glycol can also be attached to polypeptides using a number of different intervening linkers. For example, U.S. Pat. No. 5,612,460, the entire disclosure of which is incorporated herein by reference, discloses urethane linkers for connecting polyethylene glycol to polypeptides. Polypeptide-polyethylene glycol conjugates wherein the polyethylene glycol is attached to the polypeptide by a linker can also be produced by reaction of polypeptides with compounds such as MPEG-succinimidylsuccinate, MPEG activated with 1,1'-carbonyldiimidazole, MPEG-2,4,5-trichlorophenylcarbonate, MPEG-p-nitrophenolcarbonate, and various MPEG-succinate derivatives. A number of additional polyethylene glycol derivatives and reaction chemistries for attaching polyethylene glycol to polypeptides are described in WO 98/32466, the entire disclosure of which is incorporated herein by reference. Pegylated BLyS binding polypeptide products produced using the reaction chemistries set out herein are included within the scope of the invention.

The number of polyethylene glycol moieties attached to each polypeptide of the invention (i.e., the degree of substitution) may also vary. For example, the pegylated polypeptides of the invention may be linked, on average, to 1, 2, 3, 4, 5, 6, 7, 8, 9, 10, 12, 15, 17, 20, or more polyethylene glycol molecules. Similarly, the average degree of substitution may range within ranges such as 1–3, 2–4, 3–5, 4–6, 5–7, 6–8, 7–9, 8–10, 9–11, 10–12, 11–13–15, 14–16, 15–17, 16–18, 17–19, or 18–20 polyethylene glycol moieties per polypeptide molecule. Methods for determining the degree of substitution are discussed, for example, in Delgado et al., *Crit. Rev. Thera. Drug Carrier Sys.*, 9:249–304 (1992).

BLyS Binding Polypeptide Multimers, Conjugates and Fusions

The present invention encompasses multivalent BLyS binding polypeptides. BLyS binding polypeptides may be monomeric, dimeric, trimeric, or higher-order multimers. In a preferred embodiment multivalent BLyS binding polypeptides are homotrimeric. In another preferred embodiment a homotrimeric BLyS binding polypeptide binds a single homotrimeric BLyS.

In another preferred embodiment, monomeric or multimeric BLyS binding polypeptides are conjugated with another polypeptide or other chemical compound. For example, BLyS binding polypeptide(s) may be conjugated to a radioactive or other toxic compound so as to target and destroy cells expressing BLyS.

The present invention also encompasses heteromeric multimers comprised of one or more BLyS binding polypeptides and one or more non-BLyS binding polypeptides or other chemical moieties. Such heteromeric multimers may be monomeric, dimeric, trimeric, tetrameric, pentameric, or higher-order multimers. Heteromeric BLyS binding multimers may be used to target, bind, inhibit, and/or activate responses in cells expressing BLyS and receptors for the heterologous, non-BLyS binding polypeptide or other chemical moiety. Such activated responses may include, for example, apoptosis or other biologically and chemically mediated forms of cell destruction. Heteromeric BLyS binding multimers may also be used to target BLyS expressing cells so as to introduce a desired molecule or compound to the cells. For example, a heteromeric BLyS binding multimer may be conjugated with a radioactive or otherwise toxic compound so as to kill BLyS expressing cells. As an alternative example, a heteromeric BLyS binding and Adenovirus-binding multimer could be used to specifically target and introduce adenovirus-mediated gene therapeutics into BLyS expressing cells.

BLyS binding polypeptide multimers may be fused or conjugated as homopolymers and heteropolymers using methods known in the art. In a preferred embodiment BLyS binding polypeptides are linked as homomultimers wherein the linker or linkers provide sufficient length and flexibility such that each BLyS binding polypeptide may simultaneously bind an individual BLyS molecule. In another preferred embodiment BLyS binding polypeptides are linked as heteromultimers wherein the linker or linkers provide sufficient length and flexibility such that each BLyS binding polypeptide may simultaneously bind individual BLyS molecules and the heterologous polypeptide or chemical moiety may simultaneously bind to its target. Numerous examples of suitable linker molecules are known in the art. (See, for example, Todorovska et al., *J. Immunol. Methods*, 248(1–2):47–66 (2001); Mehvar, *J. Control Release*, 69(1): 1–25 (2000); Francis et. al., *Int. J. Hematol.*, 68(1):1–18 (1998).) In specific embodiments, the linker is a member selected from the group consisting of: (a) a peptide linker; (b) a glutamate linker; and (c) a polyethylene glycol linker. The length of linkers to be used according to the methods of the invention may routinely be determined using techniques known in the art. In specific embodiments, the linker is 5–60 angstroms in length. In other embodiments, the linker is 10–50, 10–40, 10–30, or 10–20 angstroms in length. In further embodiments, the linker is about 5, 10, 15, 20, 25, 30, 35, 40, 45, 50, 55, 60, 65, 70, 75, 80, 85, 90, 95, or 100 angstroms in length. In this context "about" includes the recited length, and/or lengths that are larger or smaller by several (5, 4, 3, 2, or 1) angstroms. In other embodiments, the linker is at least 5, 10, 15, 20, 25, 30, 35, 40, 45, 50, 55, 60, 65, 70, 75, 80, 85, 90, 95, or 100 angstroms in length.

In a preferred embodiment, BLyS binding polypeptides may be fused with human serum albumin (HA). See, e.g., U.S. application Ser. No. 09/833,245, filed Apr. 12, 2001, which is hereby incorporated by reference herein. In one embodiment, the albumin fusion protein comprises HA as the N-terminal portion, and a BLyS binding polypeptide as the C-terminal portion. In another embodiment the albumin fusion protein comprise HA as the C-terminal portion, and a BLyS binding polypeptide as the N-terminal portion.

In other embodiments, the albumin fusion protein has a BLyS binding polypeptide fused to both the N-terminus and the C-terminus of albumin. In one preferred embodiment, the BLyS binding polypeptides fused at the N- and C-termini are the same BLyS binding polypeptides. In another preferred embodiment, the BLyS binding polypeptides fused at the N- and C-termini are different BLyS binding polypeptides. In another preferred embodiment, a BLyS binding polypeptide is fused at either the N- or C-terminus of HA and a different (non-BLyS binding) polypeptide is fused at either the C- or N-terminus, respectively.

In addition to albumin fusion proteins in which the BLyS binding polypeptide(s) is (are) fused to the N-terminus and/or C-terminus of HA, BLyS binding polypeptide/albumin fusion proteins of the invention may also be produced by inserting the BLyS binding polypeptide into an internal region or regions of HA. For instance, within the protein sequence of the HA molecule a number of loops or turns exist between the end and beginning of α-helices, which are stabilized by disulphide bonds (see FIGS. 9–11 in U.S. application Ser. No. 09/833,245). The loops, as determined from the crystal structure of HA (FIG. 13 of U.S. application Ser. No. 09/833,245) (PDB identifiers 1A06, 1BJ5, 1BKE, 1BM0, 1E7E to 1E7I and 1UOR) for the most part extend away from the body of the molecule. These loops are useful for the insertion, or internal fusion, of therapeutically active peptides (particularly those requiring a secondary structure to be functional) or therapeutic proteins, to essentially generate an albumin molecule with specific biological activity.

Loops in human albumin structure into which binding polypeptides of the invention may be inserted to generate albumin fusion proteins of the invention include: Val54–Asn61, Thr76–Asp89, Ala92-Glu100, Gln170-Ala176, His 247-Glu252, Glu 266-Glu277, Glu 280-His288, Ala362-Glu368, Lys439-Pro447, Val462–Lys475, Thr478-Pro486, and Lys560-Thr566. In more preferred embodiments, polypeptides of the invention are inserted into the Val54–Asn61, Gln170-Ala176, and/or Lys560-Thr566 loops of mature human serum albumin (SEQ ID NO:445).

In specific embodiments, BLyS binding polypeptides of the invention are attached to macrocyclic chelators useful for conjugating radiometal ions, including but not limited to, $^{111}$In, $^{177}$Lu, $^{90}$Y, $^{166}$Ho, and $^{153}$Sm, to polypeptides. In a preferred embodiment, the radiometal ion associated with the macrocyclic chelators attached to BLyS binding polypeptides of the invention is $^{111}$In. In another preferred embodiment, the radiometal ion associated with the macrocyclic chelator attached to BLyS binding polypeptides of the invention is $^{90}$Y. In specific embodiments, the macrocyclic chelator is 1,4,7,10-tetraazacyclododecane-N,N',N",N'"-tetraacetic acid (DOTA). In other specific embodiments, the DOTA is attached to the BLyS binding polypeptides of the invention via a linker molecule. Examples of linker molecules useful for conjugating DOTA to a polypeptide are commonly known in the art—see, for example, DeNardo et al., *Clin. Cancer Res.*, 4(10):2483–90 (1998); Peterson et al., *Bioconjug. Chem.*, 10(4):553–7 (1999); and Zimmerman et al, *Nucl. Med. Biol.*, 26(8):943–50 (1999), which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties. Though U.S. Pat. Nos. 5,652,361 and 5,756,065 focus on conjugating chelating agents to antibodies, one skilled in the art would be readily able to adapt the method disclosed therein in order to conjugate chelating agents to other polypeptides.

The BLyS binding polypeptides of the invention can be recovered and purified by known methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

The BLyS binding polypeptides may also be modified with a detectable label, including, but not limited to, an enzyme, prosthetic group, fluorescent material, luminescent material, bioluminescent material, radioactive material, positron emitting metal, nonradioactive paramagnetic metal ion, and affinity label for detection and isolation of BLyS target. The detectable substance may be coupled or conjugated either directly to the polypeptides of the invention or indirectly, through an intermediate (such as, for example, a linker known in the art) using techniques known in the art. Examples of suitable enzymes include horseradish peroxidase, alkaline phosphatase, beta-galactosidase, glucose oxidase or acetylcholinesterase; examples of suitable prosthetic group complexes include streptavidin/biotin and avidin/biotin; examples of suitable fluorescent materials include biotin, umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include a radioactive metal ion, e.g., alpha-emitters such as, for example, $^{213}$Bi, or other radioisotopes such as, for example, iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin.

In a specific embodiment, BLyS binding polypeptides of the invention are labeled with biotin.

Uses of the Binding Polypeptides and Recombinant Bacteriophage of the Invention

The BLyS binding polypeptides described herein are especially useful to detect, isolate, or remove BLyS target proteins in solutions. Such solutions may be simple dispersions or solutions of BLyS and/or BLyS-like polypeptide in water or aqueous buffer or more complex solutions, such as, a blood and other biological fluids, tissue homogenates cell extracts, or biopsy samples, and cell culture media containing BLyS or BLyS-like polypeptides. Biological fluids include, but are not limited to sera, plasma, lymph, blood, blood fractions urine, synovial fluid, spinal fluid, saliva, and mucous.

In one embodiment, the present invention provides a method for detecting a BLyS protein and/or a BLyS-like polypeptide in a solution comprising contacting the solution with a BLyS binding polypeptide of the invention and detecting binding of BLyS or BLyS-like polypeptide to the BLyS binding polypeptide. The BLyS binding polypeptide may be either free or immobilized. Preferably, the BLyS binding polypeptide is a polypeptide immobilized on a solid surface or chromatographic material or the well of a plastic microtiter assay dish.

Another embodiment of the present invention is a method for isolating BLyS protein and/or BLyS-like polypeptide from a solution containing it, comprising:
(a) contacting the solution with a BLyS binding polypeptide under conditions that permit binding of BLyS and/or BLyS-like polypeptides to BLyS binding polypeptide, and
(b) recovering the BLyS and/or BLyS-like polypeptides.

A further embodiment of the present invention is a method for isolating BLyS protein and/or BLyS-like polypeptide from a solution containing it, comprising:
(a) contacting the solution with a BLyS binding polypeptide under conditions that permit binding of BLyS and/or BLyS-like polypeptides to BLyS binding polypeptide, and
(b) separating the complex(es) formed by the BLyS binding polypeptide and BLyS and/or BLyS-like polypeptides from other components of the solution.

Preferably such method also includes the further steps of:
(c) dissociating the BLyS binding polypeptide from the BLyS and/or BLyS-like polypeptides, and
(d) recovering the dissociated, BLyS and/or BLyS-like polypeptide.

The invention also provides for kits containing a binding polypeptide of the invention for use in methods of detecting or isolating BLyS and/or BLyS-like polypeptides.

According to the invention, detection or isolation of BLyS target proteins comprises contacting a solution containing a BLyS target protein with a BLyS binding polypeptide. Depending on the particular application, the BLyS binding polypeptide may be free in solution or immobilized on a solid support or chromatographic material. Sufficient time is allowed to permit binding between the BLyS target protein and the binding polypeptides, and non-binding components in the solution or mixture are removed or washed away. The formation of a binding complex between the binding polypeptide and the BLyS target protein can then be detected, for example, by detecting the signal from a label on the binding polypeptide, which is one component of the binding complex. A label may be any label that generates a signal that can be detected by standard methods, such as a fluorescent label, a radioactive compound, or an enzyme that reacts with a substrate to generate a detectable signal. Suitable such labels are discussed above. A phage binding polypeptide according to the invention, that is, a recombinant phage displaying a BLyS binding polypeptide on its surface, may form a complex with BLyS and/or BLyS-like polypeptides that is detectable as a precipitate or sediment in a reaction tube, which can be detected visually after settling or centrifugation. Alternatively, a sandwich-type assay may be used, wherein a BLyS binding polypeptide is immobilized on a solid support such as a plastic tube or well, or a chromatographic support matrix such as agarose beads, then the solution suspected of containing the BLyS target is contacted with the immobilized binding polypeptide and non-binding materials or components are removed or washed away.

The binding polypeptides according to this invention are particularly useful for detection and/or isolation of BLyS and/or BLyS-like polypeptides by affinity chromatography methods. Any conventional method of chromatography may be employed. Preferably, a BLyS binding polypeptide of the invention will be immobilized on a solid support suitable, for example, for packing a chromatography column. The immobilized BLyS binding polypeptide affinity ligand can then be loaded or contacted with a feed stream under conditions favorable to formation of binding polypeptide/BLyS (or BLyS-like polypeptide) complexes. Non-binding materials can be washed away. Examples of suitable wash conditions can readily be determined by one of skill in the art and include but are not limited to [PBS/0.01% Tween 20, pH7.2] and [1M NaCl/10 mM Tris, pH7.5]. Tris wash buffers may be preferable since phosphates can precipitate in 50% ethylene glycol. In general, non-limiting terms, wash buffers are pH7.0, optionally containing 0.0 to 1.5 M NaCl, more preferably 1M NaCl. Additionally, wash buffers may optionally contain a mild detrgenet, such as, for example, Tween 20, Tween 80, or NP-80. BLyS or BLyS-like polypeptide can be eluted from the BLyS binding polypeptide by introducing solution conditions that favor dissociation of the binding complex. Suitable elution solutions can readily be determined by one of skill in the art and include but are not limited to [50% ethylme glycol/100 mM NaOAc]. By way of non-limiting example, useful elution buffers, for the purposes of the present invention contain 40–60% ethylene glycol, preferably 50% ethylene glycol.; and 50–100 mM NaOAc with a pH in the range of pH 4-pH7, more preferably, pH 4-pH 6 and most preferably pH 4.5-pH 5.5. Preferably, a fast flow affinity chromatographic technique is used to bind the molecules and from which purified BLyS or BLyS-like polypeptides are eluted.

Alternatively, batch chromatography can be carried out by mixing a solution containing the BLyS target and the BLyS binding polypeptide, then isolating complexes of the BLyS target and the binding polypeptides. For this type of separation, many methods are known. For example, the binding polypeptide may be immobilized on a solid support such as beads, then separated from the feed stream along with the BLyS target by filtration. In another example, the BLyS binding polypeptide may be modified with its own affinity tag, such as a polyHis tail or streptavidin binding region, which can be used to isolate the binding polypeptide after complexes have formed using an immobilized metal affinity chromatographic resin or steptavidin-coated substrate. Once separated, the BLyS target can be released from the binding polypeptide under elution conditions and recovered in a purified form.

Methods of producing BLyS or a BLyS-like polypeptides usually yield BLyS or BLyS-like polypeptides in a feed stream that additionally contains impurities (with respect to the BLyS target). One purpose of the present invention is to produce BLyS binding polypeptides and preparations (such as affinity chromatography media or surfaces) comprising BLyS binding polypeptides that allow rapid and highly specific purification of BLyS target proteins from a feed stream. BLyS binding polypeptides obtained herein may easily be tailored to isolate BLyS target protein from a particular feed stream, using or routinely modifying conditions and techniques known in the art. If an alternate production method for BLyS is used, producing a different feed stream, a different set of BLyS binding polypeptides and/or conditions may be necessary to achieve the same level of purification. The new set of BLyS binding polypeptides and/or conditions can be readily obtained following or modifying procedures outlined herein, or otherwise known in the art.

Kits

The present invention is also directed to an assay kit which can be useful in screening for the presence of BLyS and/or quantitating BLyS concentrations in a fluid, such as, for example, a biological fluid (e.g,. blood, serum, or synovial fluid).

In a particular embodiment of the present invention, an assay kit is contemplated which comprises in one or more containers of BLyS binding polypeptide(s) according to the invention and, optionally, a detection means for determining the presence of a BLyS target/BLyS binding polypeptide interaction or the absence thereof. The kit further optionally contains BLyS protein that may be used, for example as a control or standard. The BLyS binding polypeptide may be free or expressed on the surface of a host cell or on the surface of a bacteriophage.

In a specific embodiment, either the BLyS binding polypeptide or the BLyS protein is labeled. As further discussed herein, a wide range of labels can be used in accordance with the present invention, including but not limited to conjugating the recognition unit to biotin by conventional means. Alternatively, the label may comprise, e.g., a fluorogen, an enzyme, an epitope, a chromogen, or a radionuclide. Preferably, the biotin is conjugated by covalent attachment to either the BLyS binding polypeptide or the BLyS protein. Preferably, the BLyS binding polypeptide is immobilized on a solid support. The detection means employed to detect the label will depend on the nature of the label and can be any known in the art, e.g., film to detect a radionuclide; an enzyme substrate that gives rise to a detectable signal to detect the presence of an enzyme; antibody to detect the presence of an epitope, etc.

Methods of Screening for BLyS Binding Molecules

The present invention also encompasses screening methods for identifying polypeptides and nonpolypeptides that bind BLyS, and the BLyS binding molecules identified thereby. This method comprises the steps of:

(a) contacting a BLyS protein or BLyS-like protein with a plurality of molecules; and (b) identifying a molecule that binds the BLyS protein or BLyS-like protein.

The step of contacting the BLyS protein or BLyS-like protein with the plurality of molecules may be effected in a number of ways. For example, one may contemplate immobilizing the BLyS protein or BLyS-like protein on a solid support and bringing a solution of the plurality of molecules in contact with the immobilized BLyS protein or BLyS-like protein. Such a procedure would be akin to an affinity chromatographic process, with the affinity matrix being comprised of the immobilized BLyS protein or BLyS-like polypeptide. The molecules having a selective affinity for the BLyS protein or BLyS-like polypeptide can then be purified by affinity selection. The nature of the solid support, process for attachment of the BLyS protein or BLyS-like polypeptide to the solid support, solvent, and conditions of the affinity isolation or selection are largely conventional and well known to those of ordinary skill in the art.

Alternatively, one may also separate a plurality of polypeptides into substantially separate fractions comprising a subset of or individual polypeptides. For instance, one can separate the plurality of polypeptides by gel electrophoresis, column chromatography, or like method known to those of ordinary skill for the separation of polypeptides. The individual polypeptides can also be produced by a transformed host cell in such a way as to be expressed on or about its outer surface (e.g., a recombinant phage). Individual isolates can then be "probed" by the BLyS protein or BLyS-like polypeptide, optionally in the presence of an inducer should one be required for expression, to determine if any selective affinity interaction takes place between the BLyS protein or BLyS-like protein and the individual clone. Prior to contacting the BLyS protein or BLyS-like protein with each fraction comprising individual polypeptides, the polypeptides could first be transferred to a solid support for additional convenience. Such a solid support may simply be a piece of filter membrane, such as one made of nitrocellulose or nylon. In this manner, positive clones could be identified from a collection of transformed host cells of an expression library, which harbor a DNA construct encoding a polypeptide having a selective affinity for BLyS protein or BLyS-like protein. Furthermore, the amino acid sequence of the polypeptide having a selective affinity for the BLyS protein or BLyS-like protein can be determined directly by conventional means or the coding sequence of the DNA encoding the polypeptide can frequently be determined more conveniently. The primary sequence can then be deduced from the corresponding DNA sequence. If the amino acid sequence is to be determined from the polypeptide itself, one may use microsequencing techniques. The sequencing technique may include mass spectroscopy.

In certain situations, it may be desirable to wash away any unbound BLyS protein or BLyS-like protein, or alternatively, unbound polypeptides, from a mixture of the BLyS protein or BLyS-like protein and the plurality of polypeptides prior to attempting to determine or to detect the presence of a selective affinity interaction. Such a wash step may be particularly desirable when the BLyS protein or BLyS-like protein or the plurality of polypeptides is bound to a solid support.

The plurality of molecules provided according to this method may be provided by way of diversity libraries, such as random or combinatorial peptide or nonpeptide libraries which can be screened for molecules that specifically bind to BLyS. Many libraries are known in the art that can be used, e.g., chemically synthesized libraries, recombinant (e.g., phage display libraries), and in vitro translation-based libraries. Examples of chemically synthesized libraries are described in Fodor et al., *Science*, 251:767–773 (1991); Houghten et al., *Nature*, 354:84–86 (1991); Lam et al., *Nature*, 354:82–84 (1991); Medynski, *Bio/Technology*, 12:709–710 (1994); Gallop et al., *J. Medicinal Chemistry*, 37(9):1233–1251 (1994); Ohlmeyer et al., *Proc. Natl. Acad. Sci. USA*, 90:10922–10926 (1993); Erb et al., *Proc. Natl. Acad. Sci. USA*, 91:11422–11426 (1994); Houghten et al., *Biotechniques*, 13:412 (1992); Jayawickreme et al., *Proc. Natl. Acad. Sci. USA*, 91:1614–1618 (1994); Salmon et al., *Proc. Natl. Acad. Sci. USA*, 90:11708–11712 (1993); PCT Publication No. WO 93/20242; and Brenner and Lerner, *Proc. Natl. Acad. Sci. USA*, 89:5381–5383 (1992).

Examples of phage display libraries are described in Scott and Smith, *Science*, 249:386–390 (1990); Devlin et al., *Science*, 249:404–406 (1990); Christian et al., *J. Mol. Biol.*, 227:711–718 (1992); Lenstra, *J. Immunol. Meth.*, 152:149–157 (1992); Kay et al., *Gene*, 128:59–65 (1993); and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., *Proc. Natl. Acad. Sci. USA*, 91:9022–9026 (1994).

By way of examples of nonpeptide libraries, a benzodiazepine library (see, e.g., Bunin et al., *Proc. Natl. Acad. Sci. USA*, 91:4708–4712 (1994)) can be adapted for use. Peptoid libraries (see, Simon et al., *Proc. Natl. Acad. Sci. USA*, 89:9367–9371 (1992)) can also be used. Another example of a library that can be used, in which the amide functionalities in peptides have been permethylated to generate a chemically transformed combinatorial library, is described by Ostresh et al. (*Proc. Natl. Acad. Sci. USA*, 91:11138–11142 (1994)).

The variety of non-peptide libraries that are useful in the present invention is great. For example, Ecker and Crooke, *Bio/Technology*, 13:351–360 (1995) list benzodiazepines, hydantoins, piperazinediones, biphenyls, sugar analogs, beta-mercaptoketones, arylacetic acids, acylpiperidines, benzopyrans, cubanes, xanthines, aminimides, and oxazolones as among the chemical species that form the basis of various libraries.

Non-peptide libraries can be classified broadly into two types: decorated monomers and oligomers. Decorated monomer libraries employ a relatively simple scaffold structure upon which a variety functional groups is added. Often the scaffold will be a molecule with a known useful pharmacological activity. For example, the scaffold might be the benzodiazepine structure.

Non-peptide oligomer libraries utilize a large number of monomers that are assembled together in ways that create new molecular shapes that depend on the order of the monomers. Among the monomer units that have been used are carbamates, pyrrolinones, and morpholinos. Peptoids, peptide-like oligomers in which the side chain is attached to the alpha amino group rather than the alpha carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Screening the libraries can be accomplished by any of a variety of commonly known methods. See, e.g., the following references, which disclose screening of peptide libraries: Parmley and Smith, 1989, *Adv. Exp. Med. Biol.*, 251:215–218; Scott and Smith, 1990, *Science*, 249:386–390; Fowlkes et al., 1992; *BioTechniques*, 13:422–427; Oldenburg et al., 1992, *Proc. Natl. Acad. Sci. USA*, 89:5393–5397; Yu et al., 1994, *Cell*, 76:933–945; Staudt et al., 1988, *Science*, 241:577–580; Bock et al., 1992, *Nature*, 355: 564–566; Tuerk et al., 1992, *Proc. Natl. Acad. Sci. USA*, 89:6988–6992; Ellington et al., 1992, *Nature*, 355:850–852; U.S. Pat. No. 5,096,815, U.S. Pat. No. 5,223,409, and U.S. Pat. No. 5,198,346, all to Ladner et al.; Rebar and Pabo, 1993, *Science*, 263:671–673; and CT Publication No. WO 94/18318.

In a specific embodiment, screening to identify a molecule that binds BLyS can be carried out by contacting the library members with a BLyS protein or BLyS-like protein immobilized on a solid phase and harvesting those library members that bind to the BLyS protein or BLyS-like protein. Examples of such screening methods, termed "panning" techniques are described by way of example in Parmley and Smith, 1988, *Gene*, 73:305–318; Fowlkes et al., 1992, *BioTechniques*, 13:422–427; PCT Publication No. WO 94/18318; and in references cited herein.

In another embodiment, the two-hybrid system for selecting interacting proteins in yeast (Fields and Song, 1989, *Nature*, 340:245–246; Chien et al., 1991, *Proc. Natl. Acad. Sci. USA*, 88:9578–9582) can be used to identify molecules that specifically bind to BLyS or BLyS-like proteins.

An alternative screening method for obtaining new binding moieties capable of binding to BLyS target proteins is to employ a competition assay, in which a BLyS target is bound to a BLyS binding polypeptide according to the present invention, preferably labeled, and then the complex is exposed to one or more test moieties. Succesful new BLyS binding moieties will be test moieties capable of effectively competing for binding to the BLyS target in the presence of a known BLyS binder disclosed herein.

Polypeptides specifically binding BLyS target proteins can be conveniently selected from any peptide library, including random peptide libraries, combinatorial peptide libraries, or biased peptide libraries. The term "biased" is used herein to mean that the method of generating the library is manipulated so as to restrict one or more parameters that govern the diversity of the resulting collection of molecules, in this case peptides.

Thus, a truly random peptide library would generate a collection of peptides in which the probability of finding a particular amino acid at a given position of the peptide is the same for all 20 amino acids. A bias can be introduced into the library, however, by specifying, for example, that a lysine occur every fifth amino acid or that positions 4, 8, and 9 of a decapeptide library be fixed to include only arginine. For libraries designed to display a stable loop structure, a peptide sequence may be designed to include two invariant cysteine residues, with all other amino acid positions permitting one or more amino acid residues but excluding cysteine residues. (See, Example 1, infra.) Clearly, many types of biases can be contemplated, and the present invention is not restricted to any particular bias. Furthermore, the present invention contemplates specific types of peptide libraries, such as phage displayed peptide libraries and those that utilize a DNA construct comprising a lambda phage vector with a DNA insert.

As mentioned above, in the case of a BLyS binding molecule that is a polypeptide, the polypeptide may have about 6 to less than about 60 amino acid residues, preferably about 6 to about 10 amino acid residues, and most preferably, about 6 to about 22 amino acids. In another embodiment, a BLyS binding polypeptide has in the range of 15–100 amino acids, or 20–50 amino acids.

The selected BLyS binding polypeptide can be produced by chemical synthesis or recombinant expression, as described above.

The specific BLyS binding polypeptides disclosed herein were isolated using phage display technology, to identify BLyS binding polypeptides exhibiting particular preselected binding properties. These BLyS binding polypeptides were isolated initially by screening nine phage display libraries, that is, populations of recombinant bacteriophage transformed to express an exogenous recombinant polypeptide on their surface. In order to isolate new polypeptide binding moieties for a particular target, such as BLyS, screening of peptide libraries, for example using phage display techniques, is especially advantageous, in that very large numbers (e.g., $5 \times 10^9$) of potential binders can be tested and successful binders isolated in a short period of time.

In order to prepare a phage library of potential binding polypeptides to screen for members of the library that are BLyS binding polypeptides, a candidate binding domain is selected to serve as a structural template for the polypeptides to be displayed in the library. The phage library is made up of polypeptide analogues of this template or "parental binding domain." The parental binding domain is a polypeptide molecule that may be a naturally occurring or synthetic protein or polypeptide, or polypeptide region or domain of a protein. The parental binding domain may be selected based on knowledge of a known interaction between the parental binding domain and a target protein, but this is not critical. In fact, it is not essential that the parental binding domain have any affinity for a target at all because its purpose is to provide a structure from which a multiplicity of polypeptide analogues (a "library") can be generated, which multiplicity of polypeptide analogues will include one or more binding polypeptides that exhibit the desired binding and release properties with respect to BLyS target proteins (and any other properties selected).

Knowledge of the exact polypeptide that will serve as the parental binding domain, or knowledge of a class of proteins or domains to which the parental binding domain belongs can be useful in determining the conditions under which BLyS binding polypeptides optimally bind BLyS target proteins as well as the conditions under which BLyS binding polypeptides optimally release BLyS target proteins. Similarly, the binding and/or release conditions may be selected with regard to known interactions between a binding domain and the BLyS target protein, for example, to favor the interaction under the binding and/or release conditions, or they may be selected without regard to such known interactions. Likewise, the parental binding domain can be selected taking into account a desired binding and/or release condition or not. It is understood that if the binding domain analogues of a library are unstable under a proposed or desired binding or release condition, no useful binding polypeptides may be obtained.

In selecting the parental binding domain, the most important consideration is how the analogue domains will be presented to the BLyS target protein, that is, in what conformations the BLyS target and the polypeptide analogues will contact one another. In preferred embodiments, for example, the polypeptide analogues will be generated by insertion of synthetic DNA encoding the polypeptide analogue into a replicable genetic package, resulting in display of the domain on the surface of a microorganism, such as M13 phage, using techniques as described in Kay et al., *Phage Display of Peptides and Proteins: A Laboratory Manual* (Academic Press, Inc.; San Diego 1996) and U.S. Pat. No. 5,223,409 (Ladner et al.), incorporated herein by reference. For formation of phage display libraries, it is preferred to use structured polypeptides as the parental binding domain or template, as opposed to unstructured, linear peptides. Mutation of surface residues in a protein domain or polypeptide molecule will usually have little effect on the overall structure or general properties (such as size, stability, and temperature of denaturation) of the protein; while at the same time mutation of surface residues may profoundly affect the binding properties of the molecule. The more tightly a polypeptide segment is constrained, the less likely it is to bind to any particular target. If it does bind, however, the binding is likely to be tighter and more specific. Thus, it is preferred to select a parental binding domain wherein the parental polypetide has structure and, thereby in turn, select a structure for the polypeptide analogues of the library, which is constrained within a framework having some degree of rigidity.

Preferably the protein domain that is used as the template or parental domain for generating the library of domain analogues will be a peptide molecule that is a relatively small protein or polypeptide. Small polypeptides offer several advantages over large proteins: First, the mass per binding site is reduced. Highly stable protein domains having low molecular weights, for example, Kunitz domains (~7 kilodaltons, kDa), Kazal domains (~7 kDa), *Cucurbida maxima* trypsin inhibitor (CMTI) domains (~3.5 kDa), and endothelin (~2 kDa), can show much higher binding per gram than do antibodies (150 kDa) or single chain scFv antibodies (30 kDa). Second, the possibility of non-specific binding is reduced because there is less molecular surface available for nonspecific binding. Third, small polypeptides can be engineered to have unique tethering sites in a way that is impracticable for larger proteins or antibodies. For example, small proteins and polypeptides can be engineered to have lysines only at sites suitable for tethering to a chromatography matrix. This is not feasible for antibodies. Fourth, a constrained polypeptide structure is more likely to retain its functionality when transferred (with the structural domain intact) from one framework to another. For instance, the binding domain structure is likely to be transferable from the framework used for presentation in a library, such as displayed on a phage, to an isolated protein removed from the presentation framework or immobilized on a chromatographic substrate.

In specific embodiments, the BLyS binding polypeptides of the invention are immobilized. BLyS binding polypeptide molecules according to the invention may be immobilized, for example, on chromatographic support materials to form efficient BLyS separation or affinity chromatographic media. Immobilized BLyS binding polypeptides of the invention have uses that include, but are not limited to, detecting, isolating or removing BLyS target proteins from solutions.

One strategy for generating BLyS binding polypeptide molecules that can be immobilized, for example, on matrices, resins, or supports, involves selecting appropriate binding domain templates such that BLyS binding polypeptide molecules are generated that have one or more amino acids that may be used to covalently link the BLyS binding polypeptide to a chromatographic resin or substrate to form an affinity resin. Similarly, the N-terminal amino group or the C-terminal carboxyl group of a peptide molecule may be modified by adding a capping group to render it inert or a functional group, which permits linkage to a support medium. For example, the C-terminal carboxyl group of a protein domain may be converted to an amide or a hydrazide (—NH—NH$_2$) group for reaction with an aldehyde-functional substrate or other amine-reactive substrate. This technique is preferred. Another preferred modification of BLyS binding polypeptides useful for linking a BLyS binding polypeptide molecule of the invention to a chromatography material is a polypeptide linker comprising, or alternatively consisting of, the amino acid sequence Pro-Gly-Pro-Glu-Gly-Gly-Gly-Lys (SEQ ID NO:13).

In one non-limiting example of a screening procedure to obtain BLyS binding polypeptides encompassed by the invention, the phage in a phage display library are contacted with and allowed to bind a BLyS target protein that is immobilized on a solid support. Those phage that display non-binding polypeptides are separated from those that bind the BLyS target protein. Any of various techniques known in the art may be applied to dissociate the bound phage from the immobilized BLyS protein, and to collect and/or amplify the phage and/or their nucleic acid contents. Using these techniques it is possible to identify a BLyS binding phage that is about 1 in 20 million in the population. Libraries, displaying 10–20 million or more potential binding peptide molecules each, are rapidly screened to find high-affinity BLyS binding polypeptides.

In each round of screening, the diversity of a population falls until only efficient binding polypeptides remain, that is, the process converges. Typically, a phage display library will contain several closely related binding polypeptides (10 to 50 different binding polypeptides out of 10 million). Indications of convergence include increased binding (measured by phage titers) and recovery of closely related sequences. After a first set of binding polypeptide molecules is identified, the sequence information can be used to design other libraries biased for members having additional desired properties, for example, discrimination between different forms of BLyS (e.g., the membrane form and the soluble form of BLyS) and fragments thereof, or discrimination between BLyS and closely related impurities in a feed stream.

Such techniques make it possible not only to screen a large number of potential binding polypeptides, but make it practical to repeat the binding and elution cycles and to build secondary, biased libraries for screening polypeptide analogue-displaying phage that meet specific criteria. Using these techniques, a polypeptide analogue biased library may be screened to reveal members that bind tightly, that is, have high affinity for BLyS target protein, under the screening conditions.

In the present invention target BLyS protein molecules were biotinylated and then bound to streptavidin-coated magnetic particles. Nine phage display libraries of different design were screened for the ability to bind the immobilized BLyS. Each library was characterized by M13 phage displaying variegated peptides of different lengths and overall structure: A library designated TN6/6 ($2\times10^8$ variants) displayed a variegated 12-mer with two internal invariant cyteines to form a hexamer loop structure. A library designated TN7/4 ($2.3\times10^9$ variants) presented a variegated 13-mer having two internal invariant cyteines to form a heptamer loop structure. A library designated TN8/9 ($5\times10^9$ variants) displayed a variegated 14-mer with two internal invariant cyteines to form an octamer loop structure. A library designated TN9/4 ($3.2\times10^9$ variants) presented a variegated 16-mer having two internal invariant cyteines to form a nonamer loop structure. A library designated TN10/9 ($2.5\times10^9$ variants) displayed a variegated 16-mer with two internal invariant cyteines to form a decamer loop structure. A library designated TN12/1 ($1.4\times10^9$ variants) presented a variegated 18-mer having two internal invariant cyteines to form a dodecamer loop structure. A library designated as Substrate Phage Library #2, having a diversity of about $2\times10^8$ amino acid sequences, was designed to include a linear peptide-variegated region in the display polypeptide consisting of 13 consecutive amino acids, and the display polypeptide design allowed any amino acid residue except cysteine to occur at each position. Finally, two commercially available linear phage display libraries were also screened, designated PhD 7 and PhD 12, respectively (New England Biolabs). The PhD 7 library displayed a linear random-sequence 7-mer; the PhD 12 libary displayed a random-sequence 12-mer.

BLyS binding phage were isolated and collected from all of the libraries except PhD 7.

After analysis of the sequences isolated from the library screenings, several families of BLyS binding peptides were defined (see, consensus sequences A-G and H-L, above). The amino acid sequences of the BLyS-binding "hits" from the first rounds of screening are set forth in Tables 1–8 (infra).

In order to obtain BLyS binding polypeptides having an even higher affinity for BLyS targets, a specialized library was prepared, i.e., a BLyS affinity maturation library, based on variegation of high affinity examplars of the PhD 12 library (see Example 6). This library was designed to provide a population enriched with polypeptides likely to show high affinity for BLyS. The selections from this library were performed to eliminate, by prolonged competition with soluble eluants of soluble BLyS or other BLyS binding polypeptides, all but the polypeptides having the highest affinity for BLyS. A large family of high affinity BLyS binding polypeptides was isolated from four rounds of screening the affinity maturation library, and their amino acid sequences appear in Table 14 (infra).

BLyS binding polypeptides according to the invention and phage comprising such polypeptides have uses that include, but are not limited to, detecting and isolating BLYS and BLyS-like polypeptides, as described above.

Isolation of BLyS binding polypeptides and their use in accordance with this invention will be further illustrated below. The specific parameters included in the following examples are intended to illustrate the practice of the invention, and they are not presented to in any way limit the scope of the invention.

EXAMPLE 1

Screening of Phage Display Libraries

Streptavidin-coated magnetic beads (Dynal M-280) were chosen for presentation of the target during screening because of their superior binding capacity compared to that of a 96 well plate. The binding capacity of the beads for biotinylated antibodies was 5–10 μg/mg of beads as stated by the manufacturer. For this study and the screening to follow, 5 μg of biotinylated recombinant BLyS (obtained from Human Genome Sciences, Inc.) was allowed for each mg of beads. This amount of biotinylated BLyS represents a 10-fold excess of target, for saturation of the beads. Unbound BLyS was washed away. Bound biotinylated BLyS was confirmed with detection using Mab 16C9 (murine anti-BLyS, Human Genome Sciences) primary antibody and a goat anti-mouse HRP conjugate as the secondary antibody. An irrelevant monoclonal antibody (anti-TNFα) was used to probe a second set of beads to control for nonspecific binding. The color reagent TMB was used and the assay read at OD 630 nm.

Nine libraries, TN6/6, TN7/4, TN8/9, TN9/4, TN10/9, TN12/1, Substrate Phage #2, PhD7, and PhD12, were screened for BLyS binders. The makeup of these libraries was as follows:

The TN6/6 phage display library was composed of recombinant M13 phage displaying variegated peptides with the potential to form loop structures based on a polypeptide template having the structure Xaa-Xaa-Xaa-Cys-Xaa-Xaa-Xaa-Xaa-Cys-Xaa-Xaa-Xaa (SEQ ID NO:14) and providing $2.0 \times 10^8$ peptide diversity.

The TN7/4 phage display library was composed of recombinant M13 phage displaying variegated peptides with the potential to form loop structures based on a polypeptide template having the structure Xaa-Xaa-Xaa-Cys-Xaa-Xaa-Xaa-Xaa-Xaa-Cys-Xaa-Xaa-Xaa (SEQ ID NO:15) and providing $2.3 \times 10^9$ peptide diversity.

The TN8/9 phage display library was composed of recombinant M13 phage displaying variegated peptides with the potential to form loop structures based on a polypeptide template having the structure Xaa-Xaa-Xaa-Cys-Xaa-Xaa-Xaa-Xaa-Xaa-Xaa-Cys-Xaa-Xaa-Xaa (SEQ ID NO:16) and providing about $5 \times 10^9$ peptide diversity.

The TN9/4 phage display library was composed of recombinant M13 phage displaying variegated peptides with the potential to form loop structures based on a polypeptide template having the structure Xaa-Xaa-Xaa-Cys-Xaa-Xaa-Xaa-Xaa-Xaa-Xaa-Xaa-Cys-Xaa-Xaa-Xaa (SEQ ID NO:17) and providing about $3.2 \times 10^9$ peptide diversity.

The TN10/9 phage display library was composed of recombinant M13 phage displaying variegated peptides with the potential to form loop structures based on a polypeptide template having the structure Xaa-Xaa-Xaa-Cys-Xaa-Xaa-Xaa-Xaa-Xaa-Xaa-Xaa-Xaa-Cys-Xaa-Xaa-Xaa (SEQ ID NO:18) and providing $2.5 \times 10^9$ peptide diversity.

The TN12/1 phage display library was composed of recombinant M13 phage displaying variegated peptides with the potential to form loop structures based on a polypeptide template having the structure Xaa-Xaa-Xaa-Cys-Xaa-Xaa-Xaa-Xaa-Xaa-Xaa-Xaa-Xaa-Cys-Xaa-Xaa-Xaa (SEQ ID NO:19) and providing $1.4 \times 10^9$ peptide diversity.

Substrate Phage Library #2 was composed of recombinant M13 phage displaying a polypeptide insert of approximately 80 amino acids, having two streptavidin binding domains, a linear variegated segment of thirteen amino acids where all amino acids except Cys were permitted at each position, and a Factor Xa cleavage site, linked together with peptide linkers. This library provided a diversity of $2 > 10^8$ display polypeptides.

Libraries PhD7 and PhD12 were composed of recombinant M13 phage displaying randomized linear seven- and twelve-amino acid peptides, obtained commercially from New England Biolabs.

Prior to each round of screening, phage libraries or phage library pools were depleted of phage capable of binding the streptavidin beads by sequentially adding the libraries to 5 separate aliquots of streptavidin beads and allowing them to bind for 10 minutes. The depleted libraries were added to biotinylated BLyS on streptavidin magnetic beads and allowed to bind for 1 hour at room temperature. For round 1 of the screening, all the libraries were kept separate except PhD7 and PhD12 which were pooled from the beginning. After binding, the beads were washed 7 times and bound phage were incubated for 10 minutes with citrate buffered saline at pH 2.0 to elute. The eluted phage were neutralized with 2 M Tris-HCl pH 8.0 and allowed to infect *E. coli* XL-1 Blue MRF'. The infected cells were spread on a large agar plate and standard phage techniques known in the art were used to produce the starting material for the next round. For each round of screening the fraction of input recovered was calculated for each library (library pool). This is equal to the number of phage recovered divided by the number on starting phage. No further rounds of screening were done after the fraction of input recovered reached $1 \times 10^{-2}$ total phage. Pool A for round 2 of screening was a mixture of TN6/6, TN7/4 and TN8/9 round 1 outputs. Pool B for round 2 was a mixture of TN9/4, TN10/9, and TN12/1 round 1 outputs. After round 2 on Pool A and Pool B the fraction of input recovered was equal to or greater than $1 \times 10^{-2}$ and no further rounds were done. For the Substrate Phage Library #2 and the PhD pool a third round of screening was required.

At the conclusion of screening individual phage isolates were randomly selected and tested by ELISA for binding to BLyS. The same isolates were submitted for DNA sequence analysis to identify the nucleotide and deduced amino acid sequence of the displayed peptide. Isolates were also tested for their ability to bind to recombinant BLyS in feed streams of CHO supernatant and Sf9 supernatant (supplied by Human Genome Sciences, Inc.).

Each isolate was tested for binding to BLyS by standard ELISA techniques where bound phage were detected with a monoclonal anti-phage antibody/HRP conjugate. Approximately 90% of the isolates from the TN libraries Pool A and Pool B had binding signals on BLyS ranging from 3× to 12× above the background binding on streptavidin alone. Isolates from the Substrate Phage Library showed similar but slightly lower binding signals.

To assess the ability of the BLyS binding polypeptides to recognize the BLyS target in potential process feed streams, phage binding was determined in two feed streams: CHO and Sf9 supernatants spiked with BLyS protein. Phage were allowed to bind to BLyS in either CHO supernatant or Sf9 supernatant rather than the standard conditions of PBS plus Tween. All other wash steps were the same as the standard ELISA conditions. The binding of BLyS binding polypeptides to BLyS in PBS+Tween, CHO supernatant, and Sf9 supernatant binding was very similar under all conditions. Several BLyS binding polypeptide isolates demonstrated reduced binding of up to 50% in the CHO supernatant. Isolates of BLyS binding polypeptides binding to BLyS in the Sf9 supernatant was not significantly different from binding under the standard conditions. The PhD and Substrate Phage Library isolates were also compared in the feed streams. Remarkably, several of these isolates exhibited greater binding in the feed streams than under the standard conditions.

Amino acid sequences of the displayed peptides were derived from sequencing the phage isolate DNA inserts. Sequence data from the phage isolates were grouped by library and sorted according to the degree of similarity. The BLyS binding phage isolate peptides are shown in Tables 1–8 below. These peptides represent the translation of the DNA sequences across the varied regions of the genes encoding the phage display fusion/peptide.

TABLE 1

TN6/6 Library BLyS-binding Sequences

| Phage Isolate | Amino Acid Sequence | SEQ ID NO: |
|---|---|---|
| 453-01-B06 | HLRCWSTNCRYD | 20 |
| 453-01-A04 | VMDCLINRCDTV | 21 |

TABLE 2

TN7/4 Library BLyS-binding Sequences

| Phage Isolate | Amino Acid Sequence | SEQ ID NO: |
|---|---|---|
| 453-01-B04 | KSKCFFPWECQQA | 22 |
| 453-01-D11 | AMKCYFPWECANG | 23 |
| 453-01-A05 | NVACYFPWECHHP | 24 |
| 453-01-D01 | NAPCYFPWECFSI | 25 |
| 453-01-D03 | SVNCWFPWECVGN | 26 |
| 453-01-A08 | KEPCYFYWECAVS | 27 |

TABLE 3

TN8/9 Library BLyS-binding Sequences

| Phage Isolate | Amino Acid Sequence | SEQ ID NO: |
|---|---|---|
| 453-01-D04 | DTNCDLLTKMCGPQ | 28 |
| 453-01-C06 | GTPCDLLTKLCLLW | 29 |
| 453-01-D10 | MSECDLLTKICLMG | 30 |
| 453-01-B07 | VPFCDLLTKHCFEA | 31 |
| 453-01-B09 | VPFCDLLTKHCFEA | 32 |
| 453-01-C02 | WSACDLLTKQCVQV | 33 |
| 453-01-A06 | -DGCDELTKICGMK | 34 |
| 453-01-B03 | KSWCDELTKVCFDP | 35 |
| 453-01-B11 | KWMCDELTKQCQYV | 36 |
| 453-01-A02 | MKYCDELTKICVGW | 37 |
| 453-01-B05 | YFQCDELTKMCWQK | 38 |
| 453-01-A11 | AMHCDKLTKHCKFH | 39 |
| 453-01-A03 | VPYCDKLTKICQW- | 40 |
| 453-01-A07 | EVFCDVLTKVCFHD | 41 |
| 453-01-C09 | KPKCDVLTKMCDWL | 42 |
| 453-01-B02 | TQHCDVLTKQCFTI | 43 |
| 453-01-C01 | GHFCDRLTKYCFEP | 44 |
| 453-01-A09 | HIQCDRLTKSCLSV | 45 |
| 453-01-D05 | IKACDILTKVCWPP | 46 |
| 453-01-A01 | QFDCDILTKYCGEF | 47 |
| 453-01-C07 | KMYCDHLTGYCWPE | 48 |
| 453-01-C11 | MQSCDILTGYCFKR | 49 |
| 453-01-D12 | GPWCDILTGFCLAQ | 50 |
| 453-01-C04 | SVRCDLLTGWCPVW | 51 |
| 453-01-B10 | PADCDPLTNICFWK | 52 |
| 453-01-D02 | TNVCDPLTNVCFMN | 53 |
| 453-01-C05 | EHWCDDLTHLCFRL | 54 |
| 453-01-D08 | GYWCDVLTNNCWKI | 55 |
| 453-01-C10 | LYNCDYLTRLCFEP | 56 |
| 453-01-C08 | HVDCLLHPKACYKY | 57 |
| 453-01-D07 | VQDCLLHPKACQMQ | 58 |
| 453-01-D09 | KFDCLLKPMFCSNH | 59 |
| 453-01-C12 | FADCLIHPKSCKPL | 60 |
| 453-01-D06 | HGNCYPFPWECESK | 61 |
| 453-01-B01 | MIIVLLLRFAISR | 62 |
| 453-01-A12 | SLLVIFLLIGAGSL | 63 |

TABLE 4

TN9/4 Library BLyS-binding Sequences

| Phage Isolate | Amino Acid Sequence | SEQ ID NO: |
|---|---|---|
| 453-01-G06 | FHPCDMLTGIWCQPN | 64 |
| 453-01-H01 | SKRCDLLTKMWCETE | 65 |
| 453-01-F02 | TKFCDRLTMPKCVWK | 66 |
| 453-01-E03 | NTFCPDPLTGRCVNP | 67 |
| 453-01-E11 | DWTCDPLFHRECIFE | 68 |
| 453-01-H09 | PQPCDLLFEKKCSIK | 69 |
| 453-01-H02 | RWHCDMLINPSCLPD | 70 |
| 453-01-E04 | KIQCDIVNLSSCVYP | 71 |
| 453-01-G11 | LNACDIVHPNYCSGM | 72 |
| 453-01-F01 | AKACSIVNLESCEYL | 73 |
| 453-01-H06 | RQACSIITPWGCPIP | 74 |
| 453-01-F10 | ADNCTVATLDFCYWT | 75 |
| 453-01-E05 | KPECNITKPQFCFGE | 76 |

TABLE 5

TN10 Library BLyS-binding Sequences

| Phage Isolate | Amino Acid Sequence | SEQ ID NO: |
|---|---|---|
| 453-01-H07 | -NNCQWDELTSMCDPF | 77 |
| 453-01-F05 | SRLCHMDELTHVCVHF | 78 |
| 453-01-F09 | SRPCQIDELTKACFYN | 79 |
| 453-01-G09 | DRVCKLDFLTYNCLNH | 80 |
| 453-01-F04 | HSNCIMDLLTNRCFYD | 81 |
| 453-01-H03 | PFNCFHDPLTGLCLHS | 82 |
| 453-01-F03 | YDSCTYDRLTKQCYPS | 83 |
| 453-01-F07 | FHDCMYDALLGYCLPY | 84 |
| 453-01-G08 | NRSCDPLTRPKSCGL | 85 |
| 453-01-G04 | LSNCDWDDLIRQCLHD | 86 |
| 453-01-E01 | FWDCLFHPNSRYCVLS | 87 |
| 453-01-E10 | SRDCLLSPAMAWCGLD | 88 |

TABLE 6

TN12/1 Library BLyS-binding Sequences

| Phage Isolate | Amino Acid Sequence | SEQ ID NO: |
|---|---|---|
| 453-01-H05 | GGNCYTDSLTKLHFCMGD | 89 |
| 453-01-H04 | --MCPRDPLTKAKLCNWH | 90 |
| 453-01-G03 | PNQCQDDLTKQWYSCHYH | 91 |
| 453-01-F11 | FDMCFDALTKQNFYCRFH | 92 |
| 453-01-F06 | RNMCVDRLTKLQHGCEGA | 93 |
| 453-01-G07 | DPECLTSFDRLTKMCWPW | 94 |
| 453-01-H11 | DDECHYDYLTHYMRCDYR | 95 |
| 453-01-G05 | FGGCNIDLLTNTMMCHRN | 96 |
| 453-01-G10 | HGPCYWDELTMQWHCNHH | 97 |
| 453-01-H12 | GAMCVDLLTYTFRPCMYA | 98 |
| 453-01-E07 | SNKCWDELTHAWAECGRF | 99 |
| 453-01-E09 | RPVCYKGYDILTTQCMPW | 100 |
| 453-01-G01 | PSRCWFDLLFNKFVCKRN | 101 |
| 453-01-H08 | RSGCVYDMLLMTMYCPSN | 102 |
| 453-01-H10 | SNRCEGDQLMRPPSCRHL | 103 |
| 453-01-F08 | YRMCWWDDLLRGFVCDFH | 104 |
| 453-01-E06 | HDGCYDELLYRWTRCEHR | 105 |
| 453-01-E08 | WAWCFDELVQRYFTCFDH | 106 |
| 453-01-E02 | LPECRQYFPWEKQVCSYW | 107 |

TABLE 7

PhD 12 Library BLyS-binding Sequences

| Phage Isolate | Amino Acid Sequence | SEQ ID NO: |
|---|---|---|
| 453-02-B05 | VHYDSLTKMWTR | 108 |
| 453-02-D09 | FTDPLTKMSLHS | 109 |
| 453-02-C12 | GYDVLTKLYFVP | 110 |

TABLE 7-continued

PhD 12 Library BLyS-binding Sequences

| Phage Isolate | Amino Acid Sequence | SEQ ID NO: |
|---|---|---|
| 453-02-A05 | YYDRLTKLYSSM | 111 |
| 453-02-B06 | L?KDPLTKLYIS | 112 |
| 453-02-A04 | GYDVLTKL?FVP | 113 |
| 453-02-B03 | RLYDPLTKLVLS | 114 |
| 453-02-B01 | MFDPLTKIAFPA | 115 |
| 453-02-D04 | FYDSLTKTNLRD | 116 |
| 453-02-B02 | GIYDKLTRAWLP | 117 |
| 4S3-02-B08 | KYDPLTRAR?PL | 118 |
| 453-02-D06 | YIDQLTRLSLPS | 119 |
| 453-02-A09 | HqTFDILTRLHF | 120 |
| 453-02-B04 | WQFDVLTRSWTP | 121 |
| 453-02-A02 | GAAYDHLTRTWL | 122 |
| 453-02-D05 | YFDQLTHLSIKK | 123 |
| 453-02-A06 | AWDPLTMLVLPW | 124 |
| 453-02-D03 | ALWMDPLTGLAF | 125 |
| 453-02-B12 | WQFDVLT?SWTP | 126 |
| 453-02-A01 | WTDPLTHMEIYH | 127 |
| 453-02-C04 | WTDSLTGLWFPD | 128 |
| 453-02-C05 | YTDPLTGIV?PF | 129 |
| 453-02-D08 | YWDKLTMLHLGV | 130 |
| 453-02-D02 | YYDFLTRTVLPS | 131 |
| 453-02-A03 | RLDPLSKNDFPR | 132 |
| 453-02-A11 | LRYDPLLKS?IY | 133 |
| 453-02-D07 | LRYDPLLKSYIY | 134 |
| 453-02-A07 | YFDQFTHLSIKK | 135 |
| 453-02-C08 | YFDQ?THLSIKK | 136 |

TABLE 8

Substrate Phage Library BLyS-binding Sequences

| Phage Isolate | Amino Acid Sequence | SEQ ID NO: |
|---|---|---|
| 453-02-E04 | EHYYTDPLTGARI | 137 |
| 453-02-F01 | EHY?TDPLTGARI | 138 |
| 453-02-E09 | EHYSTDPLTGARI | 139 |
| 453-02-E07 | EHYYTDPL?G?RI | 140 |
| 453-02-G05 | EHYYTDPL?G?R? | 141 |
| 453-02-G09 | EHYYTDPL?GAR? | 142 |
| 453-02-E06 | EH?YTDPLNGAR? | 143 |
| 453-02-E05 | EHYYNDPLNGAR? | 144 |
| 453-02-F04 | ?H?YNDPLNGAR? | 145 |
| 453-02-G07 | KPYYDPITKMTHH | 146 |
| 453-02-F06 | KPYYDPITKMSHH | 147 |
| 453-02-E08 | KPYYDPISKMTHH | 148 |
| 453-02-G08 | KP??DPISKMTHH | 149 |
| 453-02-E01 | QIGYDELTKAWVT | 150 |
| 453-02-G02 | QLGYDELTKAWVT | 151 |
| 453-02-H06 | KIDEL?MQNIIIW | 152 |
| 453-02-F08 | DHTDPLIQGLTKR | 153 |
| 453-02-H01 | WHDPLKHMHFHHE | 154 |
| 453-02-F03 | KHIDMETGLILQN | 155 |
| 453-02-G03 | MQVDPETGLKYEH | 156 |
| 453-02-E03 | ?LDQHVN???YQS | 157 |
| 453-02-F10 | E???T??LTGAR? | 158 |
| 453-02-F02 | GPYNI?RL?GEr? | 159 |
| 453-02-E02 | HIKMLHQGSFVGV | 160 |
| 453-02-H08 | HPTNT??HQ?VYS | 161 |
| 453-02-H05 | HRGQV??LNGMv? | 162 |

?= amino acid unknown (all TABLES)
lower case = amino acid identity probable but not completely characterized A small number of phage isolates were selected for further characterization based upon several criteria: the strength of the ELISA signal (i.e., $OD_{630} \geq 0.8$ after 10 min.), the number of times the identical sequence was found, and the presence of a recurrent sequence motif. Some characteristics of the phage isolates that were selected are shown below. Sequence motifs found multiple times in the isolates are underlined.

| Isolate | ELISA # | signal | Sequence | SEQ ID NO: |
|---|---|---|---|---|
| TN7-01-A08 | 1 | 1.2 | KEP<u>CYFYWEC</u>AVS | 27 |
| TN7-01-D11 | 2 | 1.0 | AM<u>KCYFPWEC</u>ANG | 23 |
| TN7-01-B04 | 2 | 0.8 | KS<u>KCFFPWEC</u>QQA | 22 |
| TN8-01-C08 | 2 | 1.2 | HV<u>DCLLHPKAC</u>YKY | 57 |
| TN8-01-B07 | 2 | 1.4 | VPFC<u>DLLTK</u>HCFEA | 31 |
| TN9-01-G06 | 1 | 1.2 | FHPC<u>DMLTG</u>IWCQPN | 64 |
| TN9-01-011 | 1 | 0.8 | LN<u>ACDIV</u>HPNYCSGM | 72 |
| TN10-01-F05 | 1 | 1.0 | SRLCHM<u>DELTH</u>VCVHF | 78 |
| TN12-01-H05 | 1 | 1.0 | GGNCYT<u>DSLTKL</u>HFCMGD | 89 |
| PhD-02-B02 | 4 | 0.6 | GIY<u>DKLTRAWLP</u> | 117 |
| PhD-02-B05 | 9 | 0.6 | VHY<u>DSLTKM</u>WTR | 108 |
| PhD-02-C12 | 3 | 0.8 | GY<u>DVLTKL</u>YFVP | 110 |
| PhD-02-D05 | 3 | 0.8 | YF<u>DQ</u>LTHLSIKK | 123 |
| PhD-02-C04 | 1 | 1.0 | WT<u>DSLT</u>GLWFPD | 128 |

Various release conditions (see below) were tested, in order to discover possible elution conditions where the BLyS binding polypeptides could be used as affinity ligands for BLyS purification. For release studies, a constant number of phage were applied to wells containing biotinylated BLyS immobilized on streptavidin. After allowing the phage to bind, each phage isolate was then "eluted" from the well with two five-minute washes using various buffers. Wells were washed with standard wash buffer, and bound phage were detected with a standard phage ELISA. Elution conditions were selected based on low pH release, which was the mechanism employed during screening, and alternative elution conditions based on conditions where the BLyS product was known to be stable for at least several hours. The various elution conditions were: PBS pH 7.0, citrate buffered saline pH 5.0, citrate buffered saline pH 3.0, citrate buffered saline pH 2.0, 1 M Guanidine pH 7.0, and 1 M urea pH 7.0. Binding of several of the isolates was reduced under the standard conditions (PBS pH 7.0). This may have occurred because these experiments were performed with concentrated phage preparations rather than the overnight bacterial supernatants used for all previous experiments. It is believed that the polyethylene glycol used to concentrate the phage interfered with the binding of these isolates. For the purposes of these release studies, the phage isolates selected had a starting signal of 0.5 OD 630 nm or greater. Overall, 1 M urea, pH 7.0 appeared to be the best buffer to release bound phage.

EXAMPLE 2

Immobilization of BLyS Binding Polypeptides on Sepharose-4FF Beads

On the basis of the above results, six display phage sequences were chosen for further study:

TN7-01-A08 (SEQ ID NO:27), TN8-01-07 (SEQ ID NO:31), TN10-01-F05 (SEQ ID NO:78), TN12-01-H05

(SEQ ID NO:89), PhD-02-C04 (SEQ ID NO:128), and PhD-02-C12 (SEQ ID NO:110). In order to develop a suitable BLyS affinity ligand, the identified display peptides were synthesized to order by a commercial vendor, with slight modifications:

Two amino acids of leader were added to each binding peptide at the N-terminus, in order to avoid leaving a free amine at the first amino acid of the sequence corresponding to the variegated region of the phage display template; the N-terminus was acetylated to prevent immobilization of the peptide to the chromatographic matrix through that position; a C-terminal linker was added (i.e., -PGPEGGGK; SEQ ID NO:13); and any internal lysines in the peptide were blocked with the group: ivDde (i.e., 1-(4,4-dimethyl-2,6-dioxocyclohex-1-ylidene)-3-methyl butyl-L-lysine). This group was intact on the finished synthesized peptides and was removed after immobilization or fluorescein labeling. As an alternative modification, peptides with internal lysines were also synthesized with C-terminal hydrazide functional groups, which could be immobilized onto activated aldehyde chromatographic media.

The peptides were immobilized onto NHS-activated SEPHAROSE-4 Fast Flow agarose media (Pharmaceia) at ligand densities targeted to 2 μmol/ml. Actual ligand densities of peptides on the media ranged from 0.76 μmol/ml to 1.98 μmol/ml, as determined by amino acid analysis of immobilized peptide. All but one peptide was immobilized in aqueous conditions of 100 mM KH$_2$PO$_4$/150 mM NaCl/0.05% Tween 20, pH 7.5. For solubility reasons, the peptide DX217 (see, Table 9, below) was immobilized in 30% dimethyl formamide(DMF)/100 mM KH$_2$PO$_4$/150 mM NaCl/0.05% Tween 20. pH 7.5. Immobilization reactions were allowed to proceed for 2 hours at ambient temperature, followed by brief washing with pH 7.5 buffer. The Fast Flow SEPHAROSE media was then allowed to tumble at ambient temperature overnight to hydrolyze remaining NHS esters after which the media was washed to remove any unbound peptide. A solution of 2% hydrazine/DMF was used to de-block ligands containing ivDde-lysine. Media was then further washed with aqueous buffers and stored at 4° C. until packed into columns. Table 9 shows the sequences of the synthesized peptides and their measured densities on the agarose media.

TABLE 9

BLyS Binding Peptides Synthesizes as Affinity Ligands

| Peptide Name | Isolate source | Sequence (potential disulfide loop underlined) | SEQ ID NO: |
|---|---|---|---|
| DX212 | 01-A08 | Ac-AGKEP<u>CYFYWEC</u>AVSGPGPEGGGK | 163 |
| DX214 | 01-B07 | Ac-AGVPF<u>CDLLTKHC</u>FEAGPGPEGGGK | 164 |
| DX216 | 01-F-5 | Ac-GSSRL<u>CHMDELTHVC</u>VHFAPPGPEGGGK | 165 |
| DX217 | 01-H05 | Ac-GDGGN<u>CYTDSLTKLHFC</u>MGDEPGPEGGGK | 166 |
| DX219 | 02-C12 | Ac-GYDVLTKLYFVPGGPGPEGGGK | 167 |
| DX221 | 02-C04 | Ac-WTDSLTGLWFPDGGPGPEGGGK | 168 |

BLyS-Ligand Affinity Determination (Overview of Procedure)

Dissociation constants between the synthetic peptides and BLyS (free in solution) were measured by fluorescence anisotropy (FA). In these experiments, the concentration of the fluorescein-labeled peptide is held constant and the BLyS protein concentration was varied. The observed change in anisotropy is fit to the following equation via nonlinear regression to obtain the apparent $K_D$.

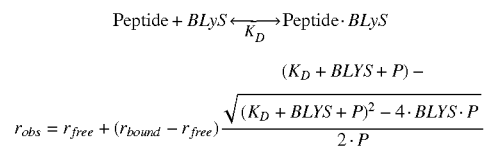

$$\text{Peptide} + BLyS \underset{K_D}{\longleftrightarrow} \text{Peptide} \cdot BLyS$$

$$r_{obs} = r_{free} + (r_{bound} - r_{free})\frac{(K_D + BLYS + P) - \sqrt{(K_D + BLYS + P)^2 - 4 \cdot BLYS \cdot P}}{2 \cdot P}$$

where:
$r_{obs}$=observed anisotrpy, $r_{free}$=anisotropy of free peptide, $r_{bound}$=anisotropy of bound peptide, $K_D$=dissociation constant, BLyS=total BLyS concentration, and P=total fluorescein labeled peptide concentration.

Binding reactions containing 50 nM fluorescein-labeled peptide and a varied concentration of BLyS in a volume between 10 and 20 μL per well were performed in 384 well microplates. Reactions were assayed using a Tecan Polarion fluorescence polarization plate reader. Cross-competition studies between peptides were performed using 50 nM fluorescein-labeled peptide and 1–2 μM BLyS in the presence and absence of 100 μM unlabeled peptide. The influence of pH on the observed $K_D$ was investigated at pH 6.0 using the primary binding buffer [15 mM sodium citrate, 120 mM NaCl, 0.01% Tween 20] and at pH 9.0 using 200 mM sodium bicarbonate, 125 mM sodium chloride. Other buffers in which dissociation constants of BLyS Binding polypeptides were detremined include: [pH 6.0, 0.01% Tween], [pH 6.0, 0.1% gelatin], [pH5.0, 0.01% Tween], [pH9.0, 0.1% Tween], [pH6.0, 15% ethylene glycol, 0.01% Tween],], [pH5.0, 15% ethylene glycol, 0.01% Tween], and [pH9.0, 15% ethylene glycol, 0.01% Tween]. All six of the peptides (DX212, DX214, DX216, DX217, DX219, and DX221) bound BLyS in solution with approximately the same affinity ($K_D$=0.4–3 μM). Cross-competition studies demonstrated that all peptides compete with each other for BLyS binding, which suggests that they all bind to the same site on BLyS.

EXAMPLE 3

Chromatographic Screening of Immobilized BLyS Binding Polypeptides

A reversed phase analytical assay was used in the assessment of the chromatographic performance of the six affinity media.

The six affinity media (BLyS binding polypeptides bound to SEPHAROSE 4 Fast Flow) and a control column, (hydrolyzed NHS-SEPHAROSE 4 Fast Flow) were packed into 3×50 mm glass Omnifit columns (350 μl). All columns were tested at 200 μl/min (170 cm/hr) using a Watson/Marlow 101 ru peristaltic pump. This setup allowed free use of numerous wash, protein and elution conditions. Detection was made using a Waters 2487 UV/VIS detector at 214 nm and 280 nm connected to a Waters Millennium workstation.

Initial screens with purified BLyS at 30 μg/ml in PBS/0.01% Tween 20, pH 7.2 showed 65% recovery in the flow-through of the control column (1 ml, 30 μg total). However, it was immediately clear that all of the columns, when tested in the same manner, bound BLyS quantitatively from solution, but did not release the protein. The columns were then tested with an array of possible elution conditions and monitored at 214 nm and 280 nm for release of BLyS. Fractions indicating possible BLyS elution based on UV absorbance were collected and analyzed by reversed phase chromatography for confirmation. Conditions tested are shown in Table 10 (below).

TABLE 10

Chromatographic Elution Conditions, BLyS Affinity Media

| Chaotropic Salts | Other Salts and pH | Other Buffers and pH | Orgainc Solvents |
|---|---|---|---|
| 1 M urea, pH 7 | 1 M NaCl, pH 7 and 5 | 30 mM H$_3$PO$_4$, pH 2 | 50% ethylene glycol, pH 4 |
| 2 M urea | 2 M NaCl, pH 7 and 5 | 200 mM NaCO$_3$, pH 10 | 50% ethylene glycol, pH 7 |
| 4 M urea, pH 7 | 2 M MgCl$_2$, pH 7.6 | 50–100 mM NaOAc, pH 5 | 20% ethanol |
| 2 M guanidine, pH 7 | 2 M CaCl$_2$, pH 6 | 2 M imidazole, pH 6 | 50% ethanol |
|  | 1 M citrate, pH 6 | 0.6 M Histidine, pH 6 | 18% butanol |
|  |  | 1 M Arginine, pH6 | 30% glycerol |
|  |  | 100 mM EGTA, EDTA |  |
|  |  | 1 M sorbitol, pH 7 |  |

Columns made with DX214, DX216, DX217, DX219 and DX221 affinity media would only release BLyS in the presence of pH 2 buffer (30 mM H$_3$PO$_4$/150 mM NaCl, pH 2). Recoveries from these columns ranged between 30% and 65%. In contrast, DX212 affinity media released BLyS with good recoveries on elution with 50% ethylene glycol, pH 4 (50% ethylene glycol/100 mM sodium acetate, pH 4) or with 50% ethylene glycol, pH 5 (50% ethylene glycol/100 mM sodium acetate, pH 5).

To determine if the elution conditions were effective at maintaining BLyS in its native trimeric form, size exclusion chromatography (SEC) was used to assay native BLyS and BLyS exposed to both pH 2 and 50% ethylene glycol/100 mM sodium acetate, pH 5. SEC analysis of BLyS following incubation at pH 2 revealed the presence of two new peaks, corresponding in size to apparent multimer and monomer forms, with no evidence of the native trimer. Incubation in 50% ethylene glycol resulted in 16% multimer, but otherwise maintained trimer. Later SEC results on material eluted from the DX212 column with 50% ethylene glycol (pH 5.0) did not show the multimer.

EXAMPLE 4

Capture of BLyS from Cell Culture Supernatants

The DX212, DX219, and DX214 affinity columns were tested for their ability to purify BLyS from cell culture supernatants. BLyS, at approximately 40 µg/ml, was spiked into thawed cell culture supernatants from CHO and Sf9 cell lines. Approximately 100 µg BLyS (2.5 ml total) was loaded onto each column. Levels of BLyS in Sf9 flow-through samples could not be determined in the reversed phase HPLC assay. BLyS was eluted with elution buffer [50% ethylene glycol, 100 mM NaAc, pH5.0]. BLyS protein recovery from these experiments ranged from 29.4% to complete recovery, with purities ranging from 76% to 96.5%.

EXAMPLE 5

Synthesis of Further BLyS Binding Peptides

Once a promising BLyS binding polypeptide has been isolated, improvements to that polypeptide can be made by changing, adding or removing individual or multiple amino acid residues from the polypeptide. Amino acid substitutions can be conservative or non conservative. Conservative amino acids exchanges include, for example, the exchange of aromatic residues (e.g., phenylalanine, tryptophan, and tyrosine) for one another, the exchange of hydrophobic residues (e.g, leucine, isoleucine, and valine) for one another, the exchange of polar residues (e.g., glutamine and asparagine) for one another, the exchange of acidic residues (e.g., arginine, lysine, and histidine) for one another, and the exchange of small residues (e.g., alanine, serine, threonine, methionine, and glycine) for one another, the exchange of aromatic residues for one another. Additionally, nonclassical amino acids, chemical amino acid analogs, or chemically modified classical amino acids can be introduced as a substitution or addition to a BLyS binding polypeptide of the invention. Non-classical amino acids include, but are not limited to, the D-isomers of the common amino acids, 2,4-diaminobutyric acid (Dbu), 4-aminobutyric acid (bAbu), 2-aminobutyric acid (Abu), 6-amino hexanoic acid (epsilon-Ahx), 2-aminoisobutyric acid (Aib), 3-aminoisobutyric acid (bAib), 3-aminopropanoic acid (bAla), ornithine (Orn), norleucine (Nle), norvaline (Nva), 3-hydroxyproline (3Hyp), 4-hydroxyproline (4Hyp), sarcosine (MeGly), citrulline, homocitrulline, cysteic acid, t-butylglycine, t-butylalanine, phenylglycine, cyclohexylalanine, fluoro-amino acids, designer amino acids such as β-methyl amino acids, Cα-methyl amino acids, Nα-methyl amino acids, and amino acid analogs in general. By way of example, four modified peptides based on the DX212 sequence have been designed:

1. Ac-AGK(Ac)EPCYFYWECAVSGPGPEGGGK (SEQ ID NO:169)—internal lysine side chain acetylated;
2. Ac-AGREPCYFYWECAVSGPGPEGGGK (SEQ ID NO:170)—arginine substitution;
3. Ac-AGQEPCYFYWECAVSGPGPEGGGK (SEQ ID NO:171)—glutamine substitution;
4. Ac-AGNleEPCYFYWECAVSGPGPEGGGK (SEQ ID NO:172)—norleucine substitution.

EXAMPLE 6

Affinity Maturation of BLyS Binding Polypeptides

In order to identify high affinity BLyS-binding polypeptides, a BLyS Affinity Maturation Library (BAML) was designed around a 14-mer linear peptide template sequence having fixed amino acid residues at 5 of the 14 positions. 3 of the 5 fixed residues corresponded to a highly conserved DxLT tetrapeptide amino acid motif (SEQ ID NO:446) isolated from both the constrained and linear peptide libraries. The design of the 14-mer allowed for some amino acid variation at each of the remaining 9 positions, however, preference was given for a particular amino acid at each of these positions. Analysis of binding affinity of the newly isolated peptides for BLyS was evaluated by direct and indirect phage ELISA and fluorescence anisotropy.

BAML was designed on a 14-mer linear (non-constrained) template peptide sequence having fixed residues at positions 1 (Ala), 5 (Asp), 7 (Leu), 8 (Thr), and 10 (Leu). The amino acid sequence of positions 3–14 in the BAML template most closely resembles a binding polypeptide isolated from the PhD 12 linear polypeptide library (see Table 7, supra). Residues An at position 1 (fixed Ala) and position 2 (variable) were included to extend the length and presentation of the BLyS-binding sequence. Positions 5–8 correspond to the DxLT motif found in peptide isolates from both the constrained and linear peptide libraries (see Tables 1–8, supra). Since hydrophobic amino acids (L, M, I, A, and G) were found at position 10 in 85% of the original isolates, a Leu residue, occurring in 42% of the isolates, was fixed at that position in the BAML template peptide.

Table 11 shows the design of the 14-mer BAML template sequence.

TABLE 11

BAML template sequence (14-mer)

| amino acid position | | | | | | | | | | | | | | SEQ ID NO: |
|---|---|---|---|---|---|---|---|---|---|---|---|---|---|---|
| 1 | 2 | 3 | 4 | 5 | 6 | 7 | 8 | 9 | 10 | 11 | 12 | 13 | 14 | |
| A | n | w | y | D | s | L | T | k | L | w | l | p | d | 184 |

Referring to Table 11, the upper case letters indicate the fixed residues at positions 1, 5, 7, 8, and 10 of the template. Lower case letters designate preferred amino acids at those positions, however the design of the variegated DNA template encoding the 14-mer allows for some sequence variation at these positions.

Table 12 shows the design of the variegated DNA template used to generate the BAML peptides.

TABLE 12

| BAML DNA template sequence (14-mer) | | | | | | | | | | | | | |
|---|---|---|---|---|---|---|---|---|---|---|---|---|---|
| codon position | | | | | | | | | | | | | |
| 1 | 2 | 3 | 4 | 5 | 6 | 7 | 8 | 9 | 10 | 11 | 12 | 13 | 14 |
| codons* | | | | | | | | | | | | | |
| GCT | eez | zjj | zez | GAT | zqz | CTT | ACT | eej | CTC | zjj | qzz | qqz | jez |

*The sequence of codons is SEQ ID NO:185.

Referring to Table 12, the nucleotide coding sequences for the fixed amino acids in the BAML 14-mer template are shown in upper case letters. The letters “e”, “j”, “q”, and “z” in the variegated DNA template each represent a particular mixture of nucleoside bases present in the input dNTPs for each position:

j=79% guanine, 7% cytosine, 7% adenine, 7% thymine q=7% guanine, 79% cytosine, 7% adenine, 7% thymine e=7% guanine, 7% cytosine, 79% adenine, 7% thymine z=7% guanine, 7% cytosine, 7% adenine, 79% thymine.

The codons of the DNA template were designed to skew the encoded variable amino acid toward the preferred amino acid at each position shown in SEQ ID NO:184 (Table 11, lower case). Later sequencing of phage isolates showed that, at any particular position, preferred residues occurred at a frequency of from 44% to 70%.

Synthetic DNA sequences fitting the DNA template were amplified by large scale PCR. The amplified DNAs were restriction digested for insertion into a M13 phage expression vector (MANP vector, Dyax Corp., Cambridge, Mass.), and vectors bearing the inserts were used to transform M13 phage by electroporation, to produce the BAML.

Recombinant phage were collected and purified by PEG precipitation and titered. A total of $3.2\times10^{13}$ PFU were amplified in BAML from $1.6\times10^{9}$ transformants.

Screening BAML

As outlined in Table 13, a two-step competition method, starting with the original BAML library, was used over 4 rounds of screening to isolate the highest affinity BLyS-binding polypeptides from the BAML. Prior to screening, the amplified BAML was contacted with Seradyn streptavidin-coated magnetic beads (MG-SA, Seradyn, Indianapolis, Ind.), to remove bead- and streptavidin-binding phage.

For screening BAML, phage were incubated in solution with biotinylated BLyS (b-BLyS) in 200 μl PBS, pH 7.4, Tween-20 (0.1%), to form phage/b-BLyS binding complexes. For the first competition step, unlabeled BLyS (1–2 μM) was added to the phage/b-BLyS binding complex mixture in solution and incubated for 1–20 hrs. (See Table 13.) The phage/b-BLyS complexes remaining in solution after incubation with unlabeled BLyS were captured by brief (10 min. on rotator) incubation with MG-SA streptavidin beads (50 μl). After capture of the phage/b-BLyS complexes on streptavidin beads, the unbound fraction was removed and beads were washed 15–20 times with 1 ml PBS-Tween 20 prior to the second competition step. The phage/unlabeled BLyS complexes from the round 1 competition step only, were collected and used as a fraction of the input phage for the second round of screening along with the bead-captured phage/b-BLyS complexes, however, in each subsequent round of screening only the bead-associated phage were collected after the first competition step for further screening, and the phage/unlabeled BLyS complexes were discarded.

For the second competition step, the competitor peptide was a polypeptide (DX221; SEQ ID NO:168) based on a BLyS-binding polypeptide isolated from the PhD 12 library in the initial screenings described above. The phage/b-BLyS complexes bound to streptavidin, collected after the first competition incubation step, were serially diluted with 50 μM DX221 BLyS-binding peptide ($K_D$=3 μM) in 300 μl PBS-Tween-20 (0.1%). A series of short incubations (3–4 per round, for 1 hour) of the phage/b-BLyS complexes with DX221 followed by a final incubation of from overnight (O/N, for rounds 1, 2, and 4) to 3 days (for round 3). (See Table 13.) The second competition step in round 4 included an incubation with 67 nM BLyS for 1 hour prior to incubation with DX221. The streptavidin bead-associated phage/b-BLyS binding complexes remaining after the DX221 competition step in round 4 were collected for further analysis.

TABLE 13

BLyS affinity maturation library (BAML) screening conditions

| Screening Round | Input phage[1] | b-BLyS[2] | First Competition Incubation Time (hrs) | Competitor (BLyS) | Second Competition Incubation Time (hrs) | Peptide Elutions |
|---|---|---|---|---|---|---|
| 1 | $1.5 \times 10^{11}$ | 100 nM | 2 | 2 μM | 1 | 50 μM DX221, 4 × 1 hr, then O/N |
| 2 | $2 \times 10^{10}$ | 100 nM | 1 | 1 μM | 20 | 50 μM DX221, 3 × 1 hr, then O/N |
| 3 | $6.5 \times 10^{10}$ | 100 pM | 16 | 1 μM | 3 | 50 μM DX221 4 × 1 hr, then 3 days |
| 4 | $6.0 \times 10^{10}$ | 10 pM | 16 | 1 μM | 2 | 67 nM BLyS, 1 hr; 50 μM DX221 + 67 nM BLyS 3 × 1 hr, O/N, then add'l 4 hrs |

[1]Input phage for round 1 was original BAML; for round 2 was amplified output phage from overnight (final) peptide elution and bead-associated phage from round 1; for round 3 was amplified bead-associated output phage from round 2; and for round 4 was amplified bead-associated output phage from round 3. All amplified phage samples were pre-cleared on streptavidin beads before incubation with biotin-BLyS in solution.
[2]b-BLyS = biotinylated BLyS ELISA Analysis Approximately four hundred BAML isolates from rounds 2, 3 and 4 of the above screening were analyzed by direct and indirect phage ELISA assays.

For indirect phage ELISA, Immulon-2HB plates (Dynex Technologies, Inc., Chantilly, Va.) were coated with 100 μl of 1 μg/ml Immunopure streptavidin (Pierce, Rockford, Ill.) diluted in PBS. 100 μl of a series of 10-fold dilutions of b-BLyS (0–0.1 μg/ml in PBS) were immobilized in the streptavidin-coated wells (1 hr, 37° C.). After washing, 1–25 μl of overnight culture of E. coli infected with the individual phage plaques were added to the appropriate wells and incubated for 1 hour, followed by 10 washes with PBS-Tween-20. Anti-M13 antibody conjugated to horseradish peroxidase (1:10,000 in PBS-Tween-20) was added to the wells (30 min., room temperature), the color reagent TMB was used and the plates read at OD 630 nm.

Individual phage isolates binding to immobilized BLyS were sequenced and the sequences analyzed. The unique sequences of the BAML BLyS-binding 14-mer display peptides are shown in Table 14.

Analysis of the peptides reveals a significant sequence "collapse" around one motif: $W_3YDPLTKLWL_{12}$ (SEQ ID NO:436) (subscripts indicate amino acid position in the 14-mer display peptide sequence). This most numerous core motif includes the four fixed residues from the original BAML template, i.e., Asp (D) at position 5, Leu (L) at position 7, Thr (T) at position 8, and Leu (L) at position 10. In addition, 5 of the 6 preferred residues from the original BAML template sequence were included in this motif (see Table 11).

73% (143 of 197) of the round 4 isolates included this core motif (SEQ ID NO:436). Single residue substitutions within the 10-mer core motif centered on positions 4 (Y→F) and 12 (L→F, I, or V), with the substitutions at position 12 being alternative hydrophobic residues for Leu.

For the three remaining variable positions (i.e., 2, 13, and 14), selection was not as stringent, although some preferences were apparent, being either built into the library or persisting through rounds of selection. For example, in round 4 isolates, 51% included Asn at position 2; 77% included Pro at position 13; and 32% included Asp at position 14. The presence of Val (27%) or Glu (19%) at position 14 was among the most highly selected in the round 4 isolates, in comparison to their theoretical proportion (4% each) at position 14 in BAML.

The sequences in Table 14 are grouped according to their degree of difference from the core sequence (SEQ ID NO:436).

TABLE 14

Sequences of BAML Phage Isolates (from Rounds 2, 3, 4)

| 14-mer amino acid position | | | | | | | | | | | | | | SEQ ID NO: |
|---|---|---|---|---|---|---|---|---|---|---|---|---|---|---|
| 1 | 2 | 3 | 4 | 5 | 6 | 7 | 8 | 9 | 10 | 11 | 12 | 13 | 14 | |
| A | n | w | y | D | s | L | T | k | L | w | l | p | d | consensus; 184 |
| A | N | W | Y | D | P | L | T | K | L | W | L | P | D | 186 |
| A | N | W | Y | D | P | L | T | K | L | W | L | P | E | 187 |
| A | N | W | Y | D | P | L | T | K | L | W | L | P | G | 188 |
| A | N | W | Y | D | P | L | T | K | L | W | L | P | V | 189 |
| A | N | W | Y | D | P | L | T | K | L | W | L | S | D | 190 |
| A | N | W | Y | D | P | L | T | K | L | W | L | N | D | 191 |
| A | N | W | Y | D | P | L | T | K | L | W | L | P | T | 192 |
| A | N | W | Y | D | P | L | T | K | L | W | L | P | A | 193 |
| A | N | W | Y | D | P | L | T | K | L | W | L | P | N | 194 |
| A | N | W | Y | D | P | L | T | K | L | W | L | V | D | 195 |
| A | N | W | Y | D | P | L | T | K | L | W | L | H | D | 196 |
| A | N | W | Y | D | P | L | T | K | L | W | L | T | D | 197 |
| A | N | W | Y | D | P | L | T | K | L | W | L | P | H | 198 |
| A | N | W | Y | D | P | L | T | K | L | W | L | T | V | 199 |
| A | N | W | Y | D | P | L | T | K | L | W | L | L | D | 200 |
| A | N | W | Y | D | P | L | T | K | L | W | L | L | E | 201 |

TABLE 14-continued

Sequences of BAML Phage Isolates (from Rounds 2, 3, 4)

14-mer amino acid position

| 1 | 2 | 3 | 4 | 5 | 6 | 7 | 8 | 9 | 10 | 11 | 12 | 13 | 14 | SEQ ID NO: |
|---|---|---|---|---|---|---|---|---|----|----|----|----|----|----|
| A | N | W | Y | D | P | L | T | K | L  | W  | L  | H  | E  | 202 |
| A | N | W | Y | D | P | L | T | K | L  | W  | L  | P  | R  | 203 |
| A | N | W | Y | D | P | L | T | K | L  | W  | L  | A  | D  | 204 |
| A | N | W | Y | D | P | L | T | K | L  | W  | L  | P  | Y  | 205 |
| A | N | W | Y | D | P | L | T | K | L  | W  | L  | P  | I  | 206 |
| A | N | W | Y | D | P | L | T | K | L  | W  | L  | I  | D  | 207 |
| A | N | W | Y | D | P | L | T | K | L  | W  | L  | R  | D  | 208 |
| A | Y | W | Y | D | P | L | T | K | L  | W  | L  | P  | D  | 209 |
| A | Y | W | Y | D | P | L | T | K | L  | W  | L  | L  | E  | 210 |
| A | Y | W | Y | D | P | L | T | K | L  | W  | L  | R  | V  | 211 |
| A | Y | W | Y | D | P | L | T | K | L  | W  | L  | P  | E  | 212 |
| A | Y | W | Y | D | P | L | T | K | L  | W  | L  | P  | V  | 213 |
| A | Y | W | Y | D | P | L | T | K | L  | W  | L  | H  | Q  | 214 |
| A | Y | W | Y | D | P | L | T | K | L  | W  | L  | P  | A  | 215 |
| A | Y | W | Y | D | P | L | T | K | L  | W  | L  | R  | V  | 216 |
| A | Y | W | Y | D | P | L | T | K | L  | W  | L  | P  | G  | 217 |
| A | Y | W | Y | D | P | L | T | K | L  | W  | L  | R  | Y  | 218 |
| A | Y | W | Y | D | P | L | T | K | L  | W  | L  | P  | Y  | 219 |
| A | Y | W | Y | D | P | L | T | K | L  | W  | L  | L  | Y  | 220 |
| A | Y | W | Y | D | P | L | T | K | L  | W  | L  | R  | D  | 221 |
| A | Y | W | Y | D | P | L | T | K | L  | W  | L  | P  | V  | 222 |
| A | Y | W | Y | D | P | L | T | K | L  | W  | L  | L  | G  | 223 |
| A | Y | W | Y | D | P | L | T | K | L  | W  | L  | T  | H  | 224 |
| A | Y | W | Y | D | P | L | T | K | L  | W  | L  | P  | T  | 225 |
| A | Y | W | Y | D | P | L | T | K | L  | W  | L  | L  | V  | 226 |
| A | Y | W | Y | D | P | L | T | K | L  | W  | L  | Y  | Y  | 227 |
| A | Y | W | Y | D | P | L | T | K | L  | W  | L  | S  | D  | 228 |
| A | S | W | Y | D | P | L | T | K | L  | W  | L  | P  | A  | 229 |
| A | S | W | Y | D | P | L | T | K | L  | W  | L  | H  | D  | 230 |
| A | S | W | Y | D | P | L | T | K | L  | W  | L  | P  | G  | 231 |
| A | S | W | Y | D | P | L | T | K | L  | W  | L  | P  | Q  | 232 |
| A | S | W | Y | D | P | L | T | K | L  | W  | L  | P  | Y  | 233 |
| A | S | W | Y | D | P | L | T | K | L  | W  | L  | P  | H  | 234 |
| A | S | W | Y | D | P | L | T | K | L  | W  | L  | P  | V  | 235 |
| A | S | W | Y | D | P | L | T | K | L  | W  | L  | P  | I  | 236 |
| A | S | W | Y | D | P | L | T | K | L  | W  | L  | P  | E  | 237 |
| A | F | W | Y | D | P | L | T | K | L  | W  | L  | R  | V  | 238 |
| A | F | W | Y | D | P | L | T | K | L  | W  | L  | P  | E  | 239 |
| A | F | W | Y | D | P | L | T | K | L  | W  | L  | L  | E  | 240 |
| A | F | W | Y | D | P | L | T | K | L  | W  | L  | P  | V  | 241 |
| A | I | W | Y | D | P | L | T | K | L  | W  | L  | P  | E  | 242 |
| A | I | W | Y | D | P | L | T | K | L  | W  | L  | P  | D  | 243 |
| A | I | W | Y | D | P | L | T | K | L  | W  | L  | H  | D  | 244 |
| A | I | W | Y | D | P | L | T | K | L  | W  | L  | T  | D  | 245 |
| A | I | W | Y | D | P | L | T | K | L  | W  | L  | P  | F  | 246 |
| A | I | W | Y | D | P | L | T | K | L  | W  | L  | L  | D  | 247 |
| A | I | W | Y | D | P | L | T | K | L  | W  | L  | P  | R  | 248 |
| A | I | W | Y | D | P | L | T | K | L  | W  | L  | P  | A  | 249 |
| A | I | W | Y | D | P | L | T | K | L  | W  | L  | T  | A  | 250 |
| A | I | W | Y | D | P | L | T | K | L  | W  | L  | A  | V  | 251 |
| A | I | W | Y | D | P | L | T | K | L  | W  | L  | P  | G  | 252 |
| A | I | W | Y | D | P | L | T | K | L  | W  | L  | R  | V  | 253 |
| A | I | W | Y | D | P | L | T | K | L  | W  | L  | P  | H  | 254 |
| A | I | W | Y | D | P | L | T | K | L  | W  | L  | R  | E  | 255 |
| A | I | W | Y | D | P | L | T | K | L  | W  | L  | S  | D  | 256 |
| A | T | W | Y | D | P | L | T | K | L  | W  | L  | P  | A  | 257 |
| A | T | W | Y | D | P | L | T | K | L  | W  | L  | A  | D  | 258 |
| A | T | W | Y | D | P | L | T | K | L  | W  | L  | T  | S  | 259 |
| A | T | W | Y | D | P | L | T | K | L  | W  | L  | P  | G  | 260 |
| A | T | W | Y | D | P | L | T | K | L  | W  | L  | P  | Y  | 261 |
| A | T | W | Y | D | P | L | T | K | L  | W  | L  | S  | G  | 262 |
| A | T | W | Y | D | P | L | T | K | L  | W  | L  | P  | V  | 263 |
| A | T | W | Y | D | P | L | T | K | L  | W  | L  | P  | D  | 264 |
| A | D | W | Y | D | P | L | T | K | L  | W  | L  | P  | V  | 265 |
| A | D | W | Y | D | P | L | T | K | L  | W  | L  | P  | K  | 266 |
| A | D | W | Y | D | P | L | T | K | L  | W  | L  | P  | D  | 267 |
| A | D | W | Y | D | P | L | T | K | L  | W  | L  | P  | E  | 268 |
| A | D | W | Y | D | P | L | T | K | L  | W  | L  | H  | Q  | 269 |
| A | E | W | Y | D | P | L | T | K | L  | W  | L  | R  | D  | 270 |
| A | E | W | Y | D | P | L | T | K | L  | W  | L  | P  | D  | 271 |
| A | E | W | Y | D | P | L | T | K | L  | W  | L  | P  | Y  | 272 |
| A | L | W | Y | D | P | L | T | K | L  | W  | L  | P  | A  | 273 |

TABLE 14-continued

Sequences of BAML Phage Isolates (from Rounds 2, 3, 4)

| 14-mer amino acid position | | | | | | | | | | | | | | |
|---|---|---|---|---|---|---|---|---|---|---|---|---|---|---|
| 1 | 2 | 3 | 4 | 5 | 6 | 7 | 8 | 9 | 10 | 11 | 12 | 13 | 14 | SEQ ID NO: |
| A | L | W | Y | D | P | L | T | K | L | W | L | P | D | 274 |
| A | L | W | Y | D | P | L | T | K | L | W | L | R | G | 275 |
| A | L | W | Y | D | P | L | T | K | L | W | L | L | G | 276 |
| A | M | W | Y | D | P | L | T | K | L | W | L | P | A | 277 |
| A | M | W | Y | D | P | L | T | K | L | W | L | Q | V | 278 |
| A | M | W | Y | D | P | L | T | K | L | W | L | L | G | 279 |
| A | A | W | Y | D | P | L | T | K | L | W | L | P | D | 280 |
| A | A | W | Y | D | P | L | T | K | L | W | L | A | D | 281 |
| A | A | W | Y | D | P | L | T | K | L | W | L | L | D | 282 |
| A | H | W | Y | D | P | L | T | K | L | W | L | T | D | 283 |
| A | H | W | Y | D | P | L | T | K | L | W | L | P | V | 284 |
| A | H | W | Y | D | P | L | T | K | L | W | L | H | D | 285 |
| A | H | W | Y | D | P | L | T | K | L | W | L | P | D | 286 |
| A | P | W | Y | D | P | L | T | K | L | W | L | H | D | 287 |
| A | P | W | Y | D | P | L | T | K | L | W | L | P | V | 288 |
| A | Q | W | Y | D | P | L | T | K | L | W | L | P | E | 289 |
| A | Q | W | Y | D | P | L | T | K | L | W | L | P | Y | 290 |
| A | Q | W | Y | D | P | L | T | K | L | W | L | P | R | 291 |
| A | K | W | Y | D | P | L | T | K | L | W | L | P | D | 292 |
| A | K | W | Y | D | P | L | T | K | L | W | L | P | V | 293 |
| A | K | W | Y | D | P | L | T | K | L | W | L | P | V | 294 |
| A | K | W | Y | D | P | L | T | K | L | W | L | N | G | 295 |
| A | W | W | Y | D | P | L | T | K | L | W | L | P | A | 296 |
| A | V | W | Y | D | P | L | T | K | L | W | L | T | D | 297 |
| A | N | W | Y | D | P | L | T | K | L | W | L | P | D | 186 |
| A | Y | E | Y | D | P | L | T | K | L | W | L | L | Y | 298 |
| A | T | K | Y | D | P | L | T | K | L | W | L | P | D | 299 |
| A | T | L | Y | D | P | L | T | K | L | W | L | P | G | 300 |
| A | I | R | Y | D | P | L | T | K | L | W | L | P | Y | 301 |
| A | E | R | Y | D | P | L | T | K | L | W | L | P | H | 302 |
| A | D | R | Y | D | P | L | T | K | L | W | L | P | Q | 303 |
| A | N | S | Y | D | P | L | T | K | L | W | L | P | E | 304 |
| A | I | L | Y | D | P | L | T | K | L | W | L | P | D | 305 |
| A | N | W | Y | D | P | L | T | K | L | W | L | P | D | 186 |
| A | N | W | F | D | P | L | T | K | L | W | L | P | Q | 306 |
| A | N | W | F | D | P | L | T | K | L | W | L | P | V | 307 |
| A | N | W | F | D | P | L | T | K | L | W | L | T | D | 308 |
| A | N | W | F | D | P | L | T | K | L | W | L | P | D | 309 |
| A | N | W | F | D | P | L | T | K | L | W | L | P | G | 310 |
| A | N | W | F | D | P | L | T | K | L | W | L | P | E | 311 |
| A | N | W | F | D | P | L | T | K | L | W | L | P | A | 312 |
| A | N | W | F | D | P | L | T | K | L | W | L | P | N | 313 |
| A | N | W | F | D | P | L | T | K | L | W | L | S | E | 314 |
| A | N | W | F | D | P | L | T | K | L | W | L | H | D | 315 |
| A | N | W | F | D | P | L | T | K | L | W | L | V | D | 316 |
| A | Y | W | F | D | P | L | T | K | L | W | L | P | D | 317 |
| A | Y | W | Y | D | P | L | T | K | L | W | L | P | V | 318 |
| A | Y | W | F | D | P | L | T | K | L | W | L | P | A | 319 |
| A | Q | W | F | D | P | L | T | K | L | W | L | P | D | 320 |
| A | H | W | F | D | P | L | T | K | L | W | L | P | D | 321 |
| A | T | W | Y | D | P | L | T | K | L | W | L | P | V | 322 |
| A | N | W | Y | D | P | L | T | K | L | W | L | P | D | 186 |
| A | Y | W | Y | D | P | L | T | K | L | W | L | P | V | 323 |
| A | Y | W | Y | D | S | L | T | K | L | W | L | H | D | 324 |
| A | N | W | Y | D | S | L | T | K | L | W | I | P | D | 325 |
| A | N | W | Y | D | S | L | T | K | L | W | L | P | V | 326 |
| A | N | W | Y | D | S | L | T | K | L | W | L | P | D | 327 |
| A | N | W | Y | D | S | L | T | K | L | W | L | A | D | 328 |
| A | N | W | Y | D | S | L | T | K | L | W | L | P | A | 329 |
| A | N | W | Y | D | S | L | T | K | L | W | L | Y | E | 330 |
| A | N | W | Y | D | P | L | T | K | L | W | L | P | D | 186 |
| A | G | W | Y | D | S | L | T | K | L | W | L | P | D | 331 |
| A | V | W | Y | D | S | L | T | K | L | W | L | T | D | 332 |
| A | N | W | Y | D | A | L | T | K | L | W | L | P | V | 333 |
| A | Y | W | Y | D | T | L | T | K | L | W | L | P | N | 334 |
| A | N | W | Y | D | P | L | T | K | L | W | L | P | D | 186 |
| A | F | W | Y | D | P | L | T | N | L | W | L | L | E | 335 |
| A | Y | W | Y | D | P | L | T | G | L | W | L | L | G | 336 |
| A | Y | W | Y | D | P | L | T | G | L | W | L | L | Y | 337 |
| A | Y | W | Y | D | P | L | T | G | L | W | L | R | V | 338 |
| A | Y | W | Y | D | P | L | T | E | L | W | L | R | L | 339 |
| A | N | W | Y | D | P | L | T | K | L | W | L | P | D | 186 |

TABLE 14-continued

Sequences of BAML Phage Isolates (from Rounds 2, 3, 4)

| 1 2 3 4 | 5 6 7 8 9 | 10 | 11 | 12 | 13 | 14 | SEQ ID NO: |
|---|---|---|---|---|---|---|---|
| A M W Y | D P L T K | L | S | L | P | D | 340 |
| A Y W Y | D P L T K | L | S | L | L | V | 341 |
| A I W Y | D P L T K | L | S | L | T | V | 342 |
| A I W Y | D P L T K | L | S | L | L | V | 343 |
| A D W Y | D P L T K | L | S | L | L | L | 344 |
| A Y W Y | D P L T K | L | R | L | L | E | 345 |
| A D W Y | D P L T K | L | 4 | L | L | V | 346 |
| A D W Y | D P L T K | L | R | L | I | V | 347 |
| A I W Y | D P L T K | L | Y | L | P | D | 348 |
| A I W Y | D P L T K | L | G | L | L | V | 349 |
| A N W Y | D P L T K | L | T | L | L | V | 350 |
| A N W Y | D P L T K | L | L | L | P | N | 351 |
| A N W Y | D P L T K | L | W | L | P | D | 186 |
| A S W Y | D P L T K | L | W | F | P | D | 352 |
| A N W Y | D P L T K | L | W | F | P | D | 353 |
| A N W Y | D P L T K | L | W | F | S | D | 354 |
| A S W Y | D P L T K | L | W | F | P | V | 355 |
| A D W Y | D P L T K | L | W | F | P | V | 356 |
| A S W Y | D P L T K | L | W | F | P | K | 357 |
| A K W Y | D P L T K | L | W | F | P | D | 358 |
| A S W Y | D P L T K | L | W | F | L | E | 359 |
| A N W Y | D P L T K | L | W | F | P | A | 360 |
| A T W Y | D P L T K | L | W | F | P | D | 361 |
| A I W Y | D P L T K | L | W | F | P | E | 362 |
| A I W Y | D P L T K | L | W | F | P | D | 363 |
| A I W Y | D P L T K | L | W | F | P | G | 364 |
| A Y W Y | D P L T K | L | W | F | P | H | 365 |
| A N W Y | D P L T K | L | W | F | P | V | 366 |
| A Y W Y | D P L T K | L | W | F | P | D | 367 |
| A G W Y | D P L T K | L | W | F | P | D | 368 |
| A I W Y | D P L T K | L | W | F | P | T | 369 |
| A K W Y | D P L T K | L | W | F | P | A | 370 |
| A Y W Y | D P L T K | L | W | F | F | D | 371 |
| A N W Y | D P L T K | L | W | F | A | D | 372 |
| A N W Y | D P L T K | L | W | L | P | D | 186 |
| A N W Y | D P L T K | L | W | F | P | Y | 373 |
| A D W Y | D P L T K | L | W | F | R | D | 374 |
| A N W Y | D P L T K | L | W | V | P | D | 375 |
| A D W Y | D P L T K | L | W | V | P | A | 376 |
| A N W Y | D P L T K | L | W | V | P | N | 377 |
| A N W Y | D P L T K | L | W | V | P | E | 378 |
| A N W Y | D P L T K | L | W | V | P | Q | 379 |
| A E W Y | D P L T K | L | W | V | P | K | 380 |
| A Q W Y | D P L T K | L | W | V | P | V | 381 |
| A N W Y | D P L T K | L | W | V | P | Y | 382 |
| A L W Y | D P L T K | L | W | V | P | Y | 383 |
| A N W Y | D P L T K | L | W | V | P | G | 384 |
| A S W Y | D P L T K | L | W | I | P | Y | 385 |
| A D W Y | D P L T K | L | W | I | P | G | 386 |
| A N W Y | D P L T K | L | W | I | P | Y | 387 |
| A K W Y | D P L T K | L | W | I | P | Y | 388 |
| A I W Y | D P L T K | L | W | I | P | N | 389 |
| A T W Y | D P L T K | L | W | I | P | Q | 390 |
| A N W Y | D P L T K | L | W | L | P | D | 186 |
| A S W Y | D P L T N | L | W | V | P | D | 391 |
| A Y E Y | D P L T N | L | W | L | L | Y | 392 |
| A Y W Y | D P L T N | L | S | L | L | V | 393 |
| A Y W Y | D P L T K | L | S | I | L | E | 394 |
| A N W Y | D S L T K | L | W | I | P | Y | 395 |
| A H W F | D P L T Q | L | K | I | R | V | 396 |
| A Y W C | D P L T K | L | C | I | L | E | 397 |
| A N S Y | D P L T K | L | W | F | P | Y | 398 |
| A N L Y | D P L T K | L | W | V | P | Y | 399 |
| A N W Y | D P L T K | L | W | L | H | D | 400 |
| A N W Y | D S L T K | L | W | F | P | D | 401 |
| A T S Y | D S L T K | L | W | L | P | A | 402 |
| A C W Y | D S L T K | L | C | H | R | E | 403 |
| A I G N | D P L T K | L | W | I | P | Y | 404 |
| A N W Q | D C L T K | L | C | L | A | G | 405 |
| A Y W F | D P L T N | L | W | L | L | E | 406 |
| A Y W Y | D P L T N | L | S | L | L | V | 407 |
| A N C F | D S L T R | L | W | L | C | D | 408 |

TABLE 14-continued

Sequences of BAML Phage Isolates (from Rounds 2, 3, 4)

| 1 | 2 | 3 | 4 | 5 | 6 | 7 | 8 | 9 | 10 | 11 | 12 | 13 | 14 | SEQ ID NO: |
|---|---|---|---|---|---|---|---|---|----|----|----|----|----|-----------|
| A | C | A | Y | D | A | L | T | K | L  | C  | L  | P  | A  | 409 |
| A | N | W | Y | D | P | L | T | N | L  | S  | L  | L  | L  | 410 |
| A | Y | W | Y | D | P | L | T | Q | L  | S  | L  | L  | V  | 411 |
| A | Y | R | Y | D | A | L | T | G | L  | W  | L  | L  | Y  | 412 |
| A | Y | W | N | D | P | L | T | K | L  | K  | L  | R  | L  | 413 |
| A | Y | W | Y | D | P | L | T | Q | L  | S  | L  | L  | V  | 414 |
| A | Y | R | Y | D | A | L | T | G | L  | W  | L  | L  | Y  | 415 |
| A | Y | R | Y | D | S | L | T | N | L  | W  | L  | L  | Y  | 416 |
| A | Y | W | Y | D | P | L | T | K | L  | S  | I  | L  | E  | 417 |
| A | S | C | Y | D | P | L | T | K | L  | C  | F  | P  | V  | 418 |
| A | F | W | F | D | P | L | T | G | L  | W  | L  | L  | E  | 419 |
| A | N | W | Y | D | P | L | T | K | L  | W  | L  | P  | D  | 186 |
| A | H | W | Y | D | P | L | T | K | L  | S  | I  | R  | V  | 420 |
| A | P | W | Y | D | S | L | T | K | L  | W  | F  | P  | S  | 421 |
| A | N | C | Y | D | T | L | T | K | L  | W  | L  | T  | C  | 422 |
| A | N | W | Y | D | S | L | T | K | L  | S  | L  | P  | D  | 423 |
| A | Y | A | Y | D | F | L | T | Q | L  | S  | L  | P  | D  | 424 |
| A | F | R | Y | D | S | L | T | G | L  | W  | L  | R  | Y  | 425 |
| A | N | C | Y | D | S | L | T | K | L  | W  | L  | P  | C  | 426 |
| A | N | G | Y | D | L | L | T | N | L  | S  | V  | S  | D  | 427 |
| A | N | W | Y | D | P | L | T | R | L  | W  | I  | P  | V  | 428 |
| A | L | K | F | D | Y | L | T | K | L  | W  | L  | P  | D  | 429 |
| A | Y | R | Y | D | S | L | T | K | L  | W  | L  | P  | G  | 430 |
| A | Y | C | Y | D | S | L | T | K | L  | W  | I  | P  | D  | 431 |
| A | S | W | E | D | S | L | T | K | L  | W  | L  | S  | K  | 432 |
| A | Y | W | Y | D | S | L | T | G | L  | S  | L  | L  | V  | 433 |
| A | Y | W | Y | D | P | L | T | Y | L  | R  | L  | R  | V  | 434 |
| A | K | C | Y | D | S | L | T | N | L  | W  | L  | C  | D  | 435 |

Nearly all of the ELISA signals of the BAML isolates were higher than those isolated in the initial screen (see Example 1). For comparison, peptide 453–01-B07 (SEQ ID NO:31) ($K_D$=700 nM) was used as a reference (positive control). Negative control MAEX (M13 phage with no insert) did not bind b-BLyS at any concentration tested.

For direct phage ELISA, the signal measured is a reflection of the ability of a set number of phage to bind to various concentrations of b-BLyS. Peptides tested by the direct phage ELISA assay were chosen based on high affinity for BLyS as determined in the indirect phage ELISA assay. For this assay, Immulon-2HB plates were coated with 0 or 1000 ng anti-Fd antibody (Sigma, St. Louis, Mo.). After washing (PBS-Tween-20), phage dilutions were added to saturate the available antibody and incubated for 1 hour, washed, then incubated with 100 µl of 10-fold dilutions of b-BLyS (0–1 µg/ml) for 1 hour at room temperature. Streptavidin-HRP (1:1000 in PBS-tween-20; Endogen, Woburn, Mass.) was added to the wells and incubated for 1 hour, developed using TMB and reading at OD 630 nm.

Determination of BAML Peptide $K_D$ by Fluoresence Anisotropy.

Several peptides containing the 10-mer core structural motif or single-position variants of that motif identified by sequence analysis were synthesized with a short Gly-Gly-Lys linker sequence and the C-terminal lysine was labeled with fluorescein. These peptides, shown in Table 15, below, were synthesized by solid phase synthesis for determination of dissociation constant with respect to BLyS. The DX815 and DX876 polypeptides were derived from DX814 (SEQ ID NO:186) by deletion of two N-terminal amino acids or the two amino acids N-terminal and C-terminal to the core peptide at (positions 3–12). DX816, DX817, DX819, and DX822 correspond to other BAML isolates (SEQ ID NOs: 189, 309, 353, 327, respectively). DX818 corresponds to isolate SEQ ID NO:340, except that Asn has been substituted for Met at position 2. The $K_D$ of several BLyS binding BAML peptides was determined by fluorescence anisotropy, performed as previously described. The sequence of DX822 without the -GGK linker (see SEQ ID NO:327) matches the BAML template sequence (see Table 11). The BAML consensus sequence found in DX822 resulted in a more than 10-fold improvement in binding affinity for BLyS, as compared to one of the highest affinity binders isolated in the initial screen (453–01-B07, SEQ ID NO:31).

TABLE 15

Dissociation Constants of Synthetic BLyS-binding Polypeptides

| Peptide | Sequence | SEQ ID NO: | $K_D$ (nM) |
|---------|----------|-----------|-----------|
| DX814 | Ac-ANWYDPLTKLWLPDGGK-fitc | 437 | 26 ±7 |
| DX815 | Ac-WYDPLTKLWLPDGGK-fitc | 438 | 31 ± 13 |
| DX876 | Ac-WYDPLTKLWLGGK-fitc | 439 | 171 ± 90 |
| DX816 | Ac-ANWYDPLTKLWLPVGGK-fitc | 440 | 44 ± 15 |
| DX817 | Ac-ANWFDPLTKLWLPDGGK-fitc | 441 | 32 ± 26 |
| DX818 | Ac-ANWYDPLTKLSLPDGGK-fitc | 442 | 342 ± 108 |
| DX819 | Ac-ANWYDPLTKLWFPDGGK-fitc | 443 | 69 ± 38 |
| DX822 | Ac-ANWYDSLTKLWLPDGGK-fitc | 444 | 79 ± 54 |

Analysis of the BAML isolates revealed a lack of sequence conservation at position 2 (varied in the BAML template, see Table 11). To examine whether the N-terminal residues at positions 1 and 2 in the BAML sequence were necessary for binding to BLyS, a truncated version of DX814 comprising only residues 3–14 (DX815; see Table 15) was synthesized and analyzed by fluorescence anisotropy. The $K_D$ for DX815 was indistinguishable from that of DX814, suggesting that residues 1–2 are not required for high affinity binding to BLyS. Further truncation of DX814 to the minimal core (residues 1–10, DX876) increased the $K_D$ to 171 nM, indicating a contribution from Pro at position 13 and/or Asp at position 14 of the 14-mer to high affinity BLyS binding. Substitution of Val in DX816 at that position had little effect on the $K_D$ (see Table 15). In comparing the BLyS-binding polypeptide DX221 (Ac-WTDSLTGLWFP-DGGPGPEGGGK; $K_D$=3 µM; SEQ ID NO:168) with the BAML peptide closest in sequence (DX819, Ac-ANWYD-PLTKLWFPDGGK; $K_D$=69 nM; SEQ ID NO:443), differences are seen at three positions 4 (T→Y), 6 (S→P), and 9 (G→K), indicating the contribution of these residues in binding affinity.

The synthesized BAML peptides exhibited $K_D$ values in the low nanomolar range, two orders of magnitude lower than primary isolate-derived peptides (see Example 1). Phenylalanine substitutions ($F_4$→$Y_4$; $F_{12}$→$L_{12}$; Table 17) were the most common minor variations to the core sequence and these changes failed to significantly affect the dissociation constants of the synthesized peptides. A change at position 11 ($W_{11}$→$S_{11}$; DX818), however, resulted in an approximately 10-fold decrease in affinity compared to DX814.

Following the foregoing description, the characteristics important for affinity binding polypeptides permitting detection or separation of BLyS or BLyS-like polypeptides (BLyS target protein) in or from any solution can be appreciated. Additional binding polypeptide embodiments of the invention and alternative methods adapted to a particular solution or feed stream will be evident from studying the foregoing description. For instance, any spacer or linker sequences associated with BLyS binding polypeptides discussed above may be removed or substituted to yield additional BLyS binding polypeptides of this invention. Also, very high affinity polypeptide BLyS target binders suitable for in vivo therapeutic applications may be prepared, e.g., by selecting among the peptides isolated from the BAML, by selecting similar polypeptides under similarly stringent conditions from BAML or other peptide library, or by designing a polypeptide binding molecule following the descriptions above, e.g., of important structural motifs contributing to BLyS binding properties. All such embodiments and obvious alternatives are intended to be within the scope of this invention, as defined by the claims that follow.

The publications referred to above are hereby incorporated by reference in their entireties.

The invention claimed is:

1. A B lymphocyte stimulator protein (BLyS) binding polypeptide comprising an amino acid sequence of the following formula:

$$\text{Cys-}X_5\text{-Phe-}X_7\text{-Trp-Glu-Cys (residue 4–10 of SEQ ID NO:1),} \quad (H)$$

wherein $X_5$ is Phe, Trp, or Tyr; and
$X_7$ is Pro or Tyr; or $$\text{Cys-}X_2\text{-}X_3\text{-}X_4\text{-}X_5\text{-}X_6\text{-}X_7\text{-Cys (SEQ ID NO:9),} \quad (I)$$

wherein $X_2$ is Asp, Ile, Leu, or Tyr;
$X_3$ is Arg, Asp, Glu, His, Ile, Leu, Lys, Phe, Pro, Tyr, or Val;
$X_4$ is His, Leu, Lys, or Phe;
$X_5$ is Leu, Pro, or Thr;
$X_6$ is Arg, Asn, Gly, His, Ile, Lys, Met, or Trp; and
$X_7$ is Ala, Asn, Gln, Glu, Gly, His, Ile, Leu, Met, Phe, Ser, Trp, Tyr, or Val; or $$\text{Cys-}X_2\text{-}X_3\text{-}X_4\text{-}X_5\text{-}X_6\text{-}X_7\text{-}X_8\text{-Cys (SEQ ID NO:10),} \quad (J)$$

wherein $X_2$ is Asn, or Asp;
$X_3$ is Arg, Asp, Ile, Leu, Met, Pro, or Val;
$X_4$ is Ala, Ile, Leu, Pro, Thr, or Val;
$X_5$ is Asn, His, Ile, Leu, Lys, Phe, or Thr;
$X_6$ is Asn, Glu, Gly, His, Leu, Lys, Met, Pro, or Thr;
$X_7$ is Arg, Asn, Asp, Gln, Glu, Gly, Ile, Lys, Met, Pro, Ser, or Trp; and
$X_8$ is Arg, Glu, Gly, Lys, Phe, Ser, Trp, or Tyr; or $$\text{Cys-}X_2\text{-}X_3\text{-}X_4\text{-}X_5\text{-}X_6\text{-}X_7\text{-}X_8\text{-}X_9\text{-Cys (SEQ ID NO:11),} \quad (K)$$

wherein $X_2$ is Asp, Gln, His, Ile, Leu, Lys, Met, Phe, or Thr;
$X_3$ is His, Ile, Leu, Met, Phe, Pro, Trp, or Tyr;
$X_4$ is Asp, His, Leu, or Ser;
$X_5$ is Ala, Arg, Asp, Glu, Leu, Phe, Pro, or Thr;
$X_6$ is Ala, Arg, Asn, or Leu;
$X_7$ is Ile, Leu, Met, Pro, Ser, or Thr;
$X_8$ is Ala, Arg, Asn, Gly, His, Lys, Ser, or Tyr; and
$X_9$ is Ala, Arg, Asn, Gln, Leu, Met, Ser, Trp, Tyr, or Val; or $$\text{Cys-}X_2\text{-}X_3\text{-}X_4\text{-}X_5\text{-}X_6\text{-}X_7\text{-}X_8\text{-}X_9\text{-}X_{10}\text{-}X_{11}\text{-Cys (SEQ ID NO:12),} \quad (L)$$

wherein $X_2$ is Arg, Asn, Gln, Glu, His, Leu, Phe, Pro, Trp, Tyr, or Val;
$X_3$ is Arg, Asp, Gln, Gly, Ile, Lys, Phe, Thr, Trp or Tyr;
$X_4$ is Ala, Arg, Asp, Glu, Gly, Leu, Ser, or Tyr;
$X_5$ is Asp, Gln, Glu, Leu, Met, Phe, Pro, Ser, or Tyr;
$X_6$ is Asp, Leu, Pro, Thr, or Val;
$X_7$ is Arg, Gln, Gly, Ile, Leu, Lys, Met, Phe, Thr, Trp or Tyr;
$X_8$ is Ala, Arg, Asn, Gln, Glu, His, Leu, Lys, Met, or Thr;

X$_9$ is Ala, Asn, Gln, Gly, Leu, Lys, Phe, Pro, Thr, Trp, or Tyr;

X$_{10}$ is Ala, Arg, Gln, His, Lys, Met, Phe, Pro, Thr, Trp, or Tyr; and

X$_{11}$ is Arg, Gln, Glu, Gly, His, Leu, Met, Phe, Pro, Ser, Thr, Tyr, or Val.

2. The polypeptide according to claim 1, wherein (a) said polypeptide comprises an amino acid sequence of the formula: Cys-X$_5$-Phe-X$_7$-Trp-Glu-Cys (residues 4–10 SEQ ID NO:1), and the following amino acid positions are independently selected as follows: X$_2$ is Tyr; X$_4$ is Pro; or combinations of such selections; or (b) said polypeptide comprises an amino acid sequence of the following formula: Cys-X$_2$-X$_3$-X$_4$-X$_5$-X$_6$-X$_7$-Cys (SEQ ID NO:9), and the following amino acid positions are independently selected as follows: X$_2$ is Asp or Leu; X$_3$ is Glu or Leu; X$_4$ is His or Leu; X$_5$ is Thr or Pro; X$_6$ is Lys; or combinations of such selections; or (c) said polypeptide comprises an amino acid sequence of the following formula: Cys-X$_2$-X$_3$-X$_4$-X$_5$-X$_6$-X$_7$-X$_8$-Cys (SEQ ID NO:10), and the following amino acid positions are independently selected as follows: X$_2$ is Asp; X$_3$ is Ile; X$_4$ is Val or Leu; X$_5$ is Thr; X$_6$ is Leu; X$_8$ is Ser; or combinations of such selections; or (d) said polypeptide comprises an amino acid sequence of the following formula: Cys-X$_2$-X$_3$-X$_4$-X$_5$-X$_6$-X$_7$-X$_8$-X$_9$-Cys (SEQ ID NO:11), and the following amino acid positions are independently selected as follows: X$_4$ is Asp; X$_5$ is Glu or Pro; X$_6$ is Leu; X$_7$ is Thr; or combinations of such selections; or (e) said polypeptide comprises an amino acid sequence of the following formula: Cys-X$_2$-X$_3$-X$_4$-X$_5$-X$_6$-X$_7$-X$_8$-X$_9$-X$_{10}$-X$_{11}$-Cys (SEQ ID NO:12), and the following amino acid positions are independently selected as follows: X$_2$ is Trp, Tyr, or Val; X$_3$ is Asp; X$_4$ is Asp; X$_5$ is Leu; X$_6$ is Leu or Thr; X$_7$ is Lys or Thr; X$_8$ is Arg or Leu; X$_9$ is Thr or Trp; X$_{10}$ is Met or Phe; X$_{11}$ is Val; or combinations of such selections.

3. A BLyS binding polypeptide comprising an amino acid sequence of the following formula:

(A) X$_1$-X$_2$-X$_3$-Cys-X$_5$-Phe-X$_7$-Trp-Glu-Cys-X$_{11}$-X$_{12}$-X$_{13}$ (SEQ ID NO:1), (A)

wherein

X$_1$ is Ala, Asn, Lys, or Ser;
X$_2$ is Ala, Glu, Met, Ser, or Val;
X$_3$ is Ala, Asn, Lys, or Pro;
X$_5$ is Phe, Trp, or Tyr;
X$_7$ is Pro or Tyr;
X$_{11}$ is Ala, Gln, His, Phe, or Val;
X$_{12}$ is Asn, Gln, Gly, His, Ser, or Val; and
X$_{13}$ is Ala, Asn, Gly, Ile, Pro, or Ser; or X$_1$-X$_2$-X$_3$-Cys-X$_5$-X$_6$-X$_7$-X$_8$-X$_9$-X$_{10}$-Cys-X$_{12}$-X$_{13}$-X$_{14}$ (SEQ ID NO:2), (B)

wherein

X$_1$ is Ala, Asp, Gln, Glu, Gly, His, Ile, Leu, Lys, Met, Phe, Pro, Ser, Thr, Trp, Tyr, Val, or is absent;
X$_2$ is Ala, Asn, Asp, Gln, Gly, His, Ile, Leu, Lys, Met, Phe, Pro, Ser, Thr, Trp, Tyr, or Val;
X$_3$ is Ala, Arg, Asn, Asp, Gln, Glu, Gly, His, Ile, Leu, Lys, Met, Phe, Pro, Ser, Trp, Tyr, or Val;
X$_5$ is Asp, Ile, Leu, or Tyr; X$_6$ is Arg, Asp, Glu, His, Ile, Leu, Lys, Phe, Pro, Tyr, or Val;
X$_7$ is His, Leu, Lys, or Phe; X$_8$ is Leu, Pro, or Thr;
X$_9$ is Arg, Asn, Gly, His, Ile, Lys, Met, or Trp;
X$_{10}$ is Ala, Gln, Glu, Gly, His, Ile, Leu, Met, Phe, Ser, Trp, Tyr, or Val;
X$_{12}$ is Asp, Gln, Glu, Gly, Ile, Leu, Lys, Phe, Ser, Trp, Tyr, or Val;
X$_{13}$ is Ala, Arg, Asn, Asp, Gln, Glu, Gly, His, Leu, Lys, Met, Phe, Pro, Ser, Thr, Trp, Tyr, or Val; and
X$_{14}$ is Ala, Arg, Asn, Asp, Gln, Glu, Gly, His, Ile, Leu, Lys, Phe, Pro, Trp, Tyr, Val, or is absent; or X$_1$-X$_2$-X$_3$-Cys-X$_5$-X$_6$-X$_7$-X$_8$-X$_9$-X$_{10}$-X$_{11}$-Cys-X$_{13}$-X$_{14}$-X$_{15}$ (SEQ ID NO:3), (C)

wherein

X$_1$ is Ala, Arg, Asn, Asp, Leu, Lys, Phe, Pro, Ser, or Thr;
X$_2$ is Asn, Asp, Gln, His, Ile, Lys, Pro, Thr, or Trp;
X$_3$ is Ala, Arg, Asn, Gln, Glu, His, Phe, Pro, or Thr;
X$_5$ is Asn, Asp, Pro, Ser, or Thr;
X$_6$ is Arg, Asp, Ile, Leu, Met, Pro, or Val;
X$_7$ is Ala, Ile, Leu, Pro, Thr, or Val;
X$_8$ is Asn, His, Ile, Leu, Lys, Phe, or Thr;
X$_9$ is Asn, Glu, Gly, His, Leu, Lys, Met, Pro, or Thr;
X$_{10}$ is Arg, Asn, Asp, Gln, Glu, Gly, Ile, Lys, Met, Pro, Ser, or Trp;
X$_{11}$ is Arg, Glu, Gly, Lys, Phe, Ser, Trp, or Tyr;
X$_{13}$ is Gln, Glu, Ile, Leu, Phe, Pro, Ser, Tyr, or Val;
X$_{14}$ is Asn, Gly, Ile, Phe, Pro, Thr, Trp, or Tyr; and
X$_{15}$ is Asn, Asp, Glu, Leu, Lys, Met, Pro, or Thr; or X$_1$-X$_2$-X$_3$-Cys-X$_5$-X$_6$-X$_7$-X$_8$-X$_9$-X$_{10}$-X$_{11}$-X$_{12}$-Cys-X$_{14}$-X$_{15}$-X$_{16}$ (SEQ ID NO:4), (D)

wherein

X$_1$ is Asn, Asp, His, Leu, Phe, Pro, Ser, Tyr, or is absent;
X$_2$ is Arg, Asn, Asp, His, Phe, Ser, or Trp;
X$_3$ is Asn, Asp, Leu, Pro, Ser, or Val;
X$_5$ is Asp, Gln, His, Ile, Leu, Lys, Met, Phe, or Thr;
X$_6$ is His, Ile, Leu, Met, Phe, Pro, Trp, or Tyr;
X$_7$ is Asp, His, Leu, or Ser;
X$_8$ is Ala, Arg, Asp, Glu, Leu, Phe, Pro, or Thr;
X$_9$ is Ala, Arg, Asn, or Leu;
X$_{10}$ is Ile, Leu, Met, Pro, Ser, or Thr;
X$_{11}$ is Ala, Arg, Asn, Gly, His, Lys, Ser, or Tyr;
X$_{12}$ is Ala, Arg, Asn, Gln, Leu, Met, Ser, Trp, Tyr, or Val;
X$_{14}$ is Asp, Gly, Leu, Phe, Tyr, or Val; and
X$_{15}$ is Asn, His, Leu, Pro, or Tyr; and X$_{16}$ is Asn, Asp, His, Phe, Ser, or Tyr; or X$_1$-X$_2$-X$_3$-Cys-X$_5$-X$_6$-X$_7$-X$_8$-X$_9$-X$_{10}$-X$_{11}$-X$_{12}$-X$_{13}$-X$_{14}$-Cys-X$_{16}$-X$_{17}$-X$_{18}$ (SEQ ID NO:5), (E)

wherein

X$_1$ is Arg, Asp, Gly, His, Leu, Phe, Pro, Ser, Trp, Tyr, or is absent;
X$_2$ is Ala, Arg, Asn, Asp, Gly, Pro, Ser, or is absent;
X$_3$ is Arg, Asn, Gln, Glu, Gly, Lys, Met, Pro, Trp or Val;
X$_5$ is Arg, Asn, Gln, Glu, His, Leu, Phe, Pro, Trp, Tyr, or Val;
X$_6$ is Arg, Asp, Gln, Gly, Ile, Lys, Phe, Thr, Trp or Tyr;
X$_7$ is Ala, Arg, Asp, Glu, Gly, Leu, Ser, or Tyr;
X$_8$ is Asp, Gln, Glu, Leu, Met, Phe, Pro, Ser, or Tyr;
X$_9$ is Asp, Leu, Pro, Thr, or Val;
X$_{10}$ is Arg, Gln, His, Ile, Leu, Lys, Met, Phe, Thr, Trp or Tyr;
X$_{11}$ is Ala, Arg, Asn, Gln, Glu, His, Leu, Lys, Met, or Thr;
X$_{12}$ is Ala, Asn, Gln, Gly, Leu, Lys, Phe, Pro, Thr, Trp, or Tyr;
X$_{13}$ is Ala, Arg, Gln, His, Lys, Met, Phe, Pro, Thr, Trp, or Tyr;

$X_{14}$ is Arg, Gln, Glu, Gly, His, Leu, Met, Phe, Pro, Ser, Thr, Tyr, or Val;

$X_{16}$ is Arg, Asp, Gly, His, Lys, Met, Phe, Pro, Ser, or Trp;

$X_{17}$ is Arg, Asn, Asp, Gly, His, Phe, Pro, Ser, Trp or Tyr; and $X_{18}$ is Ala, Arg, Asn, Asp, His, Leu, Phe, or Trp; or $$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12} \text{ (SEQ ID NO:6),} \quad (F)$$

wherein $X_1$ is Ala, Arg, Gly, His, Leu, Lys, Met, Phe, Trp, Tyr, or Val;

$X_2$ is Ala, Arg, Gln, His, Ile, Leu, Phe, Thr, Trp, or Tyr;

$X_3$ is Ala, Asp, Lys, Phe, Thr, Trp or Tyr;

$X_4$ is Arg, Asp, Gln, Lys, Met, Phe, Pro, Ser, Tyr, or Val;

$X_5$ is Asp, Leu, Lys, Phe, Pro, Ser, or Val;

$X_6$ is His, Ile, Leu, Pro, Ser, or Thr;

$X_7$ is Arg, Gly, His, Leu, Lys, Met, or Thr;

$X_8$ is Ala, Arg, Asn, Ile, Leu, Lys, Met, or Thr;

$X_9$ is Ala, Asn, Arg, Asp, Glu, Gly, His, Leu, Met, Ser, Trp, Tyr, or Val;

$X_{10}$ is Ile, Leu, Phe, Ser, Thr, Trp, Tyr, or Val;

$X_{11}$ is Ala, Arg, Gly, His, Ile, Leu, Lys, Pro, Ser, Thr, Trp, Tyr, or Val; and $X_{12}$ is Arg, Asp, His, Leu, Lys, Met, Phe, Pro, Ser, Trp, Tyr, or Val; or $$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13} \text{ (SEQ ID NO:7),} \quad (G)$$

wherein $X_1$ is Asp, Gln, Glu, Gly, His, Lys, Met, or Trp;

$X_2$ is Arg, Gln, His, Ile, Leu, or Pro;

$X_3$ is Asp, Gly, Ile, Lys, Thr, Tyr or Val;

$X_4$ is Asn, Asp, Gln, Glu, Met, Pro, Ser, or Tyr;

$X_5$ is Asn, Asp, His, Ile, Leu, Met, Pro, Thr or Val;

$X_6$ is Asp, Glu, His, Leu, Lys, Pro, or Val;

$X_7$ is Arg, Asn, Gln, His, Ile, Leu, Met, Pro, or Thr;

$X_8$ is Gln, Gly, His, Leu, Met, Ser, or Thr;

$X_9$ is Asn, Gln, Gly, His, Leu, Lys, Ser, or Thr;

$X_{10}$ is Ala, Gly, Ile, Leu, Lys, Met, or Phe;

$X_{11}$ is Ala, Glu, His, Ile, Leu, Met, Ser, Thr, Trp, Tyr, or Val;

$X_{12}$ is Arg, Gln, Glu, Gly, His, Ile, Lys, Tyr, or Val; and $X_{13}$ is Arg, Asn, Glu, His, Ile, Ser, Thr, Trp, or Val.

4. The BLyS binding polypeptide according to claim 3, wherein (a) said polypeptide includes an amino acid sequence of the following formula: $X_1\text{-}X_2\text{-}X_3\text{-Cys-}X_5\text{-Phe-}X_7\text{-Trp-Glu-Cys-}X_{11}\text{-}X_{12}\text{-}X_{13}$ (SEQ ID NO:1), and the following amino acid positions are independently selected as follows: $X_3$ is Lys; $X_5$ is Tyr; $X_7$ is Pro; $X_{11}$ is Ala, Gln, His, Phe, or Val; $X_{12}$ is Asn, Gln, Gly, His, Ser, or Val; $X_{13}$ is Ala, Asn, Gly, Ile, Pro, or Ser; or combinations of such selections; or (b) said polypeptide includes an amino acid sequence of the following formula: $X_1\text{-}X_2\text{-}X_3\text{-Cys-}X_5\text{-}X_6\text{-}X_7\text{-}X_8\text{-}X_9\text{-}X_{10}\text{-Cys-}X_{12}\text{-}X_{13}\text{-}X_{14}$ (SEQ ID NO:2), and the following amino acid positions are independently selected as follows: $X_3$ is Asp; $X_5$ is Asp or Leu; $X_6$ is Glu or Leu; $X_7$ is His or Leu; $X_8$ is Thr or Pro; $X_9$ is Lys; or combinations of such selections; or (c) said polypeptide includes an amino acid sequence of the following formula: $X_1\text{-}X_2\text{-}X_3\text{-Cys-}X_5\text{-}X_6\text{-}X_7\text{-}X_8\text{-}X_9\text{-}X_{10}\text{-}X_{11}\text{-Cys-}X_{13}\text{-}X_{14}\text{-}X_{15}$ (SEQ ID NO:3), and the following amino acid positions are independently selected as follows: $X_3$ is Ala; $X_5$ is Asp; $X_6$ is Ile; $X_7$ is Val or Leu; $X_8$ is Thr; $X_9$ is Leu; $X_{11}$ is Ser; $X_{13}$ is Val; $X_{15}$ is Glu or Pro; or combinations of such selections; or (d) said polypeptide includes an amino acid sequence of the following formula: $X_1\text{-}X_2\text{-}X_3\text{-Cys-}X_5\text{-}X_6\text{-}X_7\text{-}X_8\text{-}X_9\text{-}X_{10}\text{-}X_{11}\text{-}X_{12}\text{-Cys-}X_{14}\text{-}X_{15}\text{-}X_{16}$ (SEQ ID NO:4), and the following amino acid positions are independently selected as follows: $X_1$ is Ser; $X_2$ is Arg; $X_3$ is Asn or Asp; $X_7$ is Asp; $X_8$ is Glu or Pro; $X_9$ is Leu; $X_{10}$ is Thr; $X_{14}$ is Leu; $X_{15}$ is His, Leu, or Pro; $X_{16}$ is Asp or Ser; or combinations of such selections; or (e) said polypeptide includes an amino acid sequence of the following formula: $X_1\text{-}X_2\text{-}X_3\text{-Cys-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-Cys-}X_{16}\text{-}X_{17}\text{-}X_{18}$ (SEQ ID NO:5), and the following amino acid positions are independently selected as follows: $X_1$ is Arg; $X_2$ is Asn, Asp, Gly, or Pro; $X_3$ is Gly or Met; $X_5$ is Trp, Tyr, or Val; $X_6$ is Asp; $X_7$ is Asp; $X_8$ is Leu; $X_9$ is Leu or Thr; $X_{10}$ is Lys or Thr; $X_{11}$ is Arg or Leu; $X_{12}$ is Thr or Trp; $X_{13}$ is Met or Phe; $X_{14}$ is Val; $X_{16}$ is Met; $X_{17}$ is Arg, His, or Tyr; $X_{18}$ is Asn or His; or combinations of such selections; or (f) said polypeptide includes an amino acid sequence of the following formula: $X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}$ (SEQ ID NO:6), and the following amino acid positions are independently selected as follows: $X_1$ is Gly, Tyr, or Val; $X_2$ is His or Tyr; $X_3$ is Asp or Tyr; $X_4$ is Asp or Gln; $X_5$ is Leu or Ser; $X_6$ is Leu or Thr; $X_7$ is Lys or Thr; $X_8$ is Leu or Lys; $X_9$ is Met or Ser; $X_{10}$ is Thr or Leu; $X_{11}$ is Pro or Thr; $X_{12}$ is Arg or Pro; or combinations of such selections; or (g) said polypeptide includes an amino acid sequence of the following formula: $X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}$ (SEQ ID NO:7), and the following amino acid positions are independently selected as follows: $X_1$ is Glu or Lys; $X_2$ is His or Pro; $X_3$ is Tyr; $X_4$ is Asp or Gln; $X_5$ is Asn or Thr; $X_6$ is Asp or Pro; $X_7$ is Ile or Pro; $X_8$ is Leu or Thr; $X_9$ is Lys; $X_{10}$ is Gly or Met; $X_{11}$ is Ala or Thr; $X_{12}$ is Arg or His; $X_{13}$ is His; or combinations of such selections.

5. The BLyS binding polypeptide according to claim 3, comprising an amino acid sequence selected from the group consisting of SEQ ID NOs:20–162 as depicted in Tables 1–8.

6. The BLyS binding polypeptide according to claim 3, comprising an amino acid sequence selected from the group consisting of:

AGKEPCYFYWECAVSGPGPEGGGK (SEQ ID NO:163),

AGVPFCDLLTKHCFEAGPGPEGGGK (SEQ ID NO:164),

GSSRLCHMDELHVCVHFAPPGPEGGGK (SEQ ID NO:165),

GDGGNCYTDSLTKLHFCMGDEPGPEGGGK (SEQ ID NO:166),

GYDVLTKLYFVPGGPGPEGGGK (SEQ ID NO:167), and

WTDSLTGLWFPDGGPGPEGGGK (SEQ ID NO:168).

7. A method for detecting BLyS or a BLyS-like polypeptide in a solution suspected of containing it comprising:

(a) contacting said solution with a polypeptide according to any of claim 1 or 3, and (b) determining whether binding has occurred between said polypeptide and BLyS or a BLyS-like polypeptide.

8. A method for purifying BLyS or a BLyS-like polypeptide comprising:
contacting a solution containing BLyS or a BLyS-like polypeptide to a support that comprises, immobilized thereon, a BLyS polypeptide according to claim 1 or 3; and,
separating the solution from said support.

9. BLyS separation media comprising:
(a) a chromatographic matrix material, and, immobilized thereon,
(b) a BLyS binding molecule comprising a BLyS binding polypeptide as defined claim 1 or 3.

10. The BLyS separation media according to claim 9, comprising:
(a) a chromatographic matrix material, and, immobilized thereon,
(b) a BLyS binding molecule comprising a BLyS binding polypeptide comprising an amino acid sequence selected from the group consisting of SEQ ID NOs: 20–162 and 186–435, as depicted in Tables 1–8 and 14.

11. A method for separating BLyS or a BLyS-like polypeptide from a solution containing it comprising:
(a) contacting said solution with separation media as defined in claim 9,
(b) removing unbound material; and
(c) eluting bound BLyS or BLyS-like polypeptide from said separation media.

12. The polypeptide according to claim 1, wherein the polypeptide comprises an amino acid sequence according to H.

13. The polypeptide according to claim 12, wherein the polypeptide comprises
$X_1$-$X_2$-$X_3$-Cys-$X_5$-Phe-$X_7$-Trp-Glu-Cys-$X_{11}$-$X_{12}$-$X_{13}$ (SEQ ID NO:1),
wherein
$X_1$ is Ala, Asn, Lys, or Ser;
$X_2$ is Ala, Glu, Met, Ser, or Val;
$X_3$ is Ala, Asn, Lys, or Pro;
$X_{11}$ is Ala, Gln, His, Phe, or Val;
$X_{12}$ is Asn, Gln, Gly, His, Ser, or Val; and
$X_{13}$ is Ala, Asn, Gly, Ile, Pro, or Ser.

14. The polypeptide according to claim 13, wherein $X_1$ is Lys.

15. The polypeptide according to claim 12, wherein $X_5$ is Tyr.

16. The polypeptide according to claim 12, wherein $X_7$ is Tyr.

17. The polypeptide according to claim 12, wherein $X_5$ is Tyr; and $X_7$ is Tyr.

18. The polypeptide according to claim 12, that comprises SEQ ID NO:22, 23, 24, 25, or 26.

19. The polypeptide according to claim 12, that comprises SEQ ID NO:27.

20. The BLyS binding polypeptide according to claim 12, wherein the polypeptide comprises the sequence AGKEP-CYFYWECAVSGPGPEGGGK (SEQ ID NO:163).

21. The BLyS binding polypeptide of claim 1, wherein the polypeptide binds BLyS with an affinity less than 3 μM.

22. The BLyS binding polypeptide of claim 12, wherein the polypeptide binds BLyS with an affinity less than 3 μM.

23. The BLyS binding polypeptide of claim 13, wherein the polypeptide binds BLyS with an affinity less than 3 μM.

24. The BLyS binding polypeptide of claim 1, wherein the polypeptide binds BLyS at least 12-fold better than the polypeptide binds strepavidin.

25. The BLyS binding polypeptide of claim 12, wherein the polypeptide binds BLyS at least 12-fold better than the polypeptide binds strepavidin.

26. The BLyS binding polypeptide of claim 1, that comprises an amino acid sequence according to formula I.

27. The BLyS binding polypeptide of claim 26, that comprises SEQ ID NO:28.

28. A method for purifying BLyS or a BLyS-like polypeptide, the method comprising:
contacting a solution containing BLyS or a BLyS-like polypeptide to a support that comprises, immobilized thereon, a BlyS binding polypeptide according to claim 12, 13, 14, 15, 16, 17, 18, 19, or 20; and, separating the solution from the support.

29. The polypeptide according to claim 1, wherein the polypeptide comprises an amino acid sequence according to formula J.

30. The polypeptide according to claim 1, wherein the polypeptide comprises an amino acid sequence according to formula K.

31. The polypeptide according to claim 1, wherein the polypeptide comprises an amino acid sequence according to formula L.

* * * * *